(12) United States Patent
Kim et al.

(10) Patent No.: US 9,938,287 B1
(45) Date of Patent: Apr. 10, 2018

(54) BLUE FLUORESCENCE DOPANT COMPOUND AND ORGANIC ELECTROLUMINESCENT DEVICE USING THE SAME

(71) Applicant: NANJING TOPTO MATERIALS CO., LTD., Nanjing (CN)

(72) Inventors: Jin Woo Kim, Nanjing (CN); Chao Qian, Nanjing (CN); Xiaowei Wang, Nanjing (CN)

( * ) Notice: Subject to any disclaimer, the term of this patent is extended or adjusted under 35 U.S.C. 154(b) by 0 days.

(21) Appl. No.: 15/828,293

(22) Filed: Nov. 30, 2017

(51) Int. Cl.
| | | |
|---|---|---|
| *C07D 493/02* | (2006.01) | |
| *C07D 405/14* | (2006.01) | |
| *H01L 51/00* | (2006.01) | |
| *C07D 493/04* | (2006.01) | |
| *C09K 11/06* | (2006.01) | |
| *H01L 51/50* | (2006.01) | |

(52) U.S. Cl.
CPC ............ *C07D 493/04* (2013.01); *C09K 11/06* (2013.01); *H01L 51/0073* (2013.01); *H01L 51/5012* (2013.01); *C09K 2211/1088* (2013.01)

(58) Field of Classification Search
CPC ...... C07D 493/02; C07D 405/14; H01L 51/00
USPC ........................... 549/456; 546/101; 313/504
See application file for complete search history.

(56) References Cited

U.S. PATENT DOCUMENTS 8,999,528 B2 * 4/2015 Kim .................... H01L 51/0072
257/40

* cited by examiner

Primary Examiner — Charanjit Aulakh
(74) Attorney, Agent, or Firm — Gokap Bayramoglu

(57) ABSTRACT

A blue fluorescence dopant is characterized by the following structural formula:

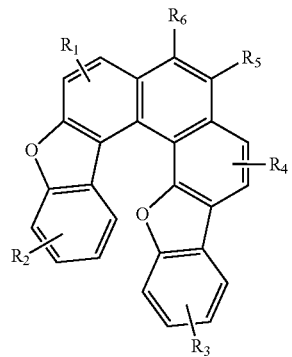

in which $R_1$, $R_2$, $R_3$, $R_4$, $R_5$ and $R_6$ are, each independently, selected from, a hydrogen atom, a C1-C10 linear or branched alkyl group, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridinyl group, a pyrimidinyl group, a quinolyl group and a triazinyl group. The blue fluorescence dopant disclosed in the present invention may facilitate to lower driving voltage and increase efficiency, brightness, heat stability, color purity, lifetime, etc. Further, an organic electroluminescent device using the blue fluorescence dopant has excellent performances of high efficiency and long lifetime.

14 Claims, No Drawings

BLUE FLUORESCENCE DOPANT COMPOUND AND ORGANIC ELECTROLUMINESCENT DEVICE USING THE SAME

CROSS REFERENCE TO RELATED APPLICATION

This application is based upon and claims priority to Chinese Patent Application No. 201610881333.9, filed on Sep. 30, 2016, the entire contents of which are incorporated herein by reference.

TECHNICAL FIELD

The present invention falls within the field of luminescent material technology and it specifically relates to an organic electroluminescent compound which could be used as blue dopant material and an organic electroluminescent device using the same.

BACKGROUND OF THE INVENTION

The electroluminescent phenomenon was first discovered in 1930s, and the luminescent material was ZnS powder. The LED technology was developed through this and now it is widely used in the energy-saving light source. However, the organic electroluminescent phenomenon was first discovered by Pope et al. in 1963. They found that the anthracene single crystal could emit a faint blue light under the drive of the voltage above 100V. Until 1987, by adopting sandwich device structure, Dr Ching W. Tang et al. of Kodak made a double layered device through vacuum evaporation of fluorescent dyes in the U.S. Pat. No. 4,356,429. The brightness of this device could reach 1000 cd/m$^2$ under the driving voltage of 10 v. This greatly promoted the research of OLED materials and devices.

Compared with inorganic luminescent material, there are the following advantages of the organic electroluminescent material: 1. The processing properties of organic material are good, which could be made into films on any substrate by means of evaporation or spinning, etc.; 2 Due to the diversity of the organic molecular structure, the improvement of the material could be achieved by the design and modification of the structure of the molecular to adjust the heat stability, mechanical properties, luminescence and electric conductivity of the material.

The luminescence principle of electromechanical emitting diodes is similar to that of inorganic luminescent diodes. Its principle is as follows: under the action of the electric field, Hole and Electron are injected respectively through the anode and cathode, the luminescence composite layer form excitons and then the excitons return to ground state by luminescence relaxation, thus the goal of luminescence is achieved.

Most of the material used in the organic electroluminescent device is pure organic material or the mixture of the organic and mental material, which could be divided into hole injection material, hole transport material, luminescent material, electron transport material, electron injection material etc. according to function. Thereinto, the organic material with p-type properties easily being oxidized and having electrochemical stability after being oxidized is often used as hole injection or hole transport material. On the other hand, the organic material with n-type properties easily being reduced and having electrochemical stability after being reduced is often used as electron injection material. The organic material with both p-type and n-type properties is preferably being used as luminescent material.

In order to achieve breakthrough in the application of organic electromechanical device, it is necessary to overcome the difficulties of low capacity of charge injection and transport. An efficient and long-lived organic electroluminescent device is usually the result of the structure of the device and the optimization of various organic materials. This provides a great opportunity and challenge for chemists to develop functionalized materials of various structures.

SUMMARY OF THE INVENTION

Technical Problem to be Solvent: the present invention provides an organic electroluminescent compound to overcome the deficiencies of prior arts. This organic compound, when used as blue dopant material for an organic electroluminescent device, may lower driving voltage and increase light-emitting efficiency, brightness, heat stability, color purity and device lifetime.

Technical Solution: the present invention provides a blue fluorescence dopant of the following structural Formula:

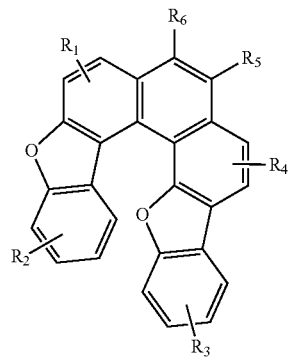

wherein $R_1$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_2$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_3$ is selected from a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_4$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_5$ and $R_6$ are, each independently, selected from a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group.

The present invention, in addition, provides an organic electroluminescent device including the above organic electroluminescent compound.

Advantageous effects: the blue fluorescence dopant provided in the present invention may facilitate to lower driving voltage and increase efficiency, brightness, heat stability, color purity, lifetime, etc. Further, an organic electroluminescent device using the blue fluorescence dopant has excellent performances of high efficiency and long lifetime.

DETAILED DESCRIPTION OF THE EMBODIMENTS

The following embodiment further describe the content of the present invention, but the scope of the present invention is not limited thereto. Without departing from the spirit and substance of the present invention, all modifications and alternatives to the methods, steps or conditions of the present invention are intended to fall within the scope thereof. All technical means employed in the embodiment are conventional means well known to persons skilled in the art, unless specifically stated.

In one respect, the present invention provides a blue fluorescence dopant of the following structural Formula:

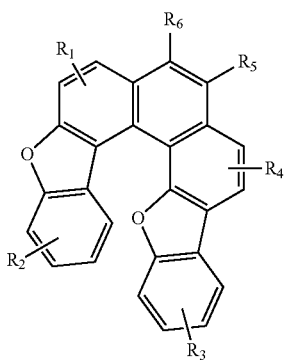

wherein $R_1$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_2$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_3$ is selected from a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_4$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_5$ and $R_6$ are, each independently, selected from a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group.

Further, R1 is selected from an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C20 linear or branched alkyl group, a C3-C24 cyclic alkyl group, a C1-C20 alkoxyl group, a halogen atom, CN, $CF_3$, a $Si(CH_3)_3$ group, or a C6-C50 aryl group.

Further, $R_2$ is selected from an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C20 linear or branched alkyl group, a C3-C24 cyclic alkyl group, a C1-C20 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

Further, $R_3$ is selected from an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, or a C6-C60 aryl group.

Further, $R_4$ is selected from an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C10 linear or branched alkyl group, a C3-C12 cyclic alkyl group, a C1-C10 alkoxyl group, a halogen atom, CN, CF$_3$, a Si(CH$_3$)$_3$ group, a naphthyl group, an anthryl group, a phenanthryl group, dibenzofuran, a fluorenyl group, a carbazolyl group, spiro fluorene, or a heteroaryl group with nuclear number of 5-20.

Further, R$_5$ and R$_6$ are, each dependently, selected from an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C10 linear or branched alkyl group, a C3-C12 cyclic alkyl group, a C1-C10 alkoxyl group, a halogen atom, CN, CF$_3$, a Si(CH$_3$)$_3$ group, a naphthyl group, an anthryl group, a phenanthryl group, dibenzofuran, a fluorenyl group, a carbazolyl group, spiro fluorene, or a heteroaryl group with nuclear number of 5-40.

The blue fluorescence dopant is any one of the following compounds:

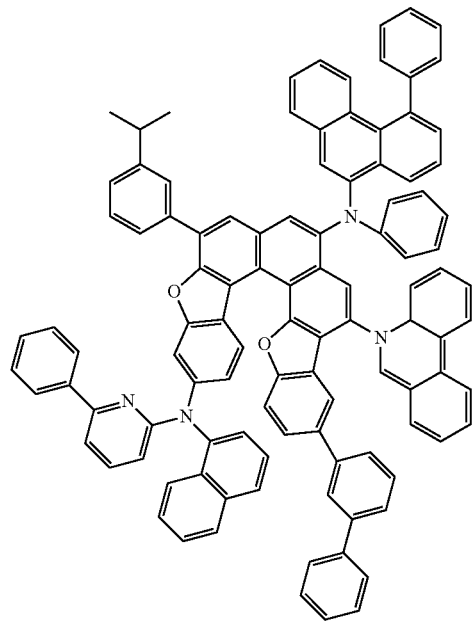

1

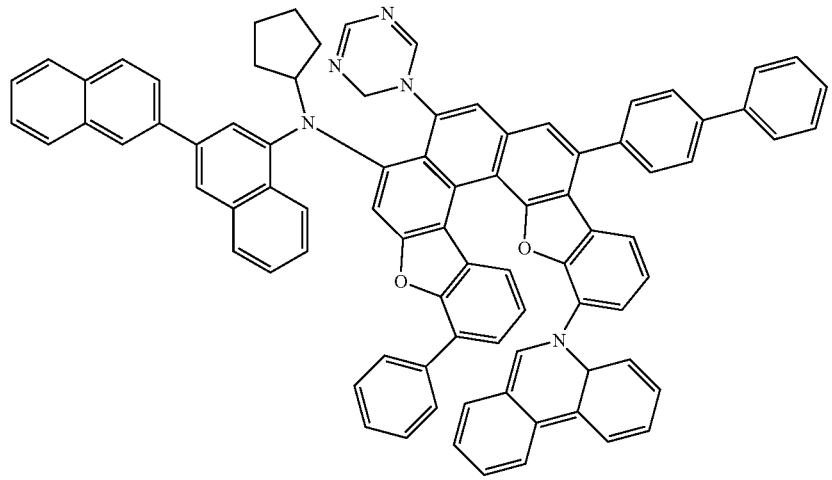

2

-continued
3
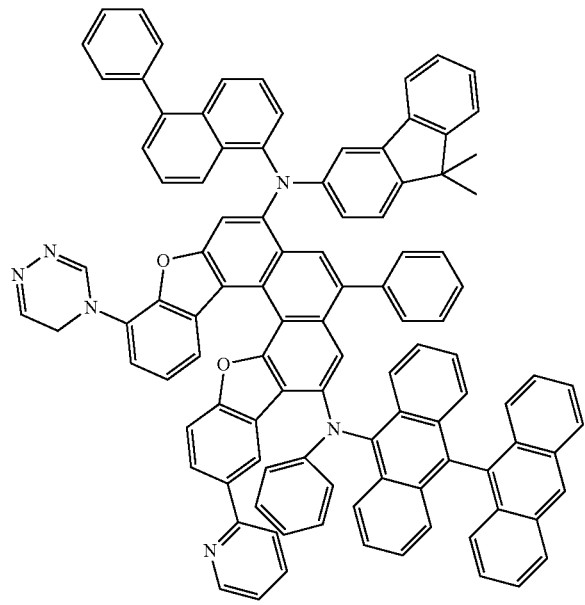
4
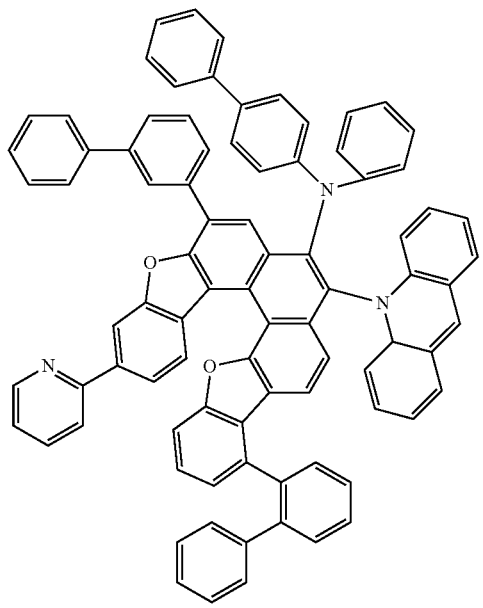
5
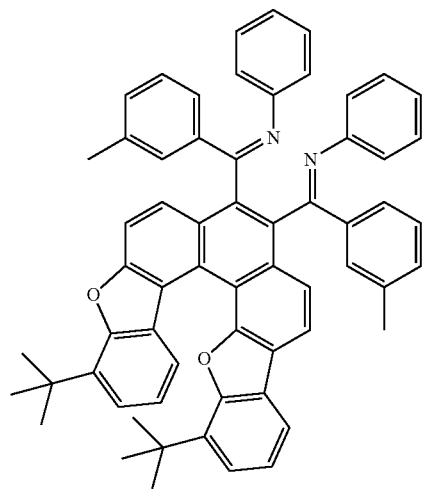
6
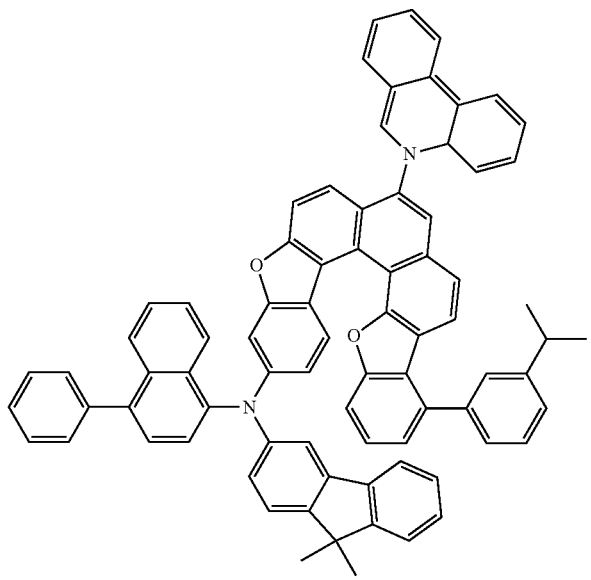

-continued
7
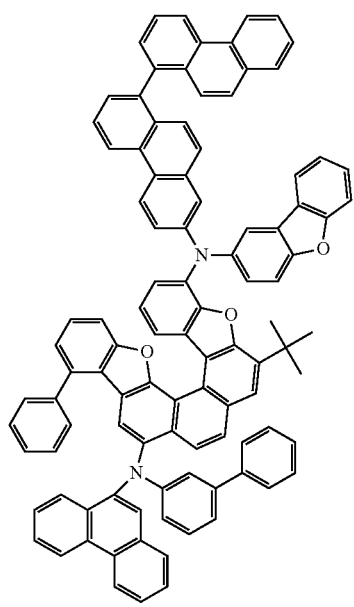
8
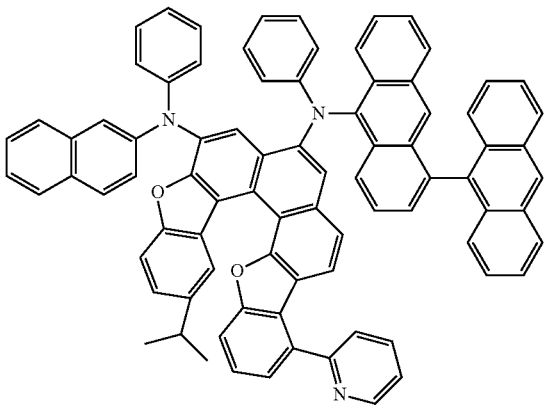
9
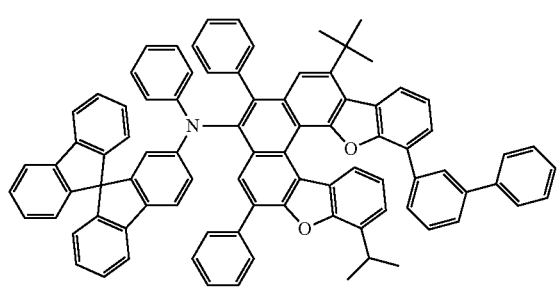
10
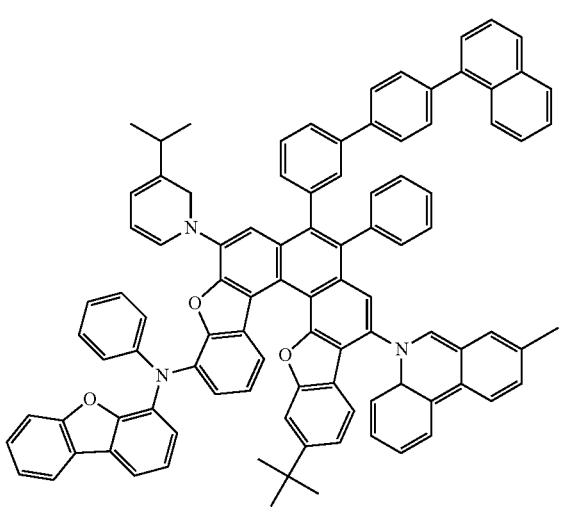

-continued
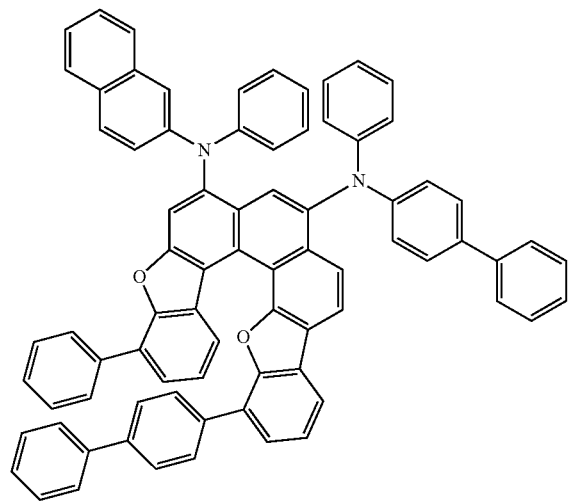
11
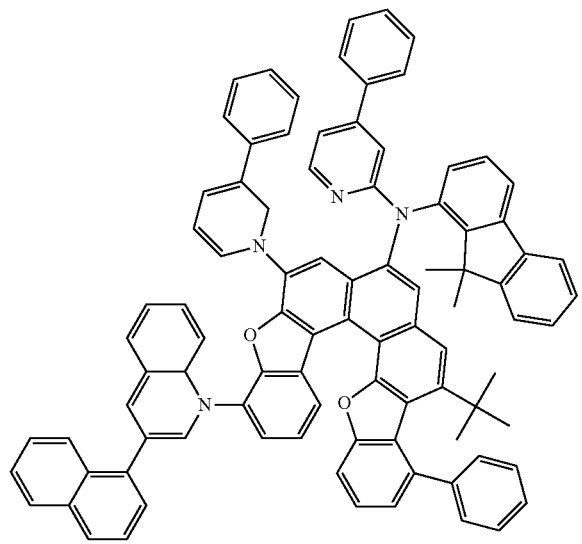
12
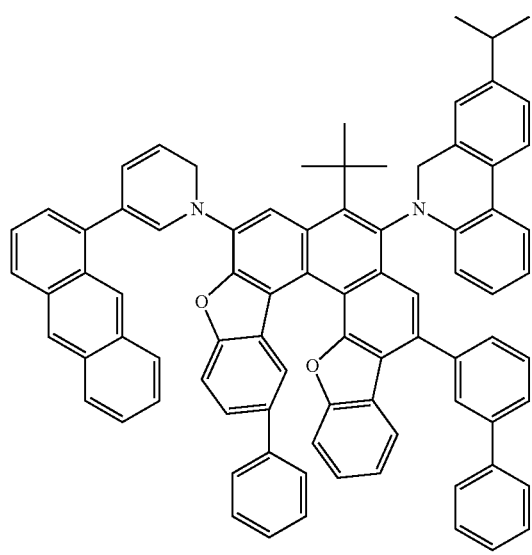
13
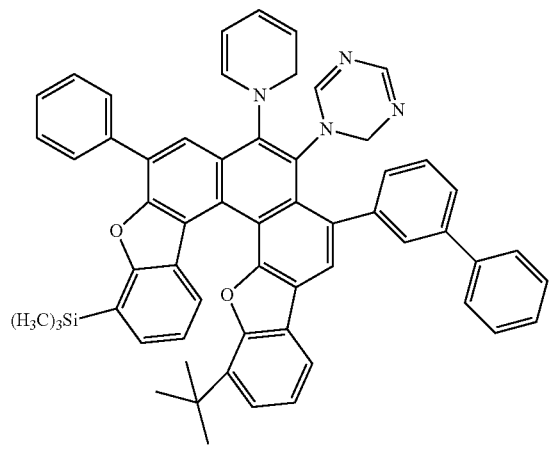
14

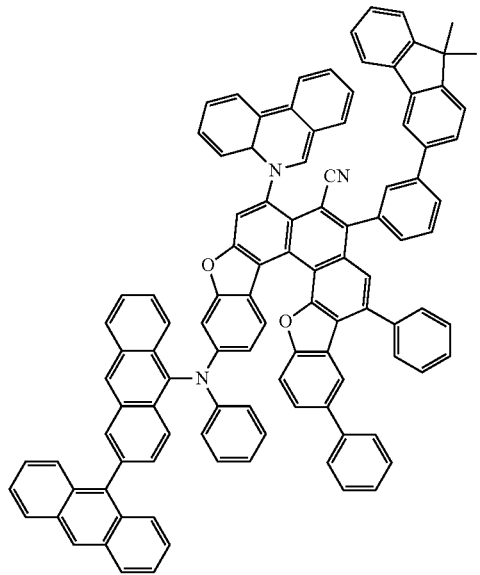
15
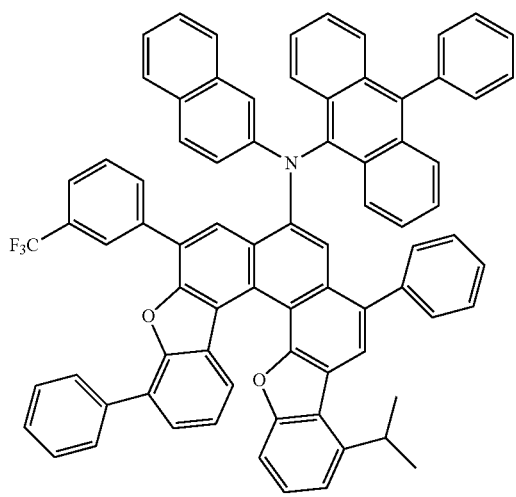
16
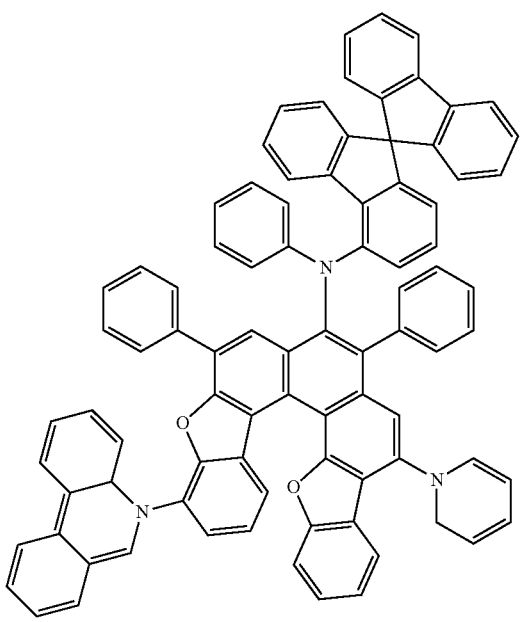
17

18
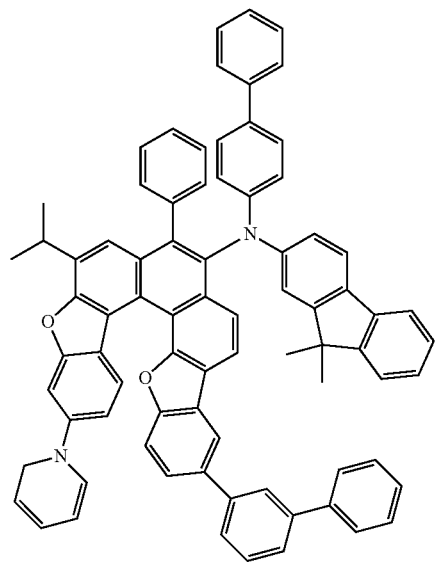
19
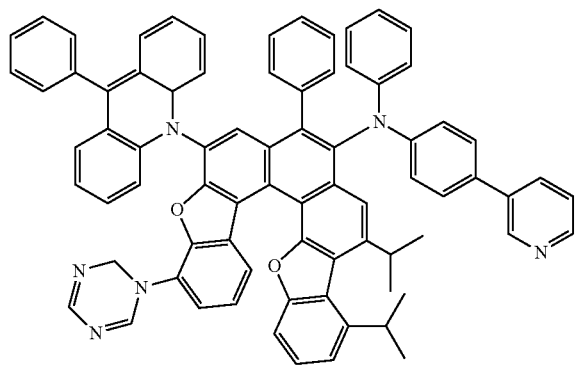
20
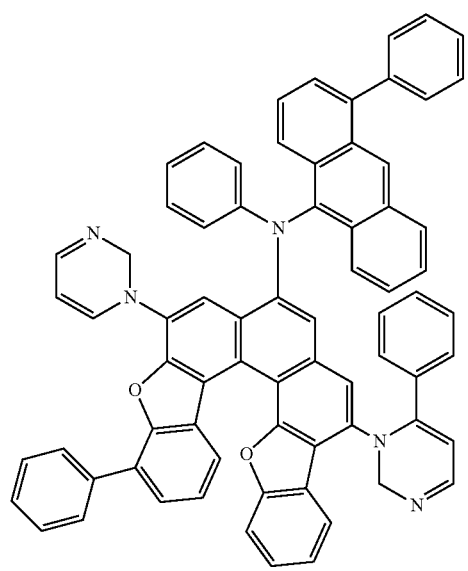
21
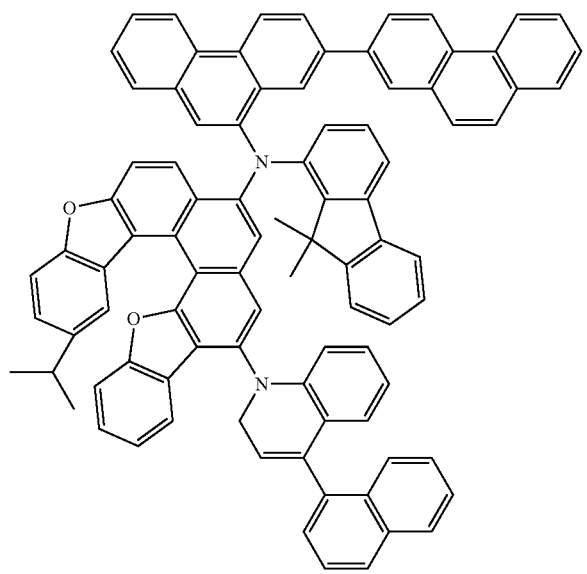

-continued
22
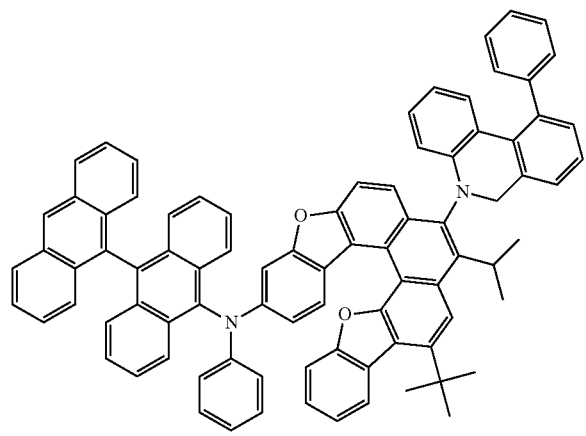
23
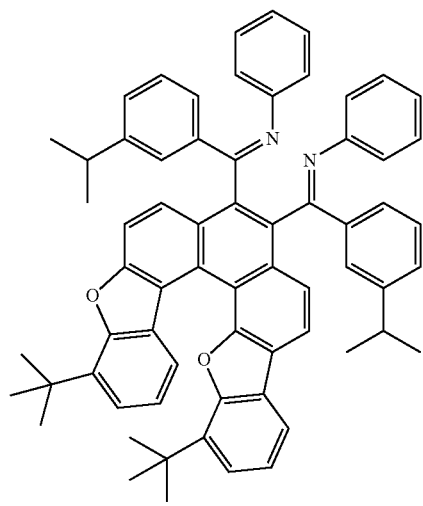
24
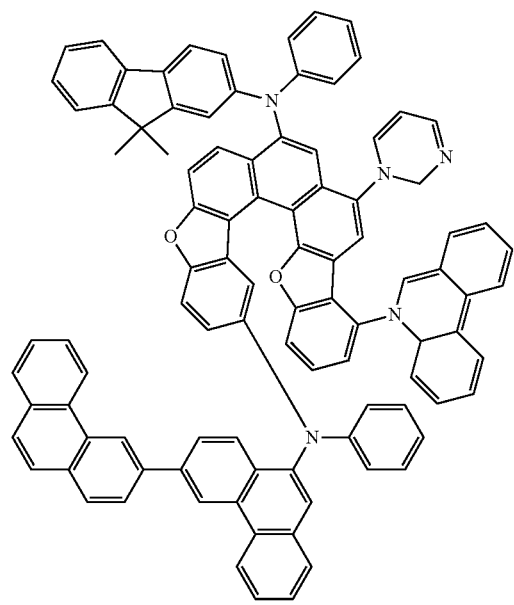
25
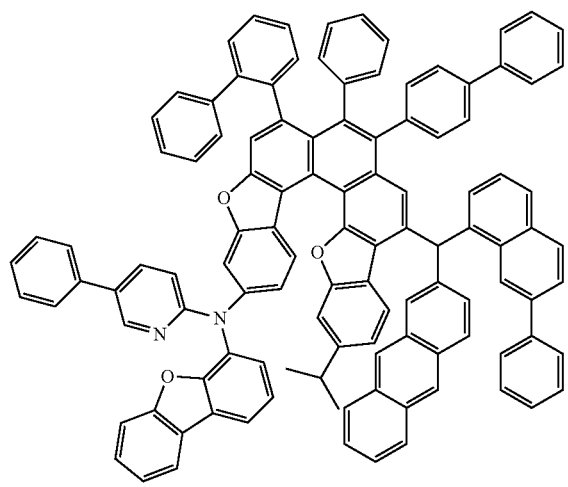

-continued
26 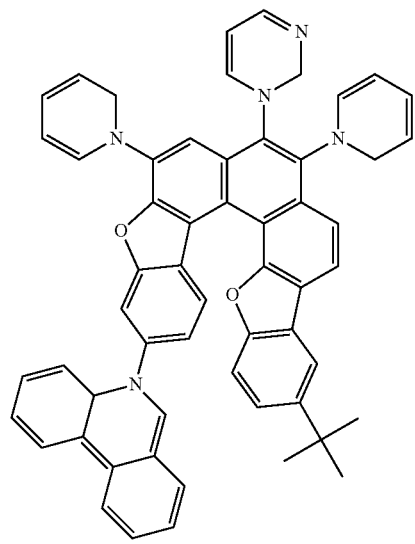
27 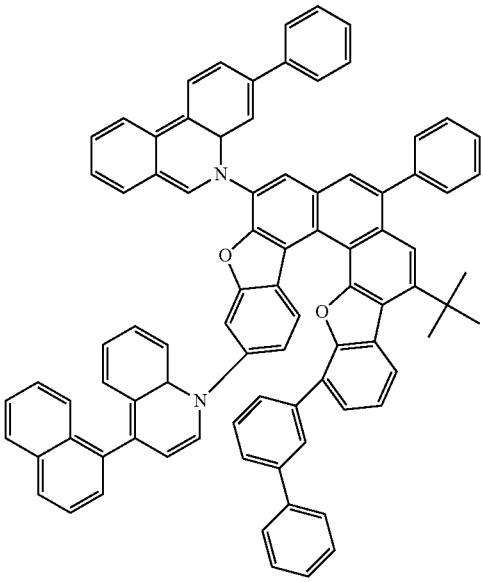
28 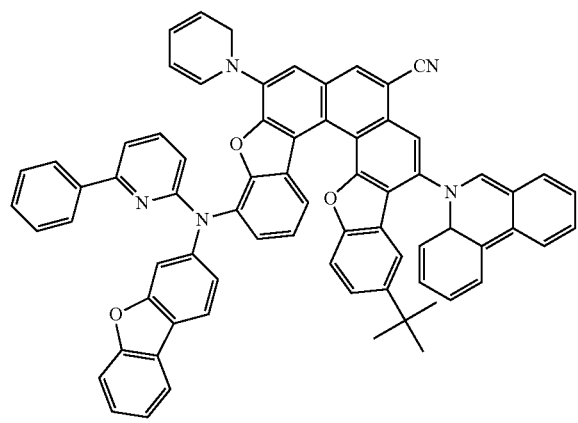
29 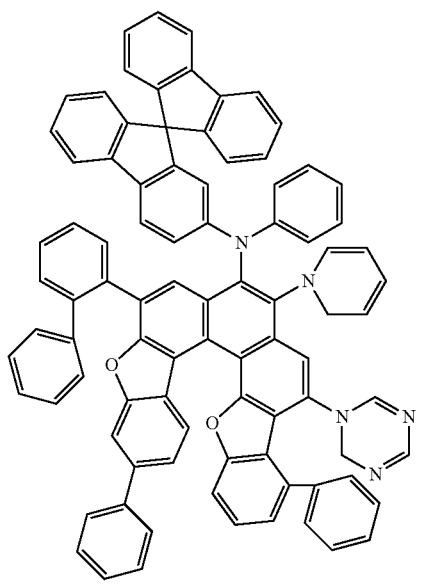

-continued
30
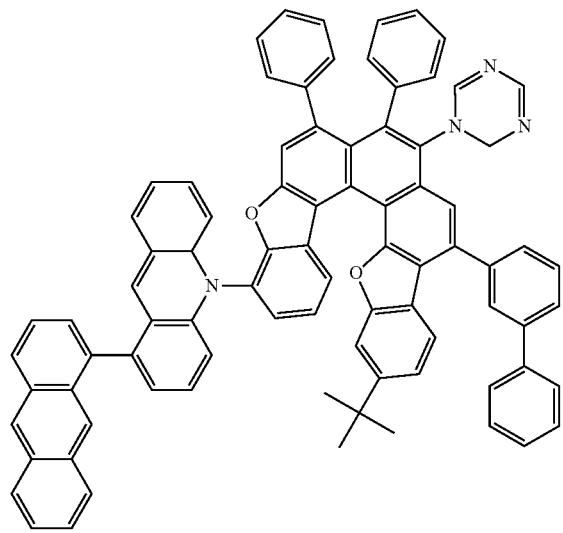
31
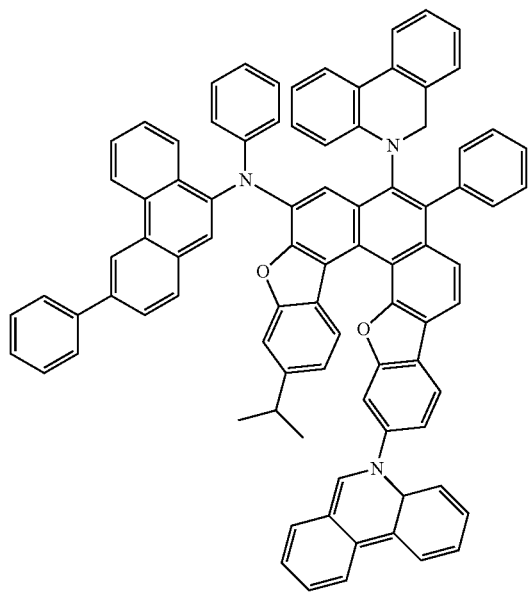
32
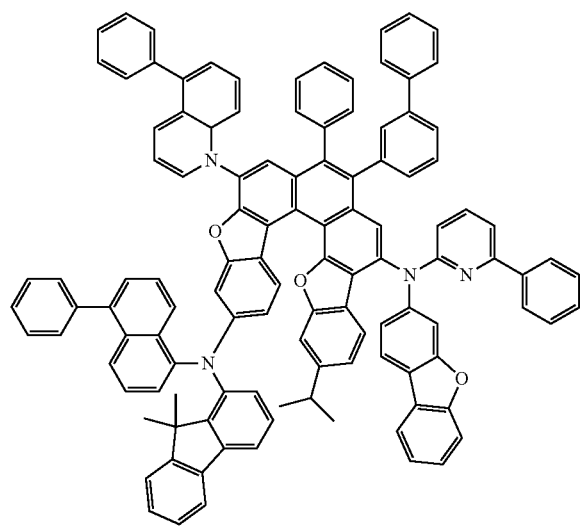
33
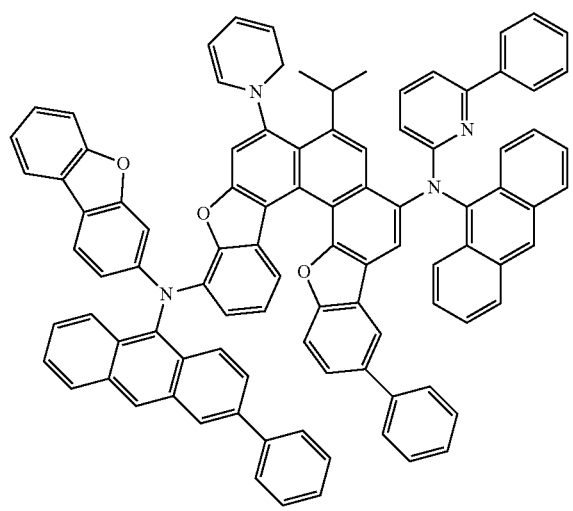

34
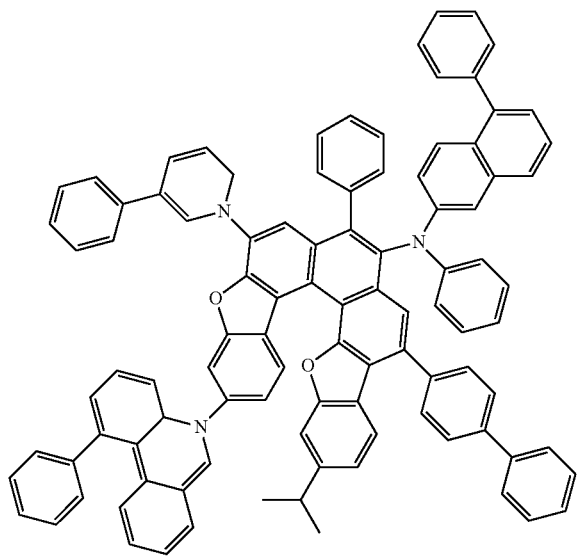
35
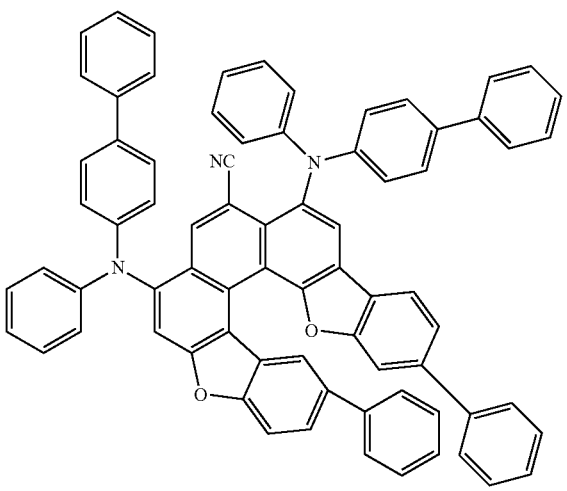
36
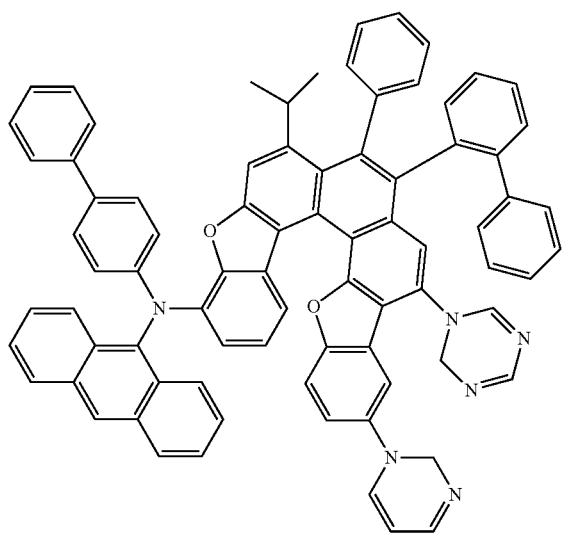
37
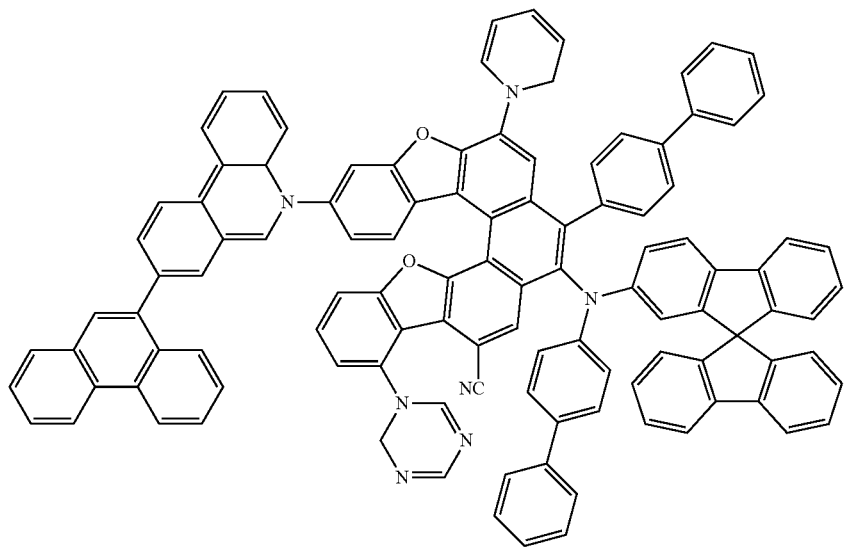

38
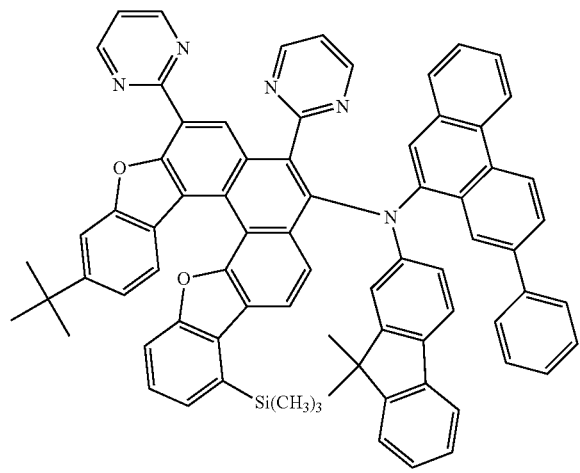
39
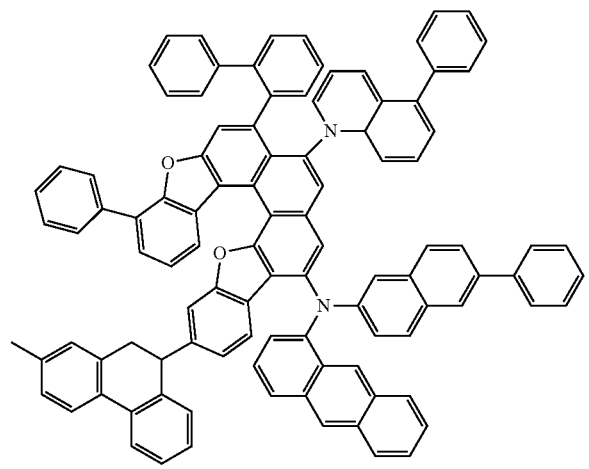
40
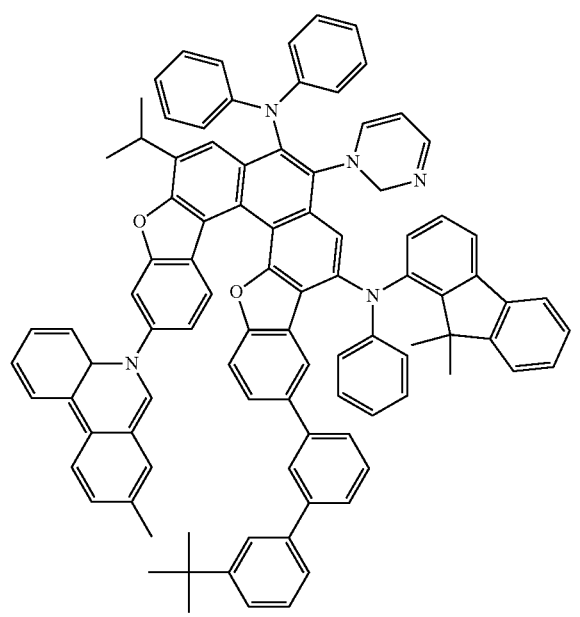
41
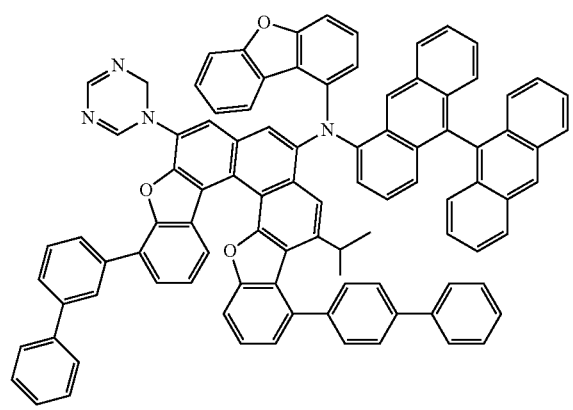

42
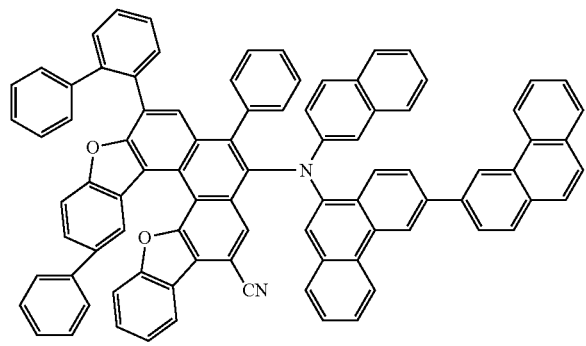
43
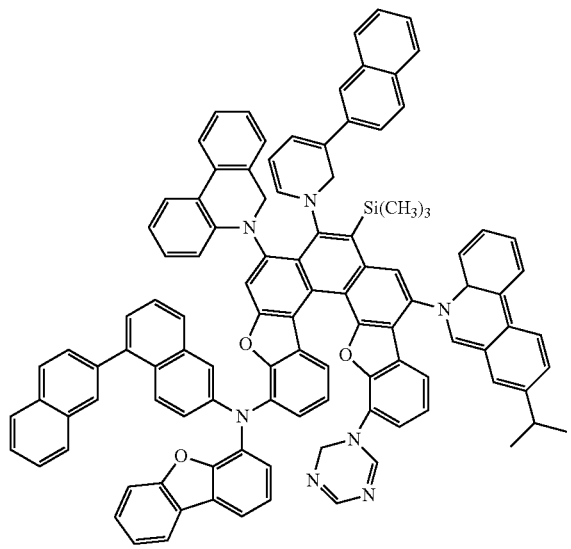
44
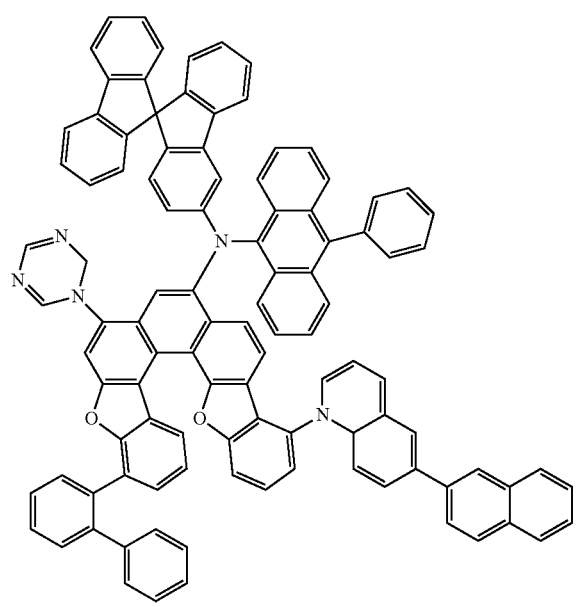

45
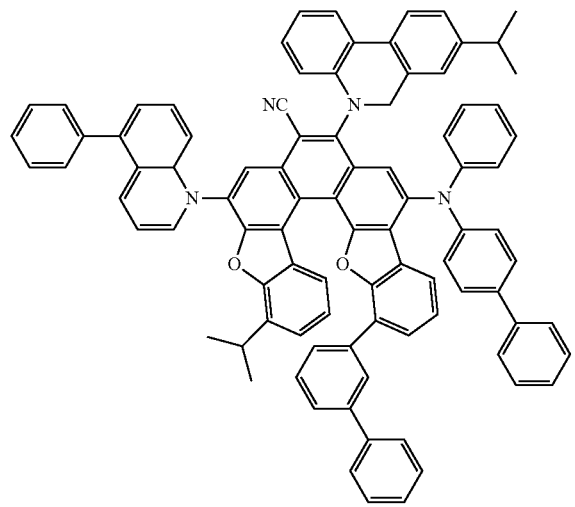
46
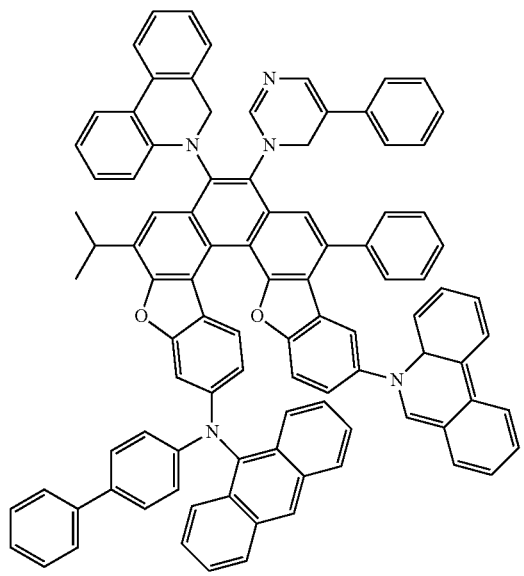
47
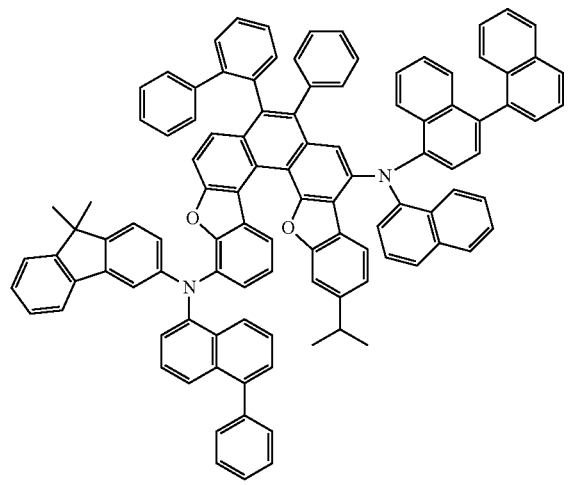
48
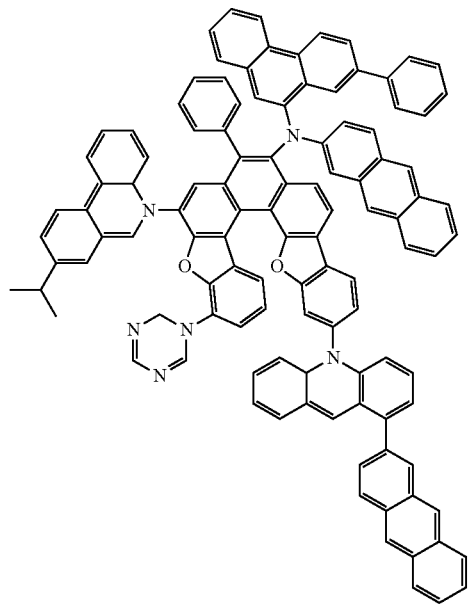

49
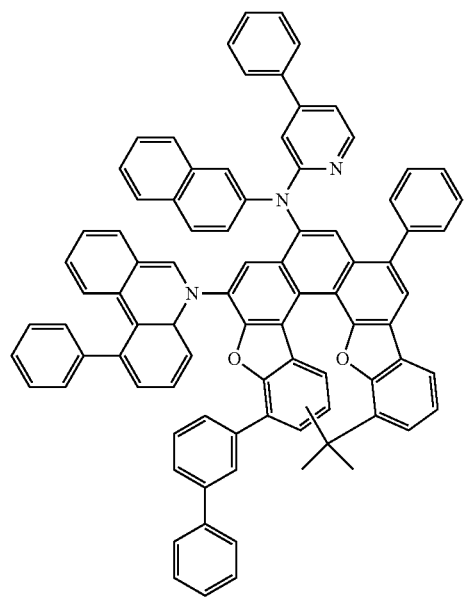
50
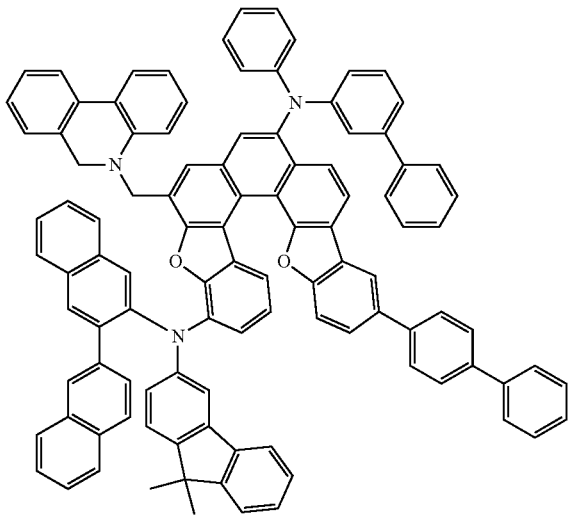
51
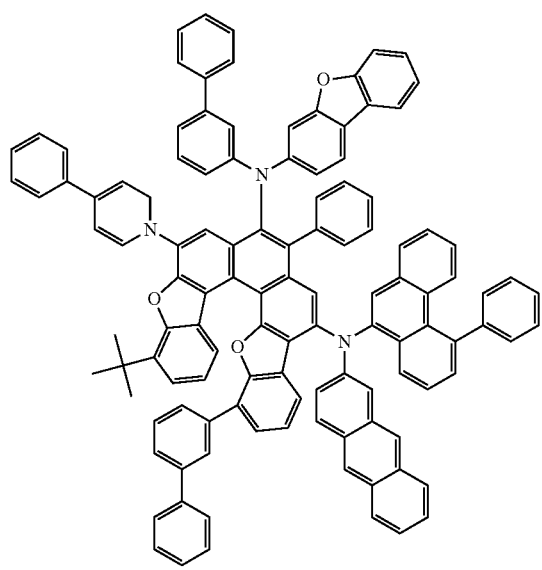
52
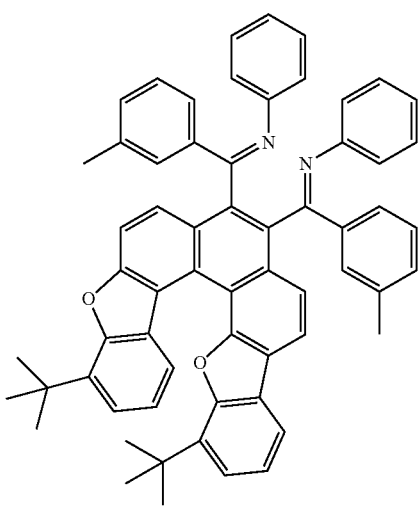

53
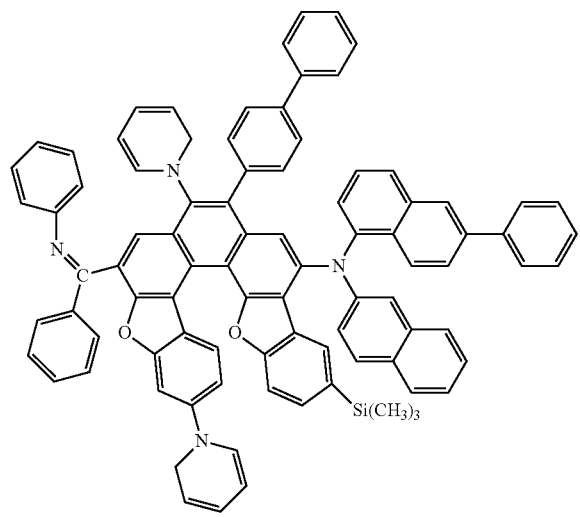
54
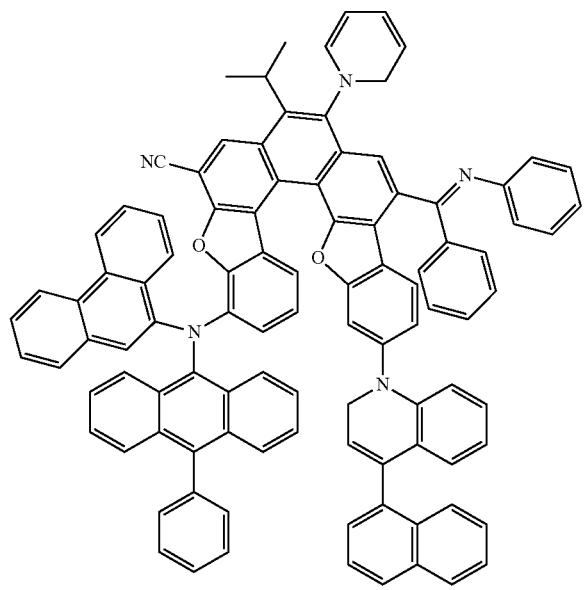
55
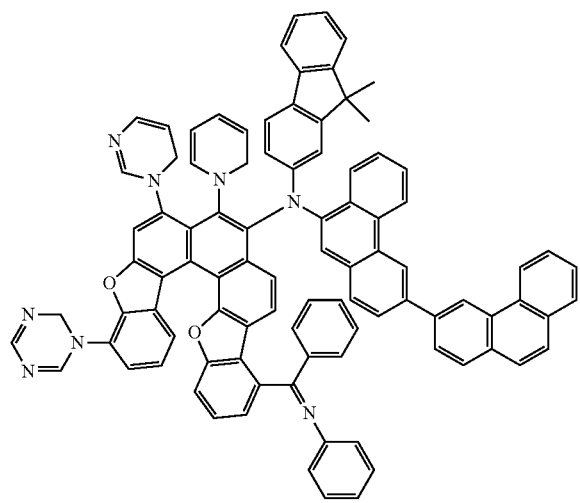
56
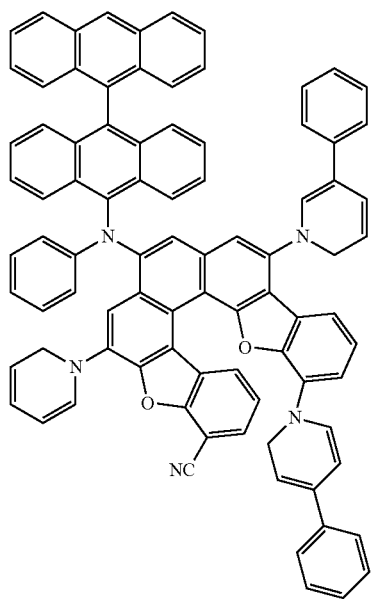

57
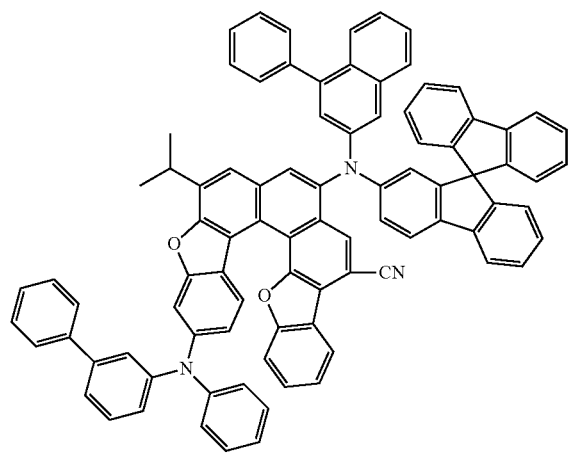
58
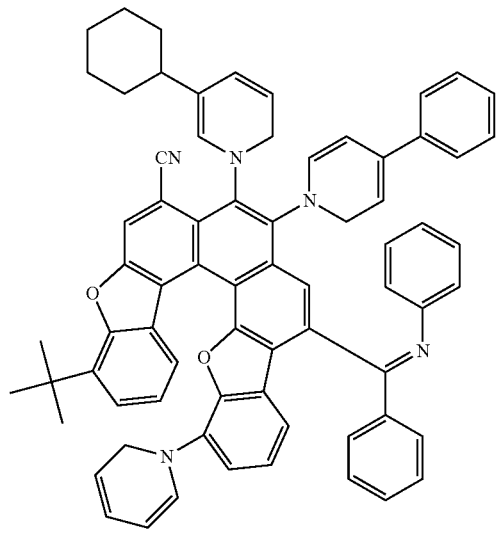
59
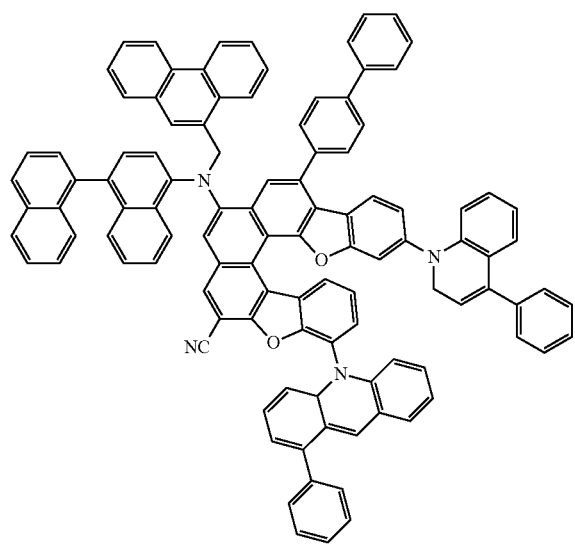
60
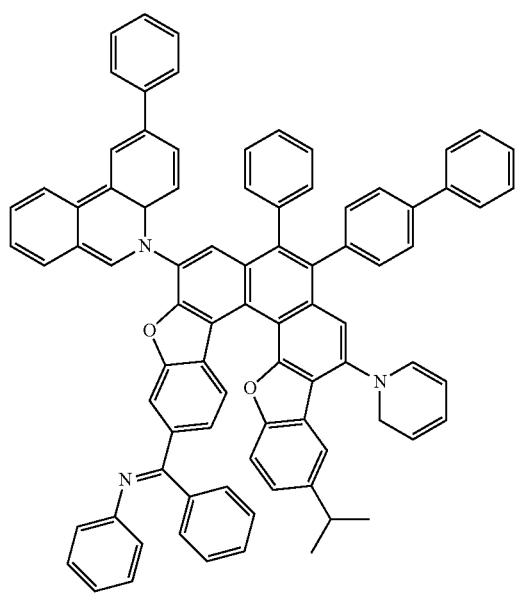

-continued
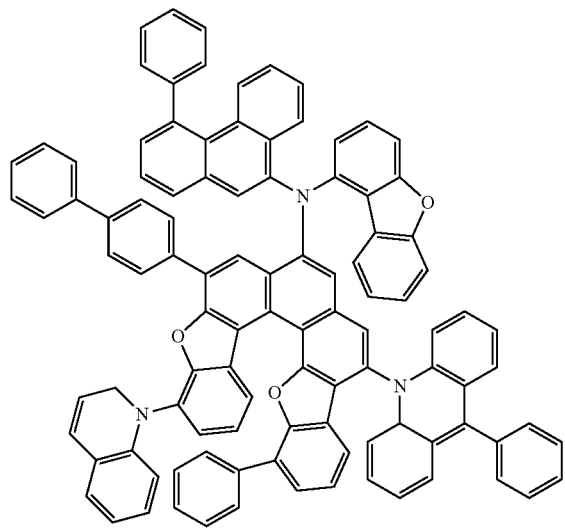
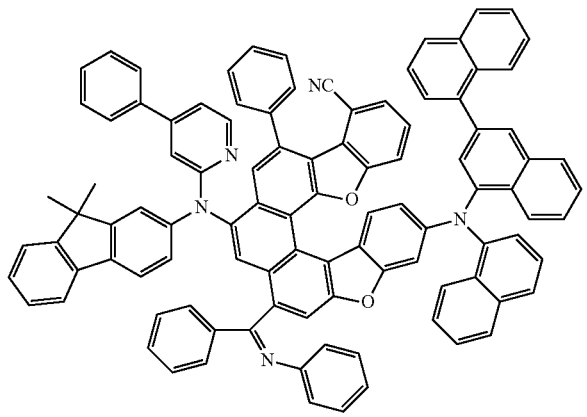
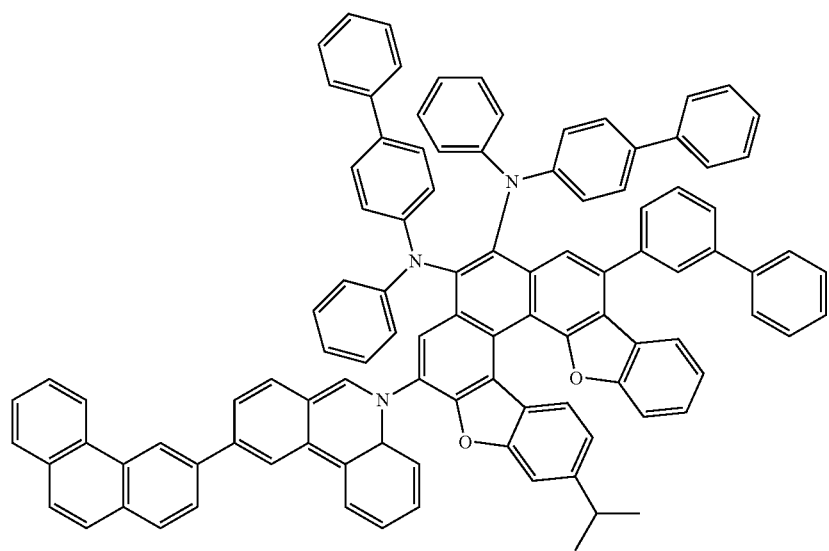

-continued
64
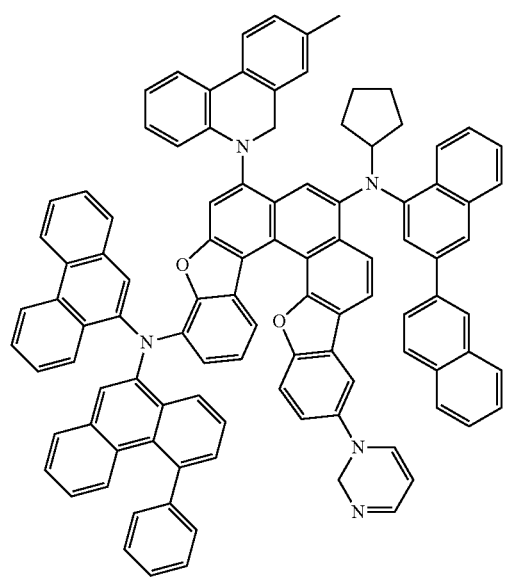
65
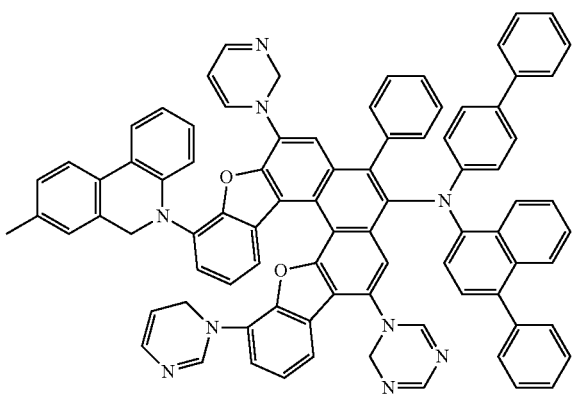
66
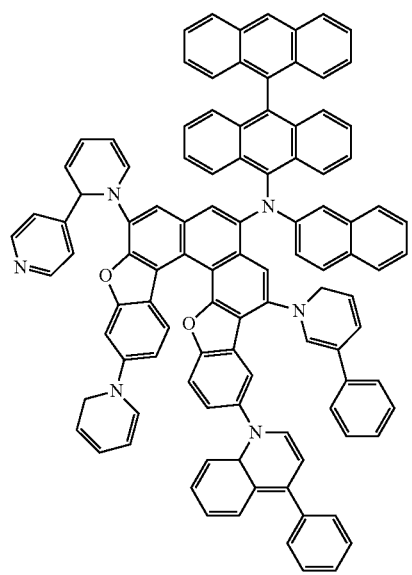
67
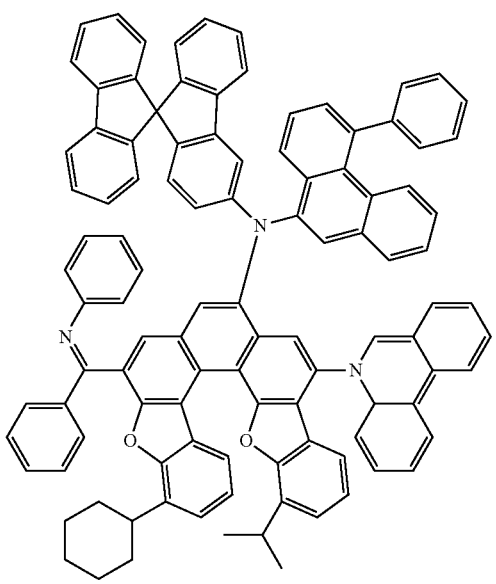

-continued
68
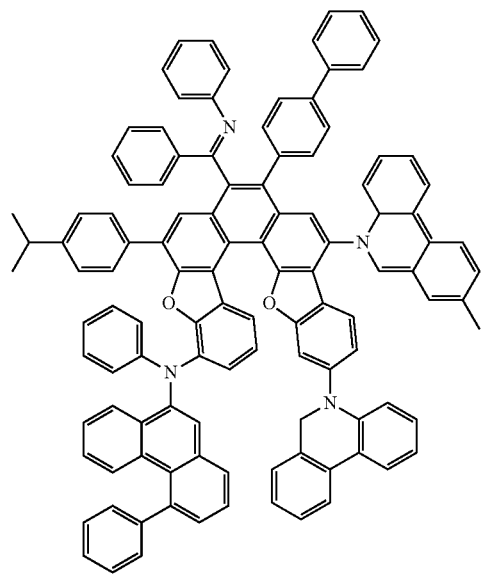
69
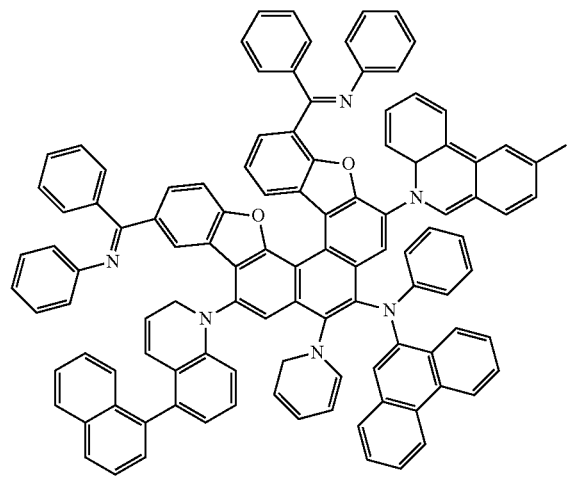
70
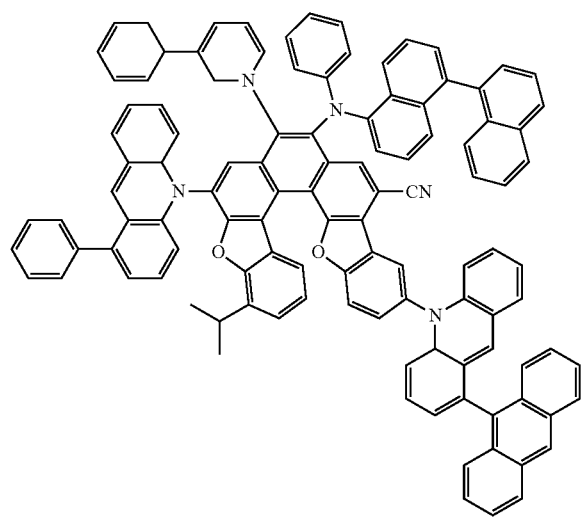
71
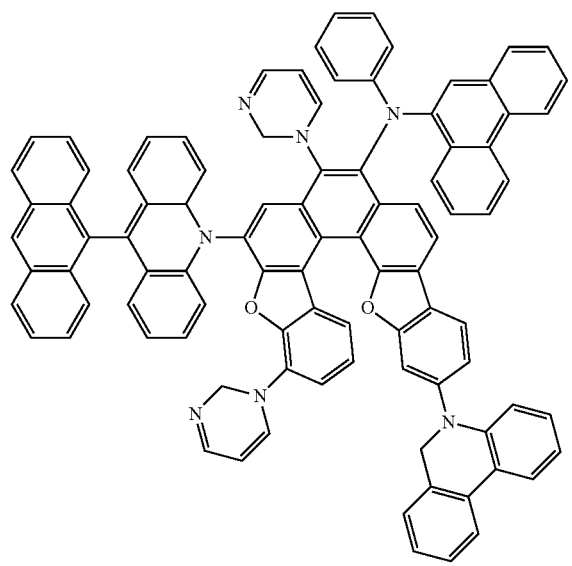

-continued
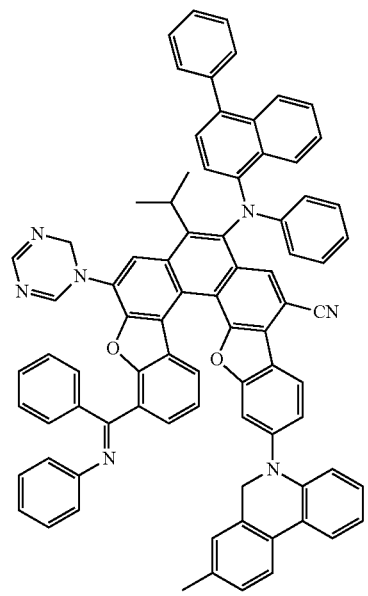
72
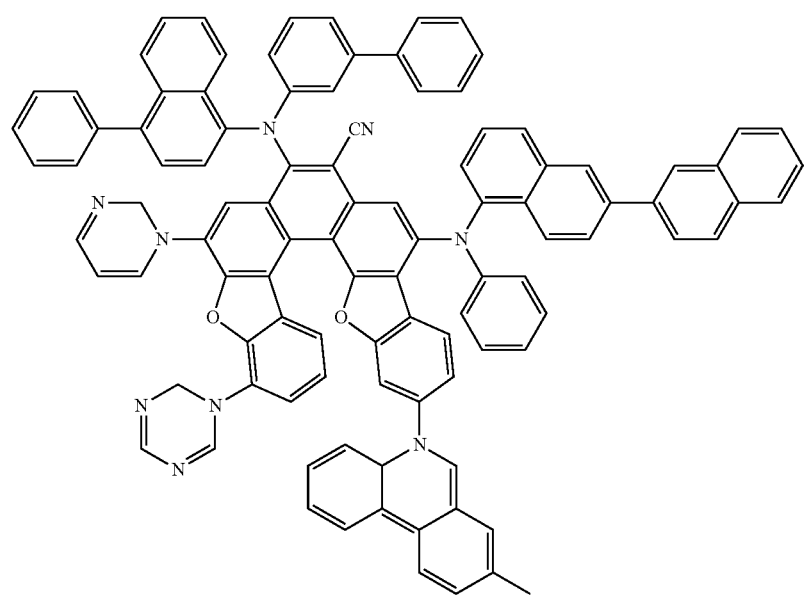
73

-continued
74
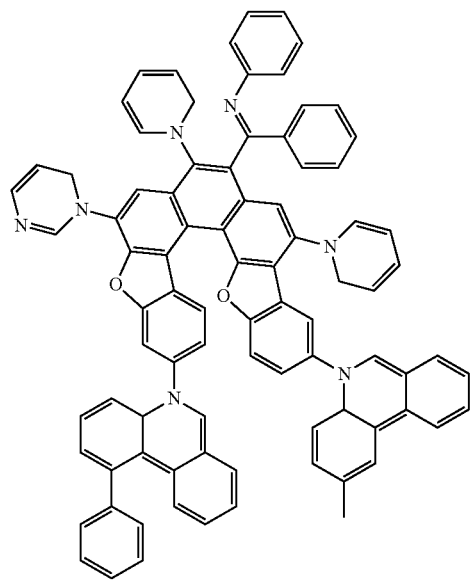
75
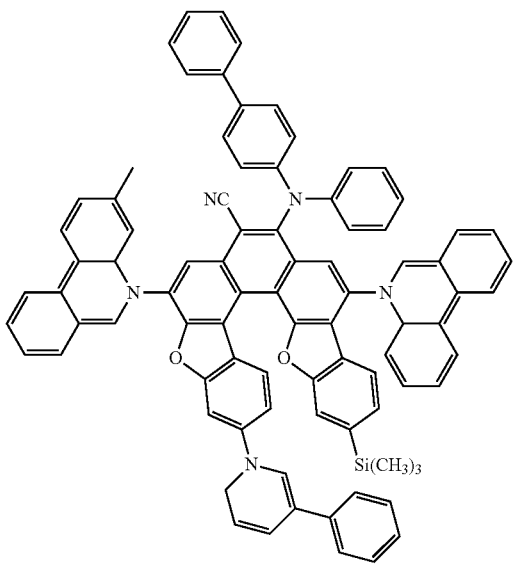
76
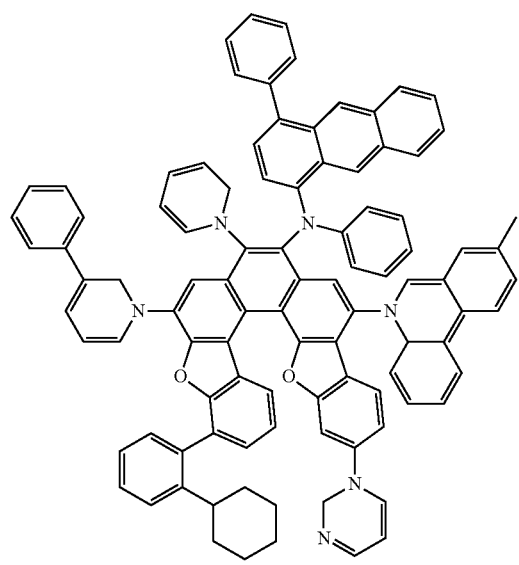
77
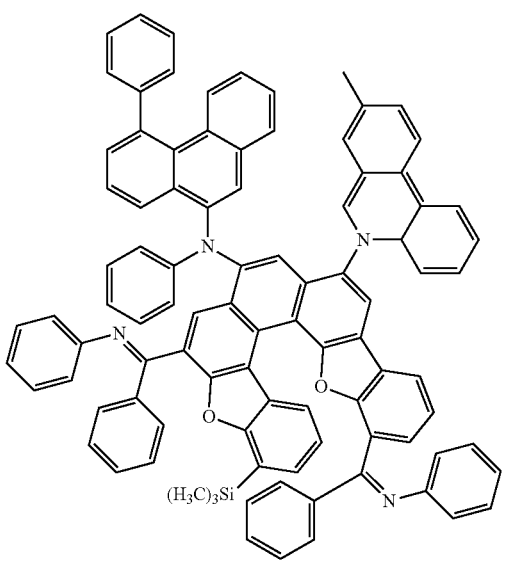

78
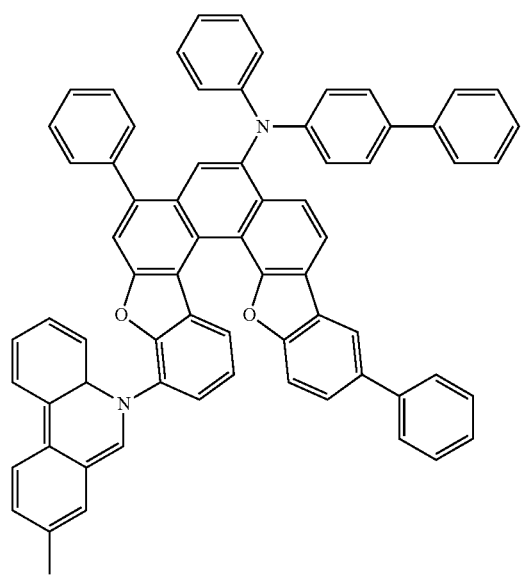
79
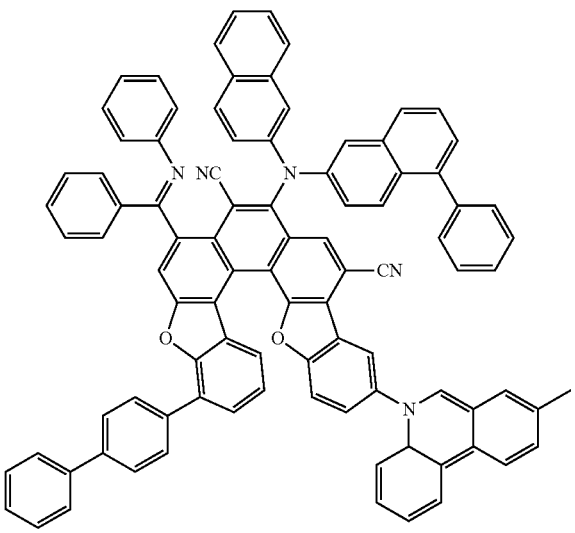
80
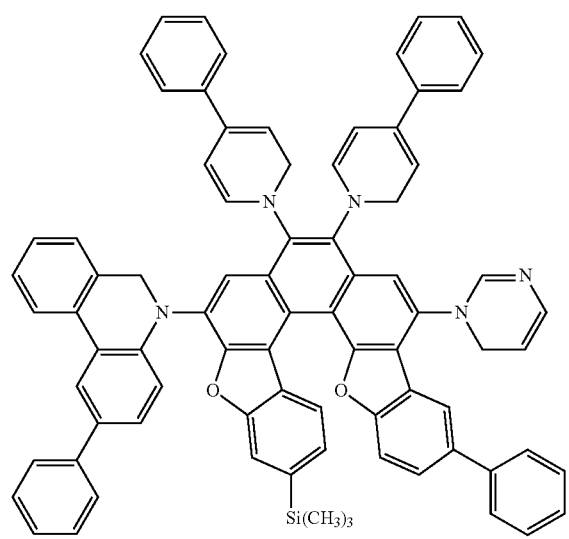
81
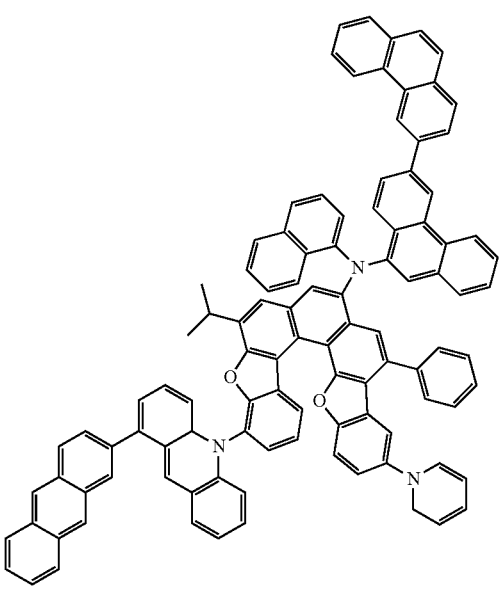

82
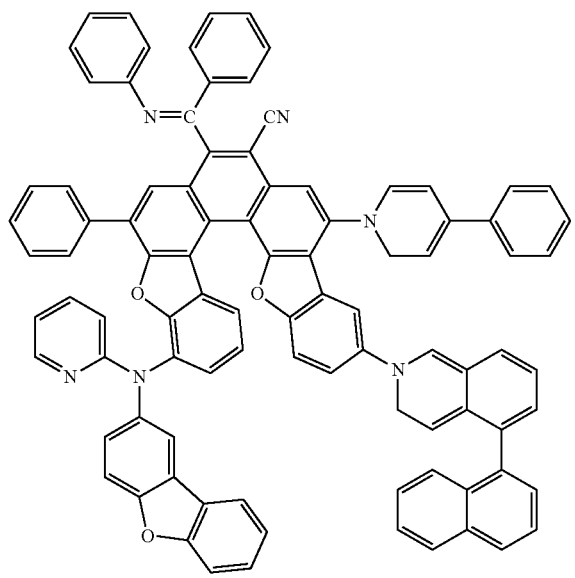
83
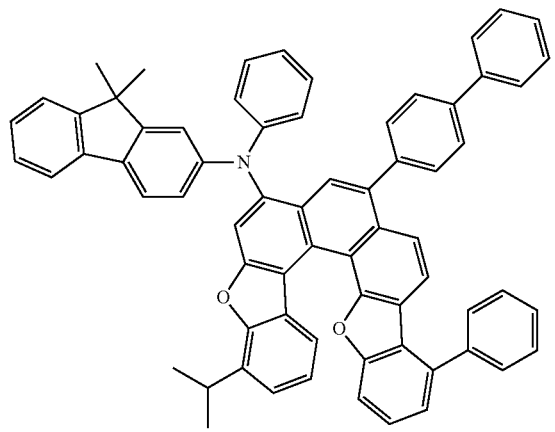
84
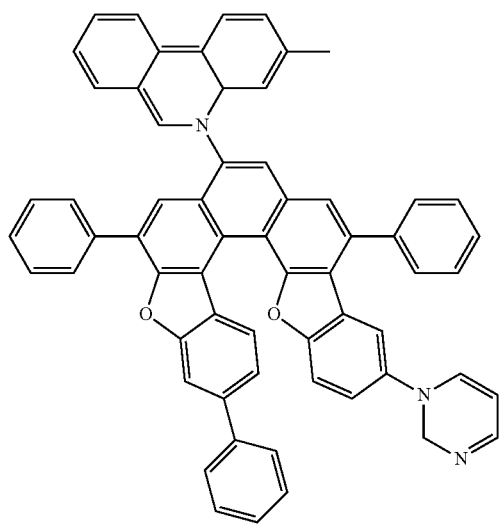
85
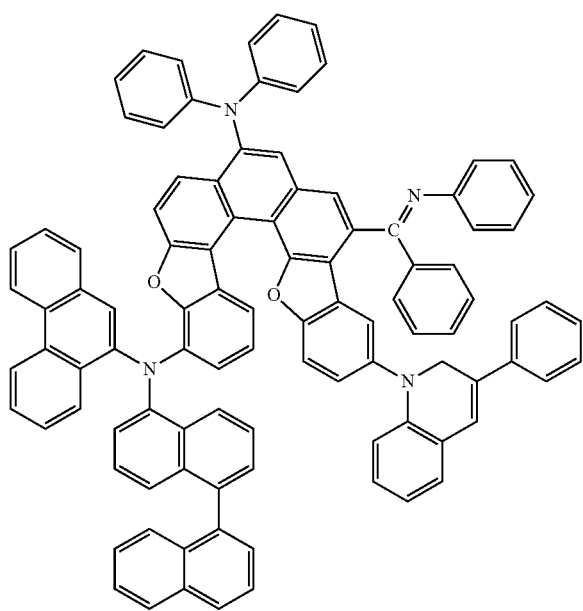

-continued
86
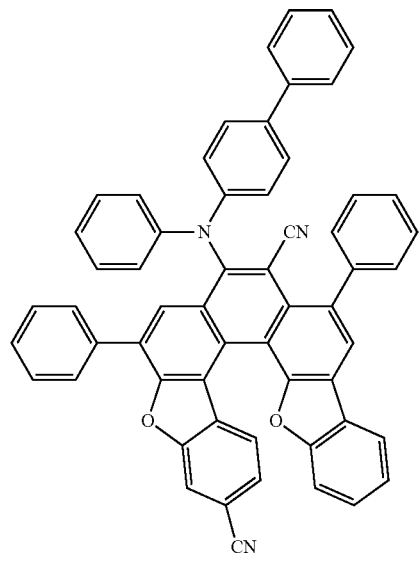
87
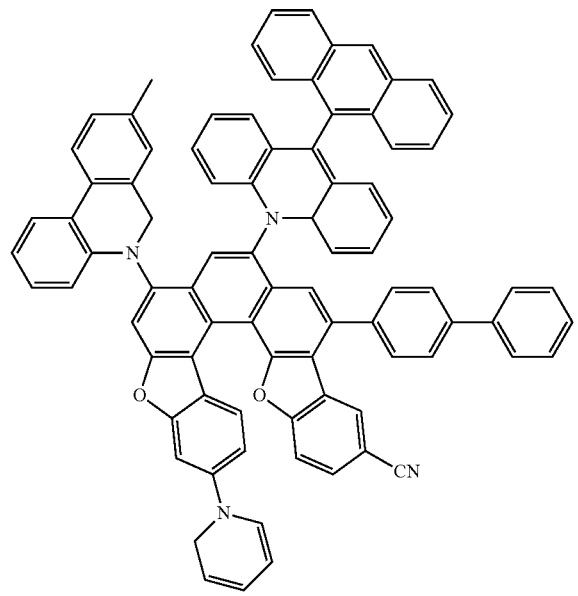
88
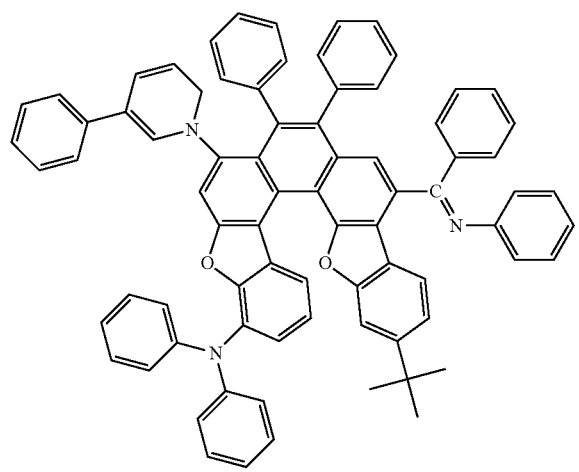
89
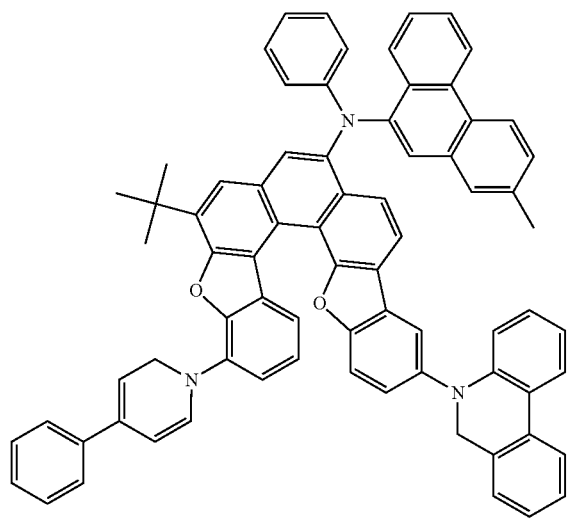

-continued
90
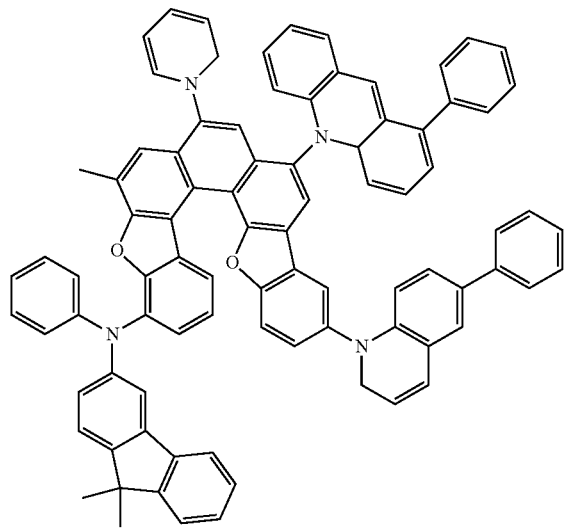
91
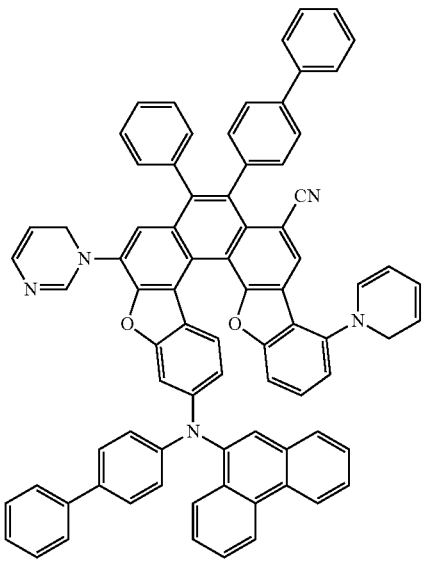
92
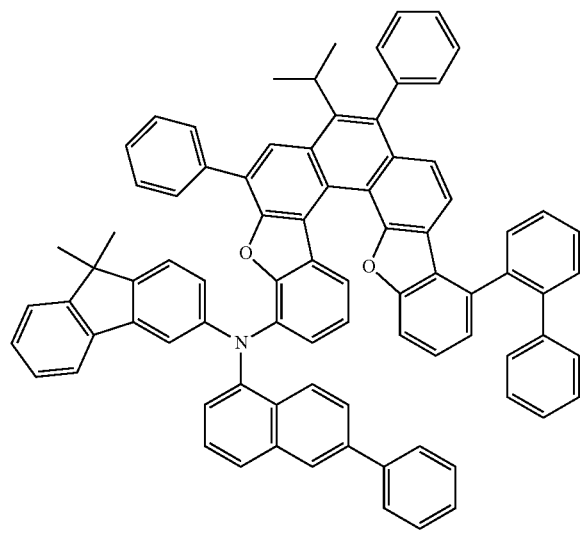
93
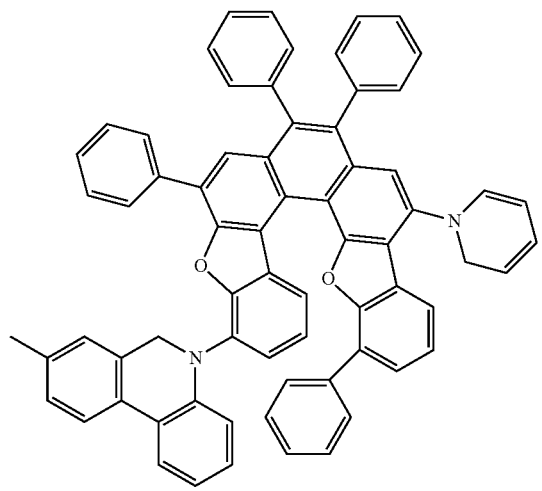
94
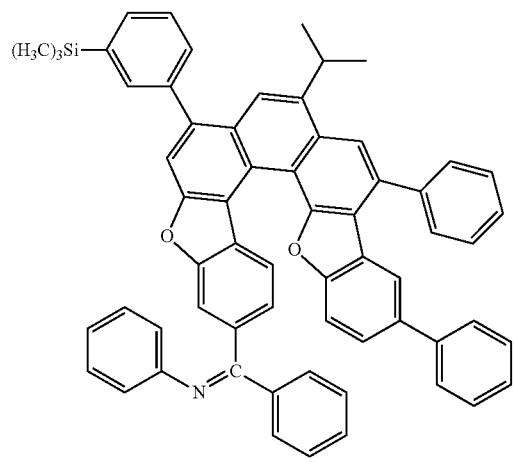
95
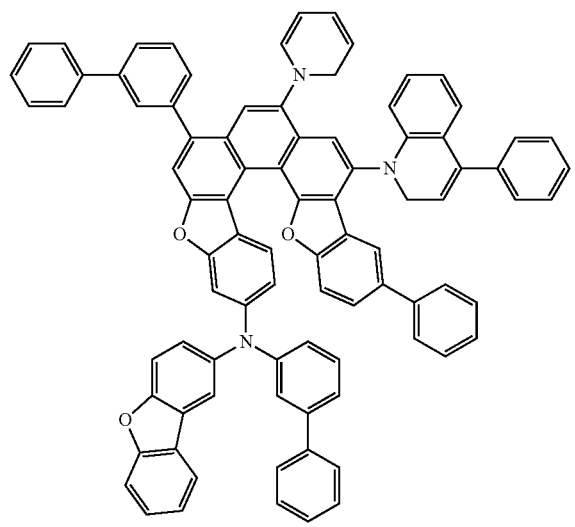

-continued
96
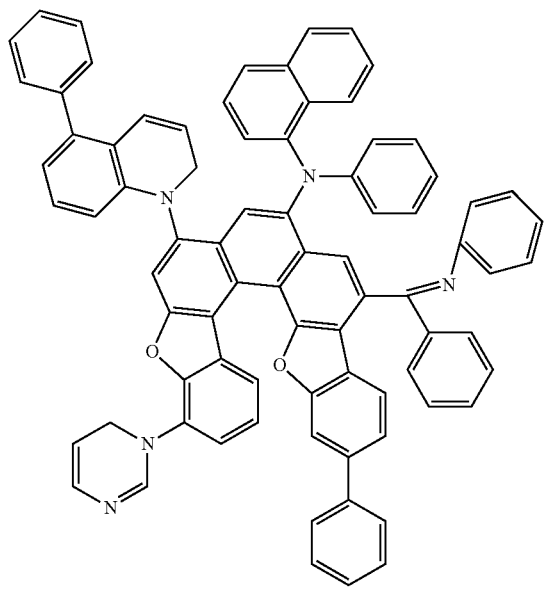
97
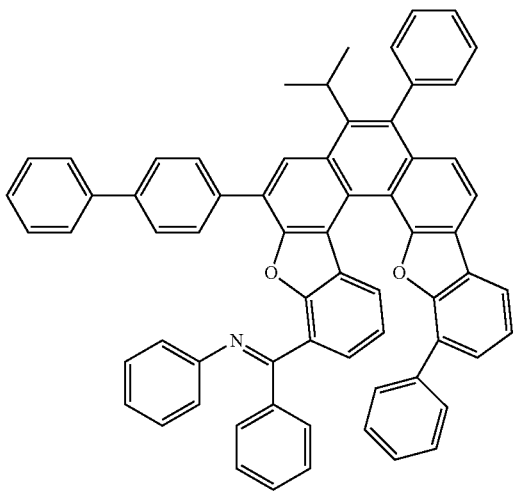
98
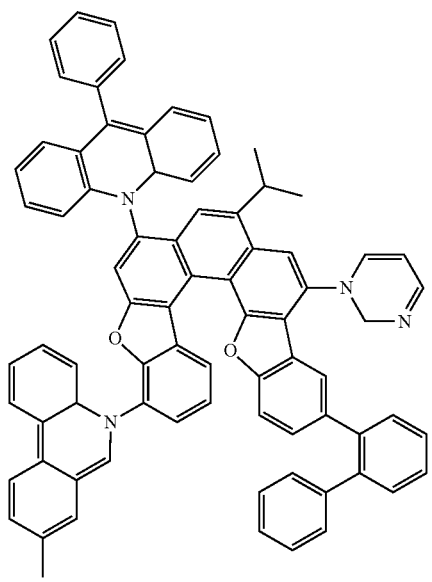
99
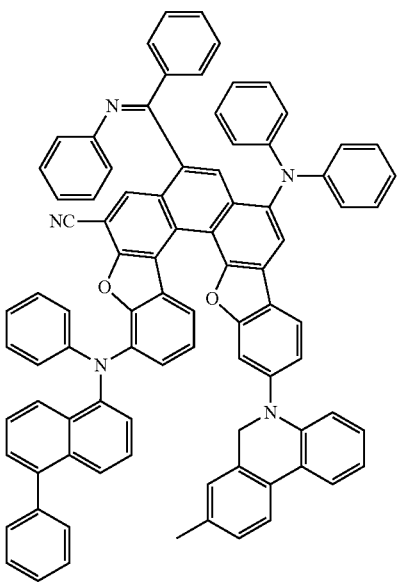

-continued
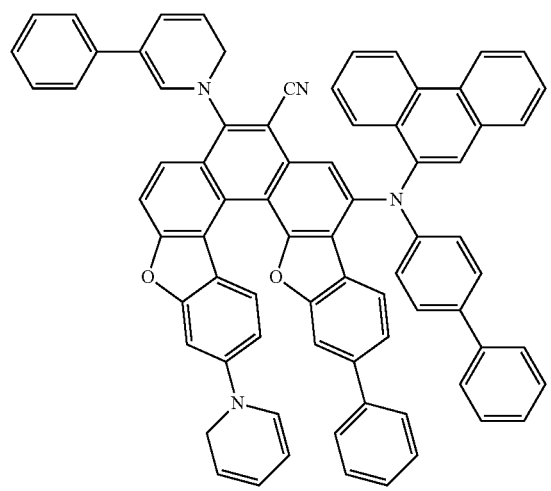
100
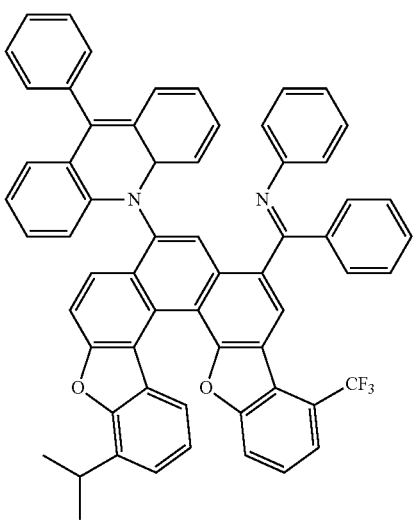
101
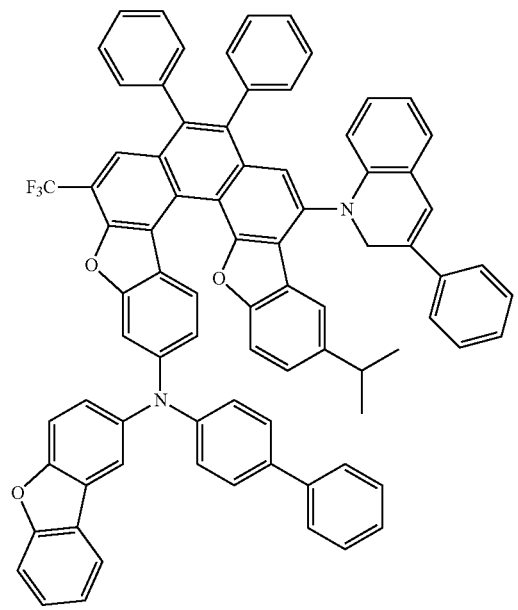
102
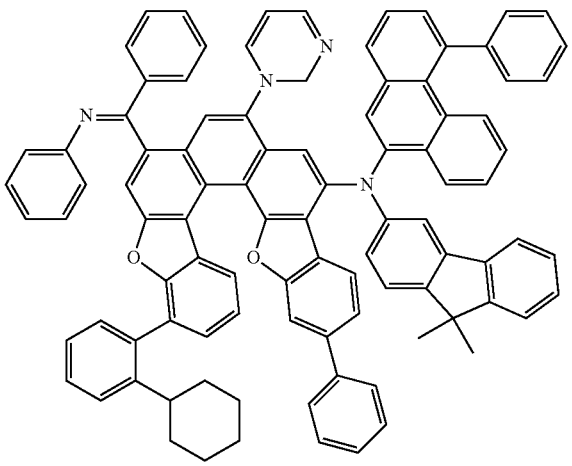
103

104
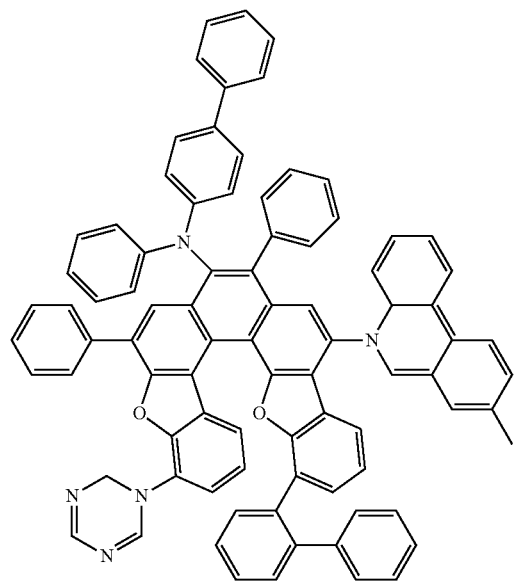
105
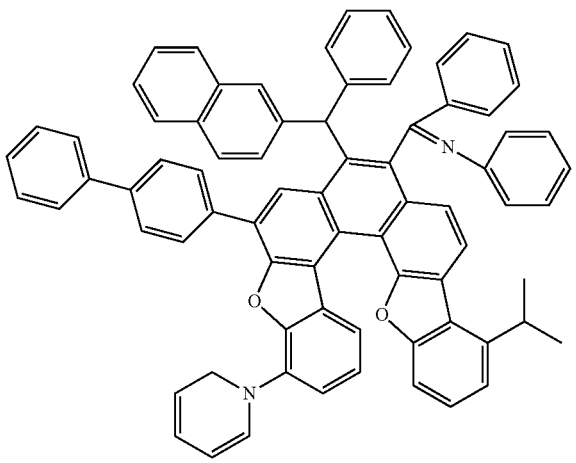
106
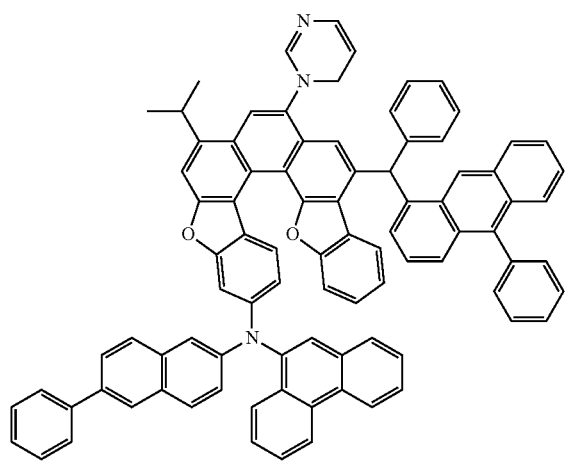
107
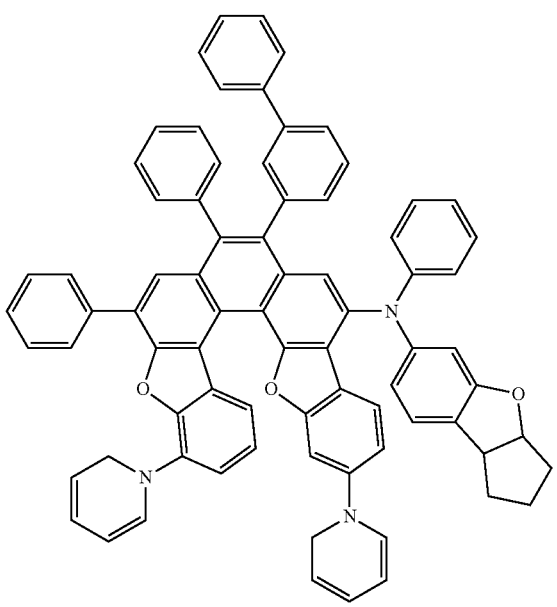

108
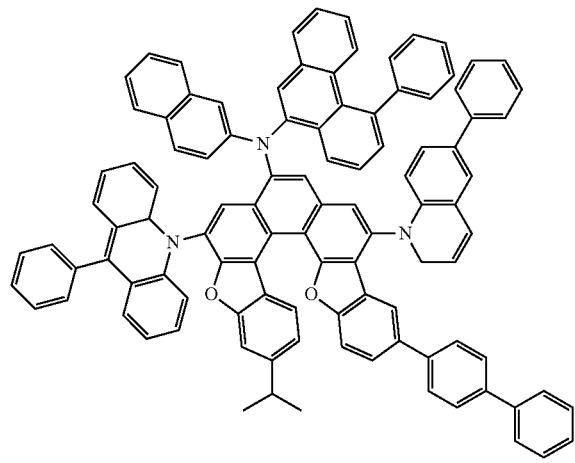
109
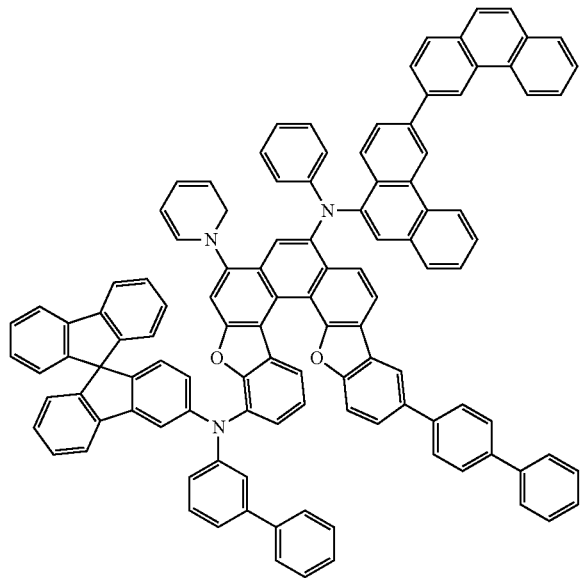
110
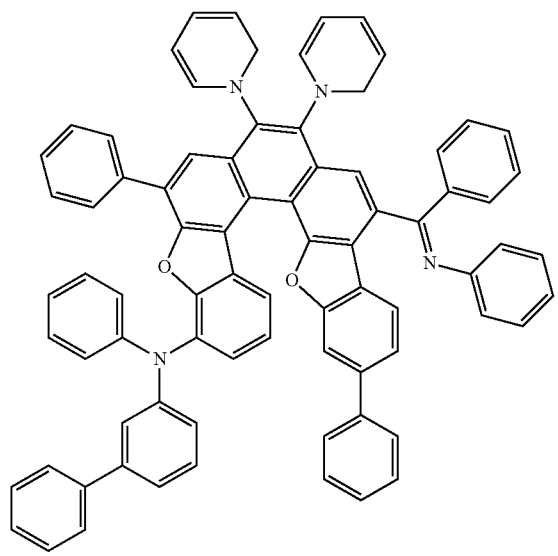
111
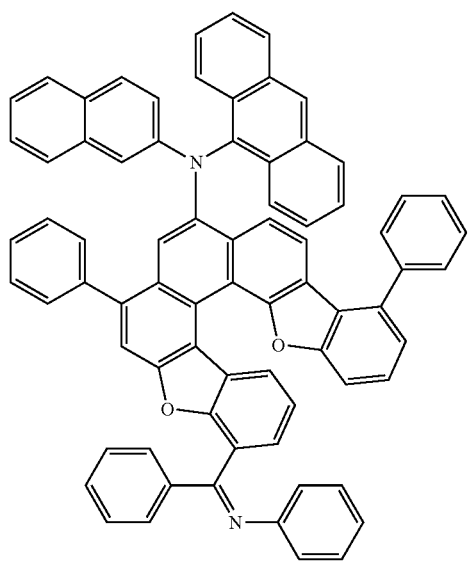

-continued
112 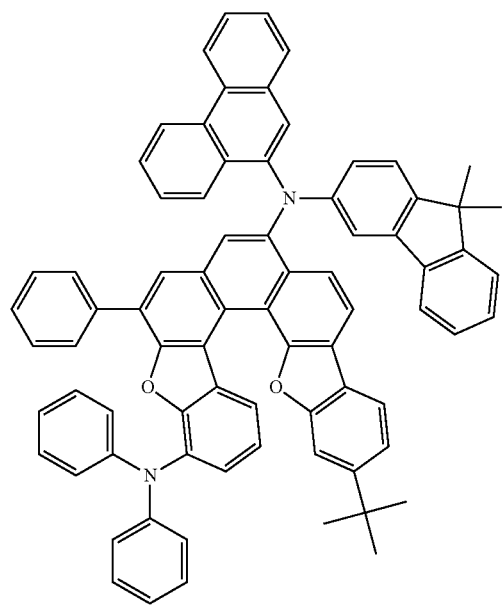
113 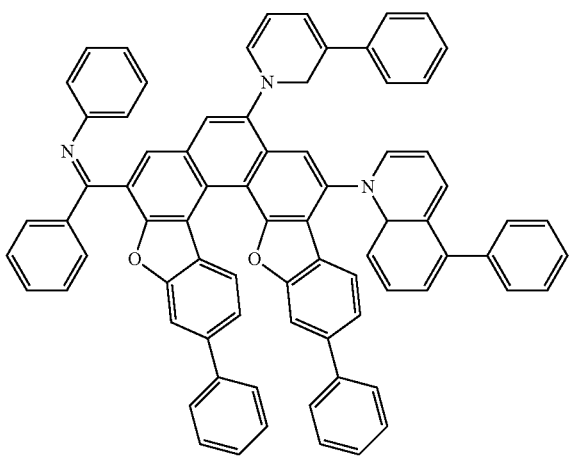
114 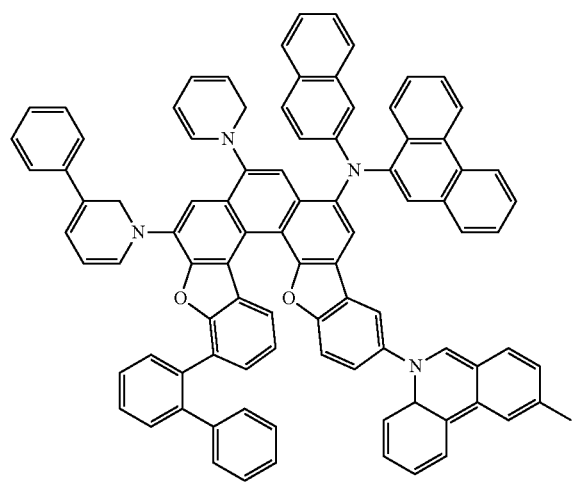
115 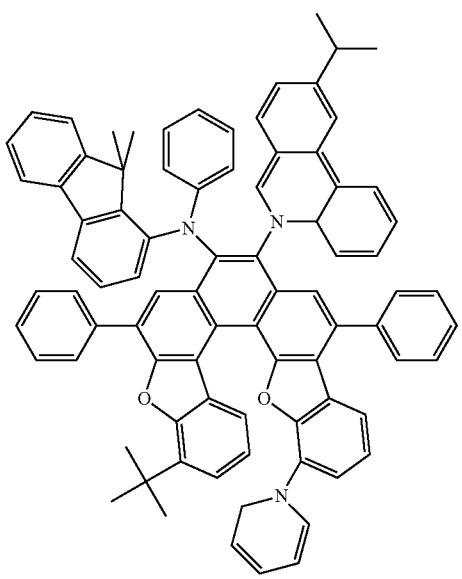

-continued
116
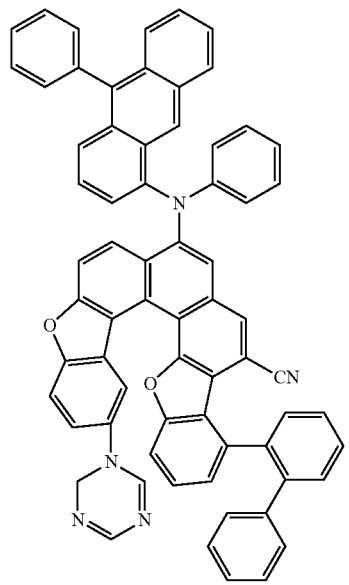
117
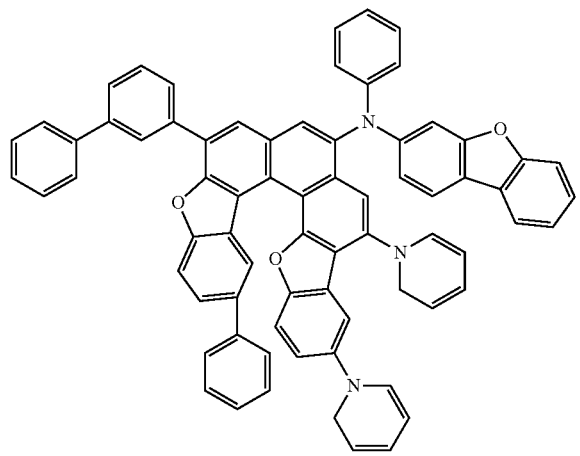
118
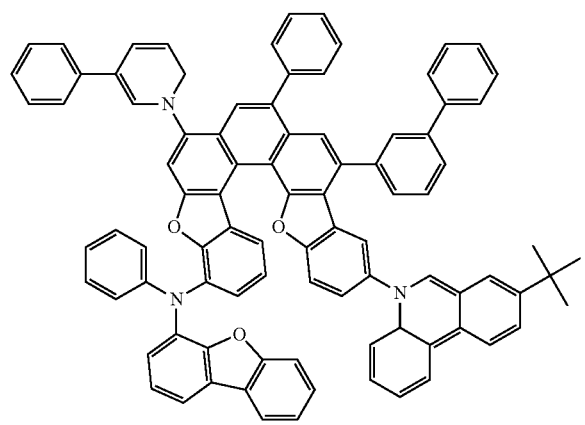
119
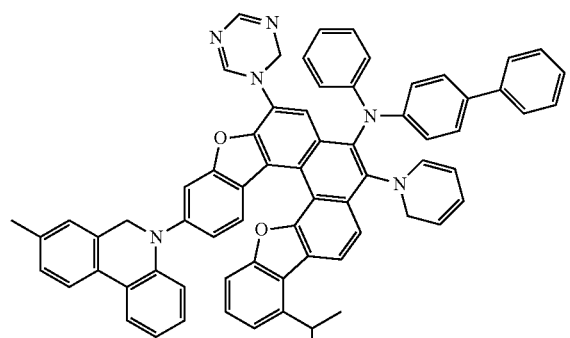

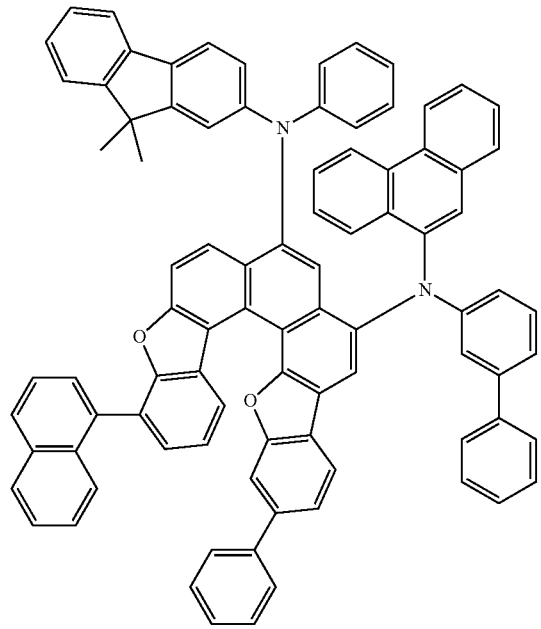

120

The present invention also provides an organic electroluminescent device including the blue fluorescence dopant. The organic electroluminescent device has a structure including an anode (a hole injection electrode), a hole injection layer (HIL), a hole transport layer (HTL), an emission layer (EML), an electron transport layer (ETL), an electron injection layer (EIL) and a cathode (an electron injection electrode) which are sequentially stacked, and if possible, an electron blocking layer (EBL) may be interposed between the anode and the emission layer, a hole blocking layer (HBL) may be interposed between the cathode and the emission layer, and a covering and protecting layer (CPL) may be added onto the surface of the cathode.

A method for manufacturing the organic electroluminescent device includes the following steps:

Step 1, the anode is formed by laminating a anode material on a substrate using a conventional method, wherein the substrate used is selected from a glass substrate or a transparent plastic substrate with excellent transparency, surface smoothness, operability and water resistance, and the anode material may be materials with excellent transparency and conductivity such as ITO, IZO, $SnO_2$, ZnO, etc.

Step 2, the hole injection layer is formed by vacuum heat depositing or spin coating a hole injection layer (HIL) material on the surface of the anode using a conventional method, wherein the hole injection layer material may be CuPc, m-MTDATA, m-MTDAPB, TCTA, 2-TNATA, or IDE406 which is available from Idemitsu Kosan, etc.

Step 3, the hole transport layer formed by vacuum heat depositing or spin coating a hole transport layer (HTL) material on the surface of the hole injection layer using a conventional method, wherein the hole transport layer material may be α-NPD, NPB or TPD.

Step 4, the EML is formed by vacuum heat depositing or spin coating an emission layer material on the surface of the hole transport layer using a conventional method, wherein the emission layer material used is a mixture of luminescent substance and the organic compound in the present invention.

Step 5, the electron transport layer is formed by vacuum heat depositing or spin coating an electron transport layer (ETL) material on the surface of the emission layer using a conventional method, wherein the electron transport layer material is not particularly limited and is preferably to be $Alq_3$.

Step 6, the electron injection layer is formed by vacuum heat depositing or spin coating an electron injection layer (EIL) material on the surface of the electron transport layer using a conventional method, wherein the electron injection layer material may be LiF, Liq, $Li_2O$, BaO, NaCl, CsF, etc.

Step 7, the cathode is formed by vacuum heat depositing or spin coating cathode material on the electron injection layer using a conventional method wherein the electron injection layer substance may be Li, Al, Al—Li, Ca, Mg, Mg—In, Mg—Ag, etc. Alternatively, a transparent cathode having light transmittance may be formed by using indium tin oxide (ITO) or indium zinc oxide (IZO).

Further, it is effective to prevent diffusion of triplet state excitons or holes into the electron transport layer by interposing a hole blocking layer (HBL) between the cathode and the emission layer along with a use of phosphorescent dopant in the emission layer. the HBL is formed by vacuum heat depositing or spin coating a hole blocking layer material on the surface of the emission layer using a conventional method, the hole blocking layer material is not particularly limited and is preferably Liq, (2-methyl-8-hydroxyquinoline-4-hydroxybiphenyl)aluminum, BCP or LiF, etc.

Compound Example 1

Synthesis of Compound 9
Synthesis of Intermediate A

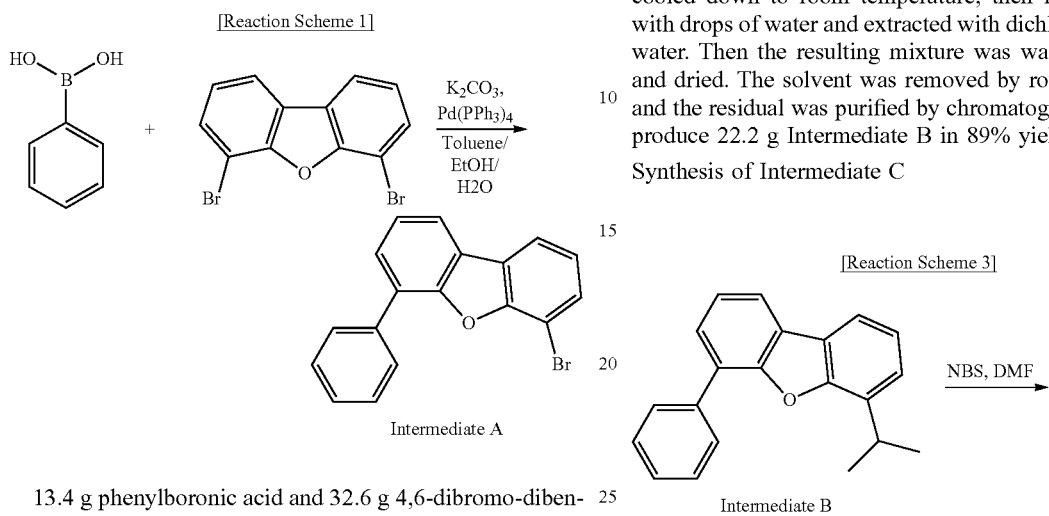

Intermediate A 13.4 g phenylboronic acid and 32.6 g 4,6-dibromo-dibenzofuran were placed into a three-neck flask (2 L), to which 700 mL toluene and 150 mL ethanol were added to dissolve the solid. The resulting mixture was aerated with nitrogen gas for 15 minutes and then, 150 mL aqueous $K_2CO_3$ solution (3.0 eq., 2M) and 2.3 g $Pd(PPh_3)_4$ (2 mol %) were sequentially added thereto. The reaction was heated up to 110° C. and performed overnight, then the reaction finished. The resulting mixture was absorbed by the added activated carbon, filtered by suction filtration and solvent removed by the rotary evaporation. The residual was dried and recrystallized with toluene and ethanol, to produce 28.1 g Intermediate A in 87% yield.

Synthesis of Intermediate B

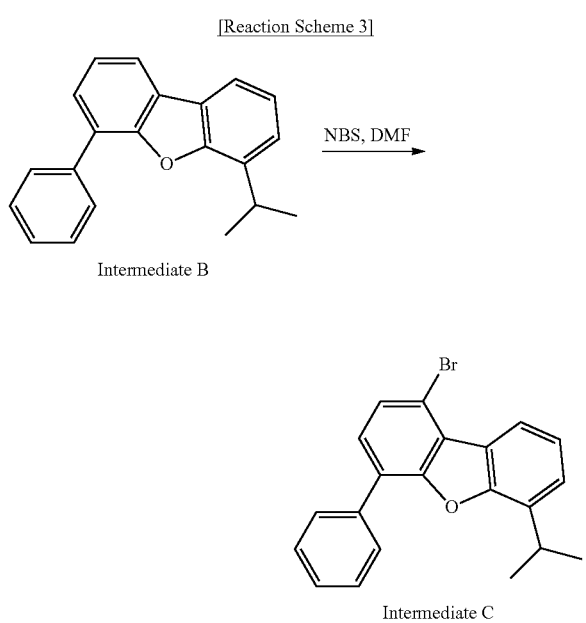

Intermediate B 3.2 g Mg, 15 mL THF (tetrahydrofuran), and 0.3 g $I_2$ were placed into a dry three-neck flask (2 L) and the mixture was heated to trigger reaction. Then a mixed solution of 13.9 g 2-bromopropane in 140 mL THF was added dropwise to the resulting mixture at room temperature. After the addition, the resulting mixture then was reacted at 55° C. for 2 hours. Thereafter, the resulting mixture was left to stand for 5 minutes, and the supernatant thereof was added dropwise to a mixed solution of 28.1 g Intermediate A in 600 mL THF, and the resulting mixture was refluxed overnight for 15 hours. After the reaction finished, the resulting mixture was cooled down to room temperature, then it was quenched with drops of water and extracted with dichloromethane and water. Then the resulting mixture was washed with water and dried. The solvent was removed by rotary evaporation and the residual was purified by chromatography column to produce 22.2 g Intermediate B in 89% yield.

Synthesis of Intermediate C

[Reaction Scheme 3]

Intermediate B → NBS, DMF →

Intermediate C 22.2 g Intermediate B was placed into a three-neck flask (2 L), to which 400 mL DMF was then added to dissolve the solid, followed by adding 15.2 g NBS (1.1 eq.). Then the resulting mixture was kept away from light and stirred overnight at room temperature. After the reaction finished, a large amount of water was added into the flask and solid matter were separated out. The solid matter was then filtered, and the filter cake was washed three times with water and dried. The residual was recrystallized with toluene and ethanol to produce 25.2 g Intermediate C in 89% yield.

Synthesis of Intermediate D

[Reaction Scheme 4]

Intermediate C → n-BuLi, THF, TMB / 4M HCl →

-continued

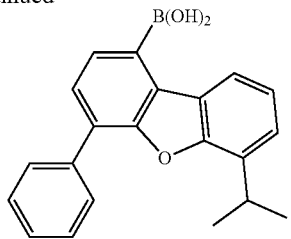

Intermediate D

All experimental instruments were fully dried beforehand. 25.2 g Intermediate C was placed into a three-neck flask (2 L), to which 500 mL dried tetrahydrofuran (THF) was added to dissolve the solid. Then the resulting mixture was cooled down to −78° C. and 30.4 mL n-BuLi (2.5M) was added dropwise thereto. After the addition, the resulting mixture was stirred at the above temperature for 1 hour, followed by dropwise addition of 9.3 g trimethyl borate. After the addition, the resulting mixture was stirred overnight at room temperature. After the reaction finished, hydrochloric acid solution (4M) was added to the resulting mixture which was then extracted with dichloromethane. The organic phase was washed with saturated aqueous NaCl solution until neutral and dried. The solvent was removed by rotary evaporation and the residual was boiled in ethyl acetate to produce crude product, which was then filtered to afford 17.1 g filter cake as Intermediate D in 75% yield.

Synthesis of Intermediate E

[Reaction Scheme 5]

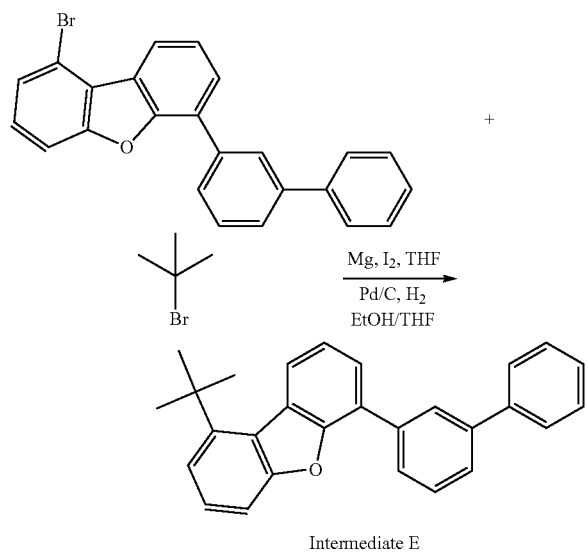

Intermediate E 2.7 g Mg (1.5 eq.), 12 mL THF, and 0.27 g $I_2$ were placed into a dry three-neck flask (2 L) and heated to trigger reaction. Then a mixed solution of 13.4 g 2-bromopropane (1.3 eq.) in 140 mL THF was added dropwise to the resulting mixture at room temperature. After the addition, the resulting mixture then was reacted at 55° C. for 2 hours. Thereafter, the resulting mixture was left to stand for 5 minutes, and the supernatant thereof was added dropwise to a mixed solution of 29.9 g halogenated compound in 600 mL THF, followed by refluxing overnight for 15 hours. After the reaction finished, the resulting mixture was cooled down to room temperature, quenched with drops of water and extracted with dichloromethane and water. The resulting mixture was washed with water and dried. The solvent was removed by rotary evaporation and the residual was purified by chromatography column to produce 24.0 g Intermediate E in 85% yield.

Synthesis of Intermediate F

[Reaction Scheme 6]

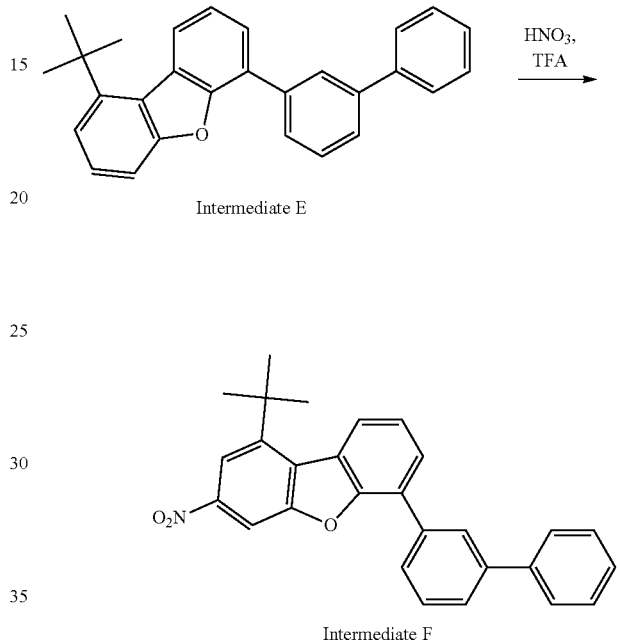

Intermediate F 24 g Intermediate E (1 eq.) was placed, with 500 mL trifluoroacetic acid as solvent, into a three-neck flask (2 L), and 4.8 g concentrated nitric acid (1.2 eq.) was then added thereto. The resulting mixture was heated up to 80° C. and refluxed overnight for 12 hours. After the reaction finished, the resulting mixture was cooled down to room temperature and 1 L of water was added. Thereto solid matter was produced. After the temperature cooling down, the mixture was filtered by the suction filtration. The obtained filter cake was washed several times with water and recrystallized with ethanol to produce 24.5 g Intermediate F in 91% yield.

Synthesis of Intermediate G

[Reaction Scheme 7]

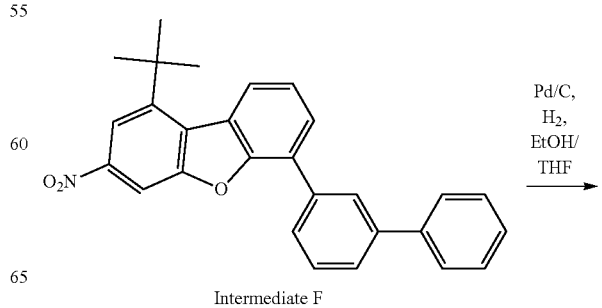

Intermediate F

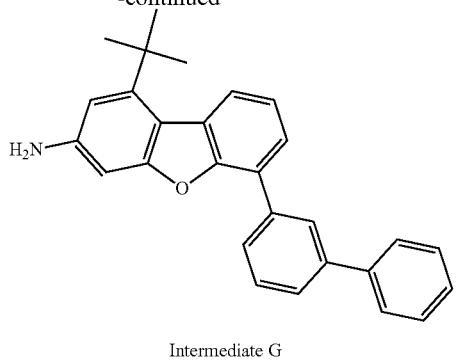

Intermediate G 24.5 g Intermediate F was placed into a three-neck flask (2 L) and nitrogen gas was aerated in and out three times through a three-way joint. A mixed solution consisting 250 mL ethanol and 50 mL THF was added as solvent, and again, nitrogen gas was aerated in and out three times, followed by a hydrogen gas flow aerated. Then, 2.5 g 5% palladium-carbon was added to the resulting mixture to react at room temperature for 5 hours. After the reaction finished, the resulting mixture was filtered by the suction filtration (diatomite), during which time water might be added properly to keep the residual from being dried out. At the last time, the moist palladium-carbon was packaged with water. After the filter liquor was removed by rotary evaporation, dried and recrystallized with ethanol, the filtrate produced 21.1 g Intermediate G in 93% yield.

Synthesis of Intermediate H

[Reaction Scheme 8]

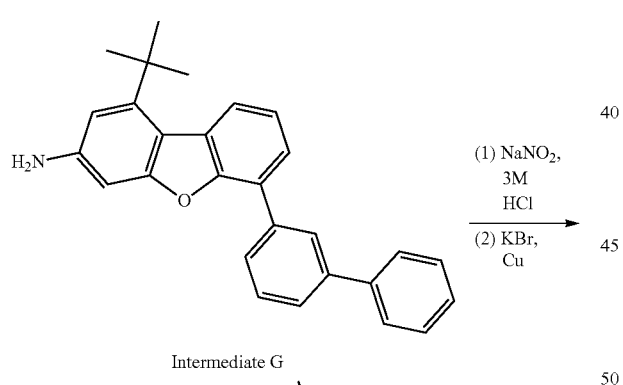

Intermediate G

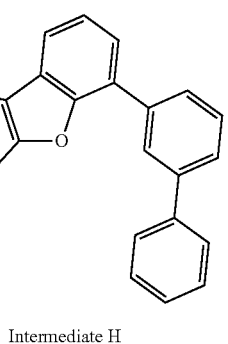

Intermediate H 21.1 g (1 eq.) Intermediate G was placed into a three-neck flask (2 L), to which 54 mL dilute hydrochloric acid (3 eq., 3M) was added to dissolve the solid. The resulting mixture was cooled down to around 0° C. (ice-salt bath), and 13.5 mL aqueous sodium nitrite solution (1 eq., 4M) was added slowly and dropwise, after which, the reaction finished in about 2 hours and solid matter separated out. The solid matter was filtered (but not drained out), washed with water until neutral and then placed in another three-neck flask. Then water, 8.3 g KBr (1.3 eq.) and a small amount of copper powder (catalyst) were added. The resulting mixture was heated up to react overnight at 80° C. After the reaction finished, the resulting mixture was cooled down to room temperature and filtered. The filtrate was extracted with dichloromethane and water. Then resulting mixture was washed with water, dried and recrystallized with toluene and ethanol to produce 20.9 g Intermediate H in 85% yield.

Synthesis of Intermediate I

[Reaction Scheme 9]

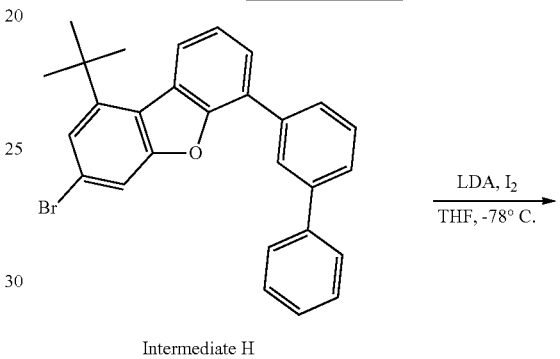

Intermediate H

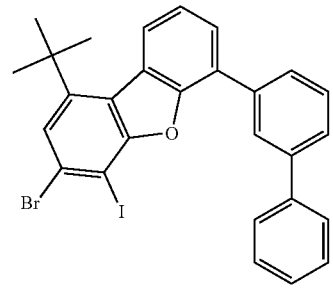

Intermediate I

All experimental instruments were fully dried beforehand. 20.9 g Intermediate H was placed into a three-neck flask (2 L), to which 400 mL dry tetrahydrofuran was added to dissolve the solid. Then the resulting mixture was cooled down to −78° C. and 24.1 mL THF solution with LDA (1.05 eq., 2M) was added dropwise thereto. After conducting the dropwise addition, the resulting mixture was stirred at the above temperature for 1 hour, followed by dropwise adding 12.8 g iodine (1.1 eq.). After conducting the dropwise addition, the resulting mixture was stirred overnight at room temperature. After the reaction finished hydrochloric acid solution (4M) was added thereto. The resulting mixture was then extracted with dichloromethane and the organic phase was washed with saturated aqueous NaCl solution until neutral. Then resulting mixture was dried, removed with solvent by rotary evaporation and recrystallized with toluene and ethanol, to produce 19.2 g Intermediate I in 72% yield.

Synthesis of Intermediate J

[Reaction Scheme 10]

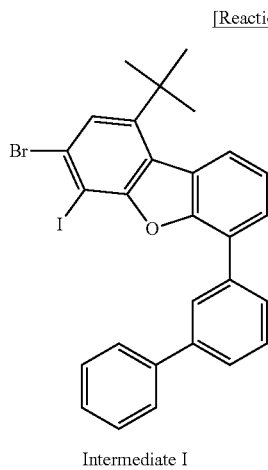

Intermediate I

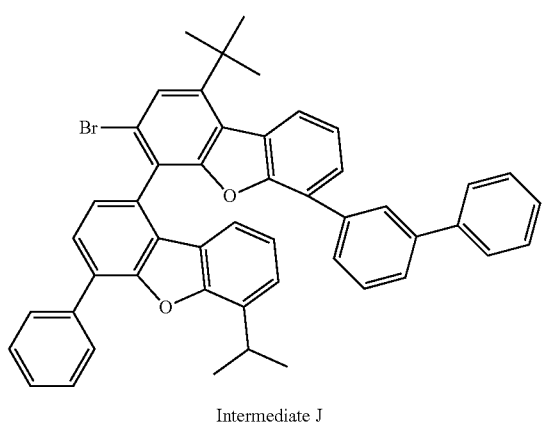

Intermediate J 12 g Intermediate D and 19.2 g Intermediate I were placed into a three-neck flask (1 L), to which 400 mL toluene and 100 mL ethanol were added to dissolve the solid. The resulting mixture was aerated with nitrogen gas for 15 minutes and then, 50 mL aqueous $K_2CO_3$ solution (3.0 eq., 2M) and 0.8 g Pd(PPh$_3$)$_4$(2 mol %) were sequentially added thereto. The reaction was performed overnight at 110° C. After the reaction finished, the resulting mixture was absorbed by activated carbon and filtered by suction filtration. The solvent was removed by rotary evaporation and the residual was dried and recrystallized with toluene and ethanol to produce 26.8 g Intermediate J in 85% yield.

Synthesis of Intermediate K

[Reaction Scheme 11]

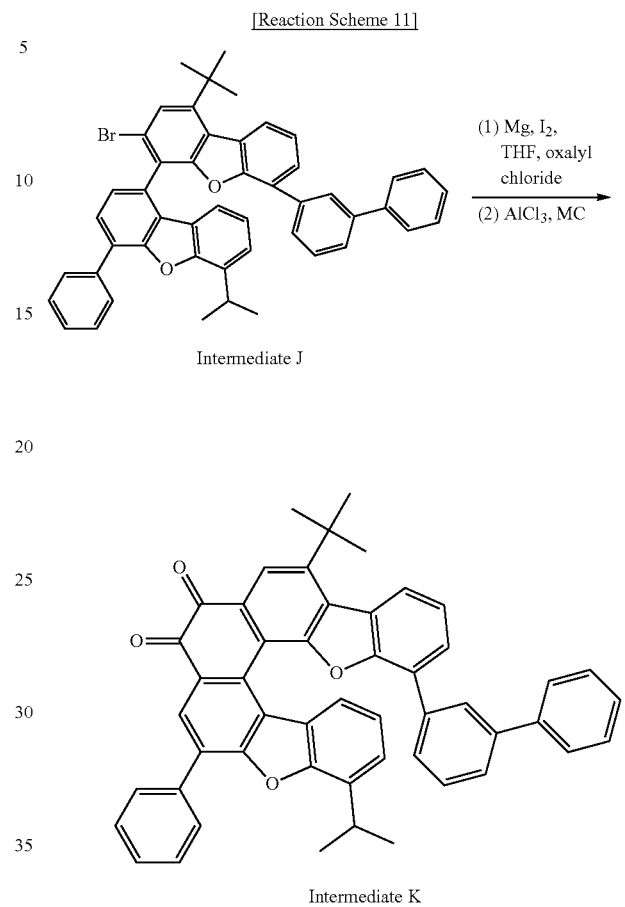

Intermediate J

Intermediate K 1.3 g Mg (1.5 eq.), 15 mL THF, and 0.2 g $I_2$ were placed into a dry three-neck flask (2 L) and the resulting mixture was heated to trigger reaction. Then a solution of 26.8 g Intermediate J in 500 mL THF was added dropwise to the resulting mixture at room temperature. After conducting the dropwise addition, the resulting mixture was reacted at 55° C. for 2 hours and was thereafter left to stand for 5 minutes. The supernatant was added dropwise to a solution of 4.1 g oxalyl chloride (0.9 eq.) in 60 mL THF, and the resulting mixture was refluxed overnight for 16 hours. After the reaction finished, the resulting mixture was cooled down to room temperature and then added dropwise, in ice-water bath, to a solution of 14.5 g aluminum trichloride in 300 mL dichloromethane. After completion of the dropwise addition, the resulting mixture was heated to reflux overnight for 15 hours. After the reaction finished, the resulting mixture was quenched with drops of ice-water to obtain a large amount of solid matter. The solid matter was then filtered by suction filtration and washed with water. Then the resulting mixture was dried and purified by chromatography column, to produce 18.4 g Intermediate K in 71% yield.

Synthesis of Intermediate L

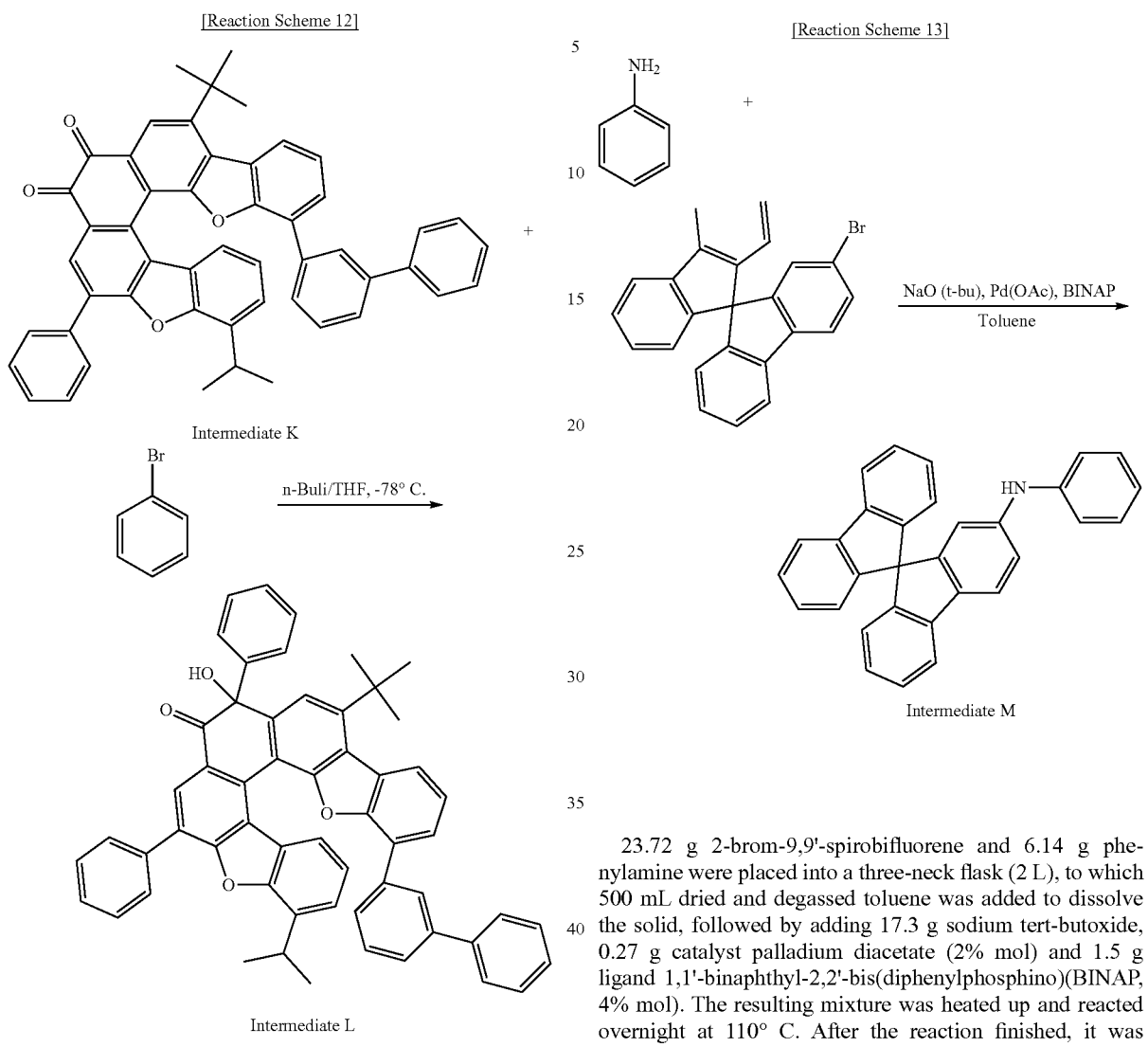

[Reaction Scheme 12]

Intermediate K

Intermediate L

All experimental instruments were fully dried beforehand. 4.4 g bromobenzene (1.1 eq.) was placed into a three-neck flask (1 L), to which 400 mL dry tetrahydrofuran was added to dissolve the solid. Then the resulting mixture was cooled down to −78° C. and 12.3 mL n-BuLi (1.2 eq., 2.5M) was added dropwise thereto. After conducting the dropwise addition, the resulting mixture was stirred at the above temperature for 1 hour and then a solution of 18.4 g Intermediate K in 400 mL THF was added dropwise thereto. After conducting the dropwise addition, the resulting mixture was stirred overnight at room temperature. After the reaction finished, hydrochloric acid solution (4M) was added to the resulting mixture which was then extracted with ethyl acetate. The organic phase was washed with saturated aqueous NaCl solution until neutral. Then the resulting mixture was dried, solvent removed by rotary evaporation and purification by chromatography column, to produce 16.3 g Intermediate L in 80% yield.

Synthesis of Intermediate M

[Reaction Scheme 13]

Intermediate M 23.72 g 2-brom-9,9'-spirobifluorene and 6.14 g phenylamine were placed into a three-neck flask (2 L), to which 500 mL dried and degassed toluene was added to dissolve the solid, followed by adding 17.3 g sodium tert-butoxide, 0.27 g catalyst palladium diacetate (2% mol) and 1.5 g ligand 1,1'-binaphthyl-2,2'-bis(diphenylphosphino)(BINAP, 4% mol). The resulting mixture was heated up and reacted overnight at 110° C. After the reaction finished, it was cooled down to room temperature. The resulting mixture was absorbed by activated carbon and filtered by suction filtration. After removal of solvent by rotary evaporation and recrystallization with toluene and ethanol, the residual produced 22.3 g Intermediate M in 91% yield.

Synthesis of Intermediate N

[Reaction Scheme 14]

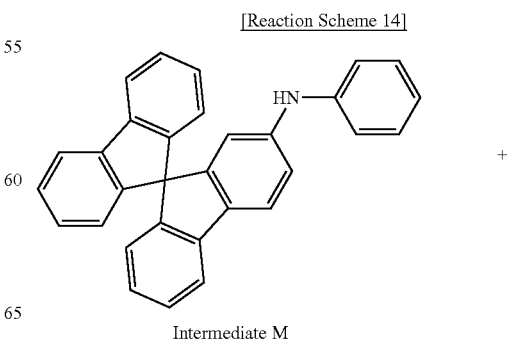

Intermediate M

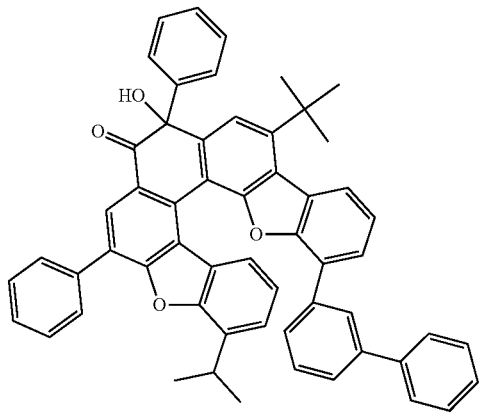

Intermediate L

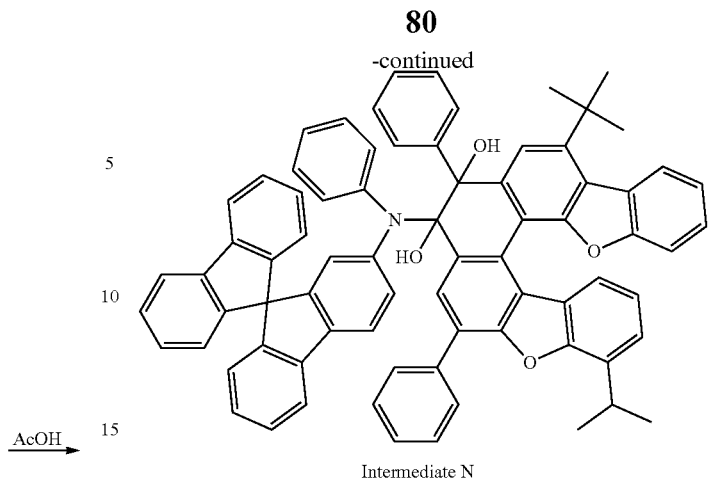

Intermediate N 16.3 g Intermediate L (1.0 eq.) and 8.4 g Intermediate M were placed into a three-neck flask (1 L), to which glacial acetic acid was added to dissolve the solid. The resulting mixture was heated to 130° C. and refluxed overnight for 18 hours, and after the reaction finished, it was cooled down to room temperature and extracted with a mixture of dichloromethane and water. The resulting mixture was then washed four times with water, followed by drying, removal of solvent by rotary evaporation and recrystallization with toluene and ethanol, to produce 19.8 g Intermediate N in 92% yield.

Synthesis of Compound 9

[Reaction Scheme 15]

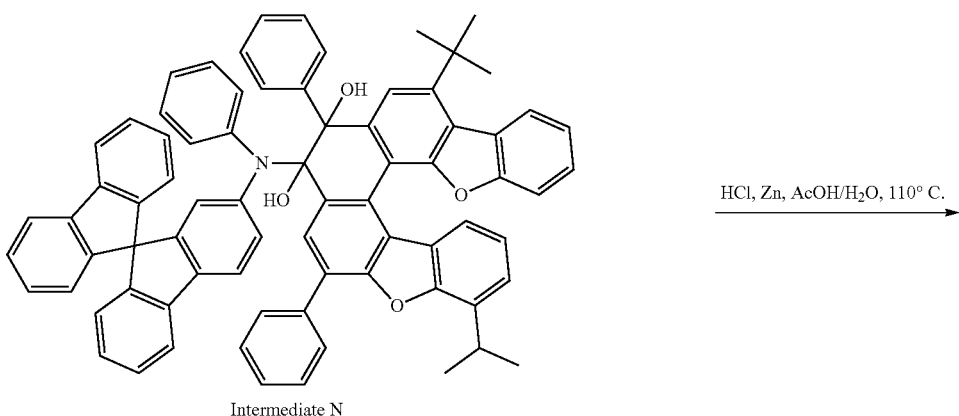

Intermediate N

HCl, Zn, AcOH/H₂O, 110° C.

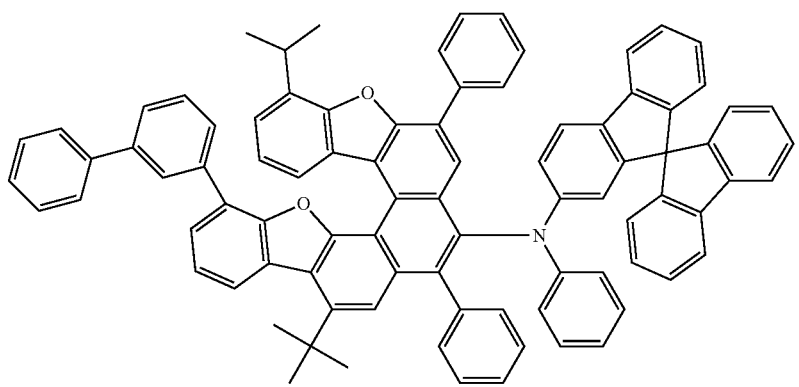

Compound 9

19.8 g Intermediate N (1.0 eq.), 300 mL glacial acetic acid, and 100 mL hydrochloric acid solution (4M) were placed into a three-neck flask (1 L), into which nitrogen gas was aerated for 30 minutes, followed by adding 1.5 g zinc powder (3.0 eq.). The resulting mixture was then heated to 110° C. and reacted overnight for 18 hours, and it was cooled down to room temperature after the reaction finished. The resulting mixture was then filtered and extracted with a mixture of dichloromethane and water. The mixture was washed with water, followed by rotary evaporation of the solvent, drying and recrystallization with toluene, to produce 19.4 g Compound 9 in 89% yield.

1H NMR (DMSO, 300 Hz): δ (ppm)=8.91-8.52 (s, 1H), 8.50-8.09 (m, 3H), 8.06-7.85 (m, 6H), 7.81-7.71 (m, 3H), 7.69-7.18 (m, 31H), 7.15-6.71 (m, 3H), 3.01-2.52 (q, 1H), 1.68-1.55 (s, 9H), 1.38-1.03 (d, 6H)

MS (FAB): 1166 (M+)

Compound Example 2

Synthesis of Compound 11
Synthesis of Intermediate O

[Reaction Scheme 16]

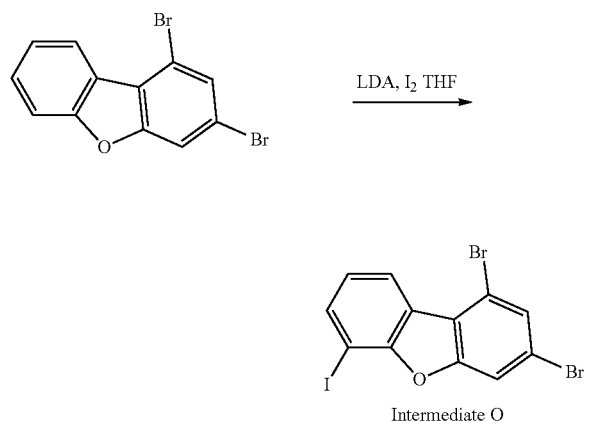

Intermediate O

All experimental instruments were fully dried beforehand. 32.6 g brominated compound (1.1 eq.) was placed into a three-neck flask (2 L), to which 600 mL dry tetrahydrofuran was added to dissolve the solid. Then the resulting mixture was cooled down to −78° C. and 52.5 mL LDA solution (1.05 eq., 2M) in THF was added dropwise thereto. After conducting the dropwise addition, the resulting mixture was stirred at the above temperature for 1 hour, to which at the same temperature 27.9 g iodine (1.1 eq.) was then added dropwise. After conducting the dropwise addition, the resulting mixture was stirred overnight at room temperature, and then after the reaction finished, hydrochloric acid solution (4M) was added thereto. The resulting mixture was extracted with dichloromethane and the organic phase was washed with saturated aqueous NaCl solution until neutral and dried. After rotary evaporation of the solvent and recrystallization with toluene and ethanol, the residual produced 36.6 g Intermediate O in 81% yield.

Synthesis of Intermediate P

[Reaction Scheme 17]

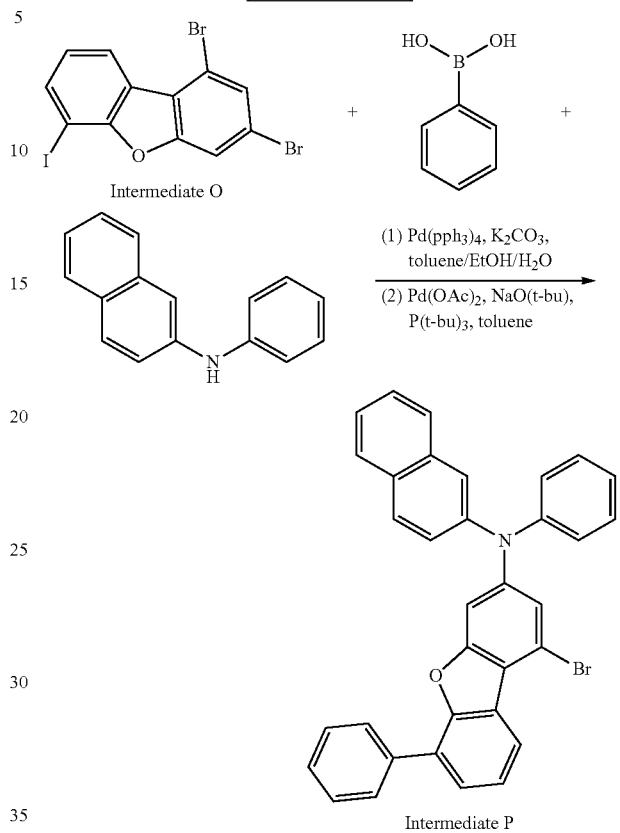

10.9 g phenylboronic acid (1.1 eq.) and 36.6 g Intermediate 0 were placed into a three-neck flask (2 L), to which 700 mL toluene and 150 mL ethanol were added to dissolve the solid. The resulting mixture was aerated with nitrogen gas for 15 minutes and then, 121.5 mL aqueous $K_2CO_3$ solution (3.0 eq., 2M) and 1.9 g Pd(PPh$_3$)$_4$(2 mol %) were sequentially added thereto. The reaction was performed overnight at 110° C. After the reaction finished, the resulting mixture was absorbed by adding activated carbon and filtered by suction filtration. The solvent was removed by rotary evaporation and the residual was dried and recrystallized with toluene and ethanol to obtain 38.7 g product for the next reaction. 38.7 g the above product and 23.2 g 2-phenylamino-naphthalene (1.1 eq.) were placed into a three-neck flask (2 L), to which 700 ml toluene was added to dissolve the solid. The resulting mixture was aerated with nitrogen gas for 15 minutes and then, 27.7 g sodium tert-butoxide (3.0 eq.), 0.39 g Pd(OAc)$_2$ (2% mol) and 2.4 g BINAP (4% mol) were added thereto. The resulting mixture was heated and reacted at 110° C. for 18 hours, then it was cooled down to room temperature, solid matter separated out. The solid matter was filtered and dissolved in toluene. The resulting mixture was then absorbed by activated carbon and filtered before cooled down. The filtrate was spin dried and recrystallized using a mixture of toluene and ethanol, producing 19.7 g Intermediate P in 43% yield.

Synthesis of Intermediate Q

[Reaction Scheme 18]

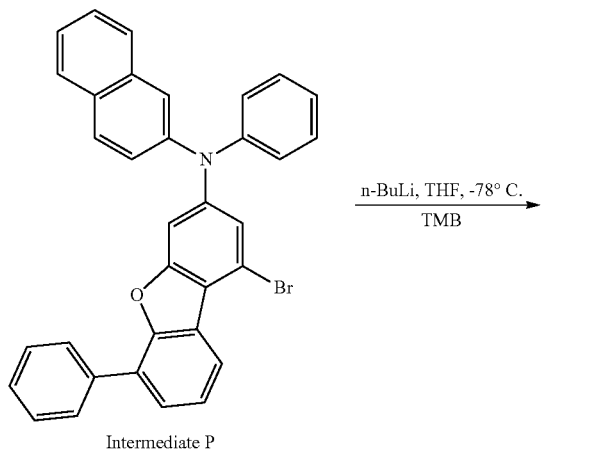

Intermediate P

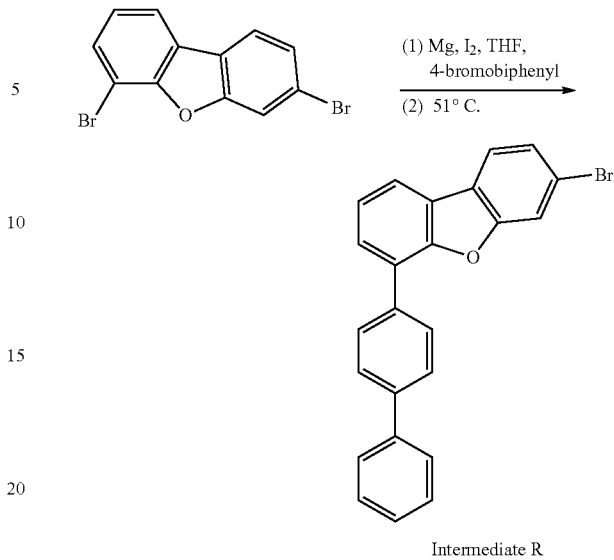

Intermediate Q

All experimental instruments were fully dried beforehand. 39 g Intermediate P was placed into a three-neck flask (2 L), to which 600 mL dry tetrahydrofuran was added to dissolve the solid. Then the resulting mixture was cooled down to −78° C. and 31.8 mL n-BuLi (2.5M) was added dropwise thereto. After conducting the dropwise addition, the resulting mixture was stirred at the above temperature for 1 hour, to which at the same temperature 9.7 g trimethyl borate (1.3 eq.) was then added dropwise. After conducting the dropwise addition, the resulting mixture was stirred overnight at room temperature, and then after the reaction finished, hydrochloric acid solution (4M) was added thereto. The resulting mixture was extracted with dichloromethane and the organic phase was washed with saturated aqueous NaCl solution until neutral, followed by drying, rotary evaporation of the solvent and boiling in ethyl acetate to get the crude product. The resulting crude product was then filtered to produce 29.2 g filter cake as Intermediate Q in 80% yield.

Synthesis of Intermediate R

[Reaction Scheme 19]

Intermediate R 3.6 g Mg (1.5 eq.), 15 mL THF, and 0.36 g I$_2$ were placed into a dry three-neck flask (2 L) and the resulting mixture was heated to trigger reaction. Then a solution of 30.3 g 4-bromobiphenyl (1.3 eq.) in 300 mL THF was added dropwise, at room temperature, to the resulting mixture. After conducting the dropwise addition, the resulting mixture was reacted at 51° C. for 2 hours and was thereafter left to stand for 5 minutes. The supernatant was added dropwise to a solution of 32.6 g 3,6-dibromodiphenylfura (1.0 eq.) in 60 mL THF, and the resulting mixture was refluxed overnight for 15 hours. Then after the reaction finished, the resulting mixture was cooled down to room temperature and quenched with drops of water. The resulting mixture was extracted with a mixture of dichloromethane and water and the resulting mixture was washed with water, dried. The solvent was removed by rotary evaporation and the residual was purified by chromatography column to produce 32.7 g Intermediate R in 82% yield.

Synthesis of Intermediate S

[Reaction Scheme 20]

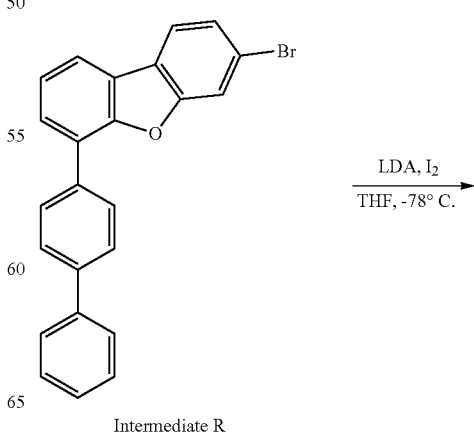

Intermediate R

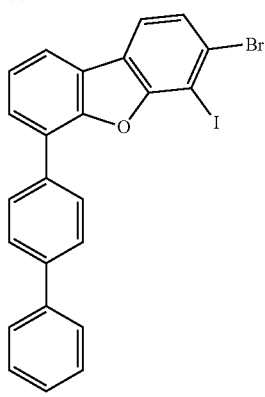

Intermediate S

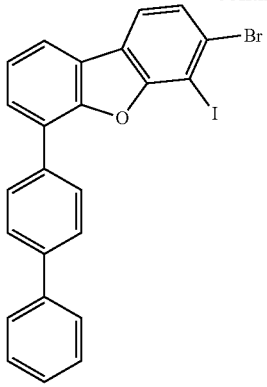

Intermediate S

Pd(PPh$_3$)$_4$, K$_2$CO$_3$
Toluene/EtOH/H$_2$O

All experimental instruments were fully dried beforehand. 32.7 g Intermediate R was placed into a three-neck flask (2 L), to which 600 mL dry tetrahydrofuran was added to dissolve the solid. Then the resulting mixture was cooled down to −78° C. and 43.1 mL LDA solution (1.05 eq., 2M) in THF was added dropwise thereto. After conducting the dropwise addition, the resulting mixture was stirred at the above temperature for 1 hour, to which 22.9 g iodine (1.1 eq.) was then added dropwise at the same temperature. After conducting the dropwise addition, the resulting mixture was stirred overnight at room temperature, and then after the reaction finished, hydrochloric acid solution (4M) was added thereto. The resulting mixture was extracted with dichloromethane and the organic phase therefrom was then washed with saturated aqueous NaCl solution until neutral and dried. Thereafter, the solvent was removed by rotary evaporation and the residual was recrystallized with toluene and ethanol to produce 35.7 g Intermediate S in 83% yield.

Synthesis of Intermediate T

[Reaction Scheme 21]

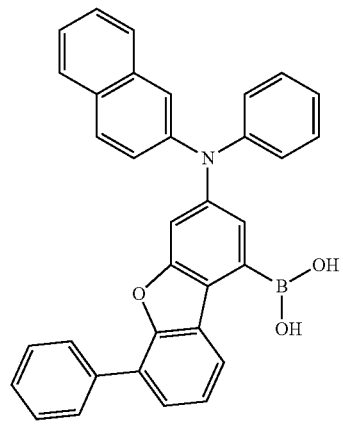

Intermediate Q

+

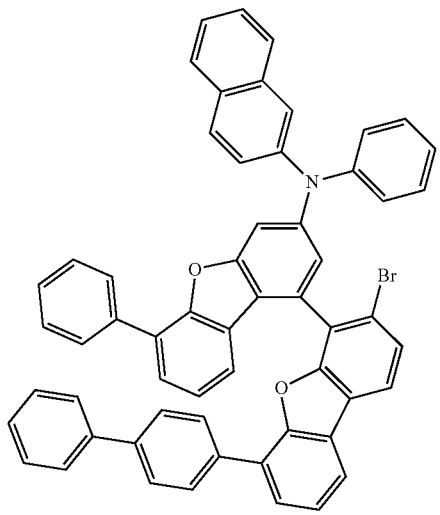

Intermediate T 29.2 g Intermediate Q (1.1 eq.) and 27.6 g Intermediate S (1.0 eq.) were placed into a three-neck flask (2 L), to which 600 mL toluene and 150 mL ethanol were added to dissolve the solid. The resulting mixture was aerated with nitrogen gas for 15 minutes and then, 78.8 mL aqueous K$_2$CO$_3$ solution (3.0 eq., 2M) and 1.2 g Pd(PPh$_3$)$_4$ (2 mol %) were sequentially added thereto. The reaction was heated up to 110° C. performed overnight, then after the reaction finished, the resulting mixture was absorbed with activated carbon and filtered by suction filtration. The solvent was removed by rotary evaporation and the residual was dried and recrystallized with toluene and ethanol to produce 36.4 g Intermediate T in 85% yield.

Synthesis of Intermediate U

[Reaction Scheme 22]

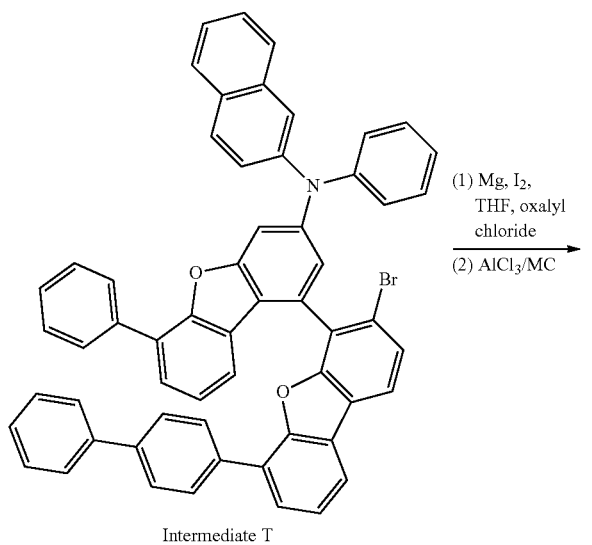

Intermediate T

Intermediate U 1.55 g Mg (1.5 eq.), 18 mL THF, and 0.16 g I2 were placed into a dry three-neck flask (2 L) and the resulting mixture was heated to trigger reaction. Then a solution of 36.4 g Intermediate T (1.0 eq.) in 700 mL THF was added dropwise, at room temperature, to the resulting mixture. After conducting the dropwise addition, the resulting mixture was reacted at 55° C. for 2 hours and was thereafter left to stand for 5 minutes. The supernatant was added dropwise to a solution of 5.0 g oxalyl chloride (0.9 eq.) in 60 mL THF, and the resulting mixture was refluxed overnight for 16 hours. After the reaction finished, the resulting mixture was cooled down to room temperature, to which a solution of 17.4 g aluminum trichloride (3 eq.) in 350 mL dichloromethane was then added dropwise in ice-water bath. After the addition was completed, the resulting mixture was heated and refluxed overnight for 15 hours, then quenched with drops of water after the reaction was completed, obtaining a large amount of solid matter. The solid matter was then filtered by suction filtration, washed with water, dried and purified by chromatography column, producing 28.1 g Intermediate U in 75% yield.

Synthesis of Intermediate V

[Reaction Scheme 23]

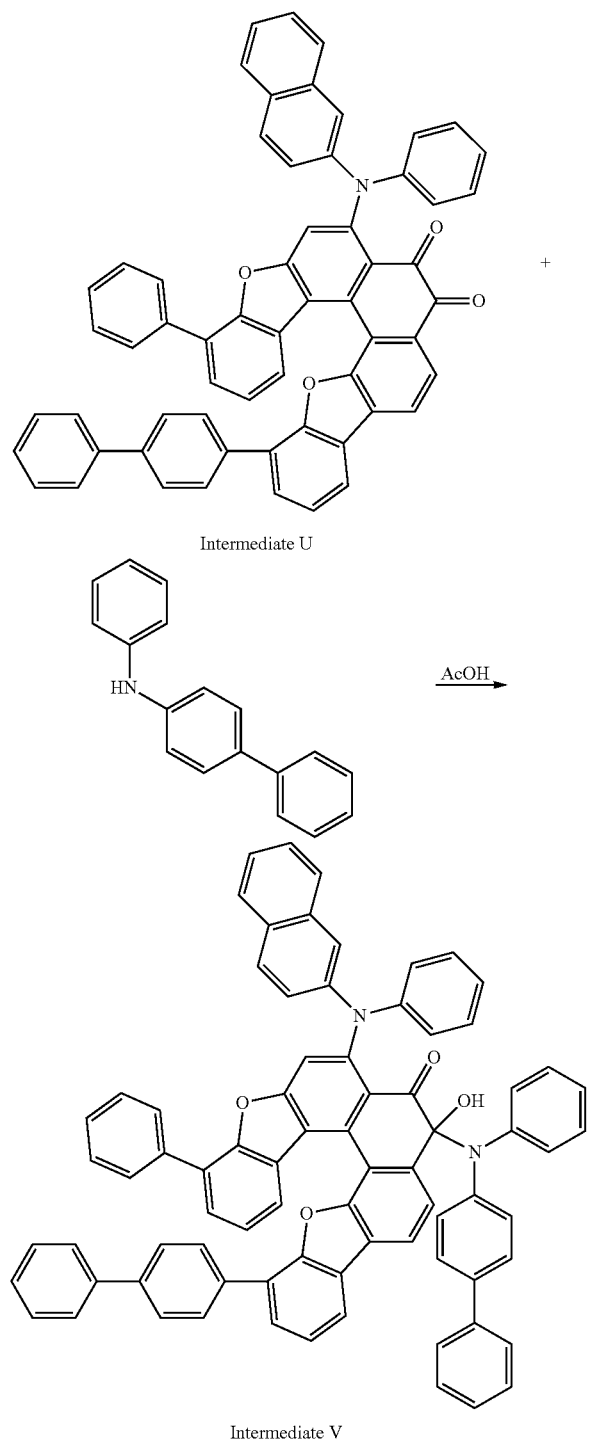

Intermediate U

Intermediate V 28.1 g Intermediate U (1.0 eq.) and 9.1 g N-phenyl-4-biphenylamine (1.1 eq.) were placed into a three-neck flask (1 L), to which glacial acetic acid was added to dissolve the solid. The resulting mixture was heated to 130° C. and refluxed overnight for 18 hours, and after the reaction finished, it was cooled down to room temperature and extracted with a mixture of dichloromethane and water. The resulting mixture was then washed four times with water and dried. The solvent was removed by rotary evaporation and the residual was recrystallized with toluene and ethanol to produce 30.9 g Intermediate V in 85% yield.

Synthesis of Intermediate W

[Reaction Scheme 24]

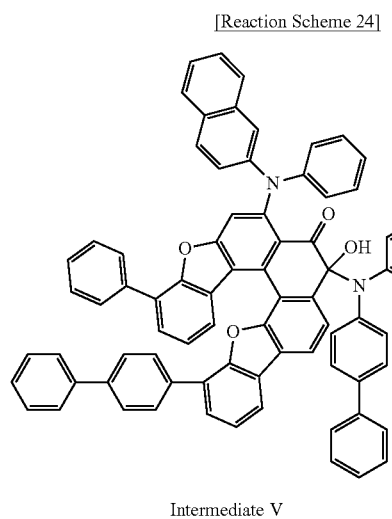

Intermediate V

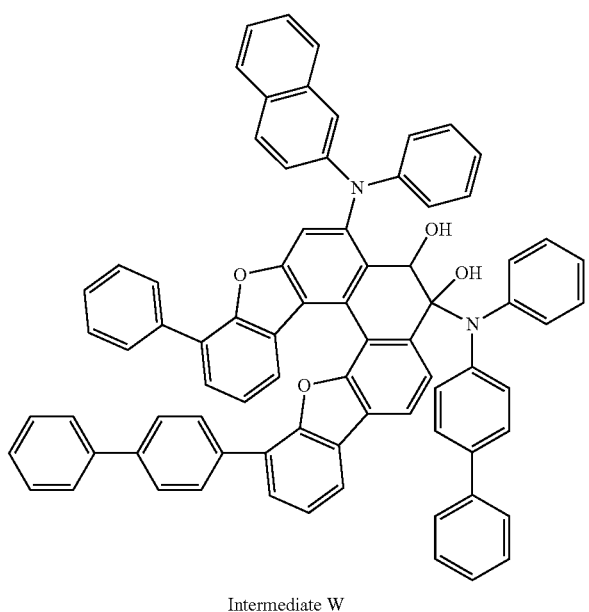

Intermediate W 30.9 g Intermediate V (1.0 eq.) and 2.2 g NaBH$_4$ (2.0 eq.) were placed into a three-neck flask (1 L) and aerated with nitrogen gas for 30 minutes. Then 450 mL ethanol and 150 mL water were added to dissolve the solid. The resulting mixture was reacted at room temperature for 24 hours, and after the reaction finished, it was filtered and the filter cake was washed with water, dried and recrystallized using a mixture of toluene and ethanol, producing 28.8 g Intermediate W in 93% yield.

Synthesis of Compound 11

[Reaction Scheme 25]

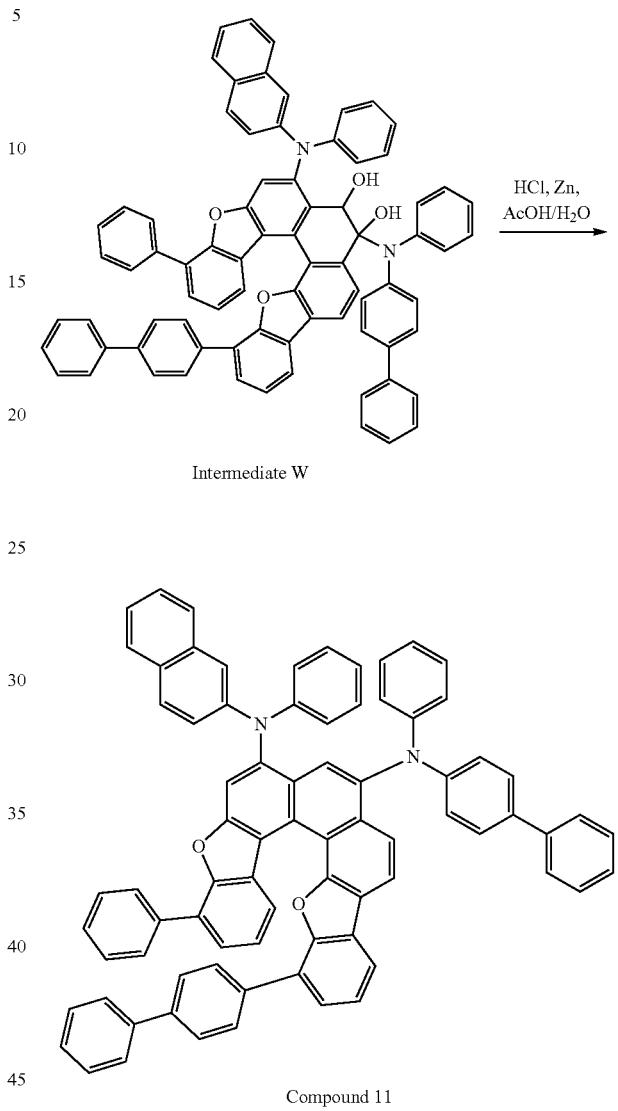

Intermediate W

Compound 11

28.8 g Intermediate W, 450 mL glacial acetic acid and 150 mL hydrochloric acid solution (4M) were placed into a three-neck flask (1 L) and aerated with nitrogen gas for 30 minutes. Then 2.2 g zinc powder (3 eq.) was added and the resulting mixture was heated to 110° C. and reacted overnight for 18 hours. After the reaction finished, the resulting mixture was cooled down to room temperature, filtered and extracted with a mixture of dichloromethane and water. The resulting mixture was then washed with water, spun to removal of solvent by rotary evaporators, dried and recrystallized using toluene, producing 22.3 g compound 11 in 80% yield.

1H NMR (DMSO, 300 Hz): δ (ppm)=8.71-8.01 (m, 5H), 7.89-7.65 (m, 7H), 7.62-7.31 (m, 23H), 7.30-7.21 (m, 8H), 7.16-6.84 (m, 7H)

MS (FAB): 1047 (M+)

Compound Example 3

Synthesis of Compound 23
Synthesis of Intermediate X

[Reaction Scheme 26]

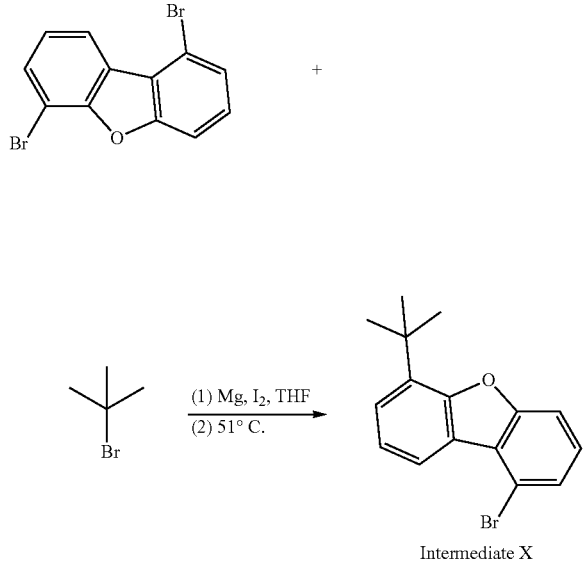

3.6 g Mg (1.5 eq.), 16 mL THF, and 0.36 g I₂ were placed into a dry three-neck flask (2 L) and the resulting mixture was heated to trigger reaction. Then a solution of 17.8 g tert-butyl bromide (1.3 eq.) in 180 mL THF was added dropwise, at room temperature, to the resulting mixture. After conducting the dropwise addition, the resulting mixture was reacted at 51° C. for 2 hours and was thereafter left to stand for 5 minutes. The supernatant was added dropwise to a solution of 32.6 g 1,6-dibromodiphenylfuran in 600 mL THF, and the resulting mixture was refluxed overnight for 15 hours, and after the reaction finished, it was cooled down to room temperature, quenched with drops of water, and extracted with a mixture of dichloromethane and water. The organic phase was washed with water and dried. The solvent was removed by rotary evaporation and the residual was purified by chromatography column to produce 27.6 g Intermediate X in 91% yield.

Synthesis of Intermediate Y

[Reaction Scheme 27]

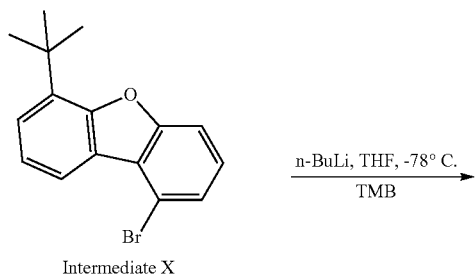

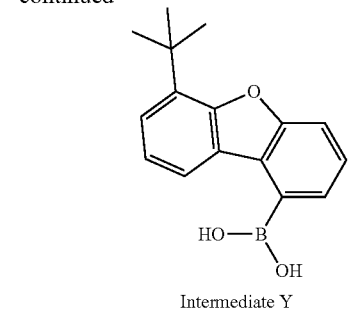

All experimental instruments were fully dried beforehand. 27.6 g Intermediate X was placed into a three-neck flask (2 L), to which 500 mL dry tetrahydrofuran was added to dissolve the solid. Then the resulting mixture was cooled down to −78° C. and 40 mL n-BuLi (2.5M) was added dropwise. Then the resulting mixture was stirred at the above temperature for 1 hour and 12.2 g trimethyl borate (1.3 eq.) was added dropwise. Then the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was boiled in ethyl acetate to obtain a crude product. The crude product was filtered to produce 19.0 g filter cake, i.e. boric acid product Immediate Y, in 78% yield.

Synthesis of Intermediate S

[Reaction Scheme 28]

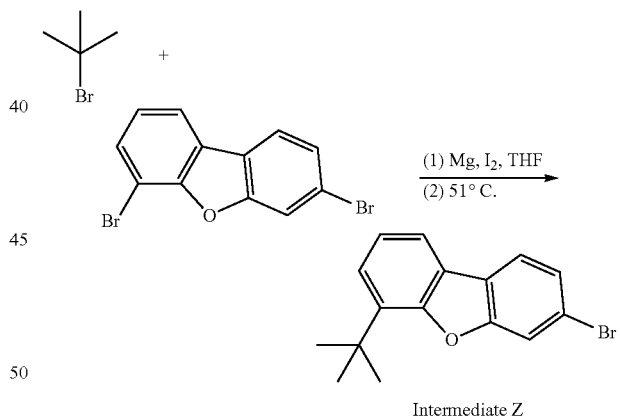

3.6 g Mg (1.5 eq.), 16 mL THF, and 0.36 g I₂ were placed into a dry three-neck flask (2 L) and the resulting mixture was heated to trigger reaction. Then a solution of 17.8 g tert-butyl bromide (1.3 eq.) in 180 mL THF was added dropwise, at room temperature, to the resulting mixture. After the addition, the resulting mixture was reacted at 51° C. for 2 hours and was thereafter left to stand for 5 minutes. The supernatant was added dropwise to a solution of 32.6 g 1,6-dibromodiphenylfuran in 600 mL THF. The resulting mixture was refluxed overnight for 15 hours, then after the reaction finished, it was cooled down to room temperature, quenched with drops of water, and extracted with a mixture of dichloromethane and water. The resulting mixture was washed with water and dried. The solvent was removed by rotary evaporation and the residual was purified by chromatography column to produce 27.9 g Intermediate Z in 92% yield.

Synthesis of Intermediate a

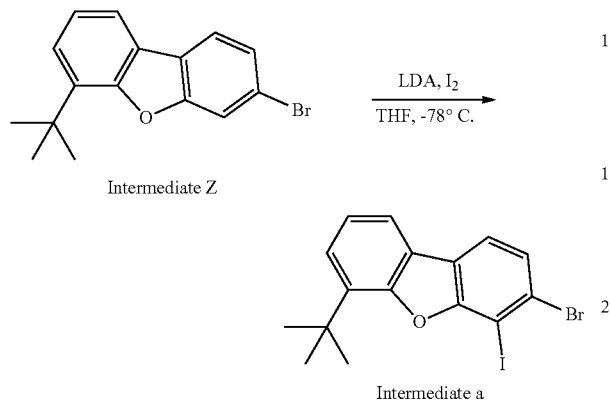

Intermediate Z

Intermediate a

All experimental instruments were fully dried beforehand. 27.9 g Intermediate Z was placed into a three-neck flask (2 L), to which 600 mL dry tetrahydrofuran was added to dissolve the solid. Then the resulting mixture was cooled down to −78° C. and 48.3 mL LDA solution (1.05 eq., 2M) in THF was added dropwise. Then the resulting mixture was stirred at the above temperature for 1 hour and 25.7 g iodine (1.1 eq.) was added. Then the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 30 g Intermediate a in 76% yield.

Synthesis of Intermediate b

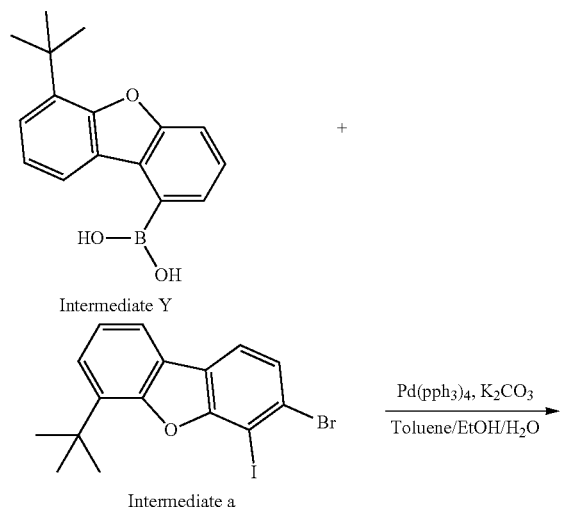

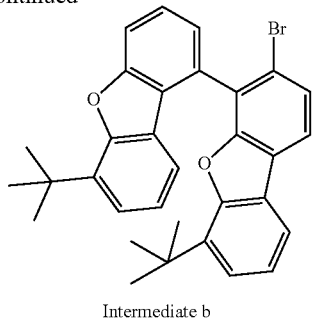

Intermediate b 20.6 g Intermediate Y and 30 g Intermediate a were placed into a three-neck flask (2 L), to which 600 mL toluene and 150 mL ethanol were added to dissolve the solid. The resulting mixture was aerated with nitrogen gas for 15 minutes and then, 105 mL aqueous $K_2CO_3$ solution (3.0 eq., 2M) and 1.6 g $Pd(PPh_3)_4$ (2 mol %) were sequentially added. The reaction was performed overnight at 110° C., and after the reaction finished, the resulting mixture was absorbed by activated carbon and filtered by suction filtration. The solvent was removed by rotary evaporation and the residual was dried and recrystallized with toluene and ethanol to produce 30.1 g Intermediate b in 82% yield.

Synthesis of Intermediate c

[Reaction Scheme 31]

Intermediate b (1) Mg, $I_2$, THF, oxalyl chloride
(2) $AlCl_3$/MC

Intermediate c 2.1 g Mg (1.5 eq.), 20 mL THF, and 0.21 g $I_2$ were placed into a dry three-neck flask (2 L) and the resulting mixture was heated to trigger reaction. Then a solution of 30.1 g Intermediate b (1.0 eq.) in 600 mL THF was added dropwise, at room temperature, to the resulting mixture. After the addition, the resulting mixture was reacted at 51° C. for 2 hours and was thereafter left to stand for 5 minutes. The supernatant was added dropwise to a solution of 6.5 g oxalyl chloride (0.9 eq.) in 80 mL THF. The resulting mixture was refluxed overnight for 16 hours, and after the reaction finished, it was cooled down to room temperature and a solution of 22.9 g aluminum trichloride (3.0 eq.) in 300 mL dichloromethane was added dropwise in an ice-water bath. After the addition, the resulting mixture was heated and refluxed overnight for 15 hours. After the reaction finished, the resulting mixture was quenched with drops of water to produce a large amount of solid matter. The solid matter was filtered by suction filtration and the residual was washed with water, dried and purified by chromatography column to produce 21.5 g Intermediate c in 75% yield.

Synthesis of Intermediate d

[Reaction Scheme 32]

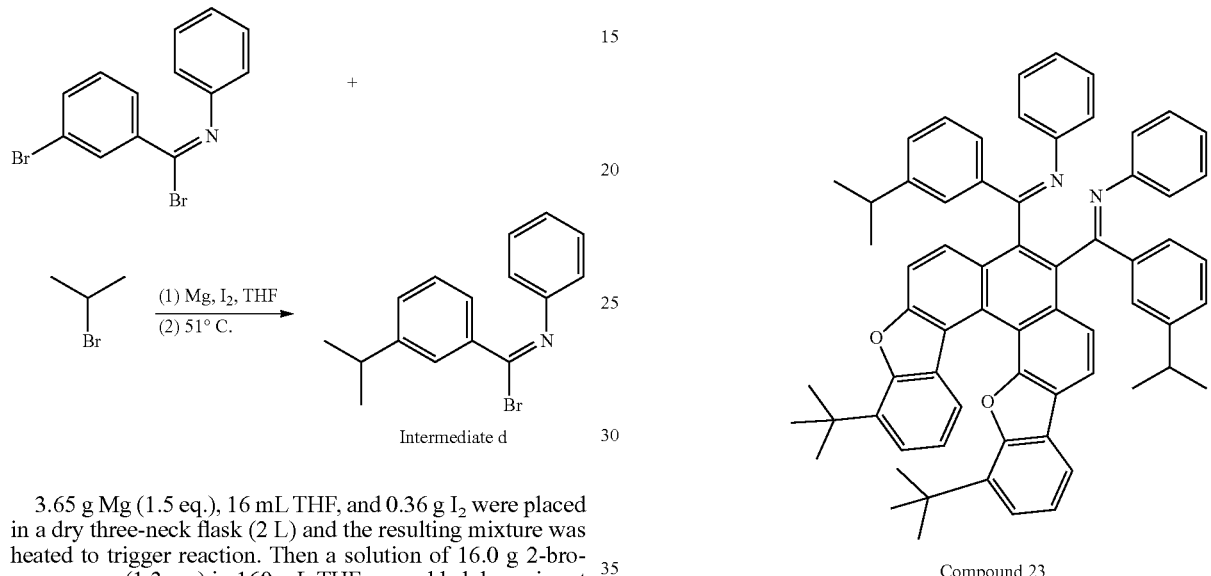

Intermediate d 3.65 g Mg (1.5 eq.), 16 mL THF, and 0.36 g I$_2$ were placed in a dry three-neck flask (2 L) and the resulting mixture was heated to trigger reaction. Then a solution of 16.0 g 2-bromopropane (1.3 eq.) in 160 mL THF was added dropwise at room temperature. After the addition, the resulting mixture was reacted at 51° C. for 2 hours and was thereafter left to stand for 5 minutes. The supernatant was added dropwise to a solution of 33.9 g 3-bromo-N-(phenylmethyl) imino bromide in 600 mL THF. The resulting mixture was refluxed overnight for 15 hours, then after the reaction finished, it was cooled down to room temperature, quenched with drops of water, and extracted with a mixture of dichloromethane and water. The residual was washed with water and dried. The solvent was removed by rotary evaporation and the residual was purified by chromatography column to produce 25.7 g Intermediate d in 85% yield.

Synthesis of Compound 23

[Reaction Scheme 33]

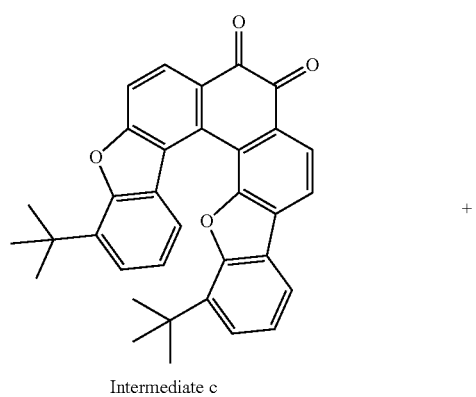

Intermediate c

+

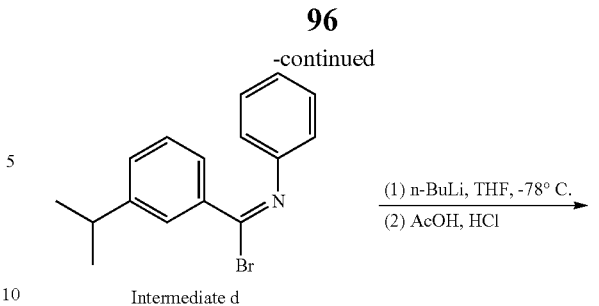

Intermediate d (1) n-BuLi, THF, -78° C.
(2) AcOH, HCl

Compound 23

All experimental instruments were fully dried beforehand. 25.7 g (2.1 eq.) Intermediate d was placed into a three-neck flask (2 L), to which 500 mL dry tetrahydrofuran was added to dissolve the solid. Then the resulting mixture was cooled down to −78° C. and 35.6 mL n-BuLi (2.2 eq., 2.5M) was added dropwise. Then the resulting mixture was stirred at the above temperature for 1 hour and 20.3 g Intermediate c (1.0 eq.) was added dropwise. Then the resulting mixture was stirred overnight at room temperature. After the reaction was finished, hydrochloric acid solution (4M) was added and the resulting mixture was extracted with dichloromethane. The organic phase was washed with saturated aqueous NaCl solution until neutral and dried. After removal of the solvent by rotary evaporation, 250 mL glacial acetic acid and 60 mL concentrated hydrochloric acid were added and the resulting mixture was heated up to 110° C. and refluxed overnight for 15 hours. After the reaction finished, the resulting mixture was cooled down to room temperature to separate out solid matter. The solid matter was filtered by suction filtration, washed with water, dried and recrystallized with toluene and ethanol to produce 34.1 g compound 23 in 92% yield.

1H NMR (DMSO, 300 Hz): δ (ppm)=8.61-8.25 (s, 1H), 8.24-8.01 (d, 1H), 7.92-7.78 (s, 2H), 7.77-7.65 (m, 4H), 7.63-7.55 (d, 2H), 7.53-7.40 (m, 4H), 7.38-7.28 (m, 4H), 7.26-7.14 (m, 4H), 7.12-7.01 (m, 2H), 6.96-6.75 (m, 4H), 3.01-2.52 (q, 2H), 1.68-1.55 (s, 18H), 1.38-1.03 (d, 12H)

MS (FAB): 913 (M+)

Compound Example 4

Synthesis of Compound 47
Synthesis of Intermediate e

[Reaction Scheme 34]

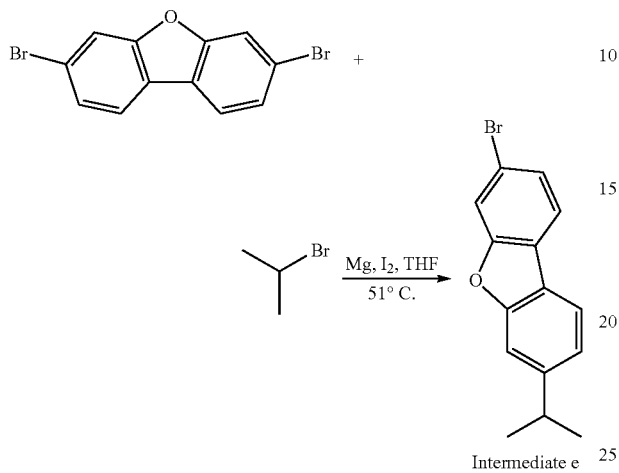

Intermediate e 3.6 g Mg (1.5 eq.), 15 mL THF, and 0.36 g I$_2$ were placed into a dry three-neck flask (2 L) and the resulting mixture was heated to trigger reaction. Then a solution of 16.0 g 2-bromopropane (1.3 eq.) in 160 mL THF was added dropwise at room temperature. After the addition, the resulting mixture was reacted at 51° C. for 2 hours and was thereafter left to stand for 5 minutes. The supernatant was added dropwise to a solution of 32.6 g 3,7-dibromodiphenylfuran in 600 mL THF. The resulting mixture was refluxed overnight for 15 hours, then after the reaction finished, it was cooled down to room temperature, quenched with drops of water, and extracted with a mixture of dichloromethane and water. The residual phase was washed with water and dried. The solvent was removed by rotary evaporation and the residual was purified by chromatography column to produce 24.6 g Intermediate e in 85% yield.

Synthesis of Intermediate f

[Reaction Scheme 35]

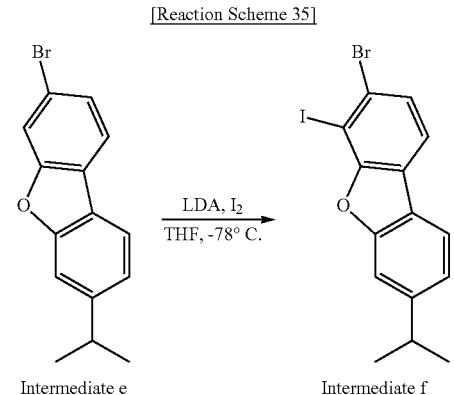 [SMILES: CC(C)c1ccc2c(c1)oc1cc(Br)ccc12 ; CC(C)c1ccc2c(c1)oc1c(I)c(Br)ccc12]

Intermediate e  Intermediate f

All experimental instruments were fully dried beforehand. 24.6 g Intermediate e was placed into a three-neck flask (2 L), to which 400 mL dry tetrahydrofuran was added to dissolve the solid. Then the resulting mixture was cooled down to −78° C. and 44.7 mL LDA solution (1.05 eq., 2M) in THF was added dropwise. After the addition the resulting mixture was stirred at the above temperature for 1 hour and 23.8 g iodine (1.1 eq.) was added dropwise. After the addition the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 26.8 g Intermediate f in 76% yield.

Synthesis of Intermediate g

[Reaction Scheme 36]

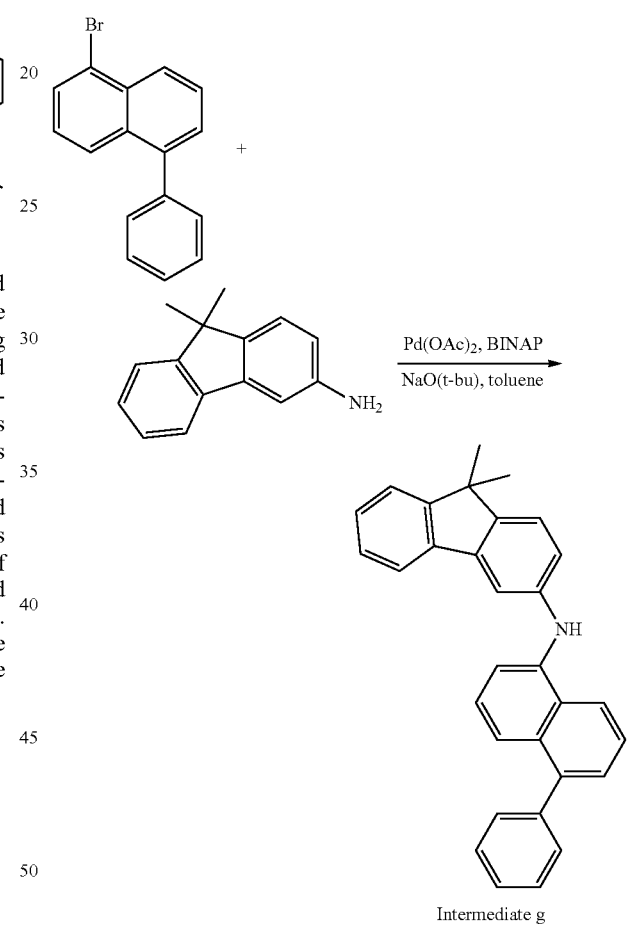

Intermediate g 28.3 g 1-bromo-5-phenylnaphthalene and 23 g 2-amino-9,9'-dimethylfluoren were placed into a three-neck flask (2 L), to which 600 mL dry and degassed toluene was added to dissolve the solid. Then, 8.8 g sodium tert-butoxide (3 eq.), 0.45 g catalyst palladium diacetate (2% mol) and 2.5 g 1,1'-binaphthyl-2,2'-bis(diphenylphosphino)(BINAP, 4% mol) ligand were added. The resulting was heated up to 110° C. and reacted overnight. After the reaction finished, the resulting mixture was absorbed with activated carbon and filtered by suction filtration. The solvent was removed by rotary evaporation and the residual was recrystallized with toluene and ethanol to produce 36.6 g Intermediate g in 89% yield.

Synthesis of Intermediate h

[Reaction Scheme 37]

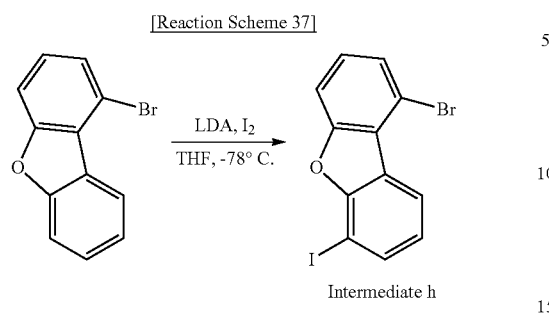

Intermediate h

All experimental instruments were fully dried beforehand. 26.3 g 1-bromobiphenylfuran was placed into a three-neck flask (2 L), to which 500 mL dry tetrahydrofuran was added to dissolve the solid. Then the resulting mixture was cooled down to −78° C. and 52.5 mL LDA solution (1.05 eq., 2M) in THF was added dropwise. After the addition the resulting mixture was stirred at the above temperature for 1 hour and 28.0 g iodine (1.1 eq.) was added dropwise. After the addition the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 38.5 g Intermediate h in 79% yield.

Synthesis of Intermediate i

[Reaction Scheme 38]

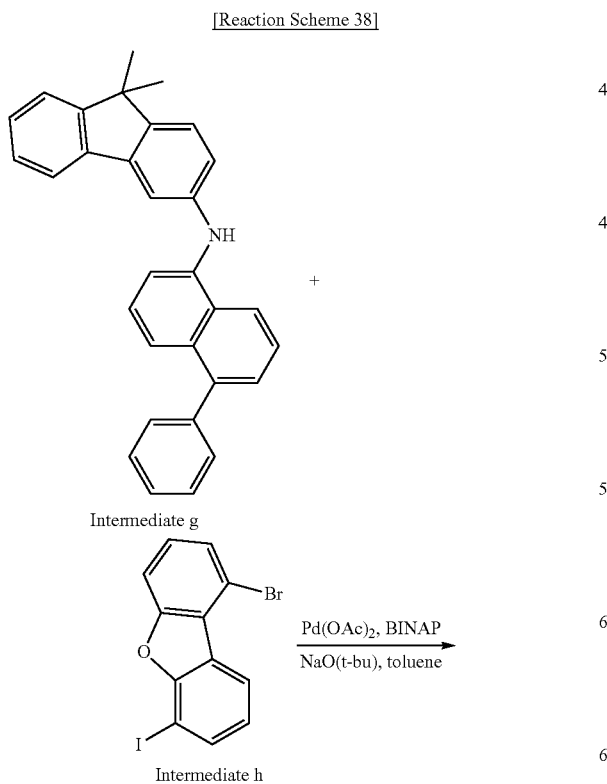

Intermediate g

+

Intermediate h

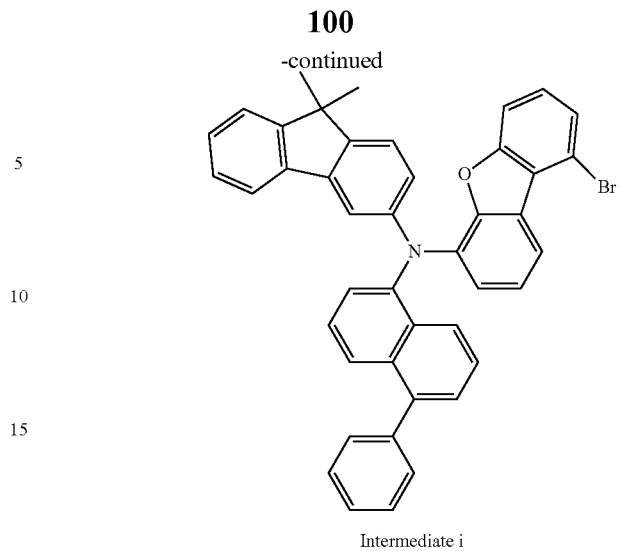

Intermediate i 38.5 g Intermediate h and 35.8 g Intermediate g were placed into a three-neck flask (2 L), to which 800 mL dry and degassed toluene was added to dissolve the solid. Then, 22.8 g sodium tert-butoxide (3 eq.), 0.36 g catalyst palladium diacetate (2% mol) and 2.0 g 1,1'-binaphthyl-2,2'-bis(diphenylphosphino)(BINAP, 4% mol) ligand were added. The resulting was heated up to 110° C. and reacted overnight. After the reaction finished, the resulting mixture was absorbed with activated carbon and filtered by suction filtration. The solvent was removed by rotary evaporation and the residual was recrystallized with toluene and ethanol to produce 47.3 g Intermediate i in 91% yield.

Synthesis of Intermediate j

[Reaction Scheme 39]

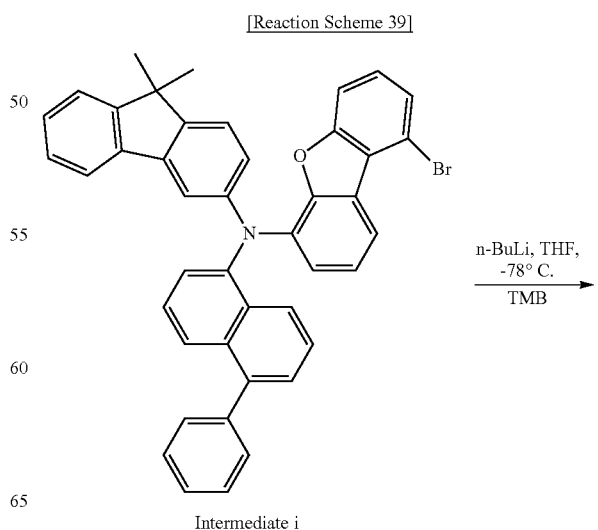

Intermediate i

-continued

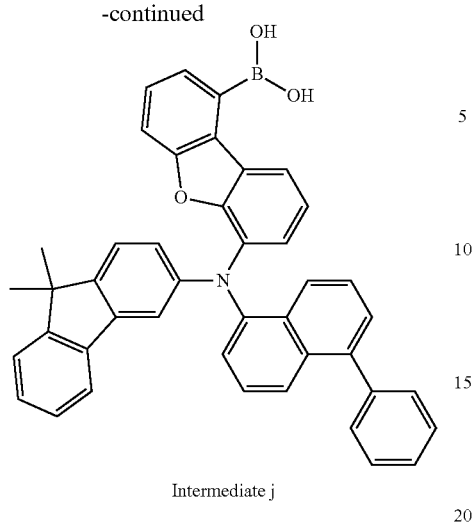

Intermediate j

All experimental instruments were fully dried beforehand. 47.3 g Intermediate i was placed into a three-neck flask (2 L), to which 1000 mL dry tetrahydrofuran was added to dissolve the solid. Then the resulting mixture was cooled down to −78° C. and 31.7 mL n-BuLi (1.1 eq., 2.5M) was added dropwise. After the addition the resulting mixture was stirred at the above temperature for 1 hour and 9.7 g trimethyl borate (1.3 eq.) was added dropwise. After the addition the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was boiled in ethyl acetate to produce a crude product. The crude product was filtered to produce 36.2 g filter cake, i.e. boric acid product Intermediate j, in 81% yield.

Synthesis of Intermediate k

[Reaction Scheme 40]

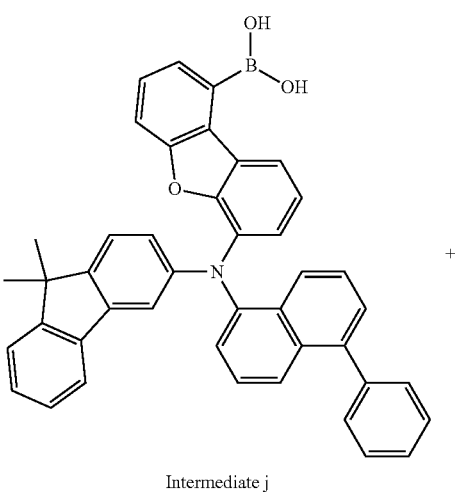

Intermediate j

+

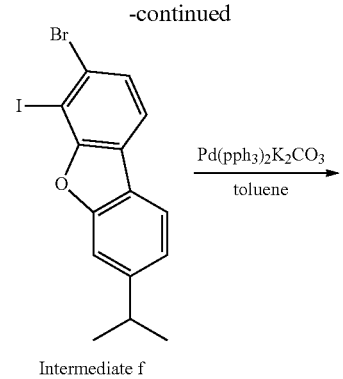

Intermediate f

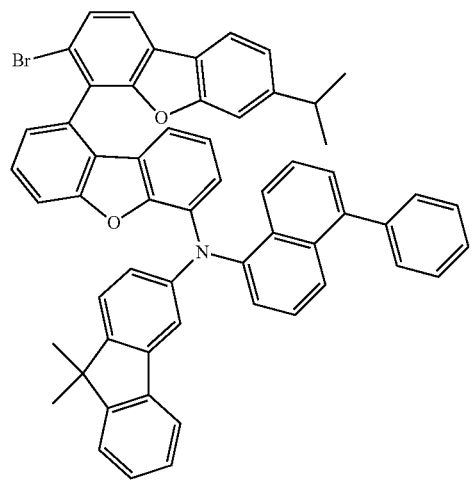

Intermediate k 36.2 g Intermediate j and 22.0 g Intermediate f were placed into a three-neck flask (2 L), to which 700 mL toluene and 150 mL ethanol were added to dissolve the solid. The resulting mixture was aerated with nitrogen gas for 15 minutes and then, 79.4 mL aqueous $K_2CO_3$ solution (3.0 eq., 2M) and 1.2 g $Pd(PPh_3)_4$ (2 mol %) were sequentially added. The reaction was performed overnight at 110° C., and after the reaction finished, the resulting mixture was absorbed with activated carbon and filtered suction filtration. The solvent was removed by rotary evaporation and the residual was dried and recrystallized with toluene and ethanol to produce 40.3 g Intermediate k in 88% yield.

Synthesis of Intermediate 1

[Reaction Scheme 41]

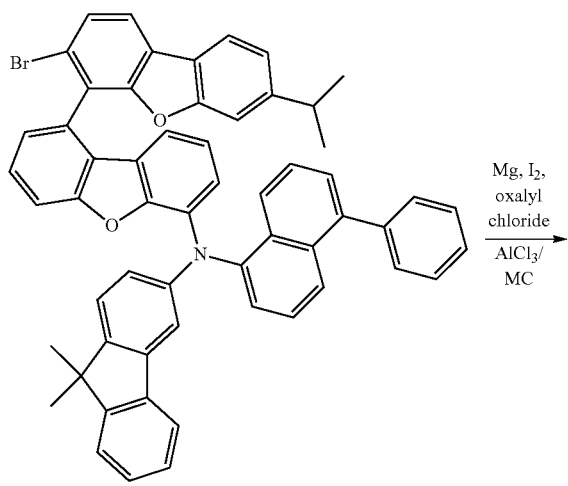

Intermediate k

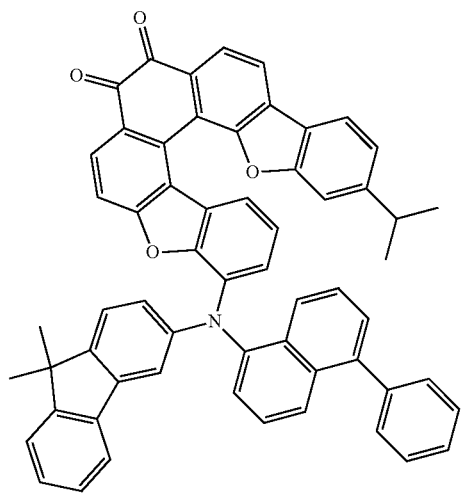

Intermediate l 1.7 g Mg (1.5 eq.), 18 mL THF, and 0.2 g I$_2$ were placed into a dry three-neck flask (2 L) and the resulting mixture was heated to trigger reaction. Then a solution of 40.3 g Intermediate k (1.0 eq.) in 400 mL THF was added dropwise, at room temperature. After the addition, the resulting mixture was reacted at 55° C. for 2 hours and was thereafter left to stand for 5 minutes. The supernatant was added dropwise to a solution of 5.3 g oxalyl chloride (0.9 eq.) in 60 mL THF. The resulting mixture was refluxed overnight for 16 hours, and after the reaction finished, it was cooled down to room temperature and was added dropwise in an ice-water bath condition into a solution of 18.6 g aluminum trichloride (3.0 eq.) in 300 mL dichloromethane. After the addition, the resulting mixture was heated and refluxed overnight for 15 hours. After the reaction was completed, the resulting mixture was quenched with drops of ice water to obtain a large amount of solid matter which was then filtered suction filtration. The solid matter was washed with water, dried and purified by chromatography column to produce 29.4 g Intermediate 1 in 75% yield.

Synthesis of Intermediate m

[Reaction Scheme 42]

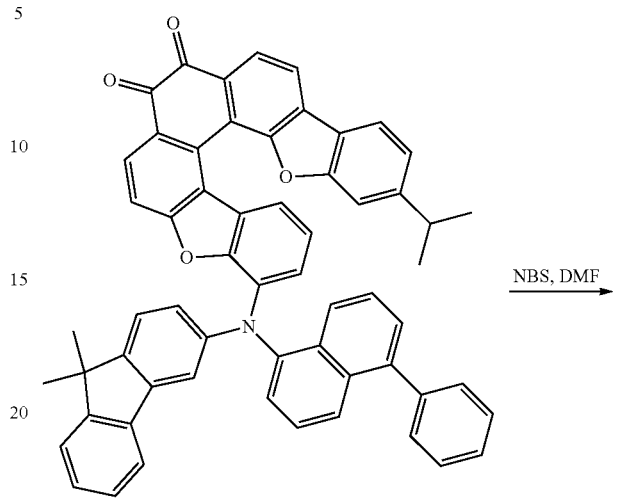

Intermediate l

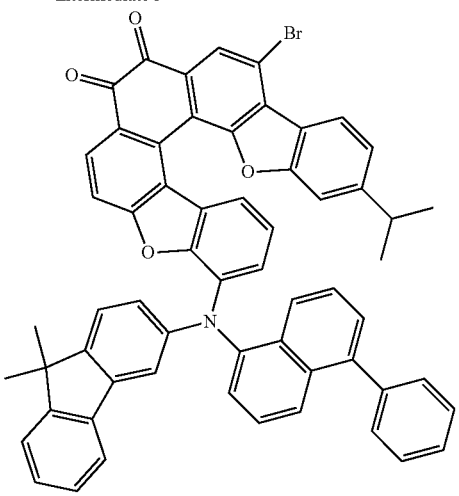

Intermediate m 29.4 g Intermediate 1 was placed into a three-neck flask (2 L), to which 600 mL DMF was added to dissolve the solid. Then, 6.9 g NBS (1.1 eq.) was added and the resulting mixture was stirred at room temperature in the dark overnight. After the reaction finished, a large amount of water was added to separate out solid matter which was then filtered. The filter cake was washed three times with water, dried and recrystallized with toluene and ethanol to produce 29.6 g Intermediate m in 92% yield.

Synthesis of Intermediate n

[Reaction Scheme 43]

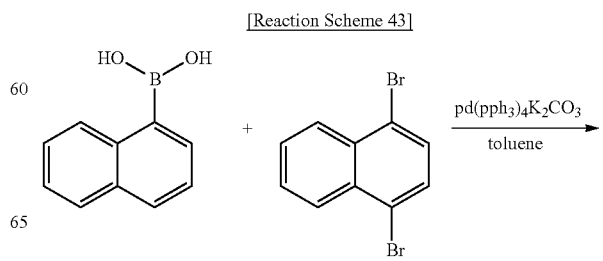

-continued

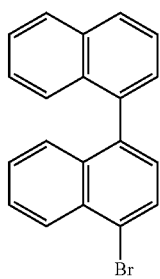

Intermediate n 28.6 g 1,4-dibromonaphalene and 17.2 g 2-naphthyl boric acid product were placed into a three-neck flask (2 L), to which 600 mL toluene and 150 mL ethanol were added to dissolve the solid. The resulting mixture was aerated with nitrogen gas for 15 minutes and then, 150 mL aqueous K$_2$CO$_3$ solution (3.0 eq., 2M) and 2.3 g Pd(PPh$_3$)$_4$(2 mol %) were sequentially added. The reaction was heated up to 110° C. performed overnight at the temperature, and after the reaction finished, the resulting mixture was absorbed with activated carbon and filtered by suction filtration. The solvent was removed by rotary evaporation and the residual was dried and recrystallized with toluene and ethanol to produce 31.0 g Intermediate n in 93% yield.

Synthesis of Intermediate o

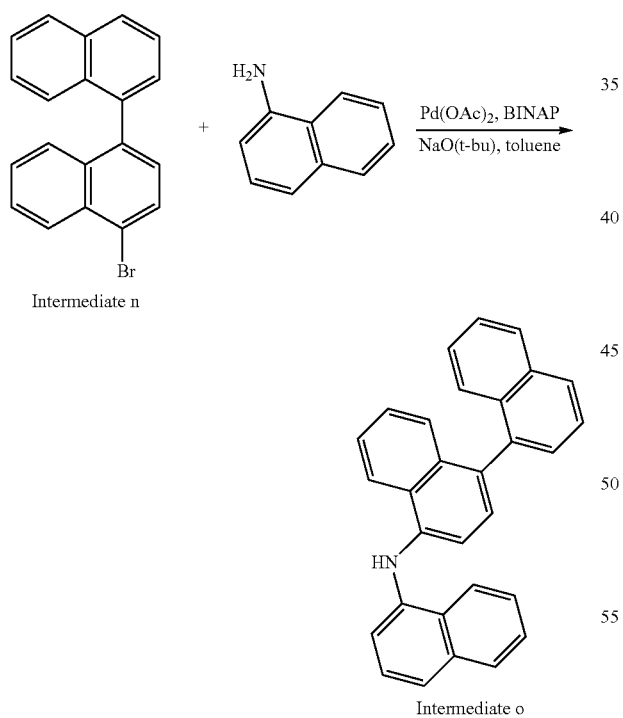

31.0 g Intermediate n and 14.7 g 2-naphthylamine were placed into a three-neck flask (2 L), to which 600 mL dry and degassed toluene was added to dissolve the solid. Then, 26.8 g sodium tert-butoxide (3 eq.), 0.42 g catalyst palladium diacetate (2% mol) and 2.3 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 32.7 g Intermediate o in 89% yield.

Synthesis of Intermediate p

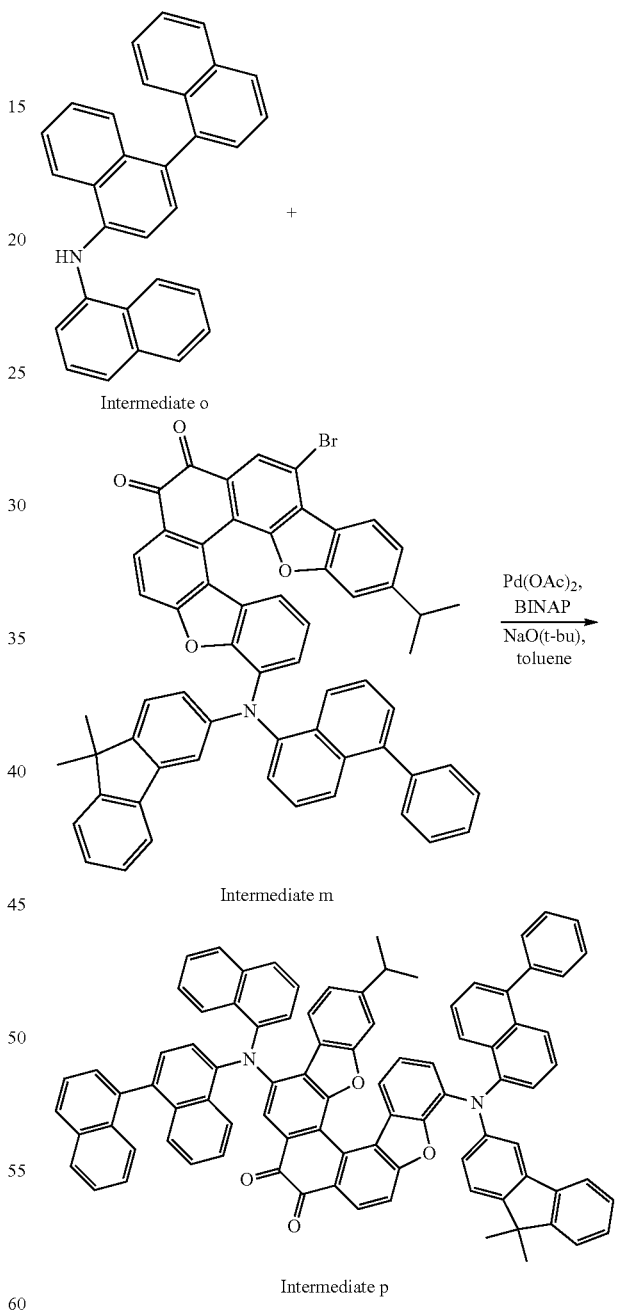

29.6 g Intermediate m and 14.0 g Intermediate o were placed into a three-neck flask (2 L), to which 600 mL dry and degassed toluene was added to dissolve the solid. Then, 9.3 g sodium tert-butoxide (3 eq.), 0.14 g catalyst palladium diacetate (2% mol) and 0.8 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 33.8 g Intermediate p in 85% yield.

Synthesis of Intermediate q

[Reaction Scheme 46]

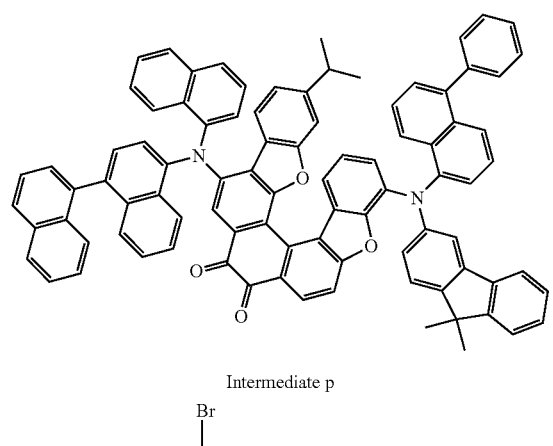

Intermediate p

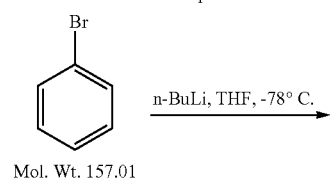

Mol. Wt. 157.01

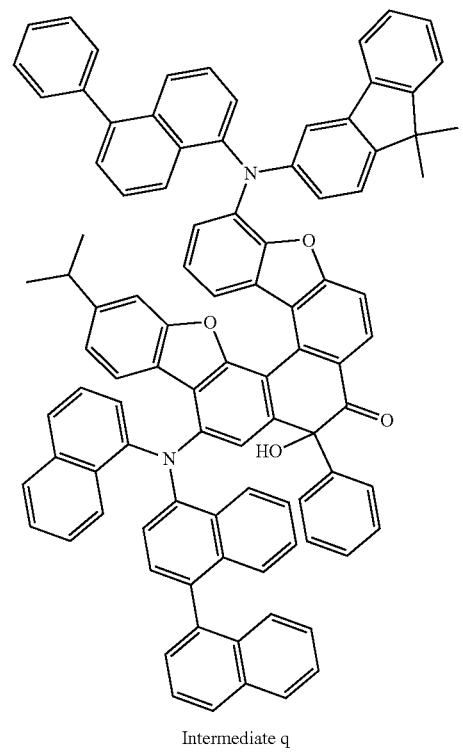

Intermediate q

All experimental instruments were fully dried beforehand. 4.7 g bromobenzene (1.1 eq.) was placed into a three-neck flask (1 L), to which 100 mL dry tetrahydrofuran was added to dissolve the solid. Then the resulting mixture was cooled down to −78° C. and 13.2 mL n-BuLi (1.2 eq., 2.5M) was added dropwise. After the addition the resulting mixture was stirred at the above temperature for 1 hour and a solution of 33.8 g Intermediate p in 400 mL THF was added dropwise. After the addition the resulting mixture was stirred overnight at room temperature. After the reaction finished, hydrochloric acid solution (4M) was added and the resulting mixture was extracted with ethyl acetate. The organic phase was washed with saturated aqueous NaCl solution until neutral and dried. The solvent was then removed by rotary evaporation and the residual was purified by chromatography column to produce 27.3 g Intermediate q in 76% yield.

Synthesis of Intermediate r

[Reaction Scheme 47]

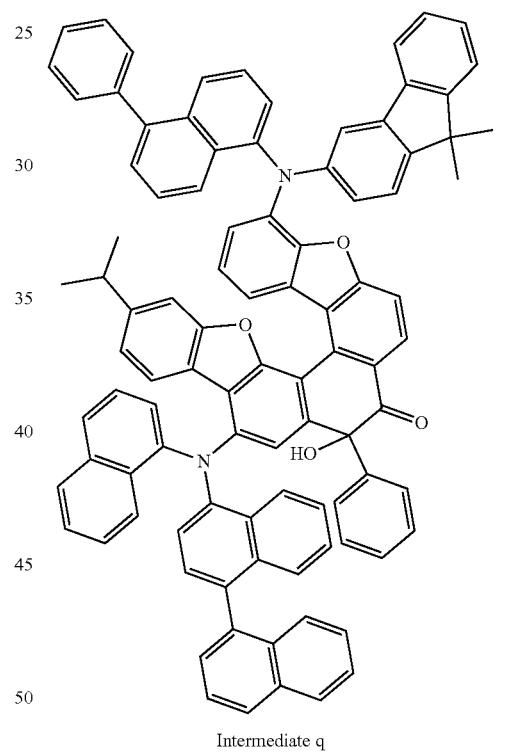

Intermediate q

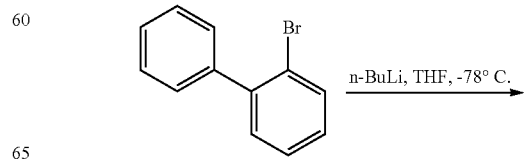

Synthesis of Compound 47

[Reaction Scheme 48]

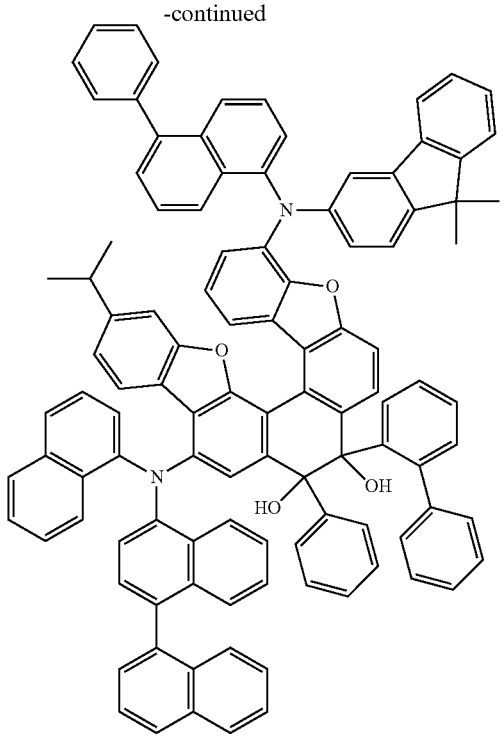

Intermediate r

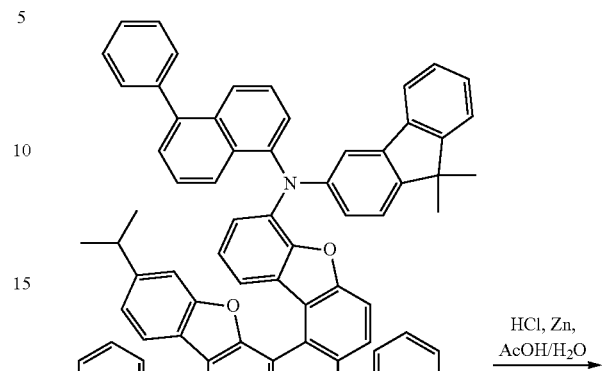

Intermediate r

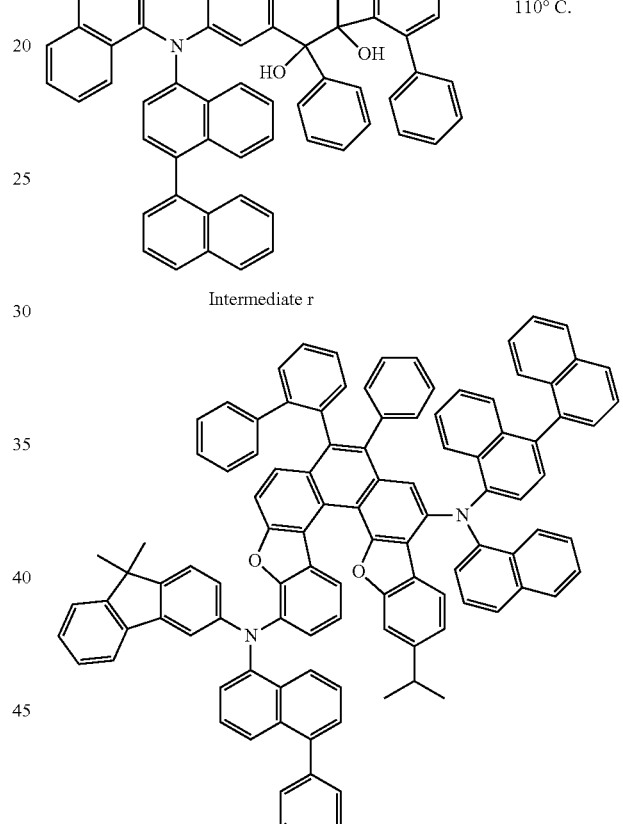

Compound 47

All experimental instruments were fully dried beforehand. 5.3 g 2-bromobiphenyl (1.1 eq.) was placed in a three-neck flask (1 L), to which 100 mL dry tetrahydrofuran was added to dissolve the solid. Then the resulting mixture was cooled down to −78° C. and 10 mL n-BuLi (1.2 eq., 2.5M) was added dropwise. After the addition the resulting mixture was stirred at the above temperature for 1 hour and a solution of 27.3 g Intermediate q in 300 mL THF was added dropwise. After the addition the resulting mixture was stirred overnight at room temperature. After the reaction finished, hydrochloric acid solution (4M) was added and the resulting mixture was extracted with ethyl acetate. The organic phase was washed with saturated aqueous NaCl solution until neutral and dried. The solvent was then removed by rotary evaporation and the residual was purified by chromatography column to produce 24.7 g Intermediate r in 81% yield.

24.7 g Intermediate r, 360 mL glacial acetic acid, and 120 mL hydrochloric acid solution (4M) were placed into a three-neck flask (1 L). The resulting mixture was aerated with nitrogen gas for 30 minutes and then, 1.4 g zinc powder (3 eq.) was added. The reaction was heated up to 110° C. and performed overnight for 18 hours. After the reaction finished, the resulting mixture was cooled down to room temperature and filtered. The filtrate was extracted with a mixture of dichloromethane and water. The residual was then washed with water, followed by rotary evaporation to remove the solvent, drying and recrystallization with toluene, to produce 20.6 g compound 47 in 85% yield.

1H NMR (DMSO, 300 Hz): δ (ppm)=9.05-8.85 (d, 2H), 8.68-8.58 (d, 1H), 8.56-8.45 (d, 2H), 8.40-8.03 (m, 7H), 7.99-7.71 (m, 13H), 7.69-7.13 (m, 34H), 7.10-6.78 (m, 2H), 3.01-2.52 (q, 1H), 1.60-1.35 (s, 6H), 1.33-1.03 (d, 6H)
MS (FAB): 1431 (M+)

Compound Example 5

Synthesis of Compound 83
Synthesis of Intermediate s

[Reaction Scheme 49]

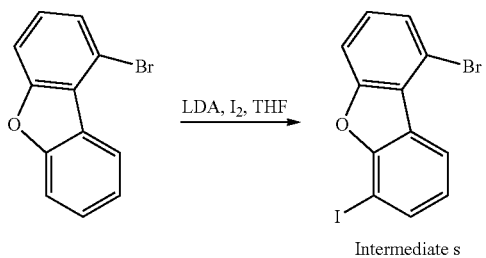

Intermediate s

All experimental instruments were fully dried beforehand. 24.7 g 1-bromobiphenylfuran was placed into a three-neck flask (2 L), to which 400 mL dry tetrahydrofuran was added to dissolve the solid. Then the resulting mixture was cooled down to −78° C. and 52.5 mL LDA solution (1.05 eq., 2M) in THF was added dropwise. After the addition, the resulting mixture was stirred at the above temperature for 1 hour and 27.9 g iodine (1.1 eq.) was added. Then the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 28.3 g Intermediate s in 76% yield.

Synthesis of Intermediate t

[Reaction Scheme 50]

2.8 g Mg (1.5 eq.), 12 mL THF, and 0.28 g I₂ were placed into a dry three-neck flask (2 L) and the resulting mixture was heated to trigger reaction. Then a solution of 12.2 g 2-bromopropane (1.3 eq.) in 120 mL THF was added dropwise at room temperature. After the addition, the resulting mixture was reacted at 51° C. for 2 hours and was thereafter left to stand for 5 minutes. The supernatant was added dropwise to a solution of 28.3 g Intermediate s in 600 mL THF. The resulting mixture was refluxed overnight for 15 hours, then after the reaction finished, it was cooled down to room temperature, quenched with drops of water, and extracted with a mixture of dichloromethane and water. The residual was washed with water and dried. The solvent was removed by rotary evaporation and the residual was purified by chromatography column to produce 18 g Intermediate t in 82% yield.

Synthesis of Intermediate u

[Reaction Scheme 51]

Intermediate t

Intermediate u

All experimental instruments were fully dried beforehand. 18 g Intermediate t was placed into a three-neck flask (2 L), to which 400 mL dry tetrahydrofuran was added to dissolve the solid. Then the resulting mixture was cooled down to −78° C. and 27.4 mL n-BuLi (2.5M) was added dropwise. After the addition, the resulting mixture was stirred at the above temperature for 1 hour and 8.4 g trimethyl borate (1.3 eq.) was added dropwise. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was boiled in ethyl acetate to produce a crude product. The crude product was filtered to produce 14.1 g filter cake, i.e. boric acid product Intermediate u, in 89% yield.

Synthesis of Intermediate v

[Reaction Scheme 52]

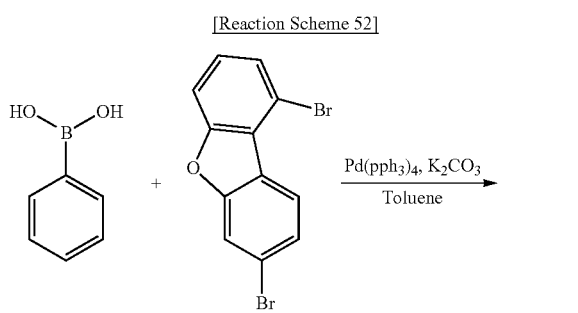

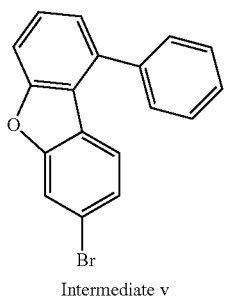

Intermediate v 13.4 g phenylboronic acid and 32.6 g 1,7-dibromo-dibenzofuran were placed in a three-neck flask (2 L), to which 700 mL toluene and 150 mL ethanol were added to dissolve the solid. The resulting mixture was aerated with nitrogen gas for 15 minutes and then, 150 mL aqueous K₂CO₃ solution (3.0 eq., 2M) and 2.3 g Pd(PPh₃)₄(2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 29.1 g Intermediate v in 90% yield.

Synthesis of Intermediate w

[Reaction Scheme 53]

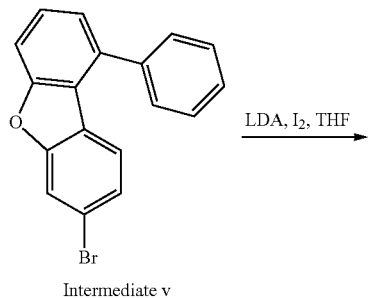

Intermediate v

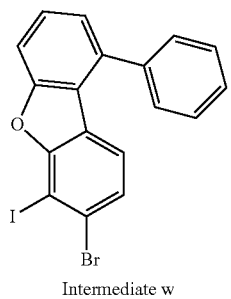

Intermediate w

All experimental instruments were fully dried beforehand. 29.1 g Intermediate v was placed in a three-neck flask (2 L), to which 600 mL dry tetrahydrofuran was added to dissolve the solid. Then the resulting mixture was cooled down to −78° C. and 47.3 mL LDA solution (1.05 eq., 2M) in THF was added dropwise. After the addition, the resulting mixture was stirred at the above temperature for 1 hour and 25.1 g iodine (1.1 eq.) was added.

After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 32.8 g Intermediate w in 81% yield.

Synthesis of Intermediate x

[Reaction Scheme 54]

Intermediate v

+

Intermediate w

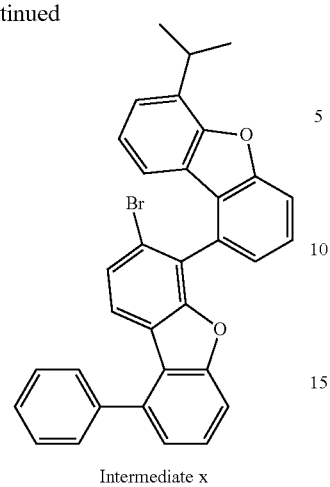

Intermediate x 14.1 g Intermediate u and 22.7 g Intermediate w were placed into a three-neck flask (2 L), to which 500 mL toluene and 150 mL ethanol were added to dissolve the solid. The resulting mixture was aerated with nitrogen gas for 15 minutes and then, 75.6 mL aqueous $K_2CO_3$ solution (3.0 eq., 2M) and 1.2 g $Pd(PPh_3)_4$ (2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 24.7 g Intermediate x in 92% yield.

Synthesis of Intermediate y

[Reaction Scheme 55]

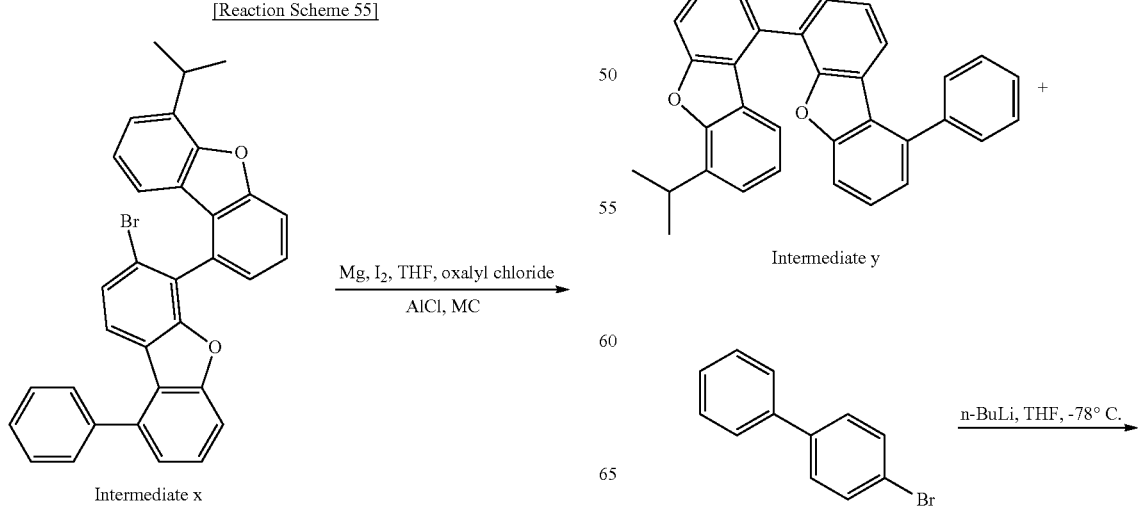

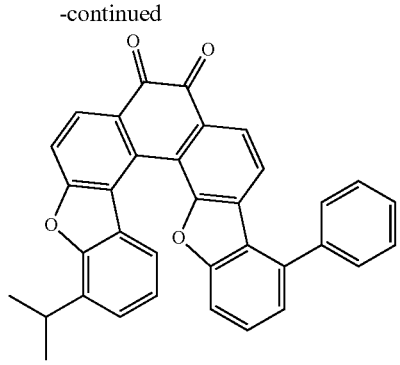

Intermediate y 1.7 g Mg (1.5 eq.), 118 mL THF, and 0.2 g $I_2$ were placed into a dry three-neck flask (2 L) and the resulting mixture was heated to trigger reaction. Then a solution of 24.7 g Intermediate x (1.0 eq.) in 400 mL THF was added dropwise at room temperature. After the addition, the resulting mixture was reacted at 55° C. for 2 hours and was thereafter left to stand for 5 minutes. The supernatant was added dropwise to a solution of 5.3 g oxalyl chloride (0.9 eq.) in 80 mL THF. The resulting mixture was refluxed overnight for 16 hours, and after the reaction finished, it was cooled down to room temperature and was added dropwise in an ice-water bath condition into a solution of 18.6 g aluminum trichloride (3.0 eq.) in 360 mL dichloromethane. After the addition, the resulting mixture was heated and refluxed overnight for 15 hours. After the reaction finished, the resulting mixture was quenched with drops of water to obtain a large amount of solid matter which was then filtered by suction filtration. The solid matter was washed with water, dried and purified by chromatography column to produce 20 g Intermediate y in 85% yield.

Synthesis of Intermediate z

[Reaction Scheme 56]

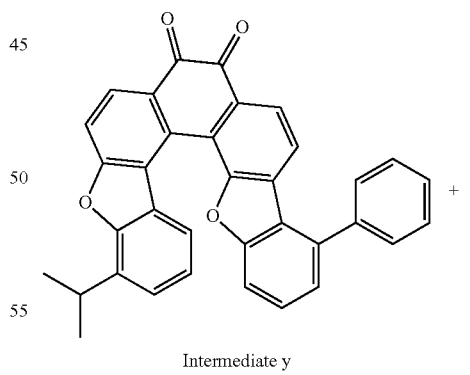

Intermediate y

-continued

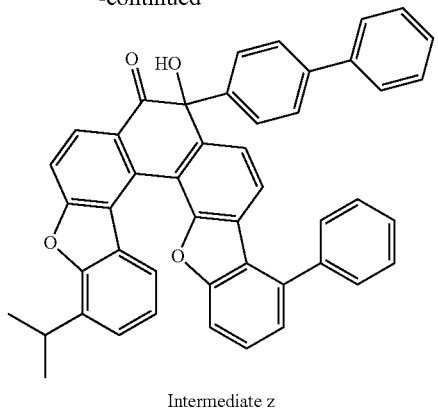

Intermediate z

All experimental instruments were fully dried beforehand. 10.1 g 4-bromobiphenyl (1.1 eq.) was placed into a three-neck flask (1 L), to which 100 mL dry tetrahydrofuran was added to dissolve the solid. Then the resulting mixture was cooled down to −78° C. and 19 mL n-BuLi (2.5M) was added dropwise. Then the resulting mixture was stirred at the above temperature for 1 hour and a solution of 20 g Intermediate y in 400 mL THF was added dropwise. Then the resulting mixture was stirred overnight at room temperature. After the reaction finished, hydrochloric acid solution (4M) was added and the resulting mixture was extracted with ethyl acetate. The organic phase was washed with saturated aqueous NaCl solution until neutral and dried. The solvent was then removed by rotary evaporation and the residual was purified by chromatography column to produce 21.7 g Intermediate z in 83% yield.

Synthesis of Intermediate AA

[Reaction Scheme 57]

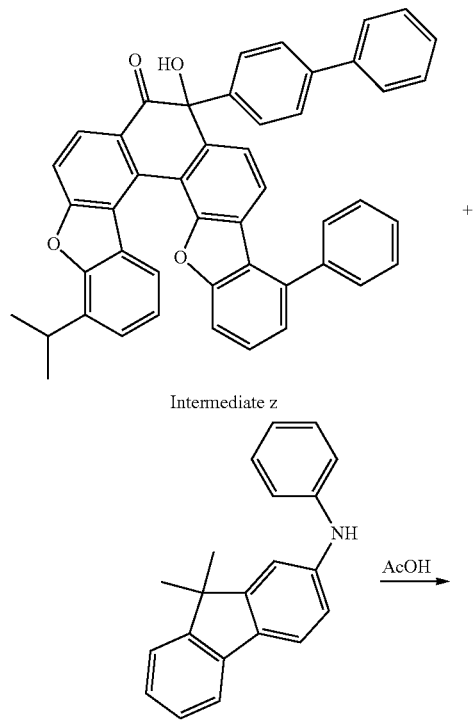

-continued

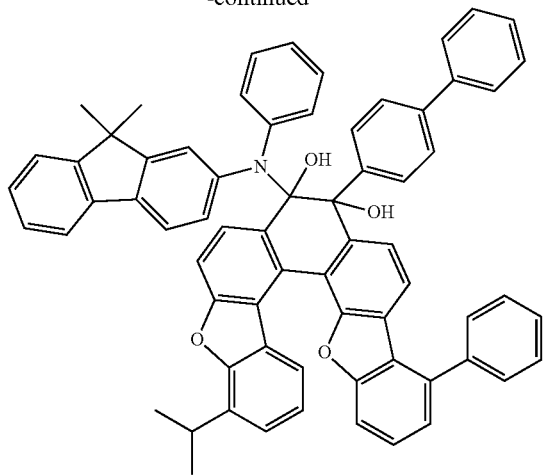

Intermediate AA 21.7 g Intermediate z (1.0 eq.) and 10.3 g 9,9-dimethyl-9H-furan-2-phenylamine (1.1 eq.) were placed into a three-neck flask (1 L), to which 300 mL glacial acetic acid was added to dissolve the solid. The resulting mixture was heated up to 130° C. and refluxed overnight for 18 hours. After the reaction finished, the resulting mixture was cooled down to room temperature and extracted with a mixture of dichloromethane and water. The residual was then washed four times with water and dried. The solvent was removed by rotary evaporation and the residual was recrystallized with toluene and ethanol to produce 27.7 g Intermediate AA in 89% yield.

Synthesis of Compound 83

[Reaction Scheme 58]

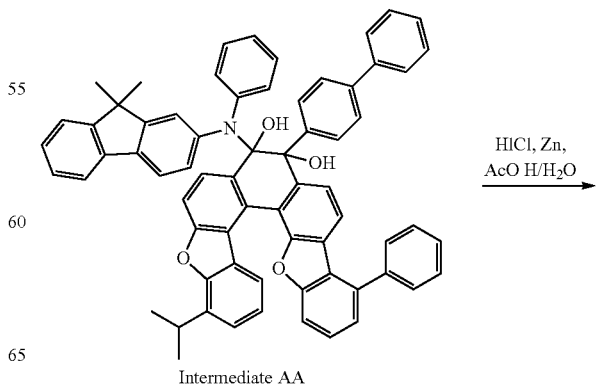

Intermediate AA

-continued

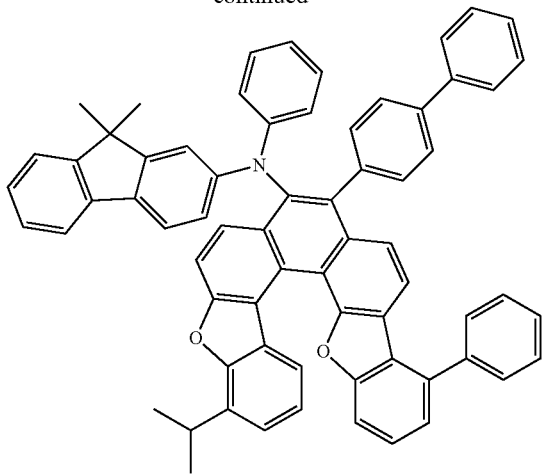

Compound 83

27.7 g Intermediate AA, 500 mL glacial acetic acid, and 160 mL hydrochloric acid solution (4M) were placed in a three-neck flask (1 L). The resulting mixture was aerated with nitrogen gas for 30 minutes and then, 2.4 g zinc powder (3 eq.) was added. The reaction was heated up to 110° C. and performed overnight for 18 hours. After the reaction finished, the resulting mixture was cooled down to room temperature and filtered. The filtrate was extracted with a mixture of dichloromethane and water. The residual was then washed with water, followed by rotary evaporation to remove the solvent, drying and recrystallization with toluene, to produce 21.6 g compound 83 in 81% yield.

1H NMR (DMSO, 300 Hz): δ (ppm)=8.51-8.05 (d, 2H), 8.01-7.67 (m, 11H), 7.65-7.15 (m, 20H), 7.13-6.76 (m, 3H), 3.01-2.52 (q, 1H), 1.60-1.35 (s, 6H), 1.33-1.03 (d, 6H)

MS (FAB): 912 (M+)

Compound Example 6

Synthesis of Compound 92
Synthesis of Intermediate AB

[Reaction Scheme 59]

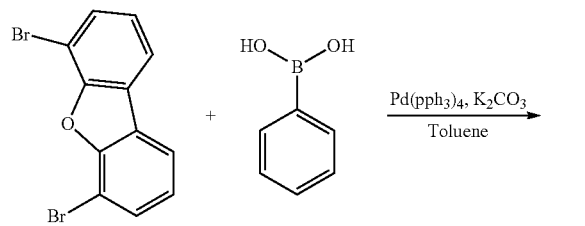

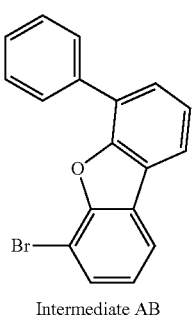

Intermediate AB 13.4 g phenylboronic acid and 32.6 g 4.6-dibromo-dibenzofuran were placed into a three-neck flask (2 L), to which 700 mL toluene and 150 mL ethanol were added to dissolve the solid. The resulting mixture was aerated with nitrogen gas for 15 minutes and then, 150 mL aqueous $K_2CO_3$ solution (3.0 eq., 2M) and 2.3 g Pd(PPh$_3$)$_4$(2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 29.7 g Intermediate AB in 92% yield.

Synthesis of Intermediate AC

[Reaction Scheme 60]

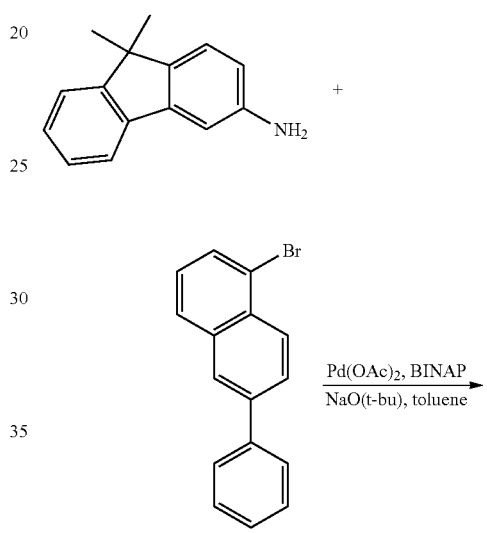

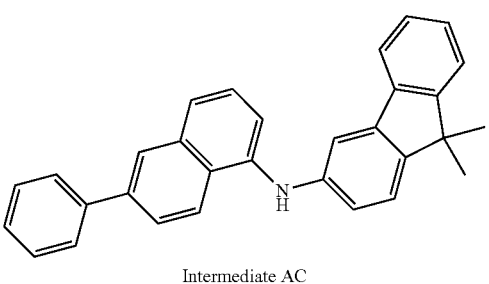

Intermediate AC 28.3 g 1-bromo-6-phenylnaphthalene and 23.0 g 3-amino-9,9'-dimethylfluorene were placed into a three-neck flask (2 L), to which 600 mL dry and degassed toluene was added to dissolve the solid. Then, 28.8 g sodium tert-butoxide (3 eq.), 0.45 g catalyst palladium diacetate (2% mol) and 2.5 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 37.0 g Intermediate AC in 90% yield.

Synthesis of Intermediate AD

[Reaction Scheme 61]

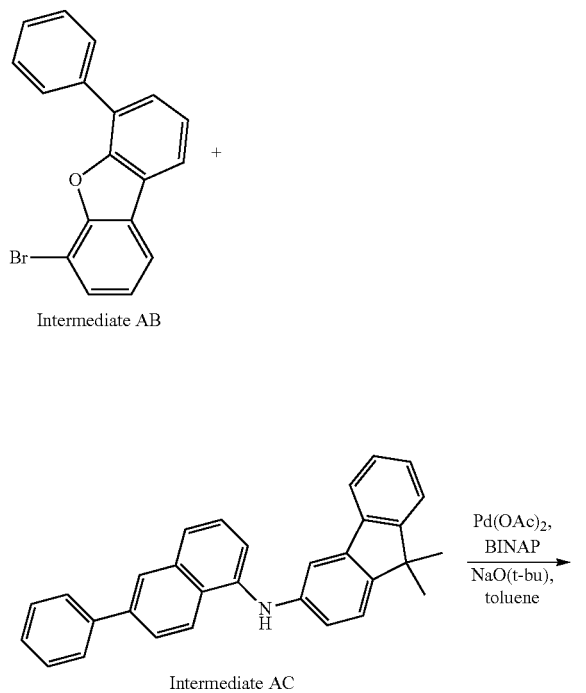

Intermediate AD

Synthesis of Intermediate AE

[Reaction Scheme 62]

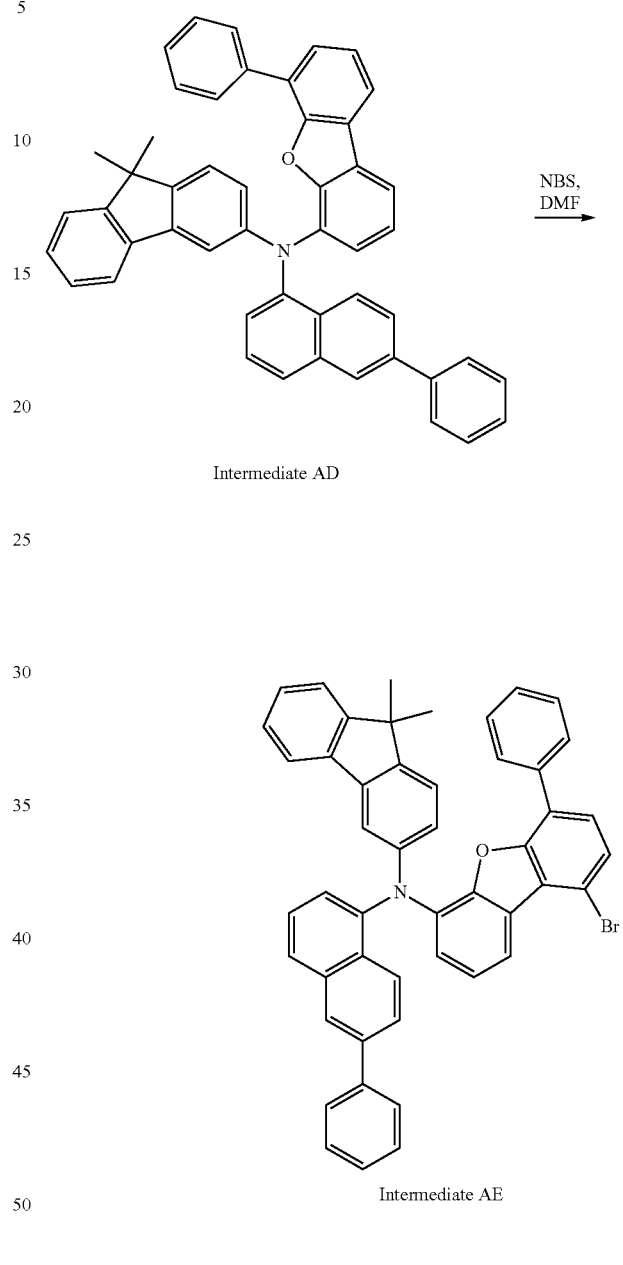

29.7 g Intermediate AC and 26.4 g Intermediate AB were placed into a three-neck flask (2 L), to which 500 mL dry and degassed toluene was added to dissolve the solid. Then, 23.6 g sodium tert-butoxide (3 eq.), 0.37 g catalyst palladium diacetate (2% mol) and 2.0 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered suction filtration. The solvent was removed by rotary evaporation and the residual was recrystallized with toluene and ethanol to produce 45.4 g Intermediate AD in 85% yield.

45.4 g Intermediate AD was placed into a three-neck flask (2 L), to which 900 mL DMF was added to dissolve the solid. Then, 13.6 g NBS (1.1 eq.) was added and the resulting mixture was stirred at room temperature in the dark overnight. After the reaction finished, a large amount of water was added to separate out solid matter which was then filtered. The filter cake was washed three times with water, dried and recrystallized with toluene and ethanol to produce 47.3 g Intermediate AE in 93% yield.

Synthesis of Intermediate AF

[Reaction Scheme 63]

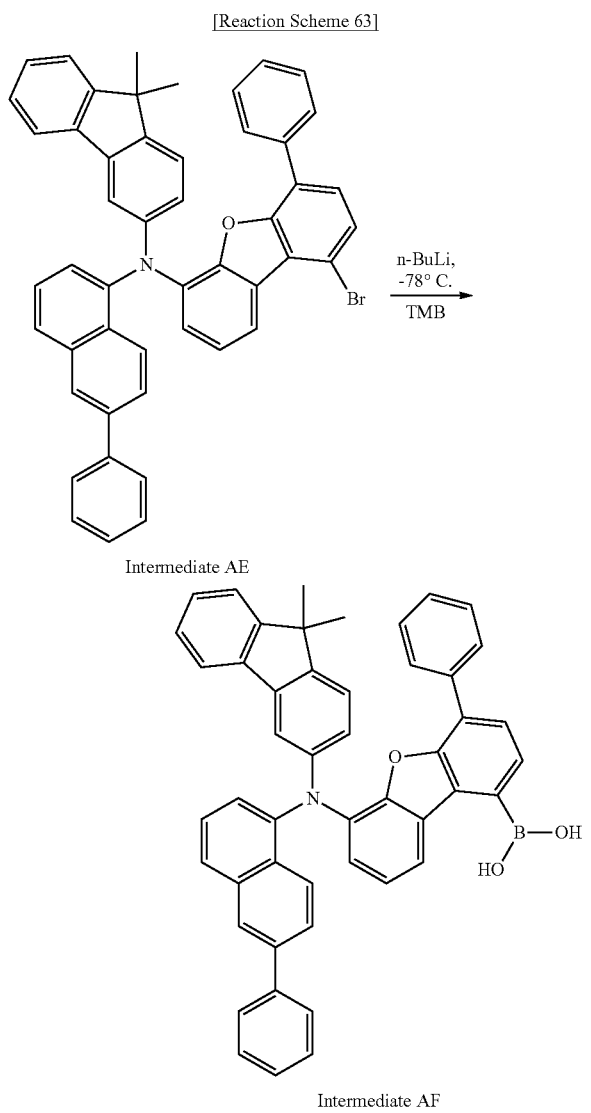

Intermediate AE

Intermediate AF

All experimental instruments were fully dried beforehand. 47.3 g Intermediate AE was placed into a three-neck flask (2 L), to which 500 mL dry tetrahydrofuran was added to dissolve the solid. Then the resulting mixture was cooled down to −78° C. and 28.4 mL n-BuLi (1.1 eq., 2.5M) was added dropwise. After the addition, the resulting mixture was stirred at the above temperature for 1 hour and 8.7 g trimethyl borate (1.3 eq.) was added dropwise. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was boiled in ethyl acetate to produce a crude product. The crude product was filtered to produce 36.1 g filter cake, i.e. boric acid product Intermediate AF, in 80% yield.

Synthesis of Intermediate AG

[Reaction Scheme 64]

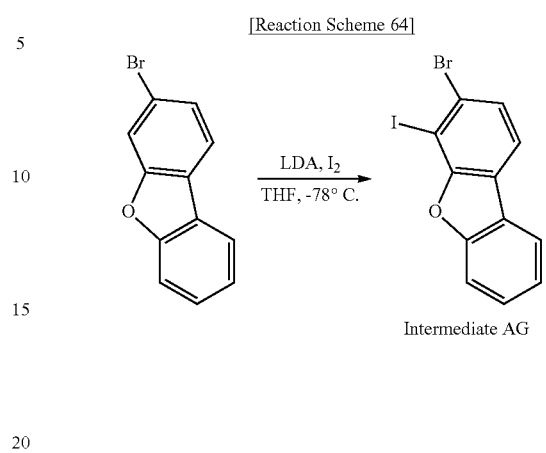

Intermediate AG

All experimental instruments were fully dried beforehand. 24.7 g 2-bromobiphenylfuran was placed into a three-neck flask (2 L), to which 500 mL dry tetrahydrofuran was added to dissolve the solid. Then the resulting mixture was cooled down to −78° C. and 52.5 mL LDA solution (1.05 eq., 2M) in THF was added dropwise. Then the resulting mixture was stirred at the above temperature for 1 hour and 27.9 g iodine (1.1 eq.) was added. Then the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 29.8 g Intermediate AG in 80% yield.

Synthesis of Intermediate AH

[Reaction Scheme 65]

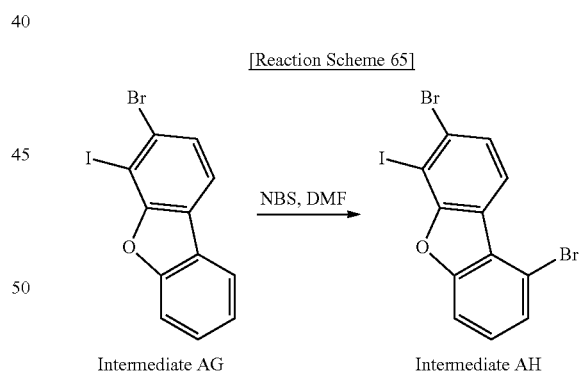

Intermediate AG

Intermediate AH 29.8 g Intermediate AG was placed into a three-neck flask (2 L), to which 600 mL DMF was added to dissolve the solid. Then, 15.6 g NBS (1.1 eq.) was added and the resulting mixture was stirred at room temperature in the dark overnight. After the reaction finished, a large amount of water was added to separate out solid matter which was then filtered. The filter cake was washed three times with water, followed by drying and recrystallization with toluene and ethanol to produce 31.1 g Intermediate AH in 86% yield.

Synthesis of Intermediate AI

Synthesis of Intermediate AJ

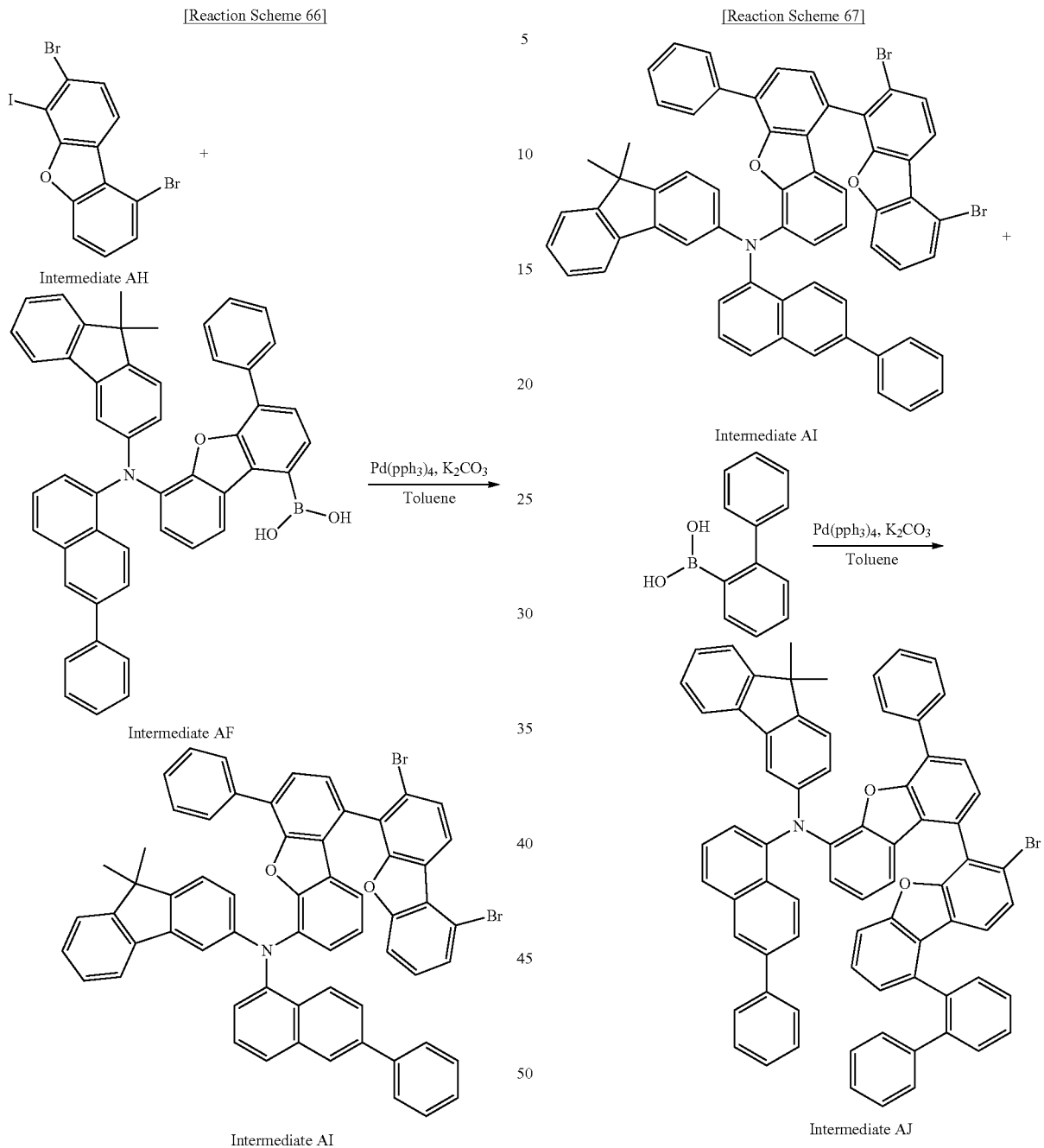

36.1 g Intermediate AF and 21.3 g Intermediate AH were placed into a three-neck flask (2 L), to which 500 mL toluene and 150 mL ethanol were added to dissolve the solid. The resulting mixture was aerated with nitrogen gas for 15 minutes and then, 70.5 mL aqueous $K_2CO_3$ solution (3.0 eq., 2M) and 1.1 g $Pd(PPh_3)_4$ (2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 40 g Intermediate AI in 87% yield.

40 g Intermediate AI and 8.9 g 2-biphenylboronic acid were placed into a three-neck flask (2 L), to which 600 mL toluene and 150 mL ethanol were added to dissolve the solid. The resulting mixture was aerated with nitrogen gas for 15 minutes and then, 61.4 mL aqueous $K_2CO_3$ solution (3.0 eq., 2M) and 0.95 g $Pd(PPh_3)_4$ (2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 37.8 g Intermediate AJ in 88% yield.

Synthesis of Intermediate AK

[Reaction Scheme 68]

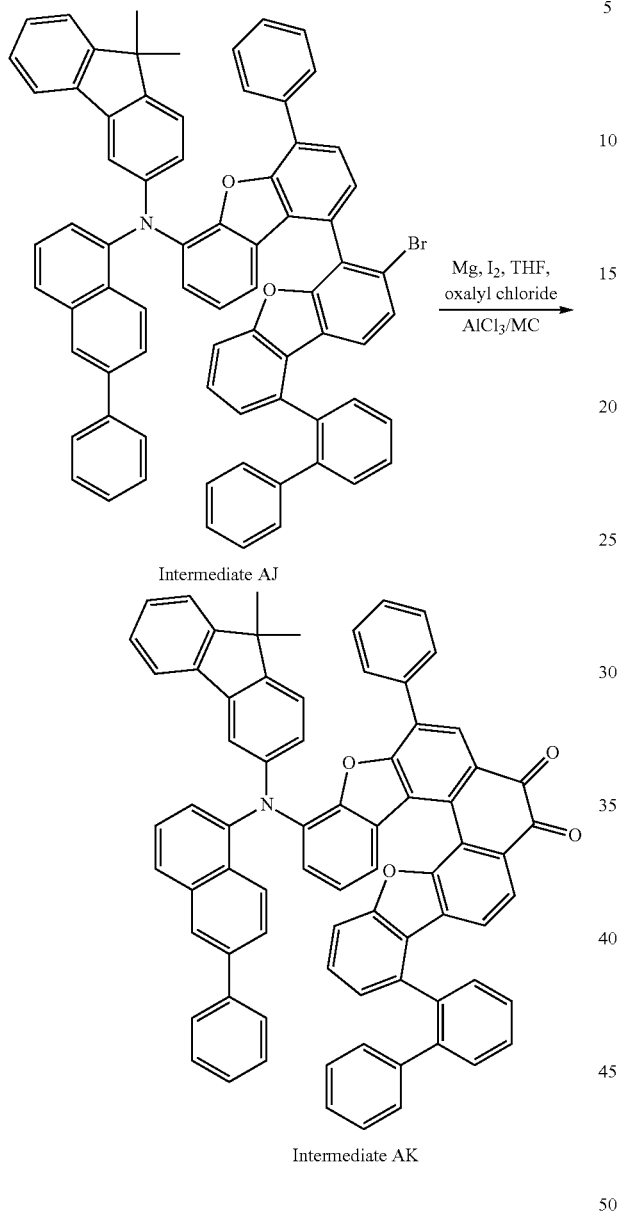

Intermediate AJ

Intermediate AK 1.3 Mg (1.5 eq.), 15 mL THF, and 0.2 g I₂ were placed into a dry three-neck flask (2 L) and the resulting mixture was heated to trigger reaction. Then a solution of 37.8 g Intermediate AJ (1.0 eq.) in 500 mL THF was added dropwise at room temperature. After the addition, the resulting mixture was reacted at 55° C. for 2 hours and was thereafter left to stand for 5 minutes. The supernatant was added dropwise to a solution of 4.1 g oxalyl chloride (0.9 eq.) in 60 mL THF. The resulting mixture was refluxed overnight for 16 hours, and after the reaction finished, it was cooled down to room temperature and was added dropwise in an ice-water bath condition to a solution of 14.4 g aluminum trichloride (3.0 eq.) in 300 mL dichloromethane. After the addition, the resulting mixture was heated and refluxed overnight for 15 hours. After the reaction finished, the resulting mixture was quenched with drops of water to obtain a large amount of solid matter which was then filtered by suction filtration. The solid matter was washed with water, dried and purified by chromatography column to produce 29.9 g Intermediate AK in 81% yield.

Synthesis of Intermediate AL

[Reaction Scheme 69]

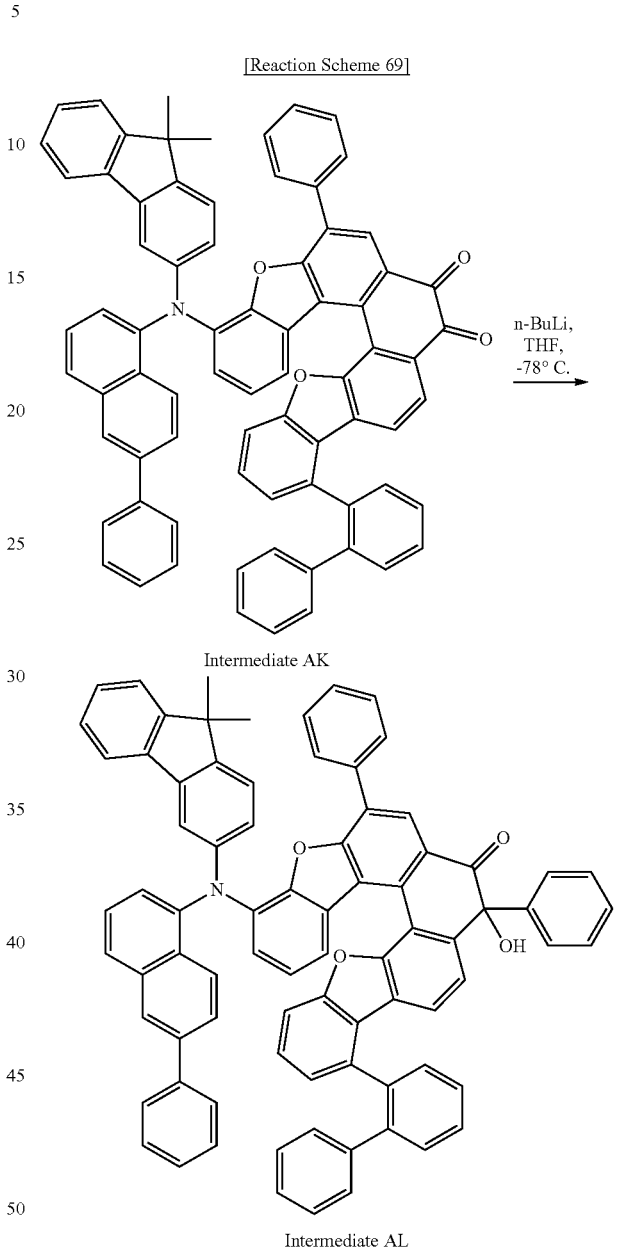

Intermediate AK

Intermediate AL

All experimental instruments were fully dried beforehand. 5.0 g bromobenzene (1.1 eq.) was placed into a three-neck flask (1 L), to which 100 mL dry tetrahydrofuran was added to dissolve the solid. Then the resulting mixture was cooled down to −78° C. and 14.0 mL n-BuLi (1.2 eq., 2.5M) was added dropwise. After the addition, the resulting mixture was stirred at the above temperature for 1 hour and a solution of 29.9 g Intermediate AK in 300 mL THF was added dropwise. After the addition, the resulting mixture was stirred overnight at room temperature. After the reaction finished, hydrochloric acid solution (4M) was added and the resulting mixture was extracted with ethyl acetate. The organic phase was washed with saturated aqueous NaCl solution until neutral and dried. The solvent was then Synthesis of Intermediate AM

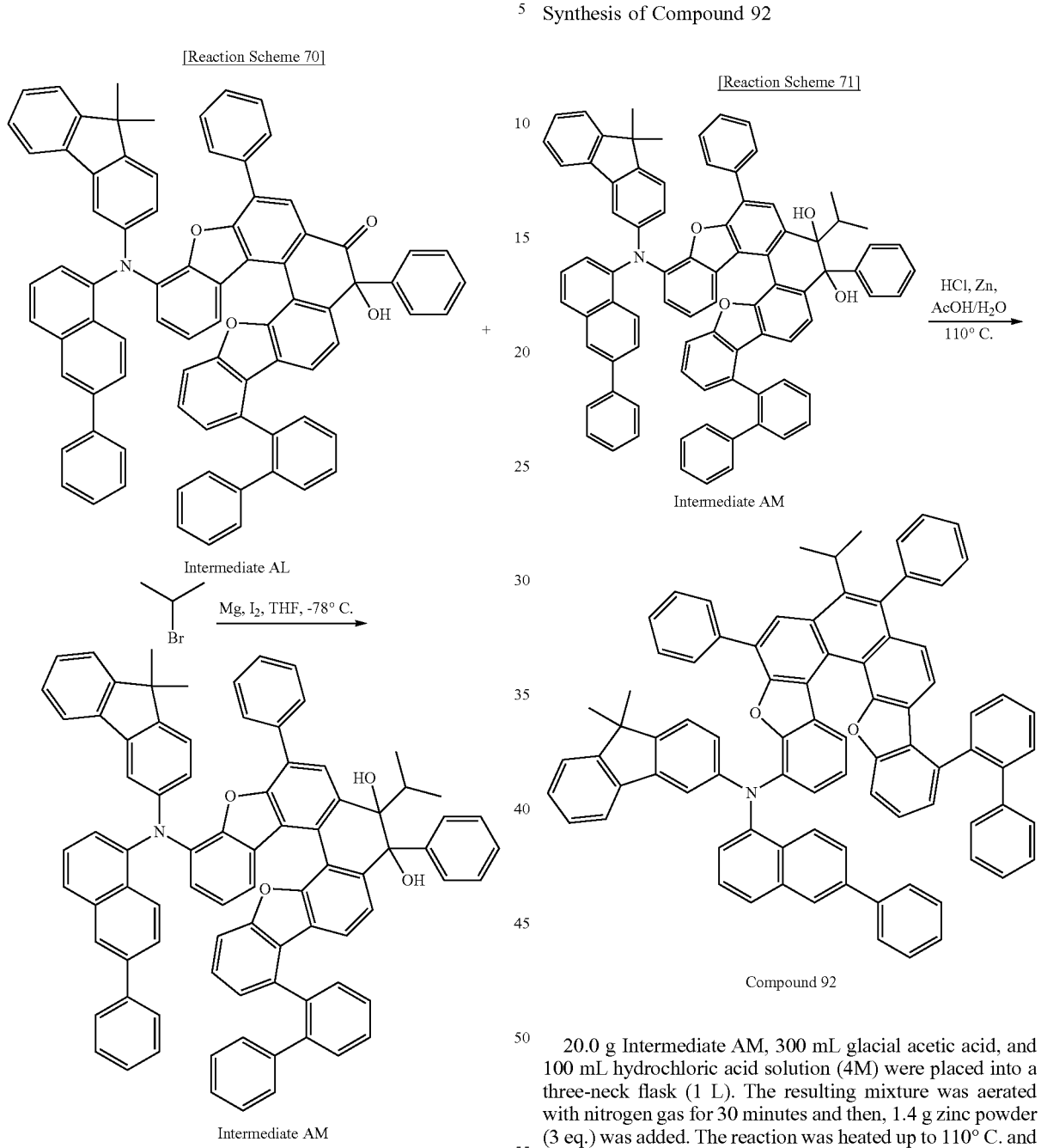

[Reaction Scheme 70]

Intermediate AL

[Reaction Scheme 71]

Intermediate AM

Compound 92

0.8 g Mg (1.5 eq.), 10 mL THF, and 0.1 g I₂ were placed into a dry three-neck flask (2 L) and the resulting mixture was heated to trigger reaction. Then 3.5 g 2-bromopropane (1.3 eq.) was added dropwise at room temperature. After the addition, the resulting mixture heated at 51° C. for 2 hours. The supernatant was added dropwise to a solution of 24.1 g Intermediate AL (1.0 eq.) in 400 mL THF. After the addition, the resulting mixture was reacted at 51° C. for 12 hours. After the reaction finished, the resulting mixture was cooled down to room temperature and quenched with drops of hydrochloric acid solution (4M) dichloromethane, followed by extraction with ethyl acetate. The residual was washed with saturated aqueous NaCl solution, dried and purified by chromatography column to produce 20.0 g Intermediate AM in 80% yield.

Synthesis of Compound 92

20.0 g Intermediate AM, 300 mL glacial acetic acid, and 100 mL hydrochloric acid solution (4M) were placed into a three-neck flask (1 L). The resulting mixture was aerated with nitrogen gas for 30 minutes and then, 1.4 g zinc powder (3 eq.) was added. The reaction was heated up to 110° C. and performed overnight for 18 hours. After the reaction finished, the resulting mixture was cooled down to room temperature and filtered. The filtrate was extracted with a mixture of dichloromethane and water. The residual was then washed with water, followed by rotary evaporation to remove the solvent, drying and recrystallization with toluene, to produce 14.7 g Compound 92 in 76% yield.

1H NMR (DMSO, 300 Hz): δ (ppm)=8.54-8.31 (m, 2H), 8.28-8.01 (m, 2H), 7.98-7.88 (m, 3H), 7.86-7.31 (m, 35H), 7.30-7.21 (m, 2H), 7.12-6.77 (m, 2H), 3.01-2.52 (q, 1H), 1.68-1.55 (s, 6H), 1.38-1.03 (d, 6H)

MS (FAB): 1114 (M+)

Compound Example 7

Synthesis of Compound 112
Synthesis of Intermediate AN

[Reaction Scheme 72]

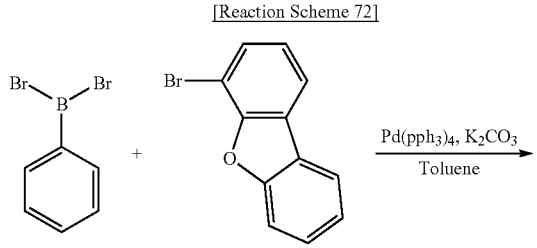

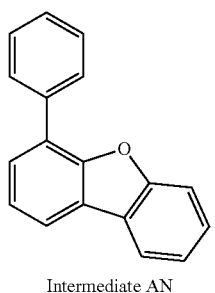

Intermediate AN 27.2 g phenylboronic acid and 24.7 g 4-bromo-dibenzofuran were placed into a three-neck flask (2 L), to which 600 mL toluene and 150 mL ethanol were added to dissolve the solid. The resulting mixture was aerated with nitrogen gas for 15 minutes and then, 150 mL aqueous $K_2CO_3$ solution (3.0 eq., 2M) and 2.3 g $Pd(PPh_3)_4$ (2 mol %) were sequentially added. The reaction was heated up to 110° C. and performed overnight at, and after the reaction finished, the resulting mixture was absorbed with activated carbon and filtered by suction filtration. The solvent was removed by rotary evaporation and the residual was dried and recrystallized with toluene and ethanol to produce 23.0 g Intermediate AN in 94% yield.

Synthesis of Intermediate AO

[Reaction Scheme 73]

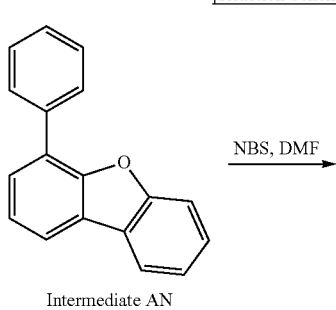

Intermediate AN

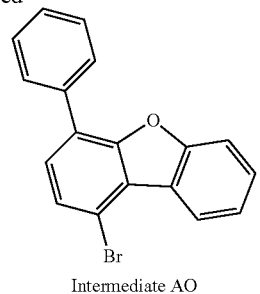

Intermediate AO 23.0 g Intermediate AN was placed into a three-neck flask (2 L), to which 300 mL DMF was added to dissolve the solid. Then, 18.4 g NBS (1.1 eq.) was added and the resulting mixture was stirred at room temperature in the dark overnight. After the reaction finished, a large amount of water was added to separate out solid matter which was then filtered. The filter cake was washed three times with water, followed by drying and recrystallization with toluene and ethanol to produce 27.7 g Intermediate AO in 91% yield.

Synthesis of Intermediate AP

[Reaction Scheme 74]

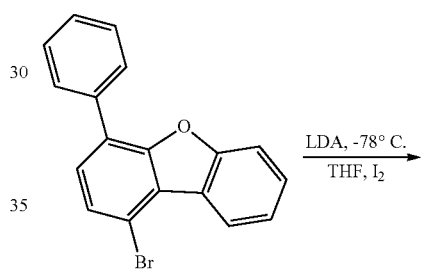

Intermediate AO

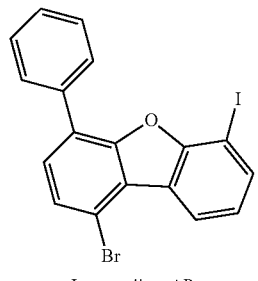

Intermediate AP

All experimental instruments were fully dried beforehand. 27.7 g Intermediate AO was placed into a three-neck flask (2 L), to which 600 mL dry tetrahydrofuran was added to dissolve the solid. Then the resulting mixture was cooled down to −78° C. and 45.0 mL LDA solution (1.05 eq., 2M) in THF was added dropwise. Then the resulting mixture was stirred at the above temperature for 1 hour and 23.9 g iodine (1.1 eq.) was added dropwise. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 33.1 g Intermediate AP in 86% yield.

Synthesis of Intermediate AQ

[Reaction Scheme 75]

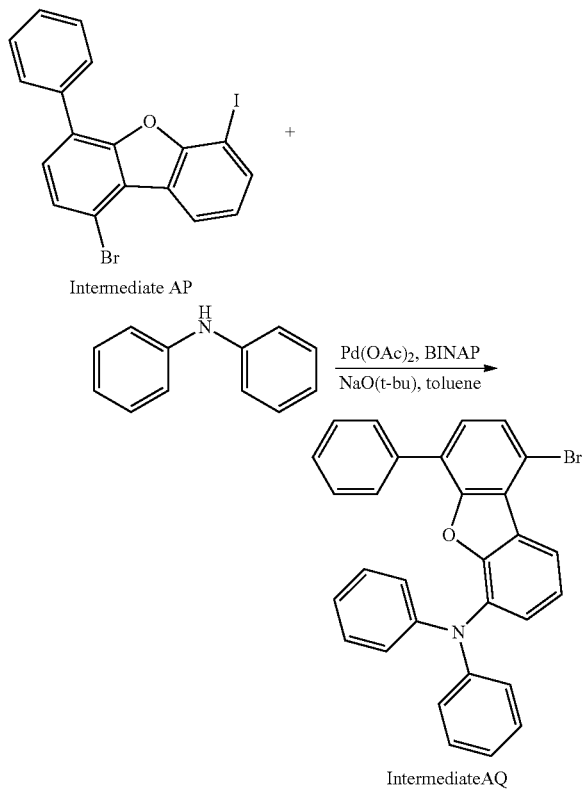

IntermediateAQ 33.1 g Intermediate AP and 13.7 g phenylamine were placed into a dry three-neck flask (2 L) to which 600 mL dry and degassed toluene was added to dissolve the solid. Then, 21.2 g sodium tert-butoxide (3 eq.), 0.33 g catalyst palladium diacetate (2% mol) and 1.8 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 30.0 g Intermediate AQ in 83% yield.

Synthesis of Intermediate AR

[Reaction Scheme 76]

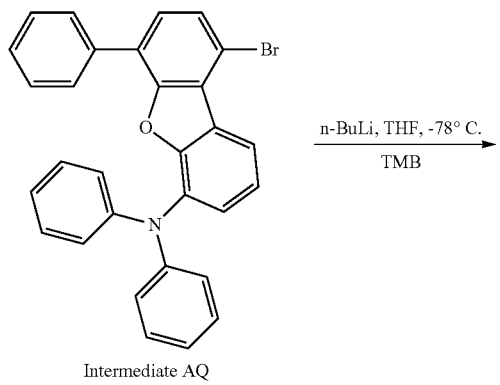

Intermediate AQ n-BuLi, THF, -78° C.
TMB

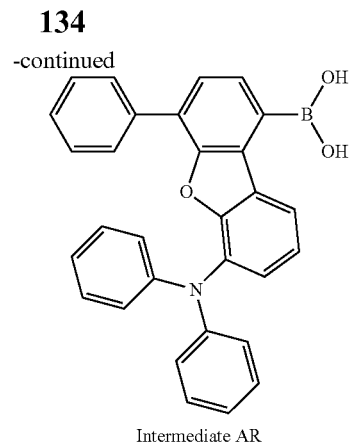

Intermediate AR

All experimental instruments were fully dried beforehand. 30.0 g Intermediate AQ was placed into a three-neck flask (2 L), to which 600 mL dry tetrahydrofuran was added to dissolve the solid. Then the resulting mixture was cooled down to -78° C. and 27.0 mL n-BuLi (1.1 eq., 2.5M) was added dropwise. After the addition, the resulting mixture was stirred at the above temperature for 1 hour and 8.3 g trimethyl borate (1.3 eq.) was added dropwise. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was boiled in ethyl acetate to produce a crude product. The crude product was filtered to produce 22.6 g filter cake, i.e. boric acid product Intermediate AR, in 81% yield.

Synthesis of Intermediate AS

[Reaction Scheme 77]

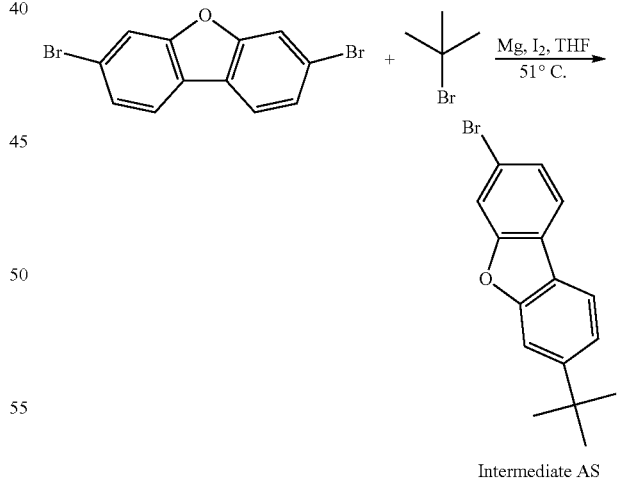

Intermediate AS 3.6 g Mg (1.5 eq.), 15 mL THF, and 0.36 g $I_2$ were placed into a dry three-neck flask (2 L) and the resulting mixture was heated to trigger reaction. Then a solution of 17.8 g tert-butyl bromide (1.3 eq.) in 170 mL THF was added dropwise at room temperature. After the addition, the resulting mixture was reacted at 51° C. for 2 hours and was thereafter left to stand for 5 minutes. The supernatant was added dropwise to a solution of 32.6 g 3,7-dibromodiphenylfuran in 600 mL THF. The resulting mixture was refluxed overnight for 15 hours, then after the reaction finished, it was cooled down to room temperature, quenched with drops of water, and extracted with a mixture of dichloromethane and water. The residual was washed with water and dried. The solvent was removed by rotary evaporation and the residual was purified by chromatography column to produce 24.0 g Intermediate AS in 79% yield.

Synthesis of Intermediate AT

[Reaction Scheme 78]

Intermediate AS    Intermediate AT

All experimental instruments were fully dried beforehand. 24.0 g Intermediate AS was placed into a three-neck flask (2 L), to which 500 mL dry tetrahydrofuran was added to dissolve the solid. Then the resulting mixture was cooled down to −78° C. and 41.6 mL LDA solution (1.05 eq., 2M) in THF was added dropwise. After the addition, the resulting mixture was stirred at the above temperature for 1 hour and 22.1 g iodine (1.1 eq.) was added. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 27.5 g Intermediate AT in 81% yield.

Synthesis of Intermediate AU

[Reaction Scheme 79]

Intermediate AR

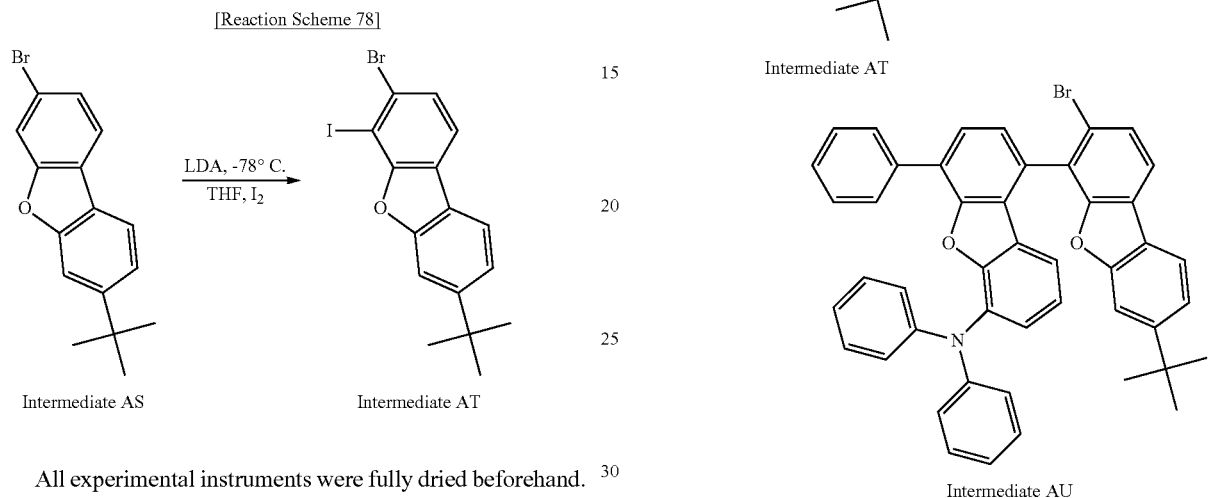

Intermediate AT

Intermediate AU 22.6 g Intermediate AR and 19.4 g Intermediate AT were placed into a three-neck flask (2 L), to which 400 mL toluene and 100 mL ethanol were added to dissolve the solid. The resulting mixture was aerated with nitrogen gas for 15 minutes and then, 67.7 mL aqueous $K_2CO_3$ solution (3.0 eq., 2M) and 1.0 g Pd(PPh$_3$)$_4$(2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 28.3 g Intermediate AU in 88% yield.

Synthesis of Intermediate AW

[Reaction Scheme 80]

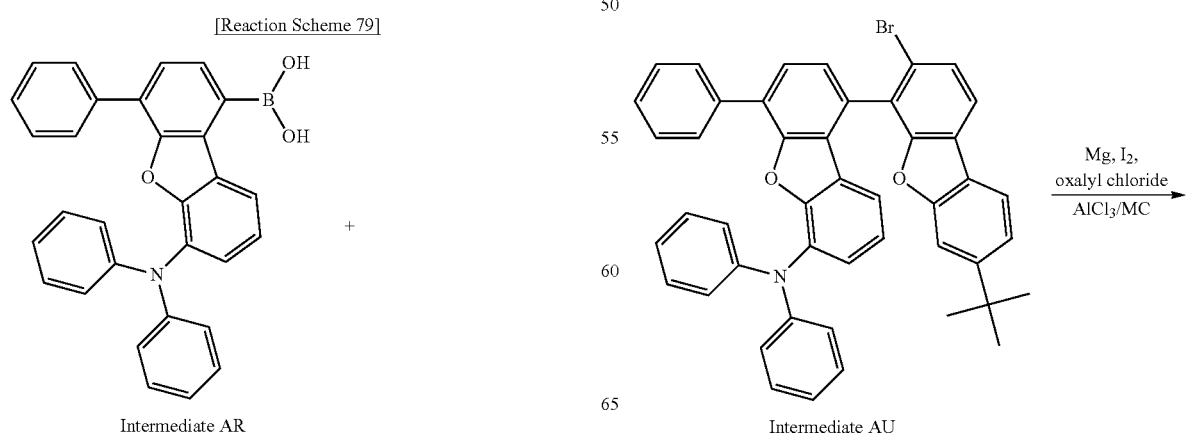

Intermediate AU

-continued

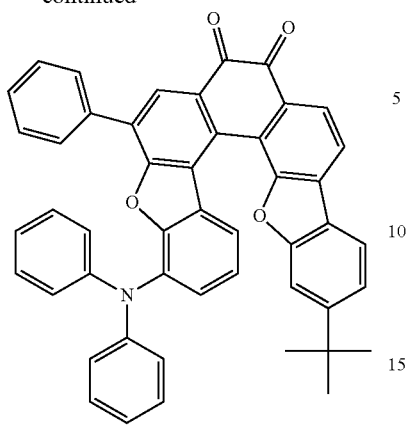

Intermediate AW 1.4 g Mg (1.5 eq.), 15 mL THF, and 0.2 g $I_2$ were placed into a dry three-neck flask (2 L) and the resulting mixture was heated to trigger reaction. Then a solution of 29.9 g Intermediate AU (1.0 eq.) in 600 mL THF was added dropwise at room temperature. After the addition, the resulting mixture was reacted at 55° C. for 2 hours and was thereafter left to stand for 5 minutes. The supernatant was added dropwise to a solution of 4.3 g oxalyl chloride (0.9 eq.) in 60 mL THF. The resulting mixture was refluxed overnight for 16 hours, and after the reaction finished, it was cooled down to room temperature and was added dropwise in an ice-water bath condition to a solution of 15.1 g aluminum trichloride (3.0 eq.) in 300 mL dichloromethane. After the addition, the resulting mixture was heated and refluxed overnight for 15 hours. After the reaction finished, the resulting mixture was quenched with drops of water to obtain a large amount of solid matter which was then filtered by suction filtration. The solid matter was washed with water, dried and purified by chromatography column to produce 21.7 g Intermediate AW in 75% yield.

Synthesis of Intermediate AX

[Reaction Scheme 81]

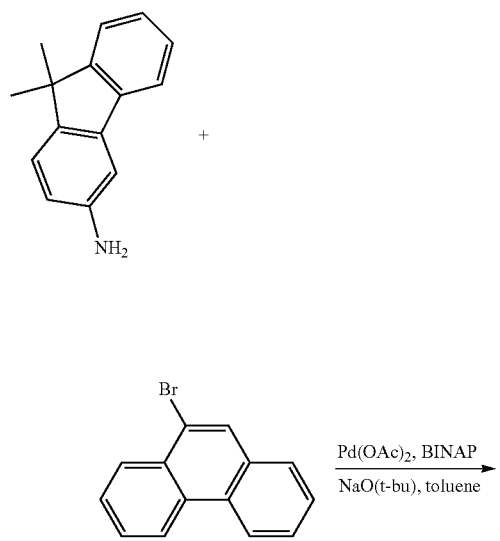

Pd(OAc)$_2$, BINAP
NaO(t-bu), toluene

-continued

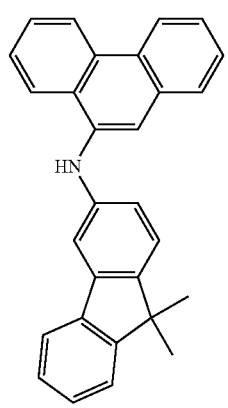

Intermediate AX 25.7 g 9-bromophenanthrene and 23.0 g 3-amino-9,9'-dimethylfluorene were placed into a dry three-neck flask (2 L), to which 500 mL dry and degassed toluene was added to dissolve the solid. Then, 28.8 g sodium tert-butoxide, 0.45 g catalyst palladium diacetate (2% mol) and 2.5 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 33.2 g Intermediate AX in 86% yield.

Synthesis of Intermediate AY

[Reaction Scheme 82]

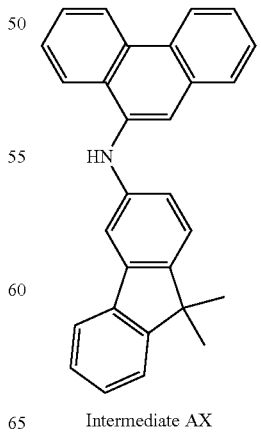

+

Intermediate AX

Synthesis of Compound 112

[Reaction Scheme 83]

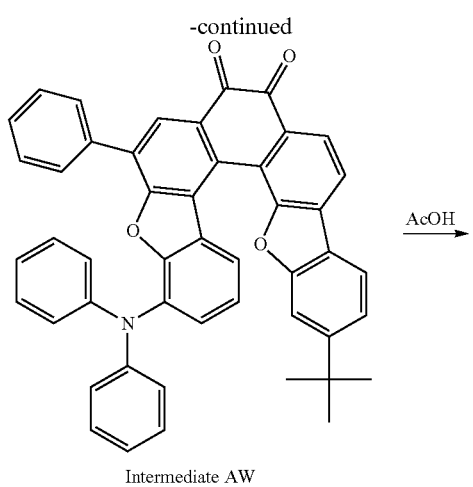

Intermediate AW

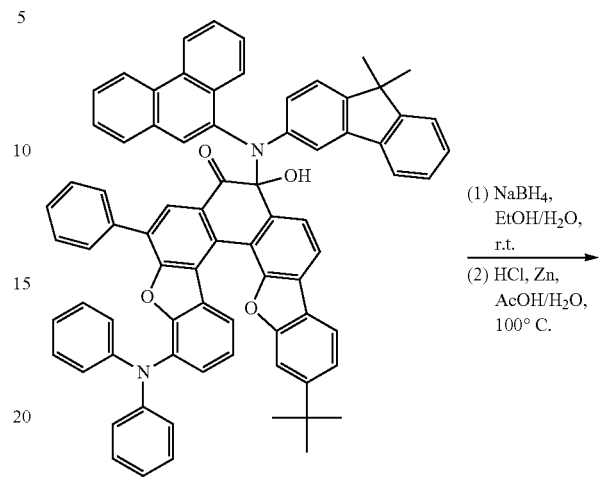

Intermediate AY (1) NaBH₄, EtOH/H₂O, r.t.
(2) HCl, Zn, AcOH/H₂O, 100° C.

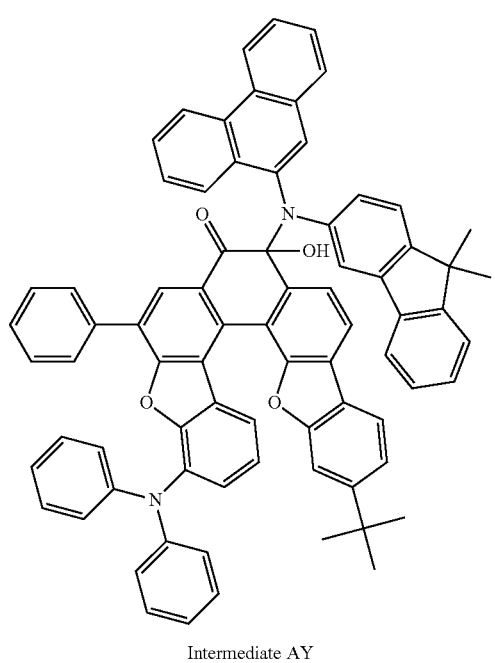

Intermediate AY

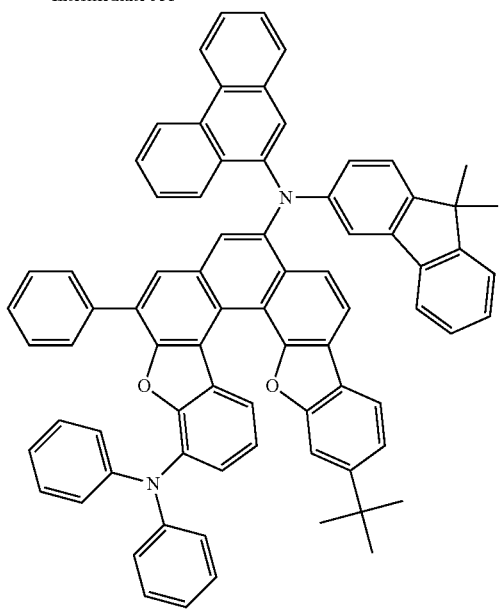

Compound 112

12 g Intermediate AX (1.0 eq.) and 21.7 g Intermediate AW were placed into a three-neck flask (1 L), to which 200 mL glacial acetic acid was added to dissolve the solid. The resulting mixture was heated up to 130° C. and refluxed overnight for 18 hours. After the reaction finished, the resulting mixture was cooled down to room temperature and extracted with a mixture of dichloromethane and water. The residual was then washed four times with water and dried. The solvent was removed by rotary evaporation and the residual was recrystallized with toluene and ethanol to produce 24.0 g Intermediate AY in 79% yield.

24.0 g Intermediate AY (1.0 eq.) and 1.7 g NaBH₄ (2.0 eq.) were placed into a three-neck flask (1 L). The resulting mixture was aerated with nitrogen gas for 30 minutes, followed by adding 500 mL ethanol and 160 mL water. The resulting mixture was reacted at room temperature for 24 hours, and after the reaction finished, it was filtered and the filter cake was washed with water and dried. The residual was recrystallized with toluene and ethanol and dried, to which 400 mL glacial acetic acid and 100 mL hydrochloric acid solution (4M) were then added. The resulting mixture was aerated with nitrogen gas for 30 minutes, followed by adding 1.8 g zinc powder (3 eq.). The reaction was heated up to 110° C. and performed overnight for 18 hours. After the reaction finished, the resulting mixture was cooled down to room temperature and filtered. The filtrate was extracted with a mixture of dichloromethane and water. The residual was then washed with water, followed by rotary evaporation to remove the solvent, drying and recrystallization with toluene, to produce 16.6 g Compound 112 in 71% yield.

1H NMR (DMSO, 300 Hz): δ (ppm)=9.02-8.91 (d, 1H), 8.88-8.78 (d, 1H), 8.61-8.42 (s, 1H), 8.23-8.03 (m, 2H), 7.94-7.82 (d, 2H), 7.53-7.40 (m, 21H), 7.38-7.12 (m, 7H), 7.10-6.79 (m, 8H), 3.01-2.52 (q, 1H), 1.68-1.55 (s, 6H), 1.38-1.03 (d, 6H)

MS (FAB): 1041 (M+)

Compound Example 8

Synthesis of Compound 120
Synthesis of Intermediate AZ

[Reaction Scheme 84]

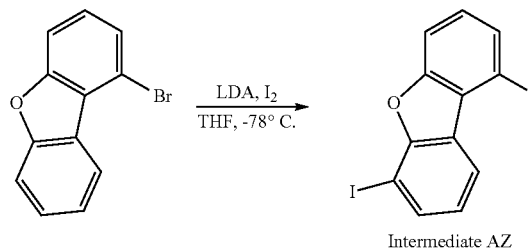

Intermediate AZ

All experimental instruments were fully dried beforehand. 24.7 g 1-bromodibenzofuran was placed into a three-neck flask (2 L), to which 500 mL dry tetrahydrofuran was added to dissolve the solid. Then the resulting mixture was cooled down to −78° C. and 52.5 mL LDA solution (1.05 eq., 2M) in THF was added dropwise. After the addition, the resulting mixture was stirred at the above temperature for 1 hour and 27.9 g iodine (1.1 eq.) was added. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was recrystallized with toluene and ethanol to produce 29.5 g Intermediate AZ in 79% yield.

Synthesis of Intermediate Aa

[Reaction Scheme 85]

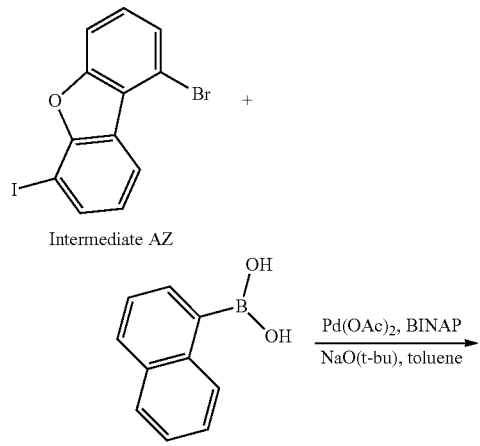

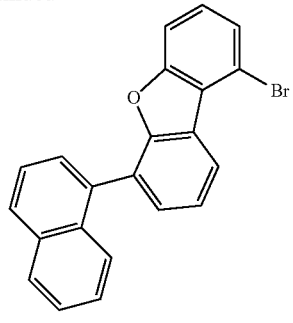

Intermediate Aa 29.5 g Intermediate AZ and 15 g 2-phenylamine were placed into a dry three-neck flask (2 L), to which 600 mL dry and degassed toluene was added to dissolve the solid. Then, 22.8 g NaO(t-bu)(3 eq.), 0.36 g catalyst palladium diacetate (2% mol) and 2.0 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 26.3 g Intermediate Aa in 89% yield.

Synthesis of Intermediate Ab

[Reaction Scheme 86]

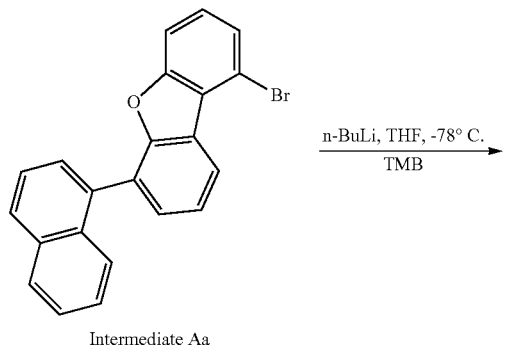

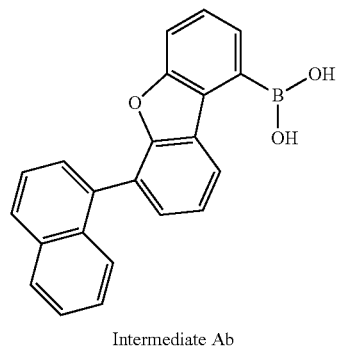

Intermediate Ab

All experimental instruments were fully dried beforehand. 26.3 g Intermediate Aa was placed into a three-neck flask (2 L), to which 500 mL dry tetrahydrofuran was added to dissolve the solid. Then the resulting mixture was cooled down to −78° C. and 31 mL n-BuLi (1.1 eq., 2.5M) was added dropwise. After the addition, the resulting mixture was stirred at the above temperature for 1 hour and 9.5 g trimethyl borate (1.3 eq.) was added dropwise. After the addition, the resulting mixture was stirred overnight at room temperature. After the reaction finished, hydrochloric acid solution (4M) was added and the resulting mixture was extracted with dichloromethane. The organic phase was washed with saturated aqueous NaCl solution until neutral and dried. The solvent was then removed by rotary evaporation and the residual was boiled in ethyl acetate to produce a crude product. The crude product was filtered to produce 18.8 g filter cake, i.e. boric acid product Intermediate Ab, in 79% yield.

Synthesis of Intermediate Ac

[Reaction Scheme 87]

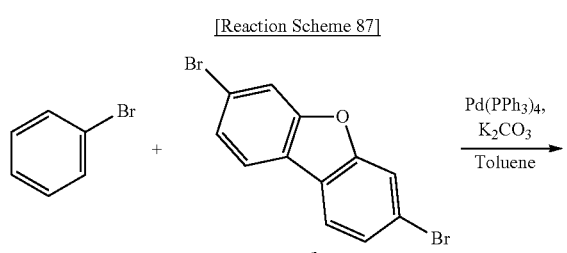

Intermediate Ac 13.4 g phenylboronic acid and 32.6 g 3,76-dibromo-dibenzofuran were placed into a three-neck flask (2 L), to which 700 mL toluene and 150 mL ethanol were added to dissolve the solid. The resulting mixture was aerated with nitrogen gas for 15 minutes and then, 150 mL aqueous $K_2CO_3$ solution (3.0 eq., 2M) and 2.3 g Pd(PPh$_3$)$_4$(2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 29.1 g Intermediate Ac in 90% yield.

Synthesis of Intermediate Ad

[Reaction Scheme 88]

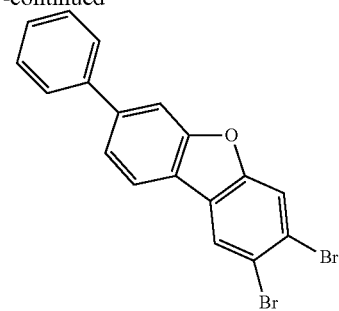

Intermediate Ad 29.1 g Intermediate Ac and 500 mL HBr were placed into a three-neck flask (2 L), followed by adding 28.7 g Br$_2$ (180.1 mmol, 2 eq.). The resulting mixture was heated up to 90° C. and reacted overnight for 18 hours. After the reaction finished, the resulting mixture was cooled down to room temperature and NaOH solution (4M) was added in an ice bath condition under stirring to obtain a large amount of solid matter. The solid matter was filtered by suction filtration and washed with water, followed by drying and recrystallization with toluene and ethanol, to produce 28.9 g Intermediate Ad in 80% yield.

Synthesis of Intermediate Ae

[Reaction Scheme 89]

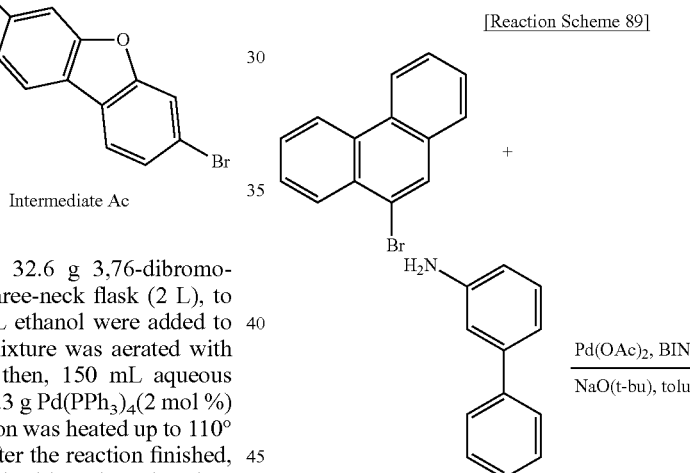

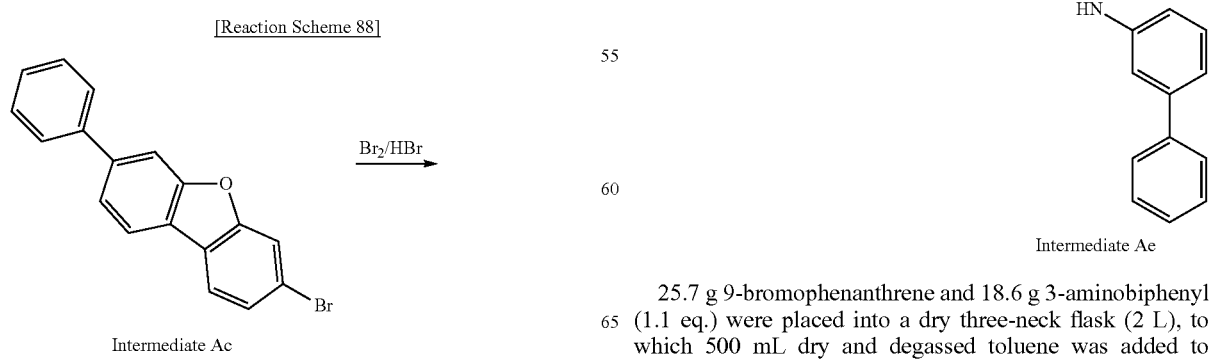

Intermediate Ae 25.7 g 9-bromophenanthrene and 18.6 g 3-aminobiphenyl (1.1 eq.) were placed into a dry three-neck flask (2 L), to which 500 mL dry and degassed toluene was added to dissolve the solid. Then, 28.8 g sodium tert-butoxide, 0.45 g catalyst palladium diacetate (2% mol) and 2.5 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 30.1 g Intermediate Ae in 87% yield.

Synthesis of Intermediate Af

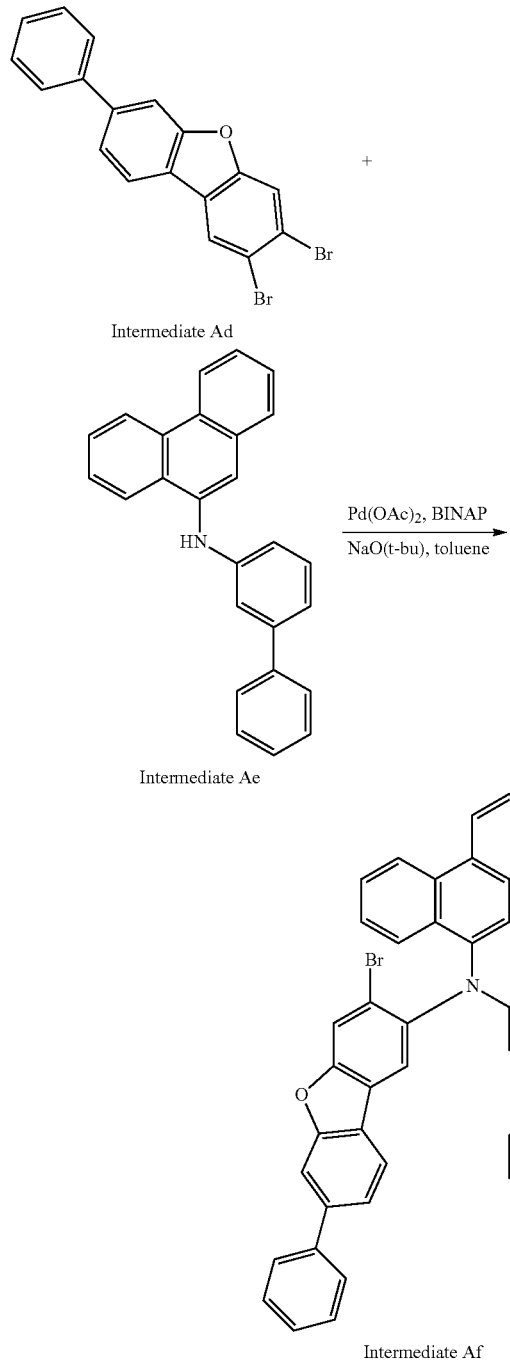

Intermediate Af 28.9 g Intermediate Ad and 27.3 g Intermediate Ae were placed into a dry three-neck flask (2 L), to which 600 mL dry and degassed toluene was added to dissolve the solid. Then, 20.7 g sodium tert-butoxide, 0.32 g catalyst palladium diacetate (2% mol) and 1.8 g 1,1'-binaphthyl-2,2'-bis(diphenylphosphino)(BINAP, 4% mol) ligand were added. The resulting was heated up to 110° C. and reacted overnight. After the reaction finished and being cooled down to room temperature, the resulting mixture was absorbed with activated carbon and filtered by suction filtration. The solvent was removed by rotary evaporation and the residual was recrystallized with toluene and ethanol to produce 44.1 g Intermediate Af in 92% yield.

Synthesis of Intermediate Ag

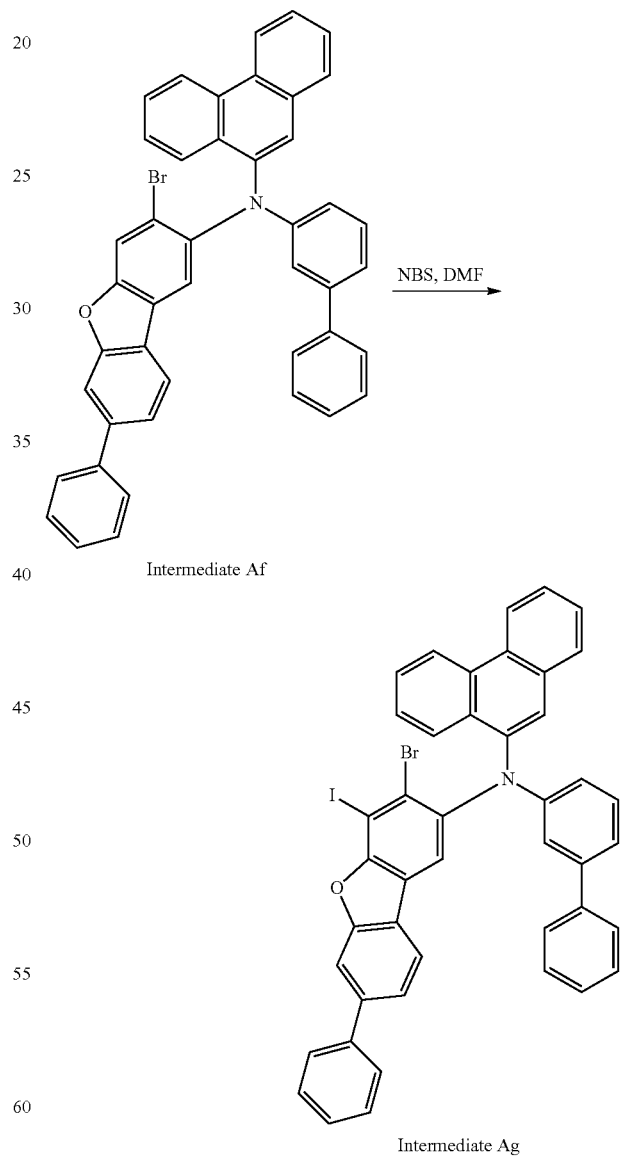

Intermediate Ag 44.1 g Intermediate Af was placed into a three-neck flask (2 L), to which 600 mL DMF was added to dissolve the solid. Then, 13.0 g NBS (1.1 eq.) was added and the resulting mixture was stirred at room temperature in the dark overnight. After the reaction finished, a large amount of water was added to separate out solid matter which was then filtered. The filter cake was washed three times with water, followed by drying and recrystallization with toluene and ethanol, to produce 45.1 g Intermediate Ag in 86% yield.
Synthesis of Intermediate Ah 18.8 g Intermediate Ab and 40.1 g Intermediate Ag were placed into a three-neck flask (2 L), to which 800 mL toluene and 200 mL ethanol were added to dissolve the solid. The resulting mixture was aerated with nitrogen gas for 15 minutes and then, 76 mL aqueous $K_2CO_3$ solution (3.0 eq., 2M) and 1.2 g $Pd(PPh_3)_4$ (2 mol %) were sequentially added. The reaction was heated up to 110° C. and performed overnight, and after the reaction finished, the resulting mixture was absorbed with activated carbon and filtered by suction filtration. The solvent was removed by rotary evaporation and the residual was dried and recrystallized with toluene and ethanol to produce 44.6 g Intermediate Ah in 92% yield.
Synthesis of Intermediate Ai

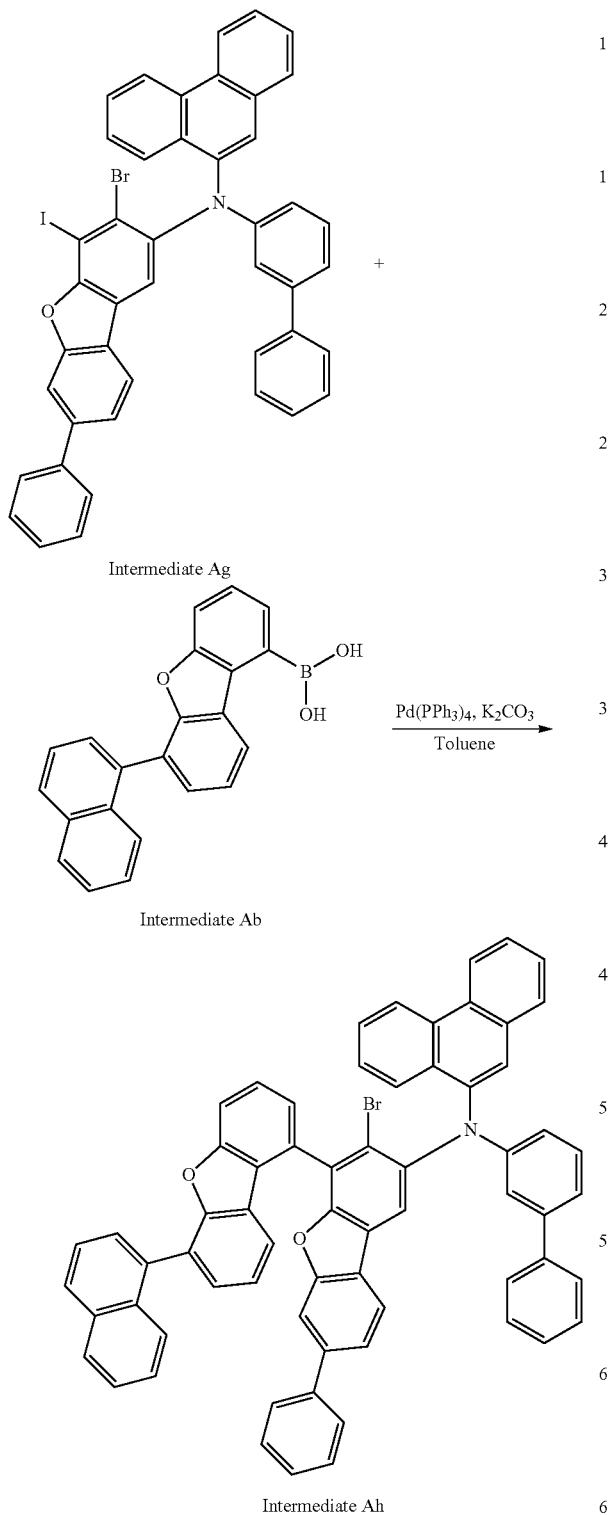

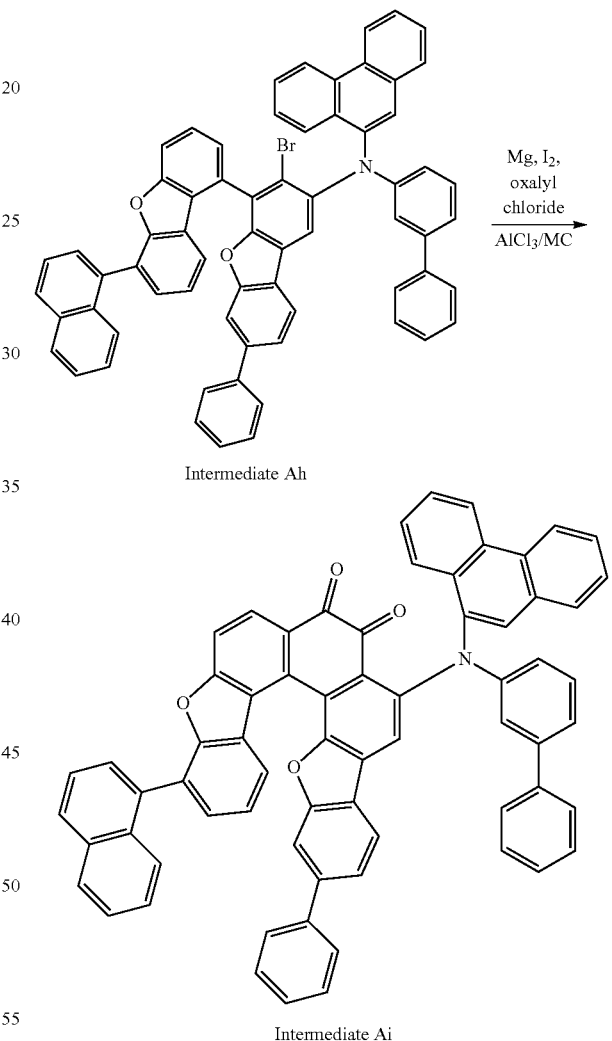

1.7 g Mg (1.5 eq.), 18 mL THF, and 0.2 g $I_2$ were placed into a dry three-neck flask (2 L) and the resulting mixture was heated to trigger reaction. Then a solution of 44.6 g Intermediate Ah (1.0 eq.) in 500 mL THF was added dropwise at room temperature. After the addition, the resulting mixture was reacted at 55° C. for 2 hours and was thereafter left to stand for 5 minutes. The supernatant was added dropwise to a solution of 5.3 g oxalyl chloride (0.9 eq.) in 60 mL THF. The resulting mixture was refluxed overnight for 16 hours, and after the reaction finished, it was cooled down to room temperature and was added dropwise in an ice-water bath condition to a solution of 18.6 g aluminum trichloride (3.0 eq.) in 300 mL dichloromethane. After the addition, the resulting mixture was heated and refluxed overnight for 15 hours. After the reaction finished, the resulting mixture was quenched with drops of water to obtain a large amount of solid matter which was then filtered by suction filtration. The solid matter was washed with water, dried and purified by chromatography column to produce 34.7 g Intermediate Ai in 80% yield.

Synthesis of Intermediate Aj

[Reaction Scheme 94]

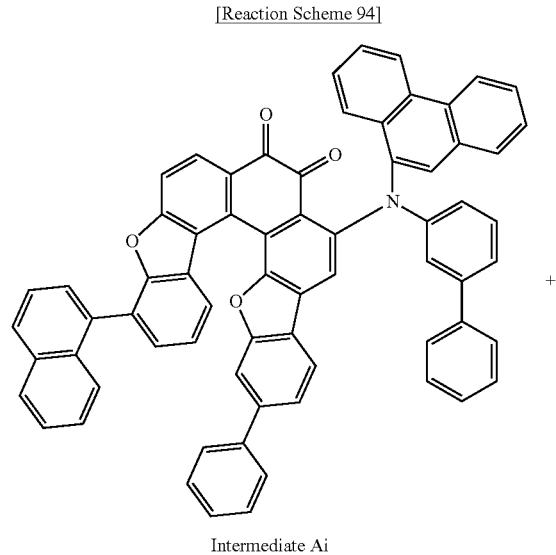

Intermediate Ai

+

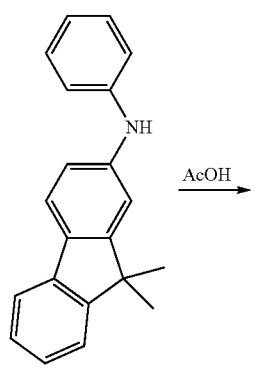

AcOH ⟶

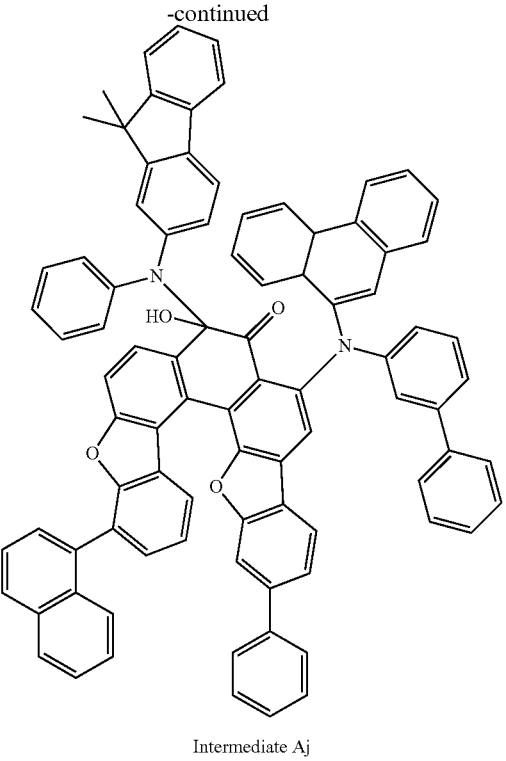

Intermediate Aj 34.7 g Intermediate Ai (1.0 eq.) and 11.7 g N-phenyl-2 (9,9-dimethyl-9H-fluorenyl) amine were placed into a three-neck flask (1 L), to which 400 mL glacial acetic acid was added to dissolve the solid. The resulting mixture was heated up to 130° C. and refluxed overnight for 18 hours. After the reaction finished, the resulting mixture was cooled down to room temperature and extracted with a mixture of dichloromethane and water. The resulting mixture was then washed four times with water and dried. The solvent was removed by rotary evaporation and the residual was recrystallized with toluene and ethanol to produce 45.5 g Intermediate Aj in 80% yield.

Synthesis of Compound 120

[Reaction Scheme 95]

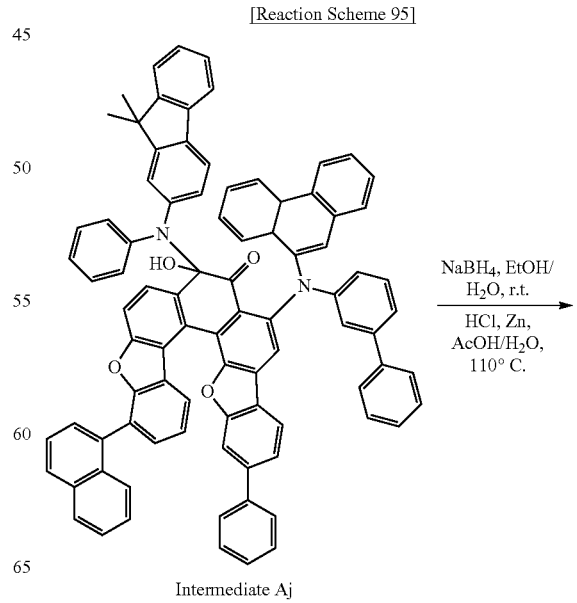

Intermediate Aj

-continued

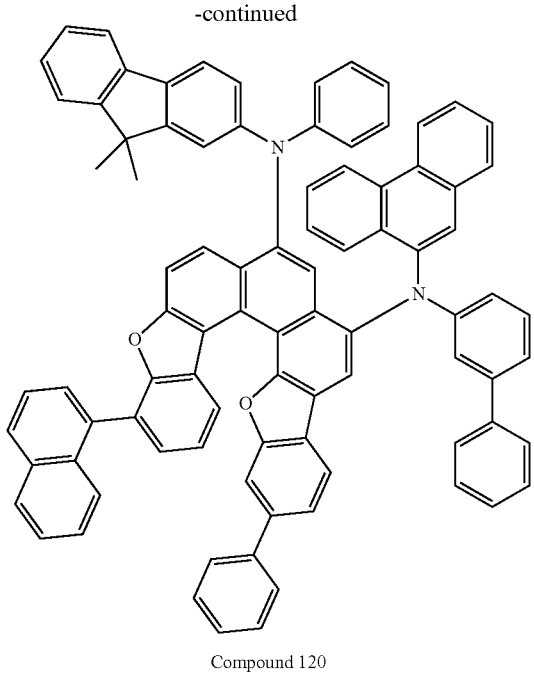

Compound 120

45.5 g Intermediate Aj (1.0 eq.) and 2.8 g NaBH$_4$ (2.0 eq.) were placed into a three-neck flask (1 L). The resulting mixture was aerated with nitrogen gas for 30 minutes, followed by adding 600 mL ethanol and 200 mL water. The resulting mixture was reacted at room temperature for 24 hours, and after the reaction finished, it was filtered and the filter cake was washed with water and dried. The residual was recrystallized with toluene and ethanol and dried, to which 500 mL glacial acetic acid and 150 mL hydrochloric acid solution (4M) were then added. The resulting mixture was aerated with nitrogen gas for 30 minutes, followed by adding 3.0 g zinc powder (3 eq.). The reaction was heated up to 110° C. and performed overnight for 18 hours. After the reaction finished, the resulting mixture was cooled down to room temperature and filtered. The filtrate was extracted with a mixture of dichloromethane and water. The residual was then washed with water, followed by rotary evaporation to remove the solvent, drying and recrystallization with toluene, to produce 30.5 g Compound 120 in 69% yield.

1H NMR (DMSO, 300 Hz): δ (ppm)=9.03-8.90 (m, 2H), 8.88-8.77 (d, 1H), 8.60-8.42 (d, 1H), 8.25-8.03 (m, 7H), 7.94-7.12 (m, 38H), 7.10-6.81 (m, 3H), 1.68-1.55 (s, 6H)

MS (FAB): 1187 (M+)

The Compounds 1-120 may be synthesized following the Reaction Schemes 1-95.

Device Example 1

An ITO anode was formed on a substrate carrying a reflecting layer and the surface of ITO anode was treated with N$_2$ plasma or UV-Ozone. A hole injection layer (HIL) was formed thereon, to a thickness of 10 nm, by vapor depositing HAT-CN as a hole injection layer material. Then, a hole transport layer was formed on top of the hole injection layer, to a thickness of 120 nm, by vapor depositing NPD under vacuum. An emission layer (EML) was formed on top of the hole transport layer, to a thickness of 25 nm, by vapor depositing a EML material comprising 9,10-di(2-naphthyl) anthracene (ADN) and Compound 5 in the present invention (5 wt %). An electron transport layer (ETL) was formed on the emission layer, to a thickness of 35 nm, by vapor depositing a mixture of anthracene derivatives (50 wt %) and Liq (50 wt %); and an electron injection layer (EIL) was formed thereon, to a thickness of 2 nm, by vapor depositing Liq. Thereafter, a cathode was formed, to a thickness of 15 nm, by vapor depositing a mixture of magnesium (Mg) (90 wt %) and Argentine (Ag) (10 wt %), and a covering and protecting layer (CPL) was formed thereon, to a thickness of 65 nm, by vapor depositing N4,N4'-bis[4-[bis(3-methylphenyl)amino]phenyl]-N4,N4'-diphenyl-[1,1-biphenyl]-4,4'-biamine (DNTPD). Finally, a water absorbent material containing UV hardening adhesive was applied thereto to protect the organic light-emitting device from being affected by the oxygen and water in the atmosphere.

The compound mentioned in this example is of the following structural formula:

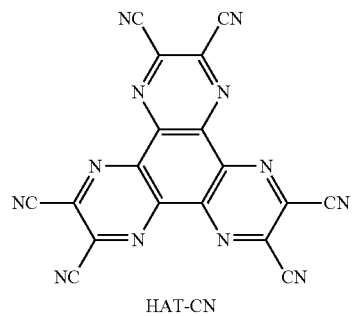

HAT-CN

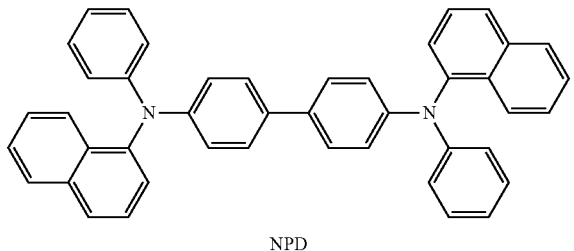

NPD

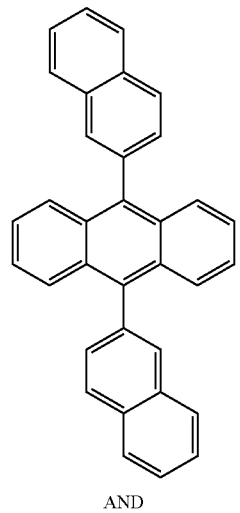

AND

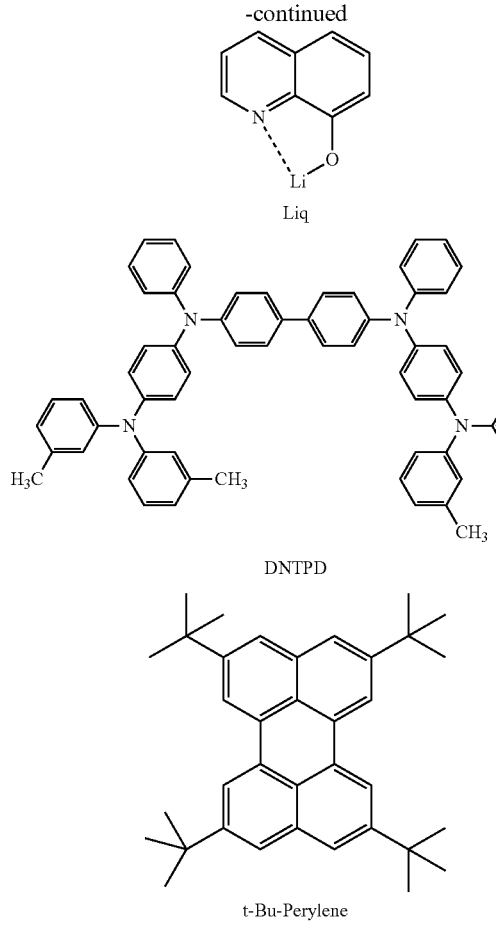

Device Examples 2-11

Device Examples 2-11 were prepared as described for Device Example 1 was replaced with Compounds 9, 11, 23, 47, 63, 83, 92, 109, 112 and 120 respectively as the dopant in the blue EML.

Comparative Device Example 1

A organic light-emitting device was prepared as described for Device Example 1 except that 2,5,8,11-tetra-butyl-Perylene (t-Bu-Perylene) was used in place of Compound 5 as the blue dopant.

Device Examples 1-11 were compared with Comparative Device Example 1 under a current density of 10 mA/cm$^2$. Results are given in the following Table.

| | Material name | electric current density (mA/cm$^2$) | voltage (V) | Efficiency (Cd/A) | CIE (X Y) |
|---|---|---|---|---|---|
| Comparative Device Example 1 | t-Bu-Perylene | 10 | 4.8 | 4.1 | (0.135 0.058) |
| Device Example 1 | Compound 5 | 10 | 4.1 | 6.1 | (0.138 0.048) |
| Device Example 2 | Compound 9 | 10 | 4.4 | 5.9 | (0.136 0.056) |
| Device Example 3 | Compound 11 | 10 | 4.3 | 5.8 | (0.135 0.057) |
| Device Example 4 | Compound 23 | 10 | 4.3 | 6.2 | (0.138 0.049) |
| Device Example 5 | Compound 47 | 10 | 4.4 | 6.1 | (0.136 0.056) |
| Device Example 6 | Compound 63 | 10 | 4.0 | 5.6 | (0.136 0.058) |
| Device Example 7 | Compound 83 | 10 | 4.4 | 5.7 | (0.136 0.057) |
| Device Example 8 | Compound 92 | 10 | 4.4 | 6.3 | (0.137 0.049) |
| Device Example 9 | Compound 109 | 10 | 4.2 | 6.0 | (0.136 0.055) |
| Device Example 10 | Compound 112 | 10 | 4.3 | 5.9 | (0.136 0.056) |
| Device Example 11 | Compound 120 | 10 | 4.2 | 6.1 | (0.137 0.052) |

As shown in the above Table, Device Examples 1-11, with the use of Compounds in the present invention as the blue dopant in the EML, presents higher light-emitting efficiency and lower driving voltage, compared with Comparative Device Example 1.

Further, from the results of CIE chromaticity coordinates (CIE x, y), the values of CIE y in Device Examples 1-11 are lower than those in Comparative Device Example 1, confirming the deep blue performance of the present material, especially the Compounds used in Device Examples 1, 4 and 8 which are, more for sure, capable of performing deep blue. Therefore, organic light-emitting devices may present lower driving voltage, higher light-emitting efficiency and deep blue performance, with use of the Compounds in the present invention as the dopants in the emission layer of the device.

We claim:

1. A blue fluorescence dopant of the following structural formula:

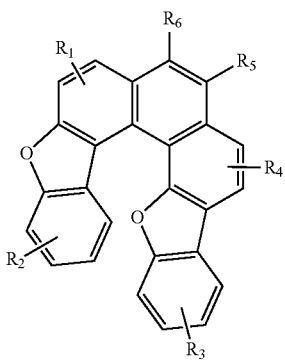

wherein $R_1$ is selected from hydrogen, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_2$ is selected from hydrogen, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_3$ is selected from hydrogen, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_4$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_5$ and $R_6$ are, each dependently, selected from, a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group.

2. The blue fluorescence dopant according to claim 1, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group or a triazinyl group among $R_1$, at least one hydrogen atom thereof is substituted with a C1-C20 linear or branched alkyl group, a C3-C24 cyclic alkyl group, a C1-C20 alkoxyl group, a halogen atom, CN, $CF_3$, a $Si(CH_3)_3$ group, or a C6-C50 aryl group.

3. The blue fluorescence dopant according to claim 1, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolinyl group and the triazinyl group among $R_2$, at least one hydrogen atom is substituted with a C1-C20 linear or branched alkyl group, a C3-C24 cyclic alkyl group, a C1-C20 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

4. The blue fluorescence dopant according to claim 1, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group among $R_3$, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, or a C6-C60 aryl group.

5. The blue fluorescence dopant according to claim 1, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, the pyrimidinyl group, the quinolyl group and the triazinyl group among $R_4$, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

6. The blue fluorescence dopant according to claim 1, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group among $R_5$ and $R_6$, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-40.

7. The blue fluorescence dopant according to claim 1, wherein the blue fluorescence dopant is any one of the following compounds:

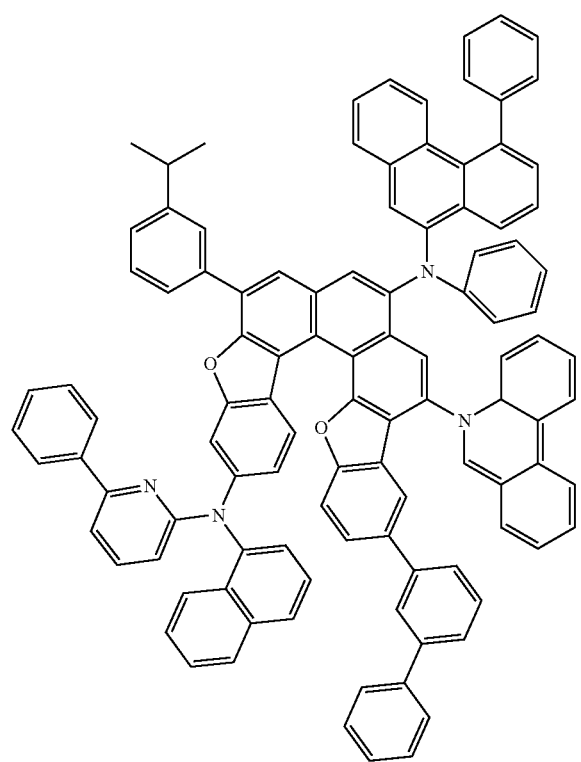
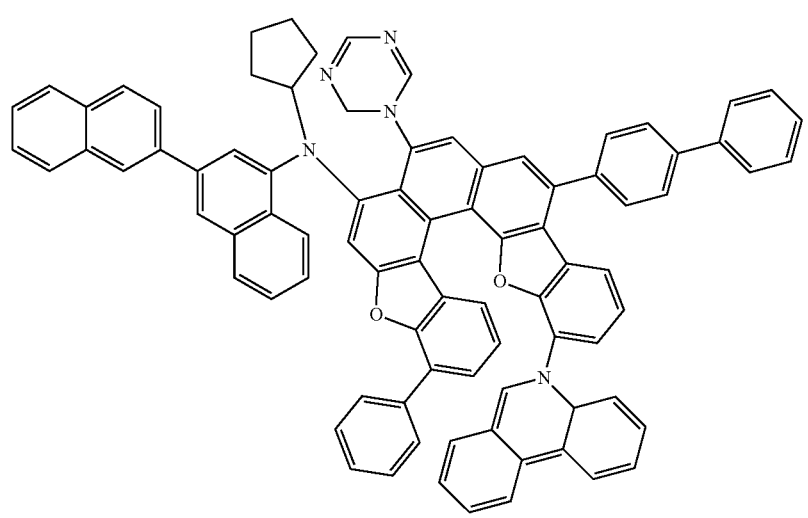

-continued
3
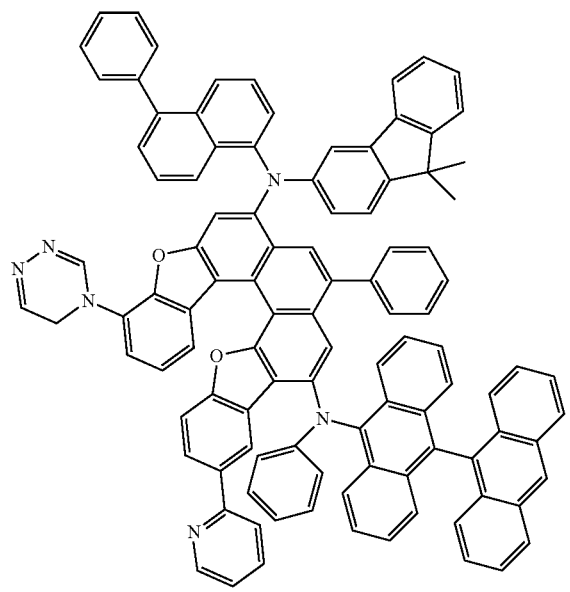
4
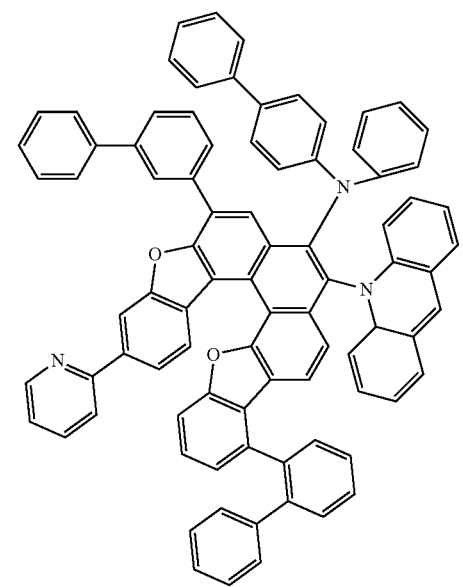
5
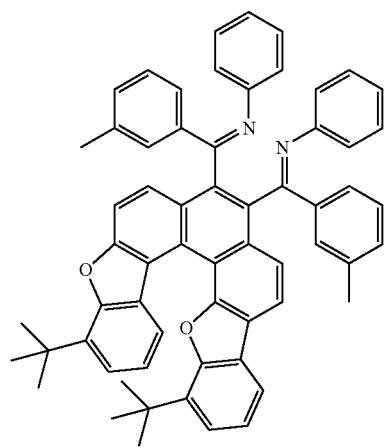
6
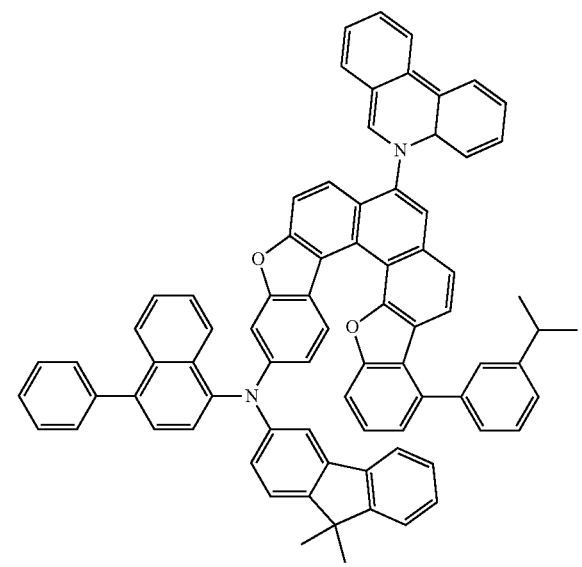

-continued
7
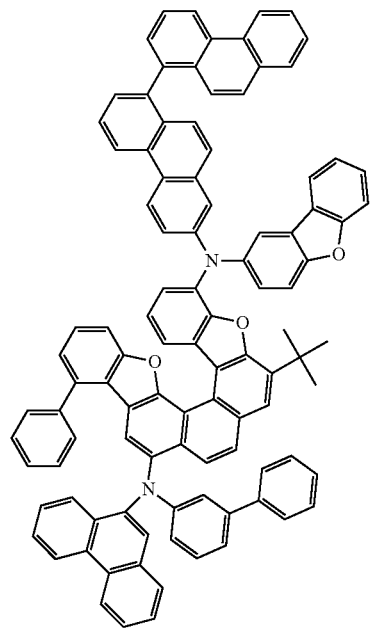
8
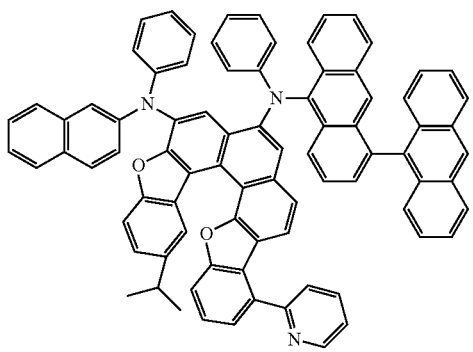
9
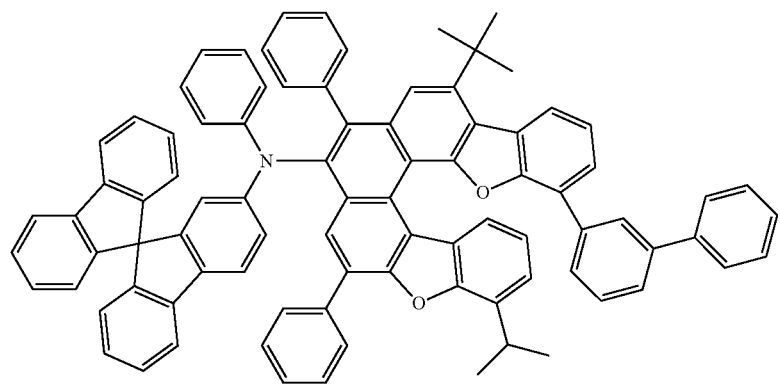
10
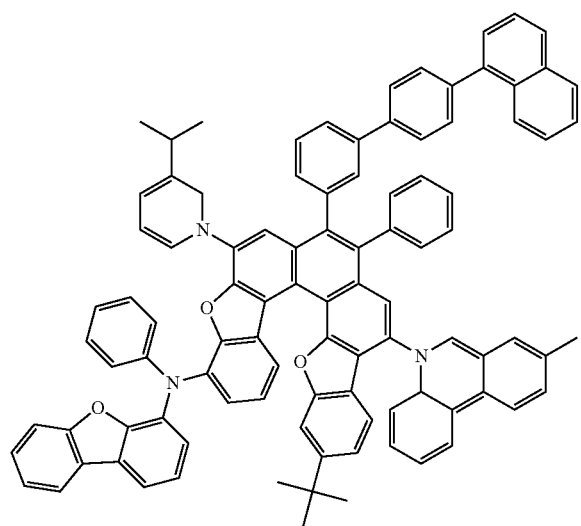
11
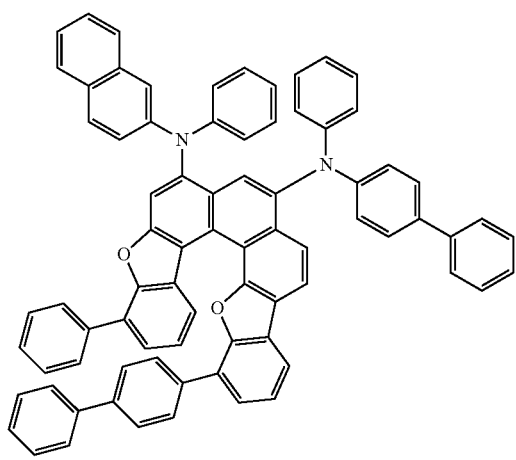

-continued
12
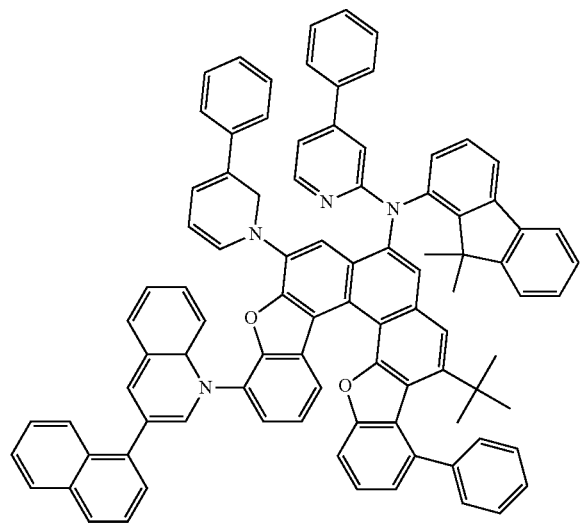
13
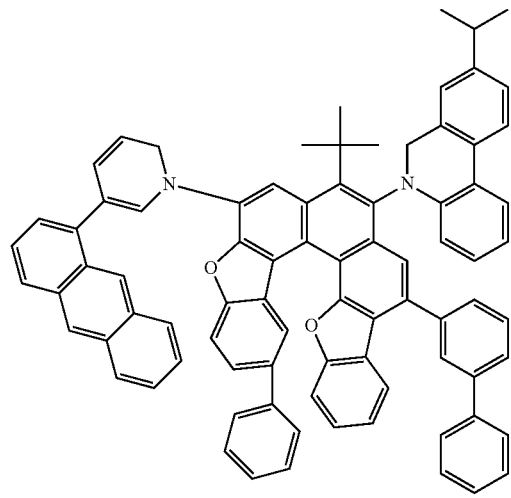
14
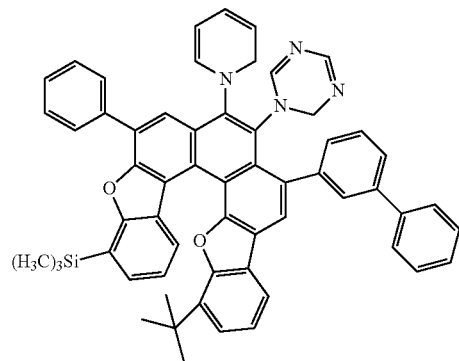
15
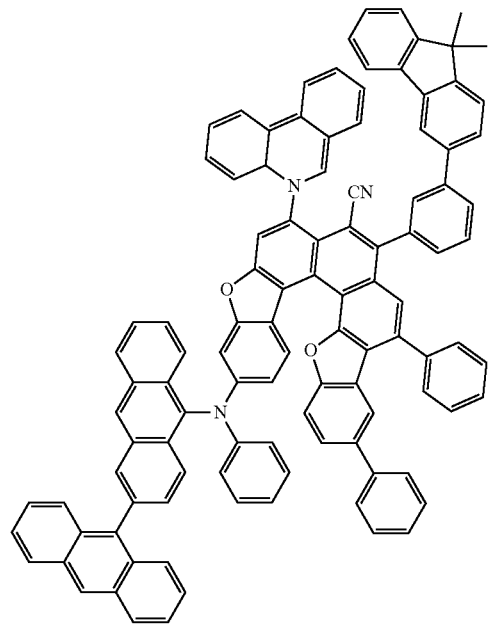

-continued
16
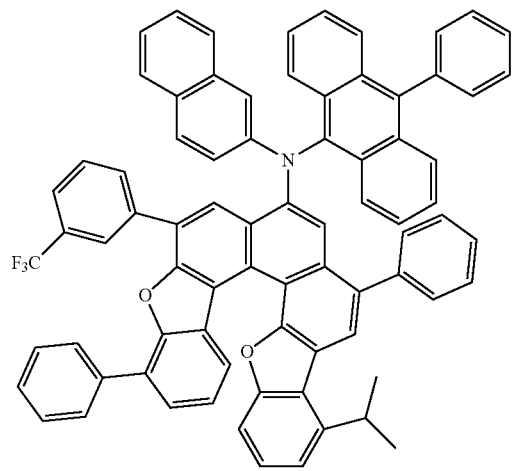
17
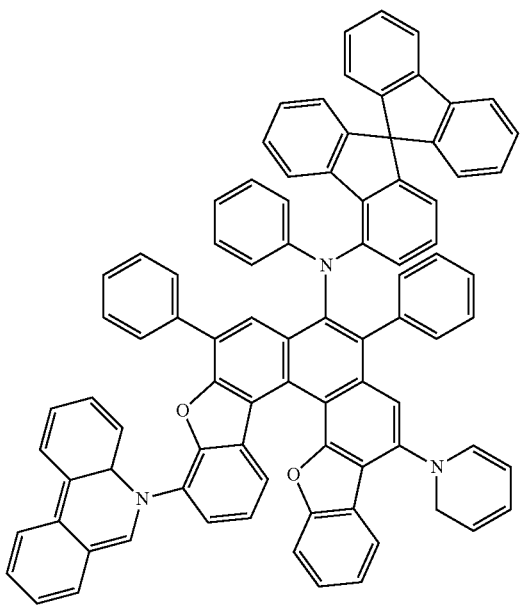
18
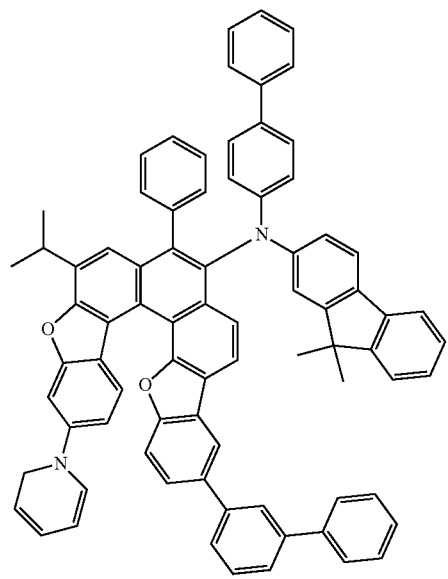
19
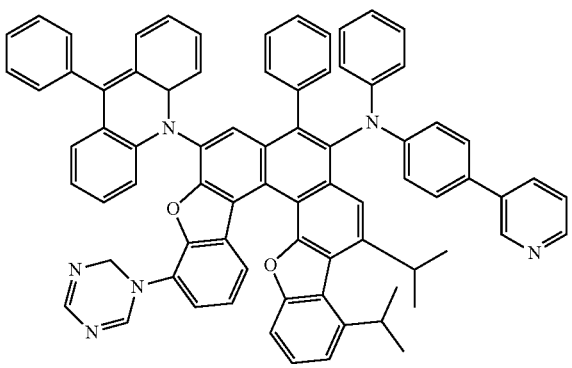

-continued
20
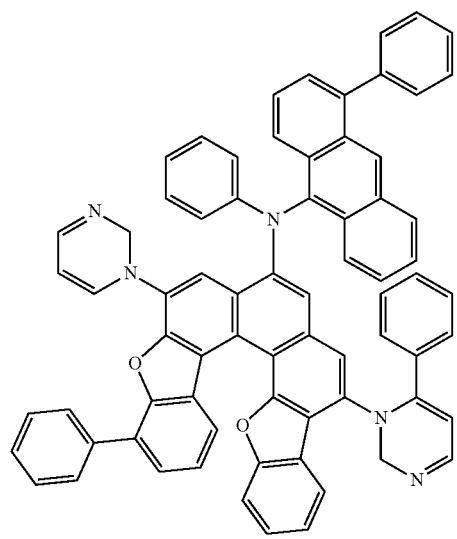
21
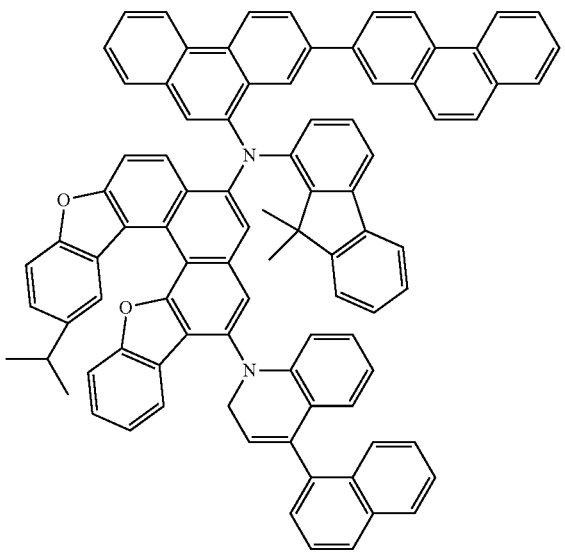
22
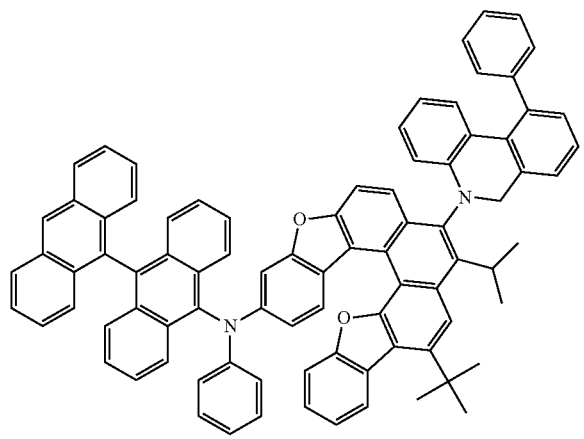
23
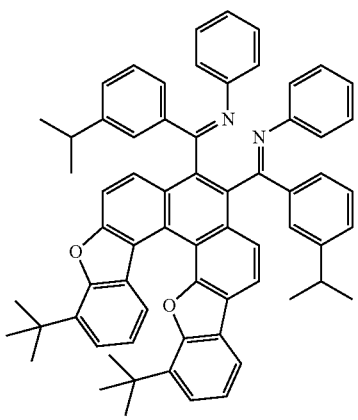
24
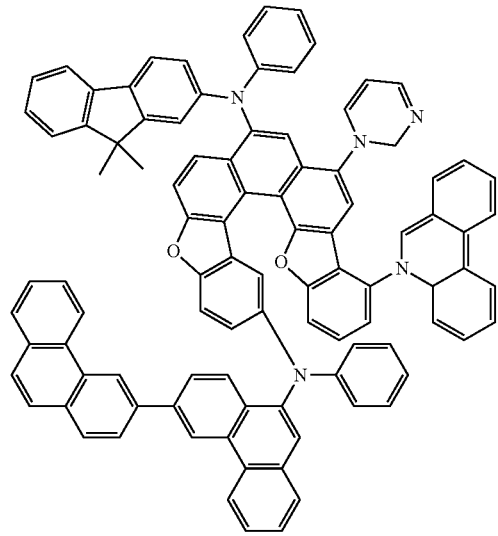
25
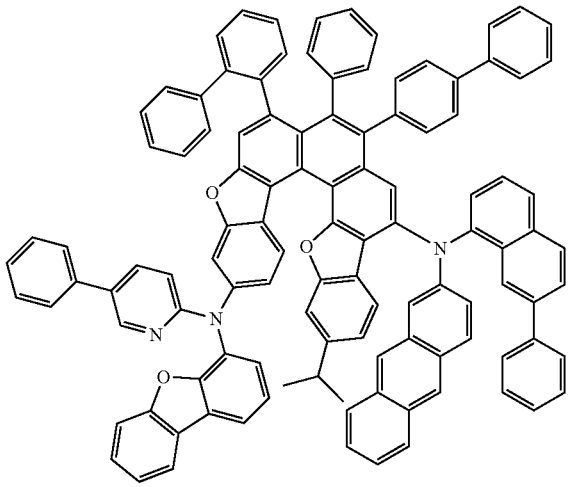

26
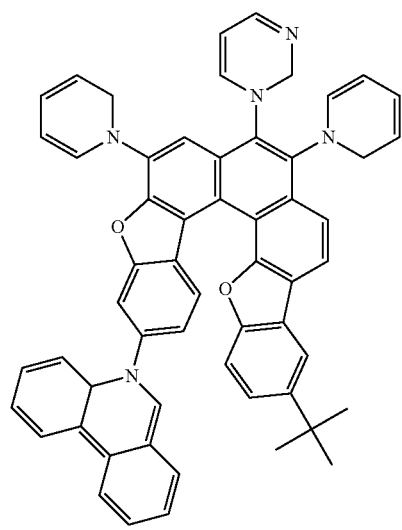
27
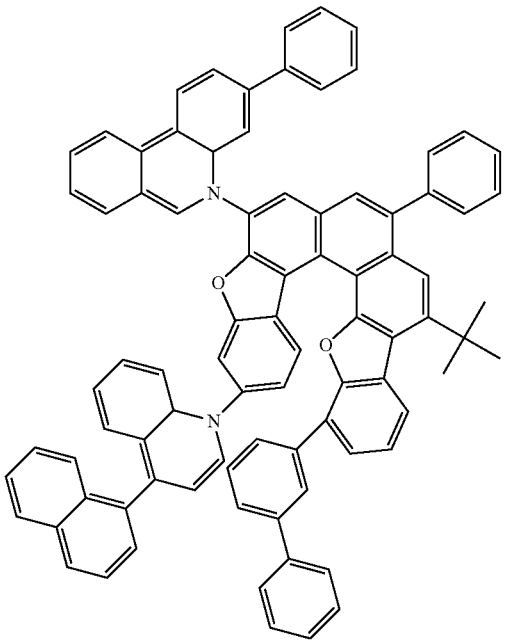
28
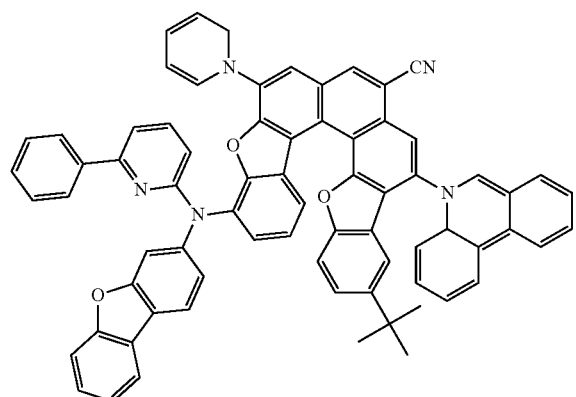
29
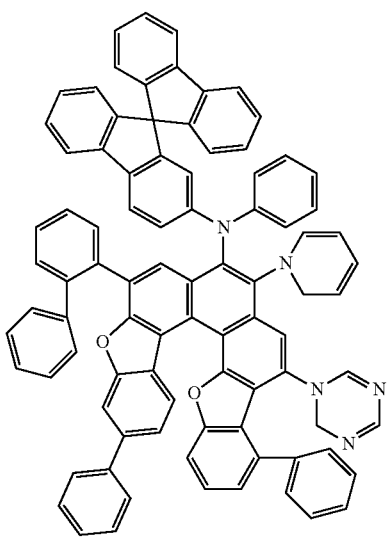

-continued
171
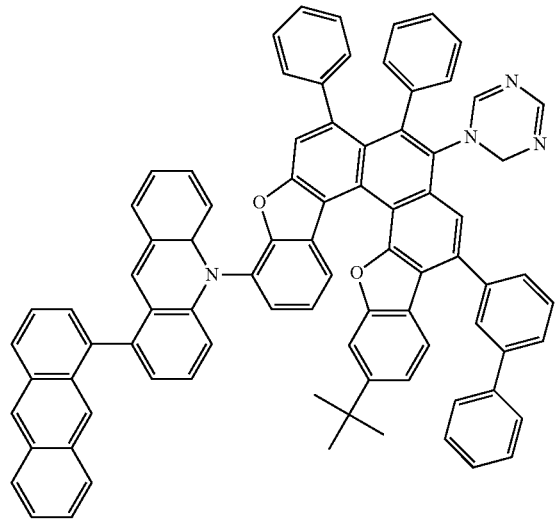
30
172
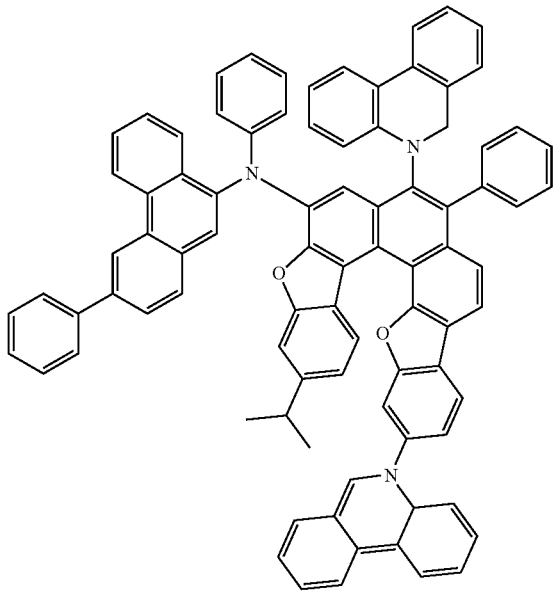
31
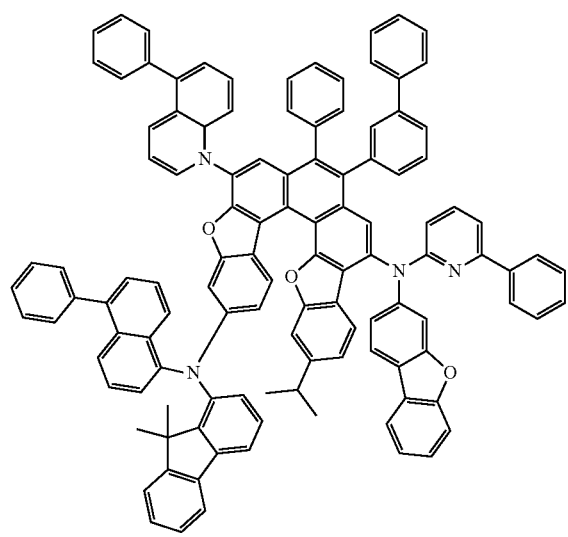
32
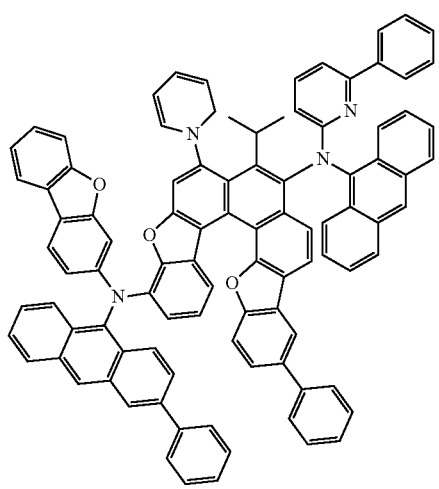
33

-continued
34
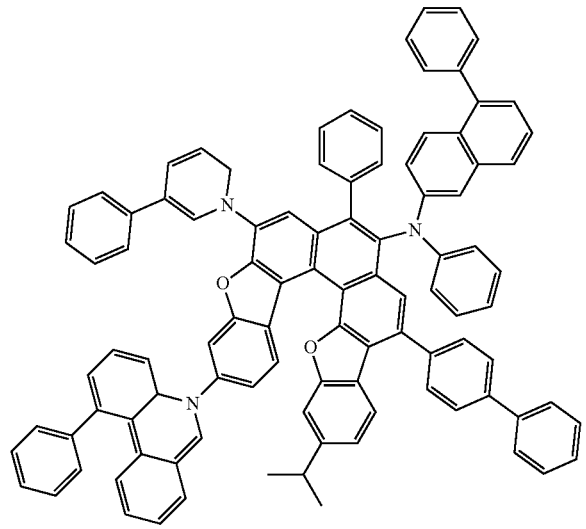
35
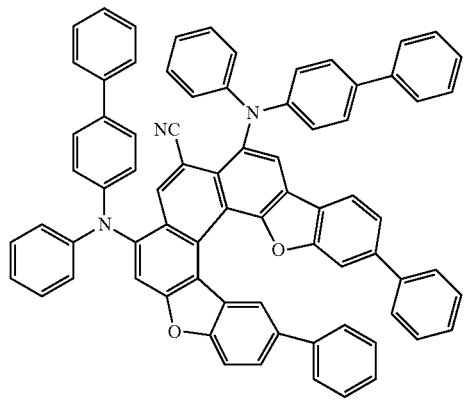
36
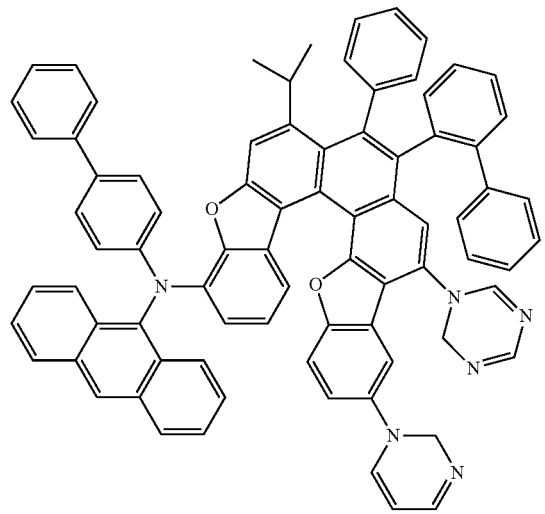
37
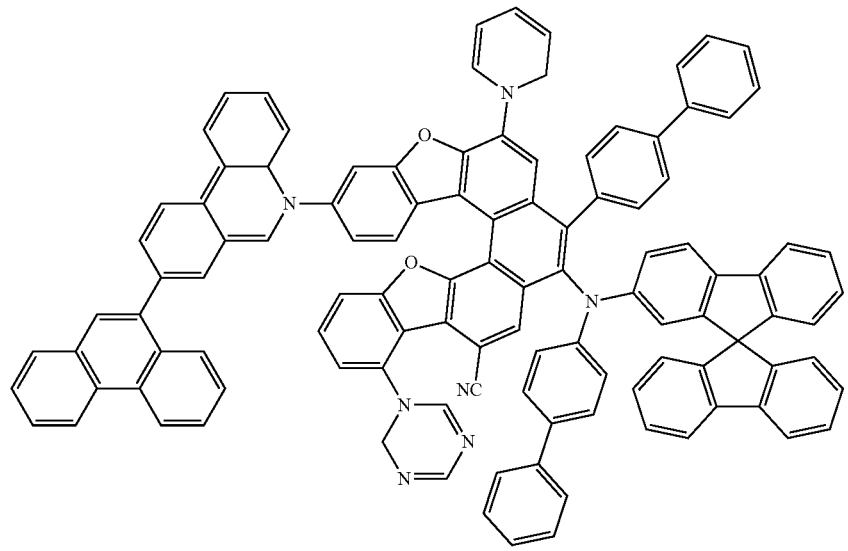

38
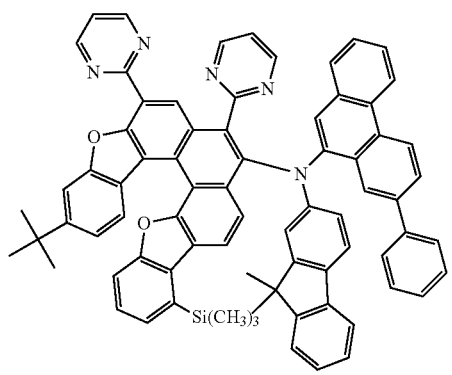
39
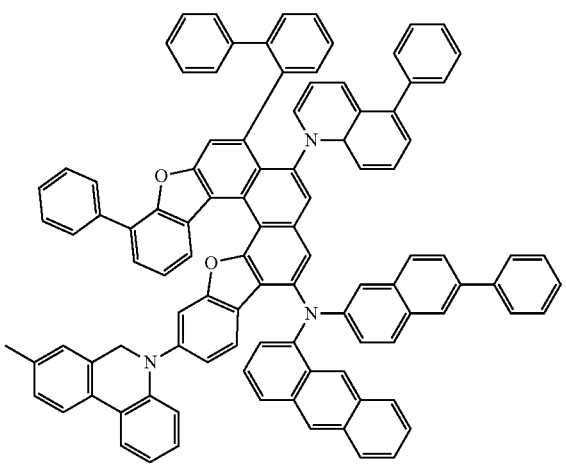
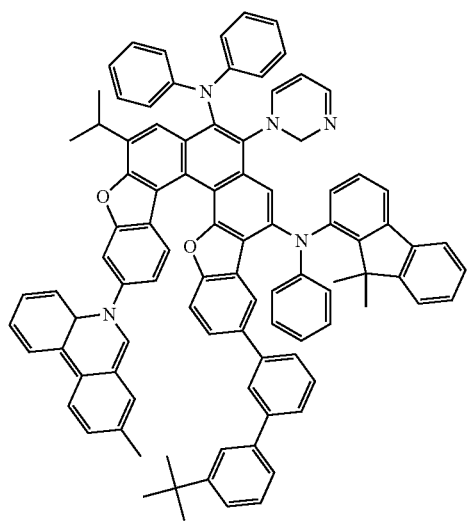
41
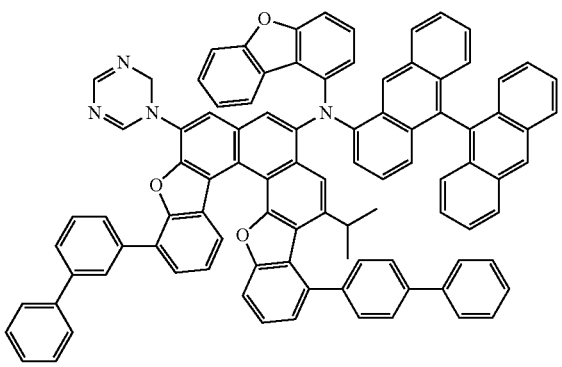
42
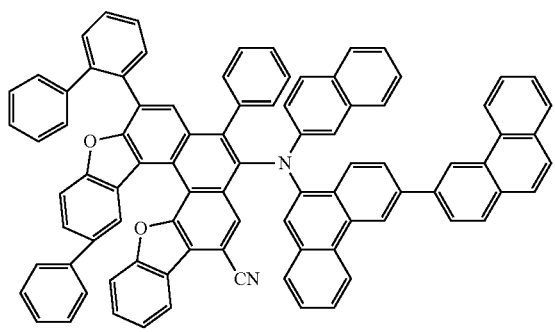
43
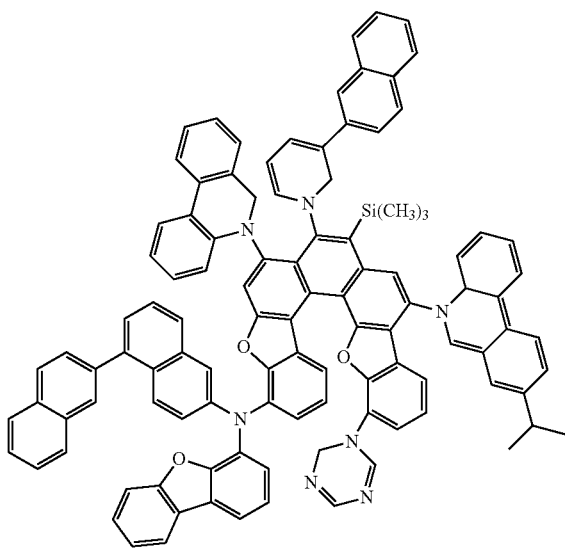

-continued
44
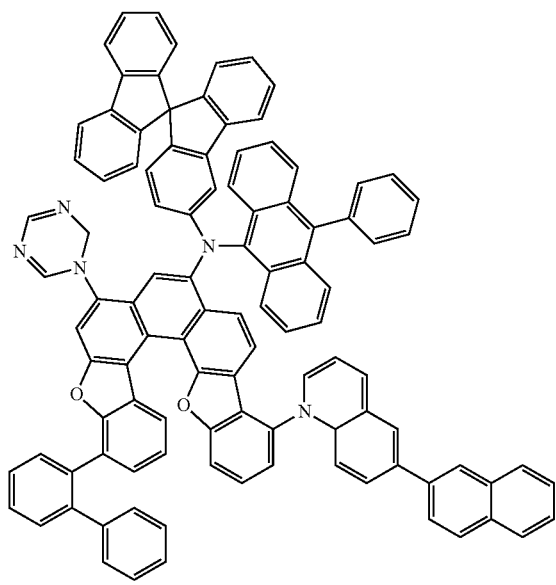
45
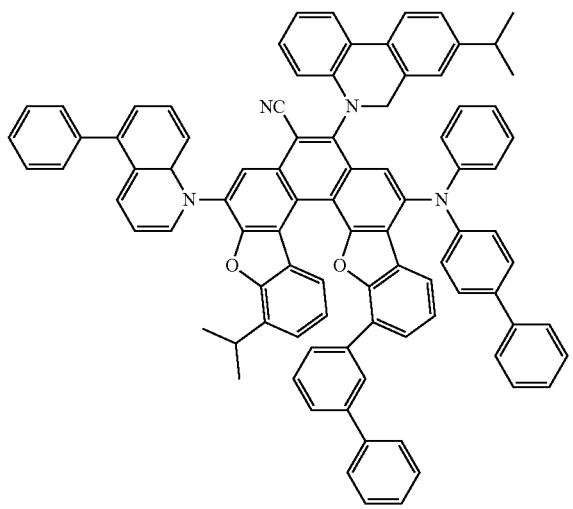
46
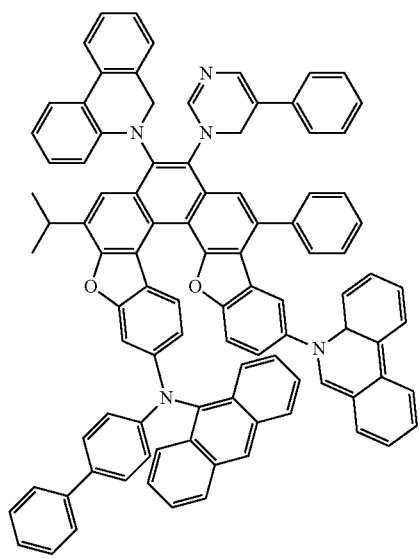
47
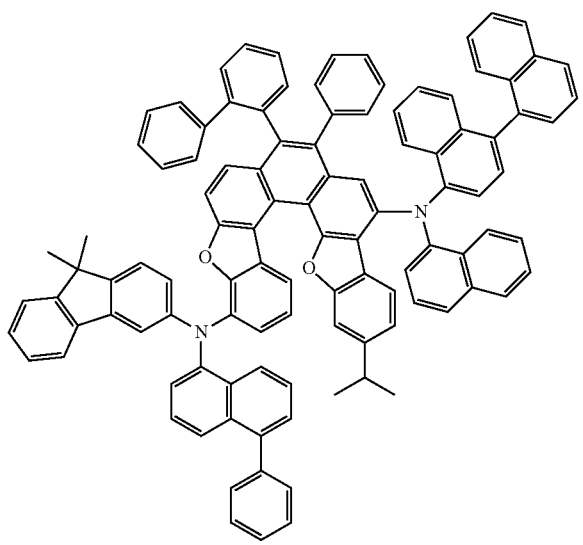

48
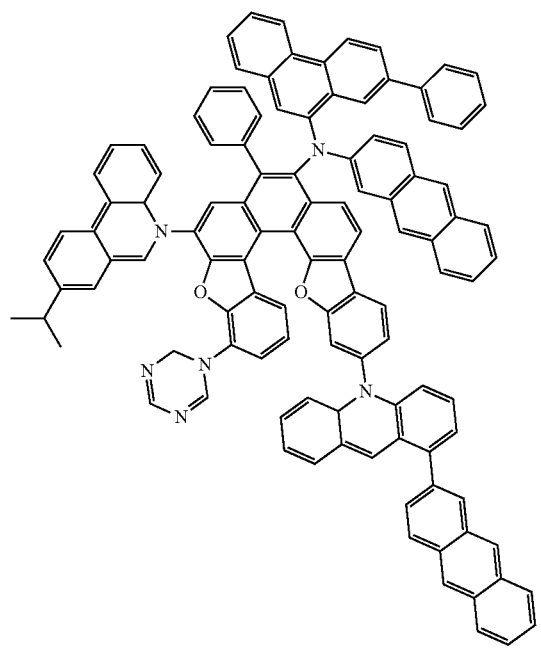
49
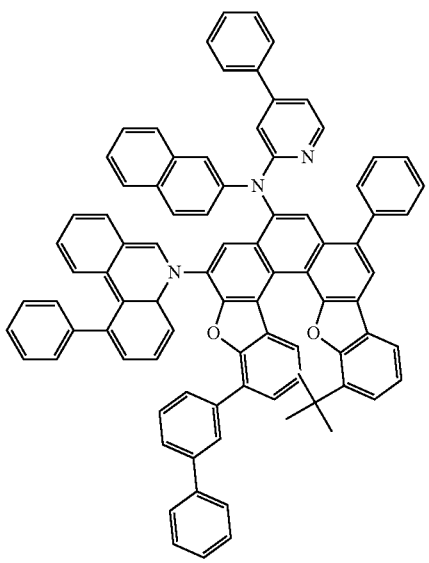
50
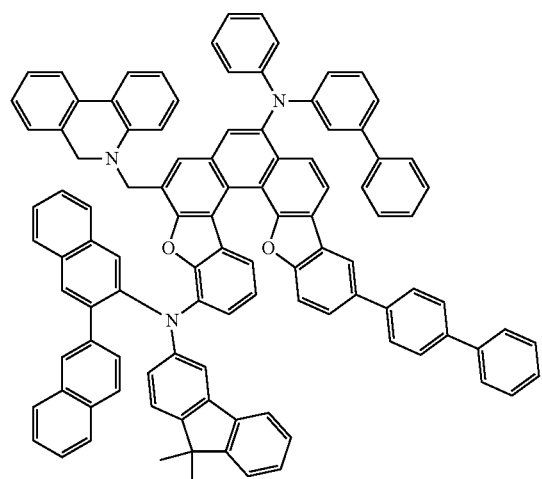
51
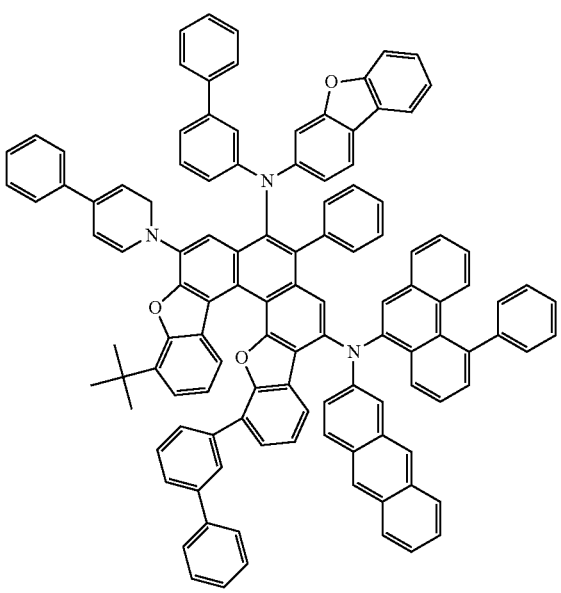

-continued
52
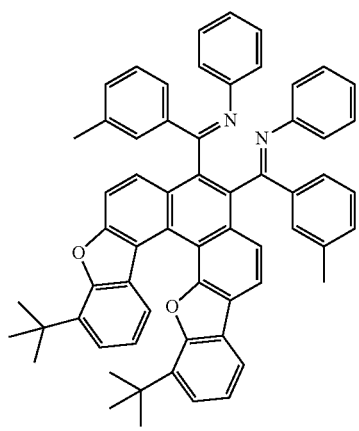
53
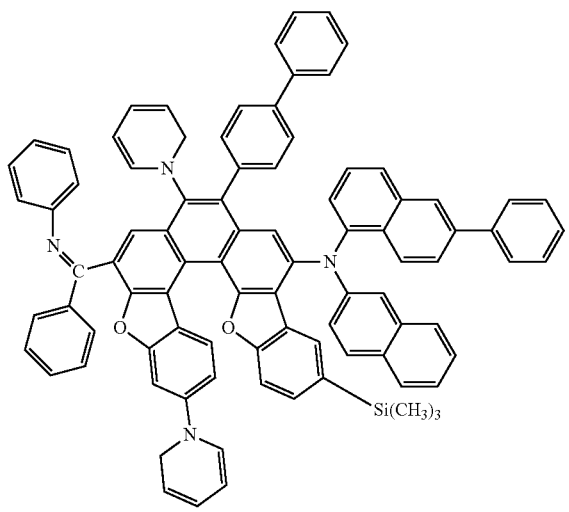
54
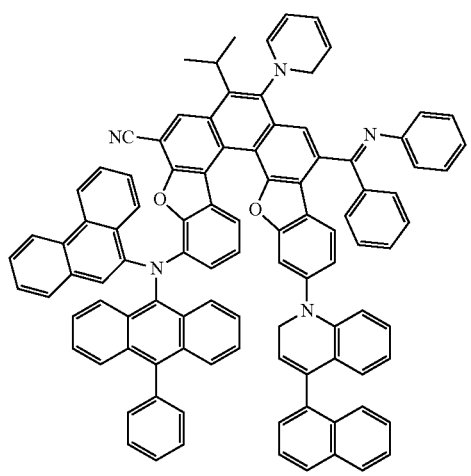
55
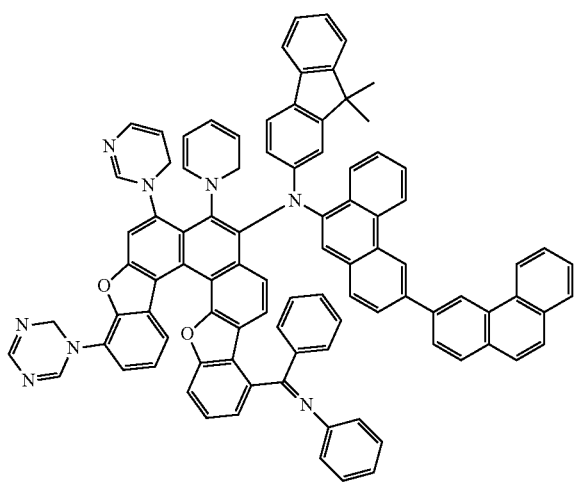
56
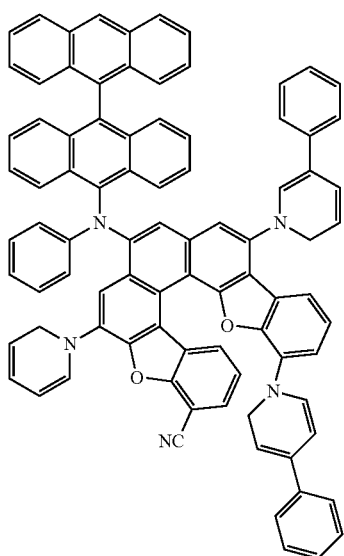
57
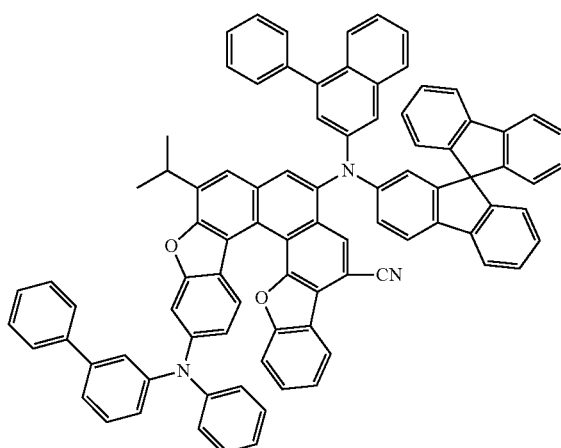

-continued
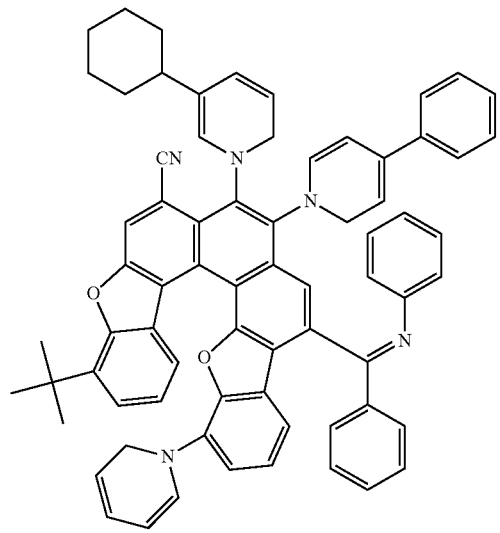
58
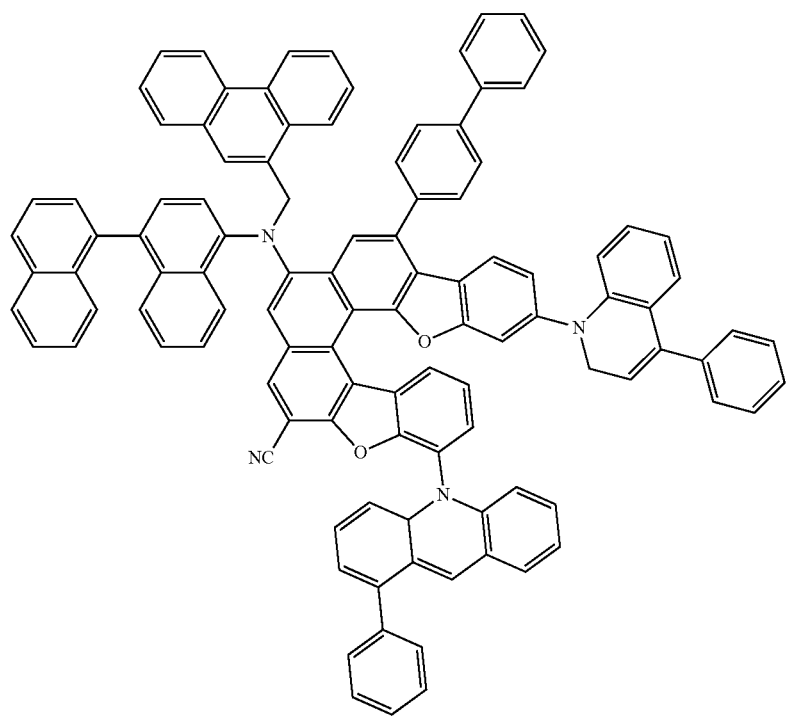
59

-continued
60
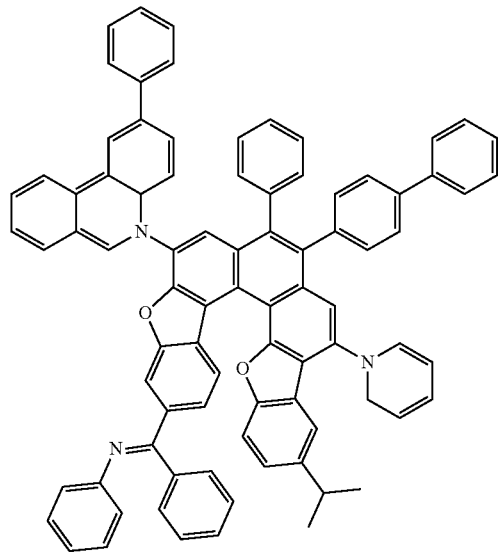
61
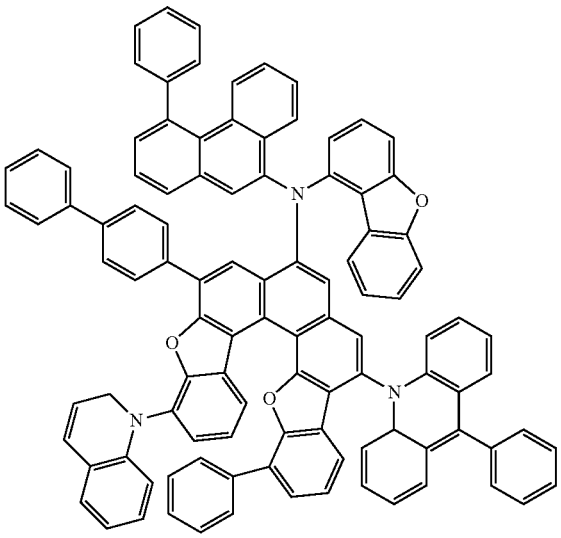
62
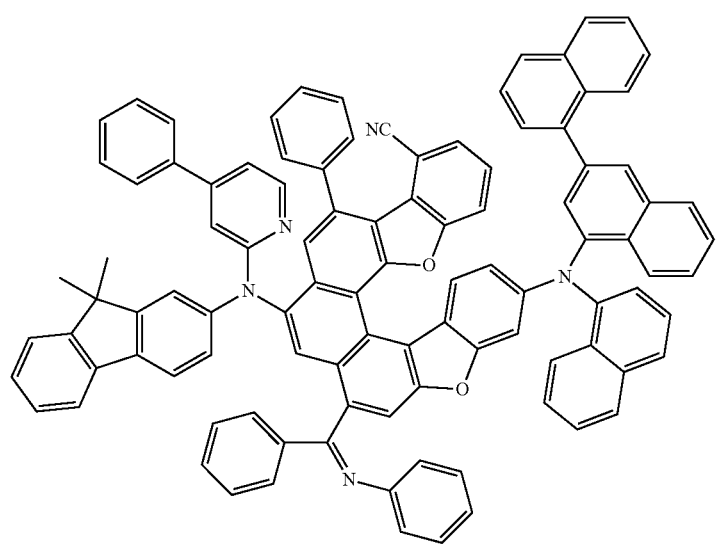
63
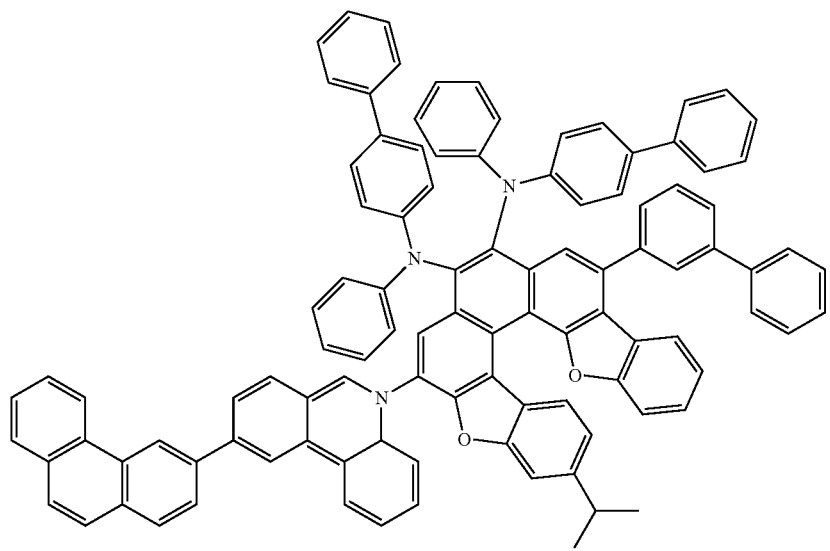

-continued
64
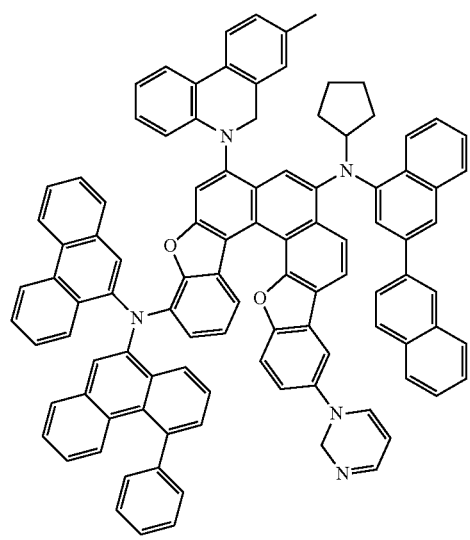
65
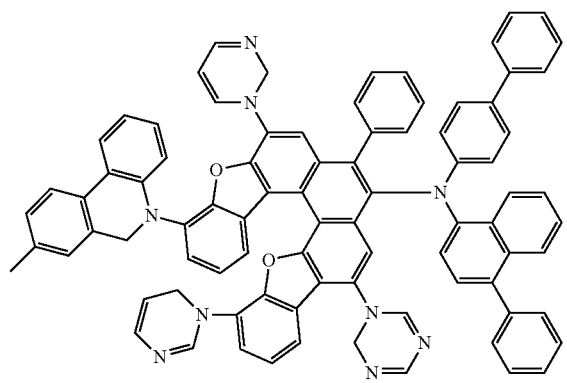
66
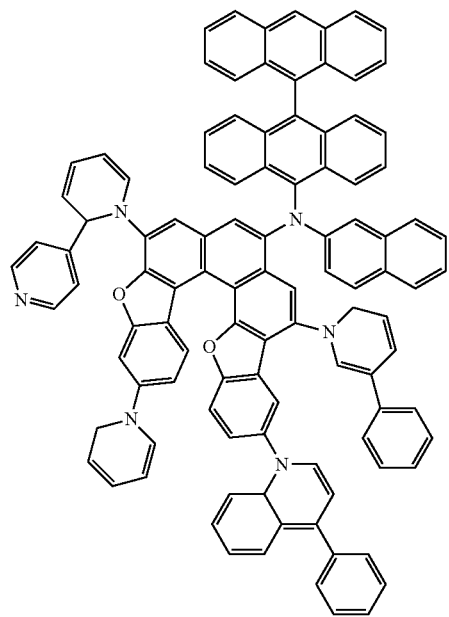
67
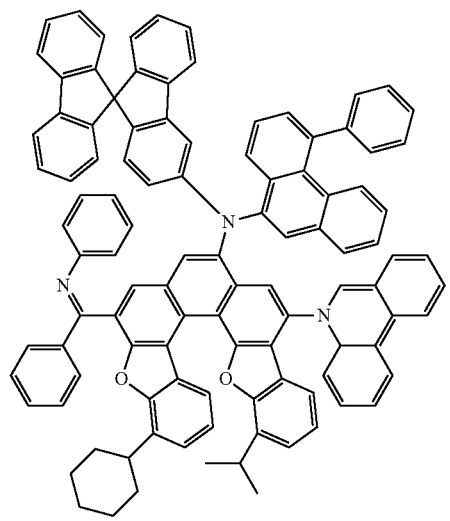

68
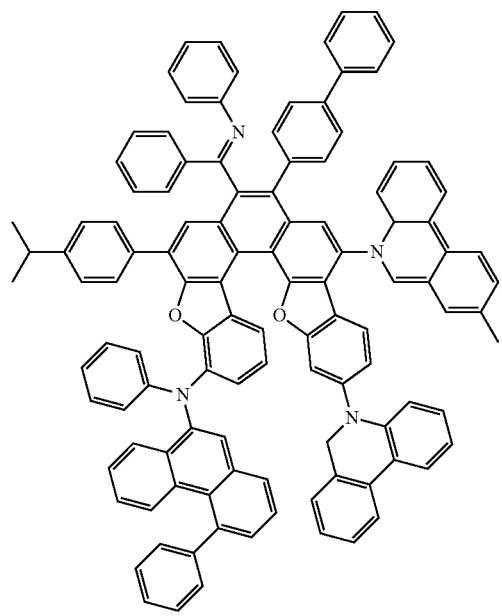
69
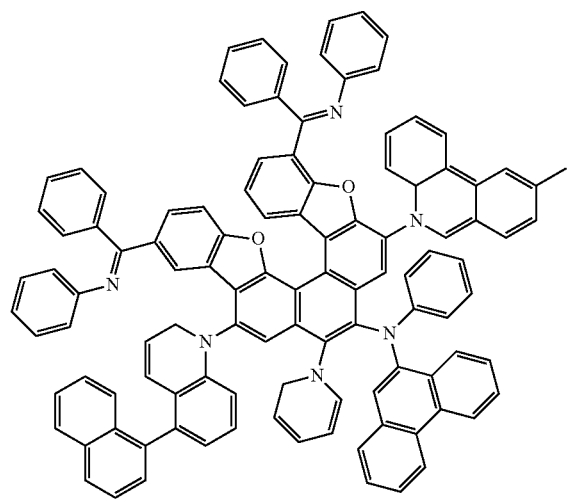
70
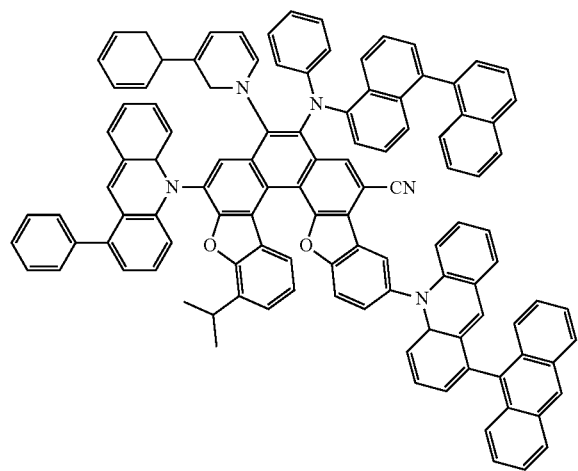
71
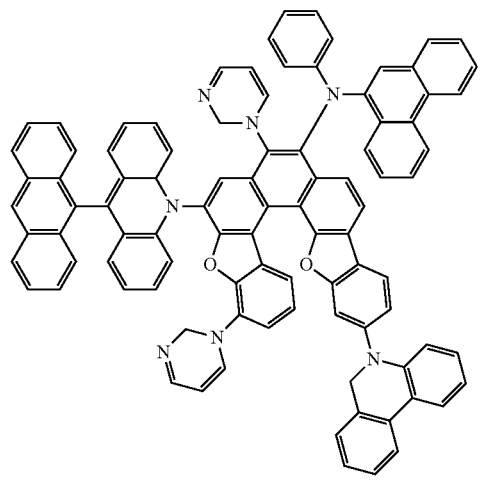

72
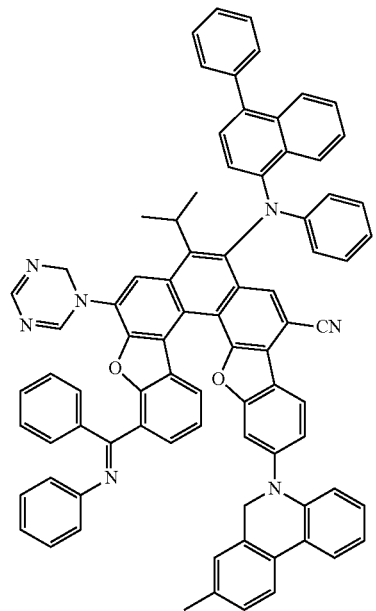
73
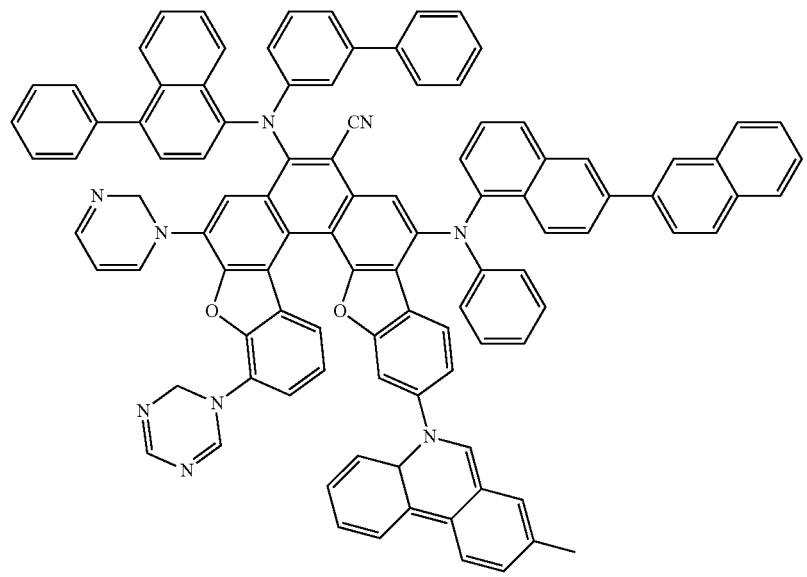

74
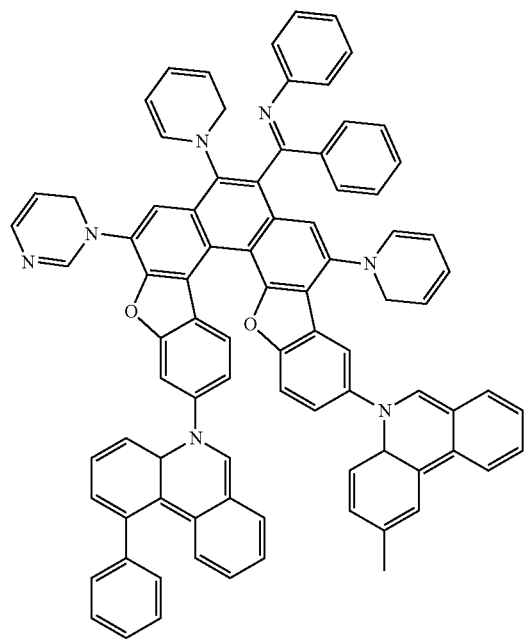
75
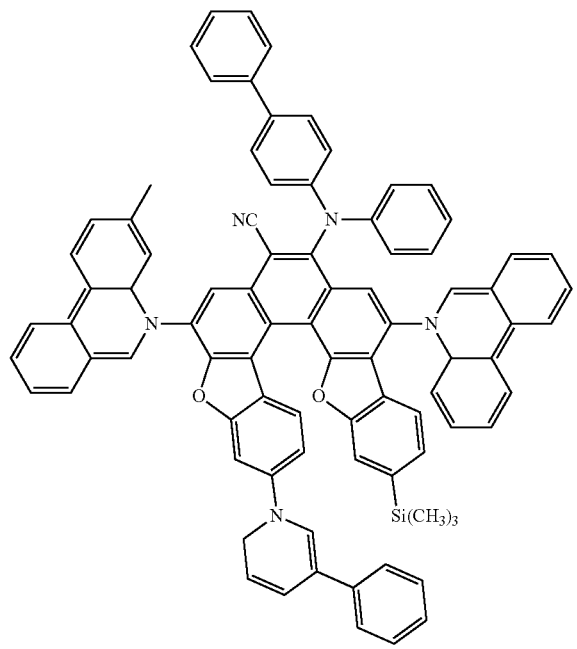
76
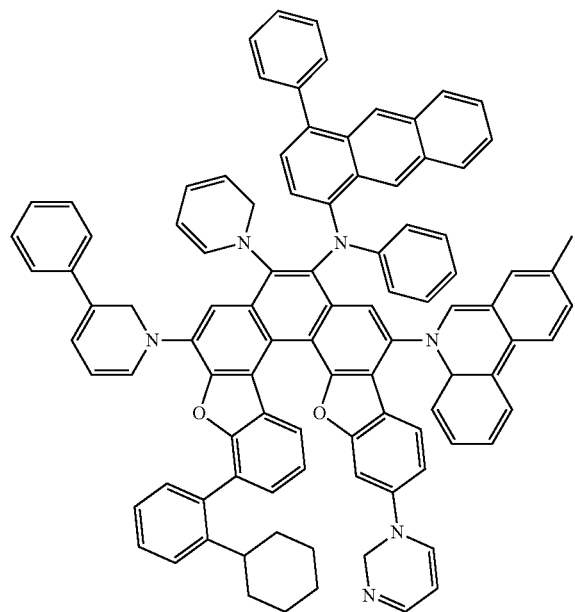
77
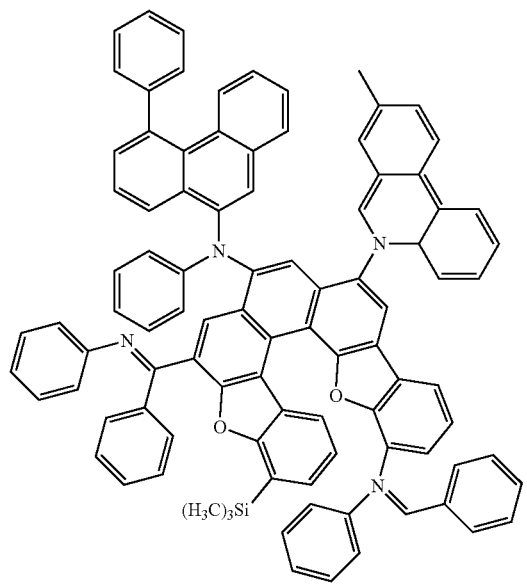

78
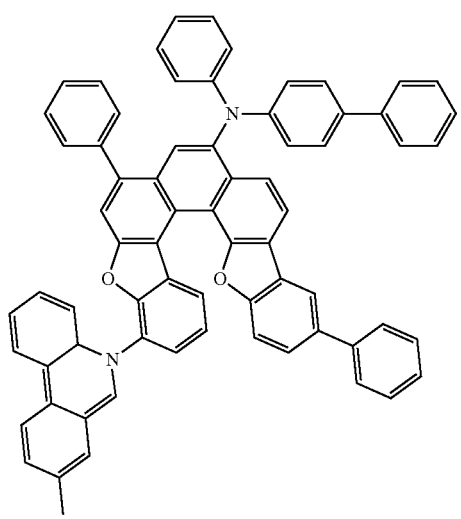
79
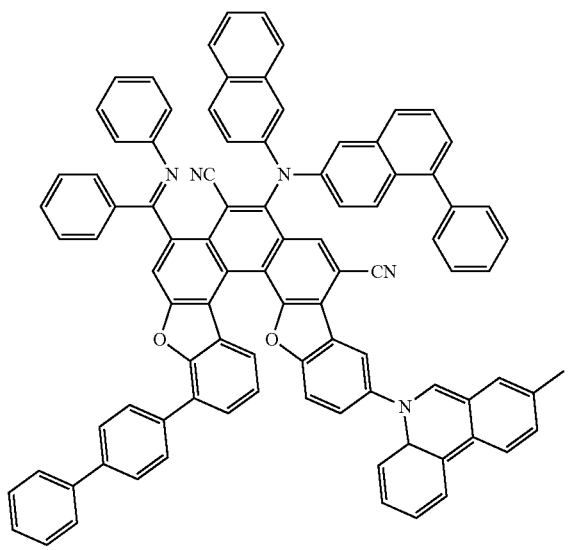
80
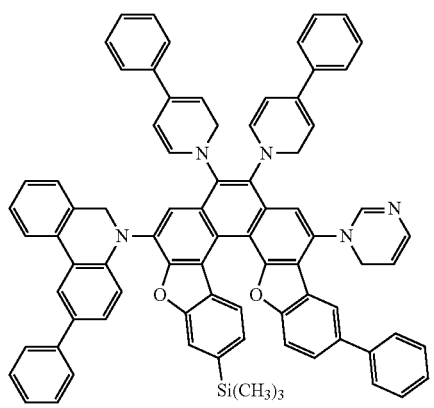
81
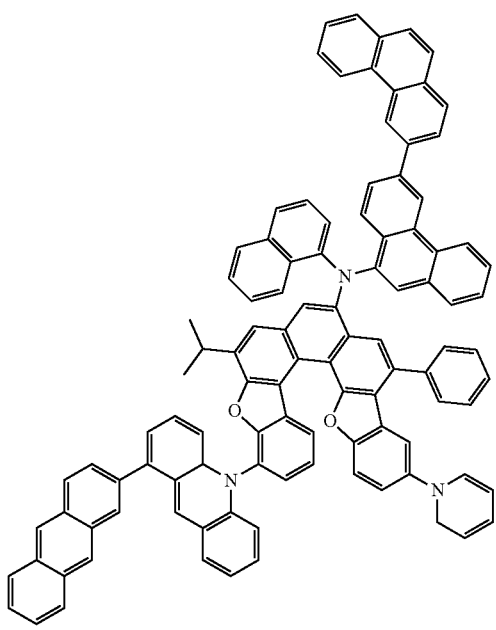

82
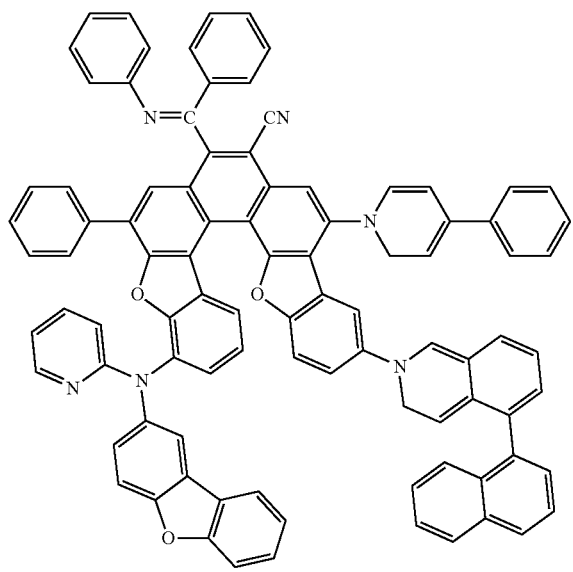
83
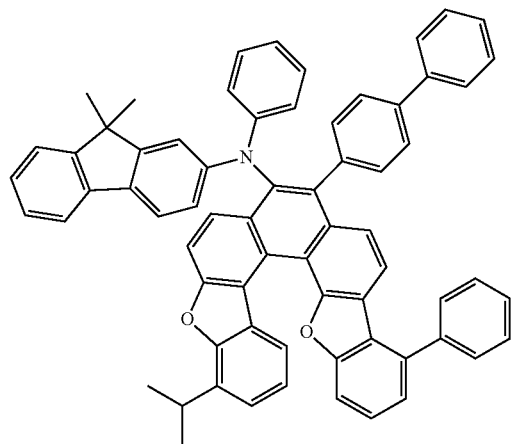
84
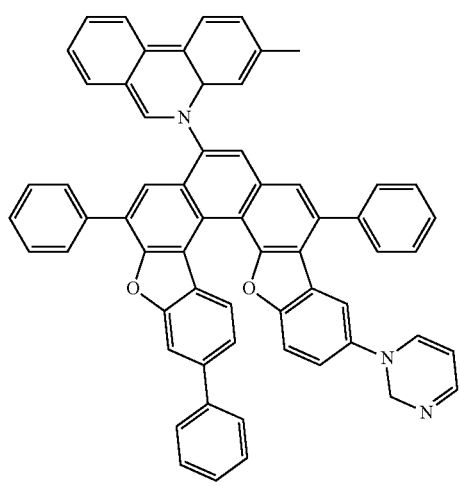
85
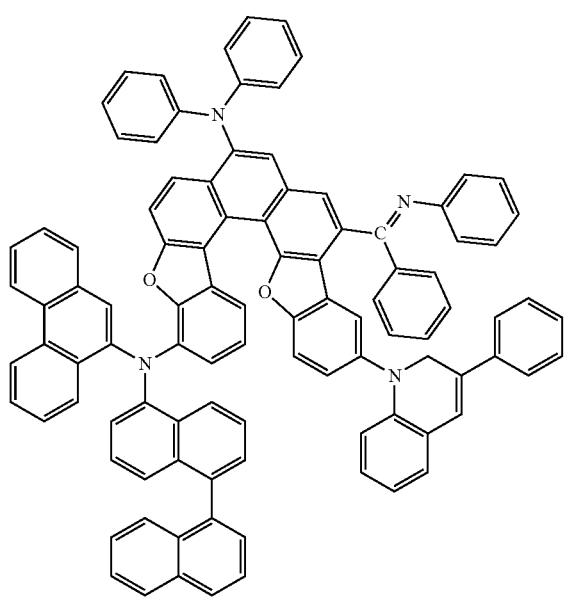

-continued
86
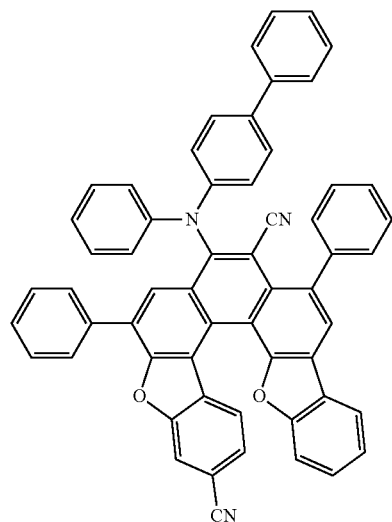
87
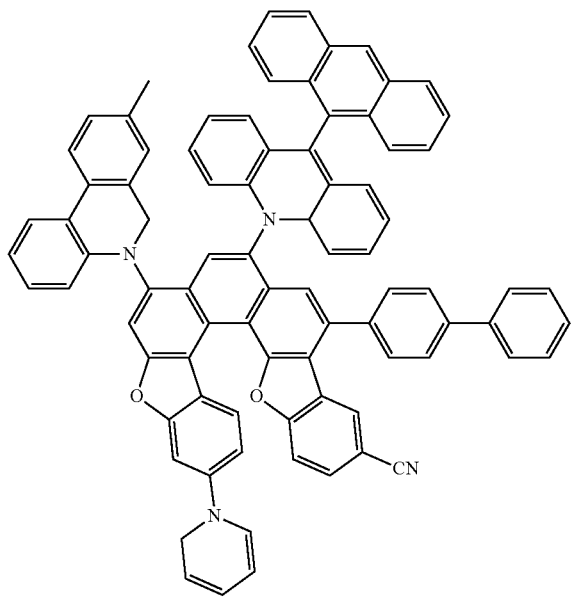
88
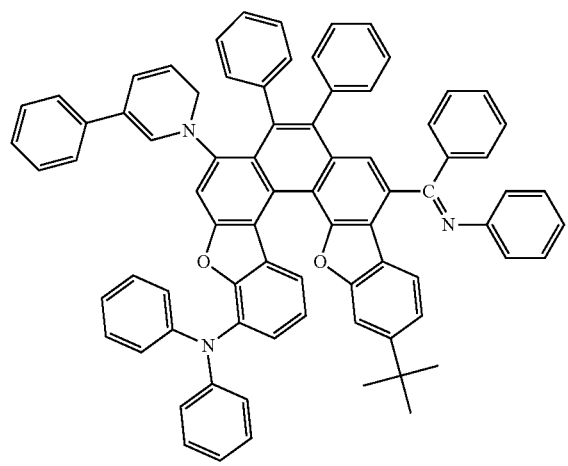
89
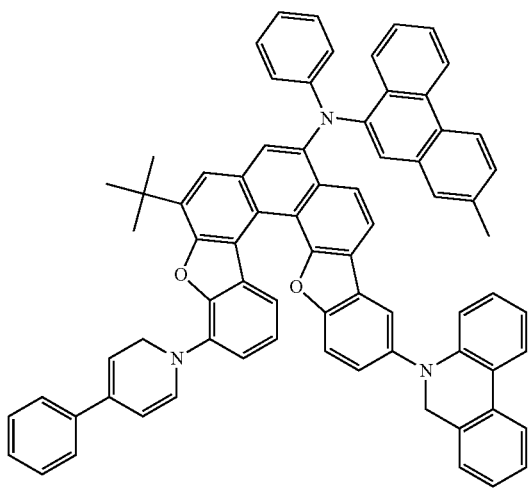

90
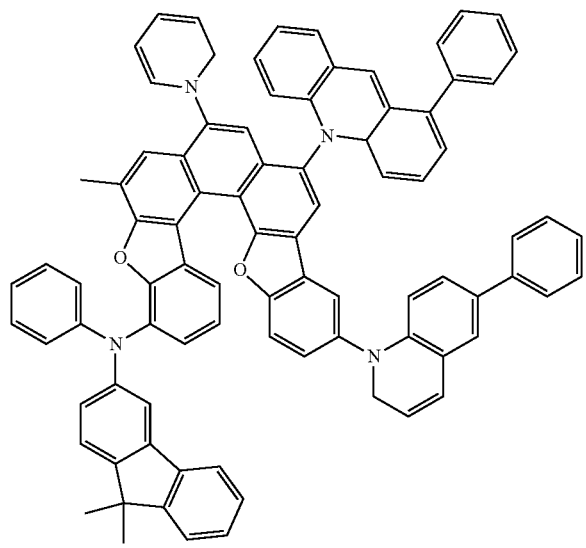
91
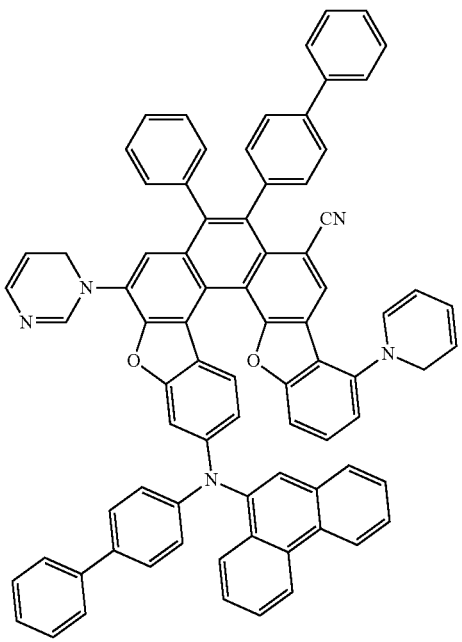
92
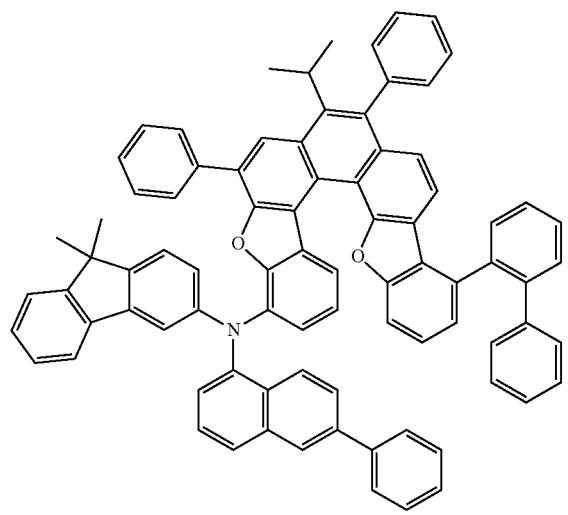
93
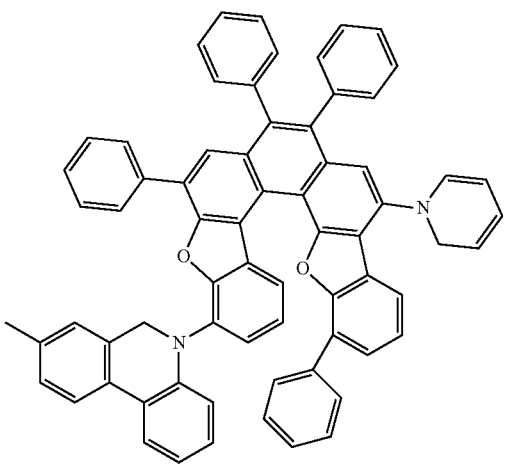

-continued
94
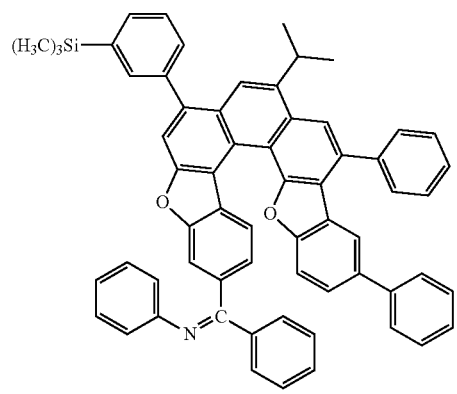
95
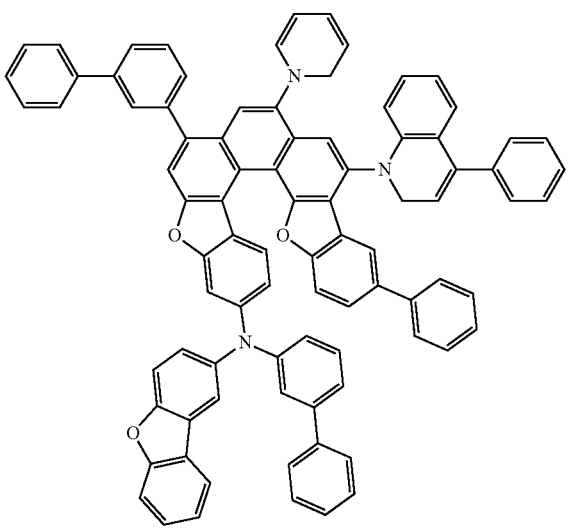
96
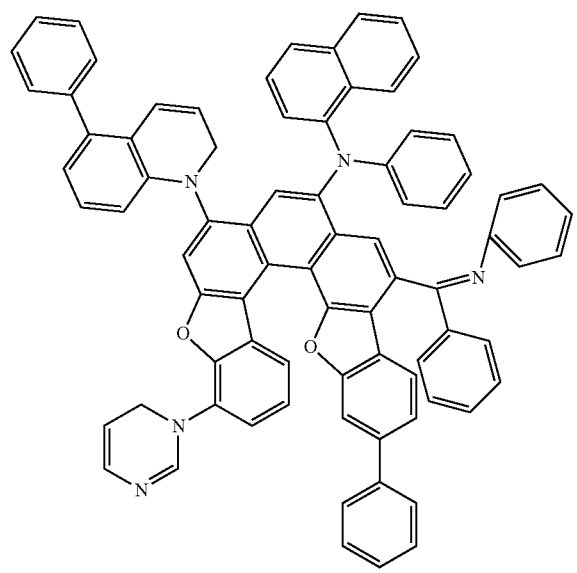
97
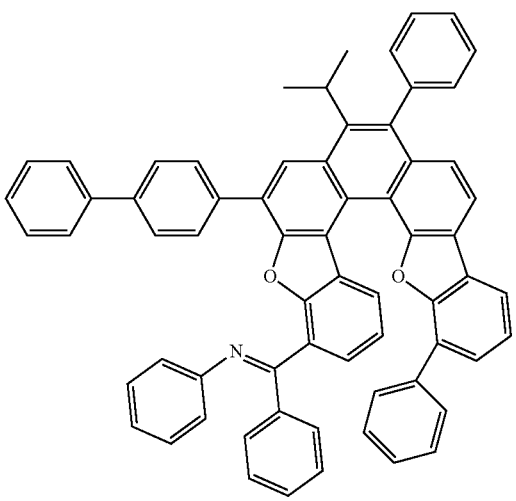

-continued
98
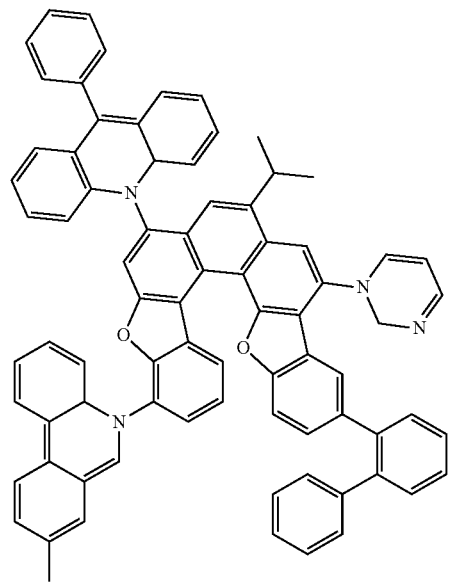
99
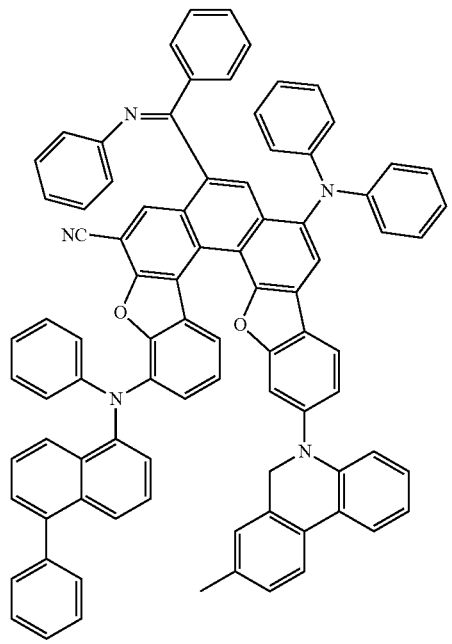
100
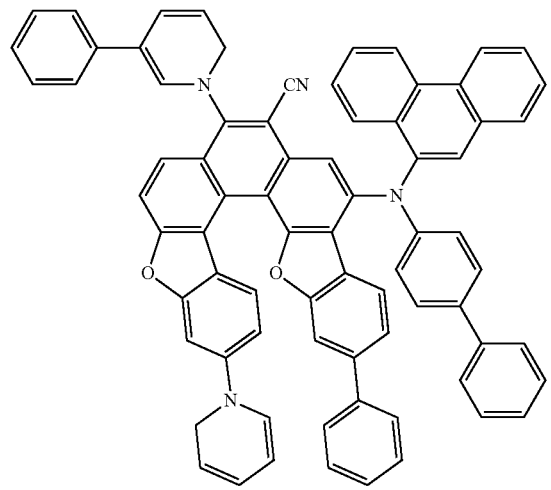
101
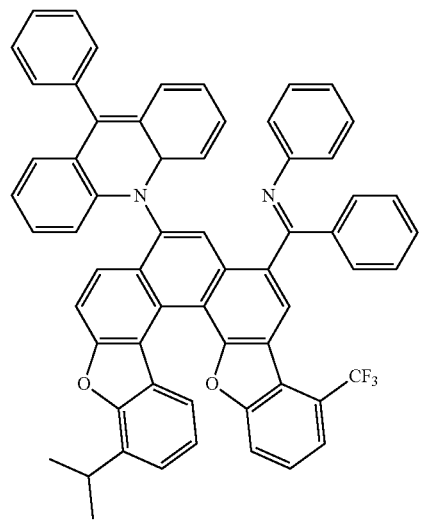

-continued
102
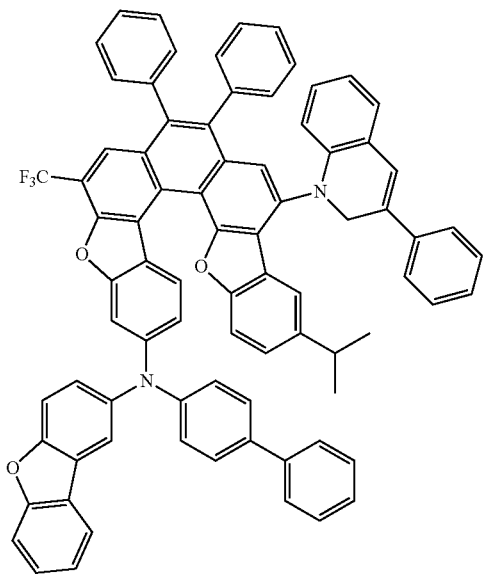
103
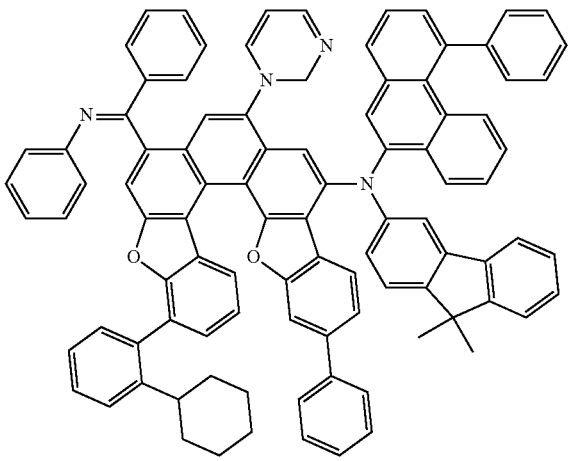
104
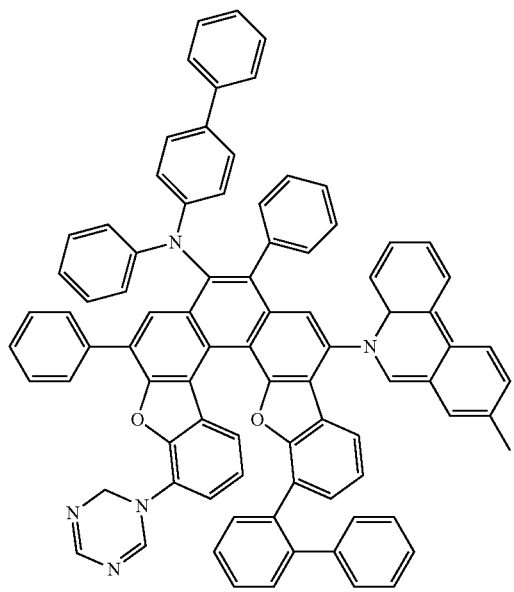
105
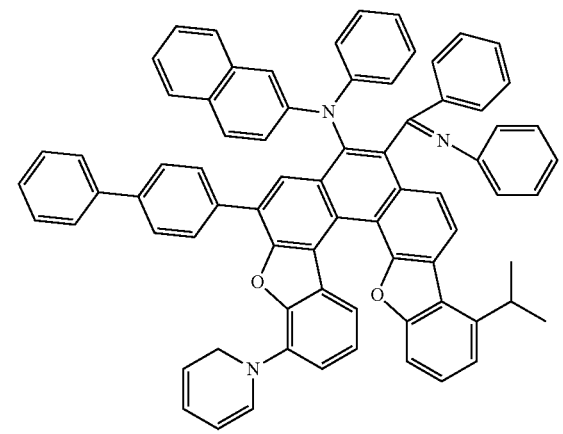
106
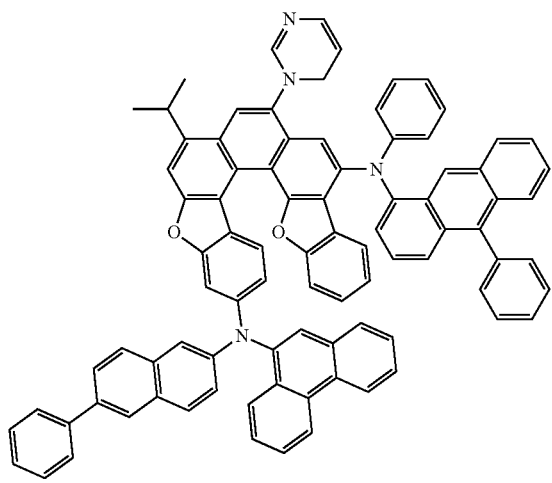
107
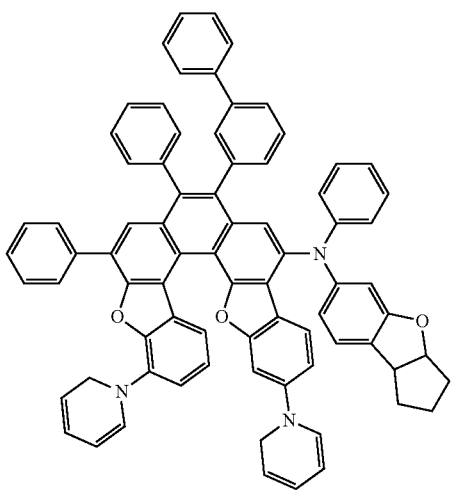

108
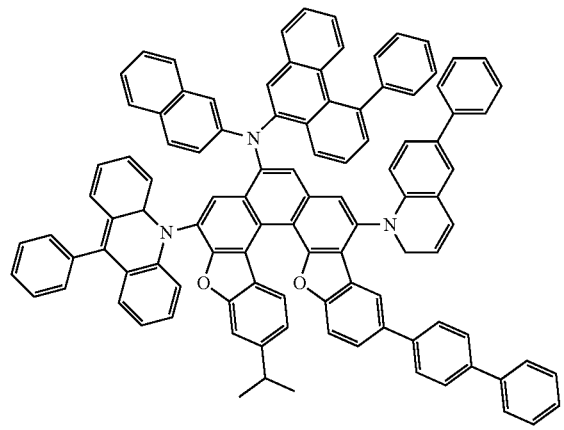
109
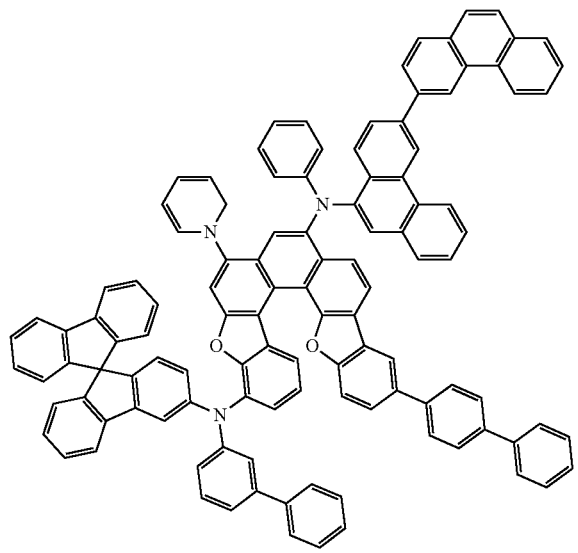
110
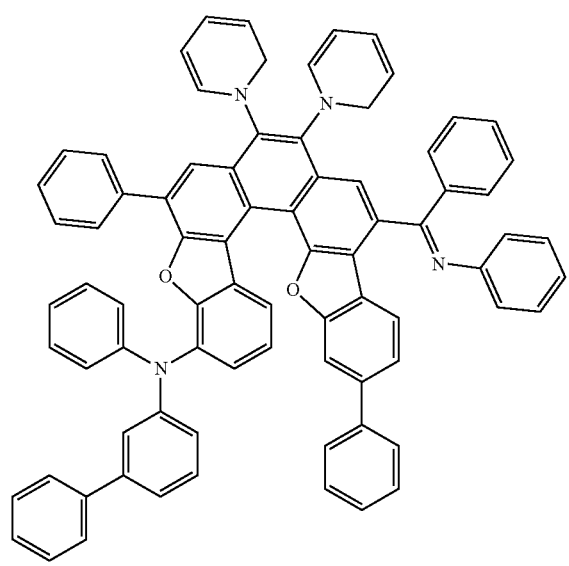
111
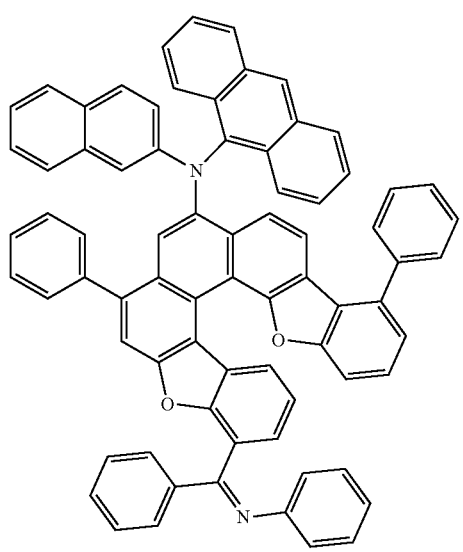

211                                                   212
-continued
112                                                   113
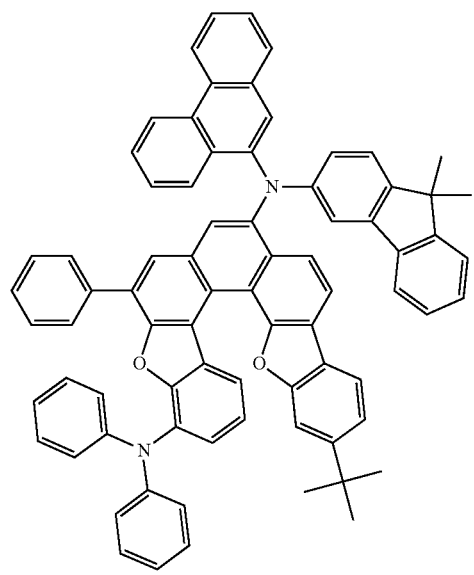    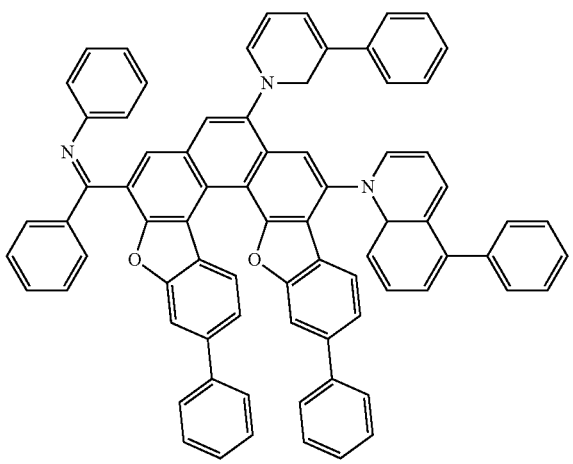
114                                                   115
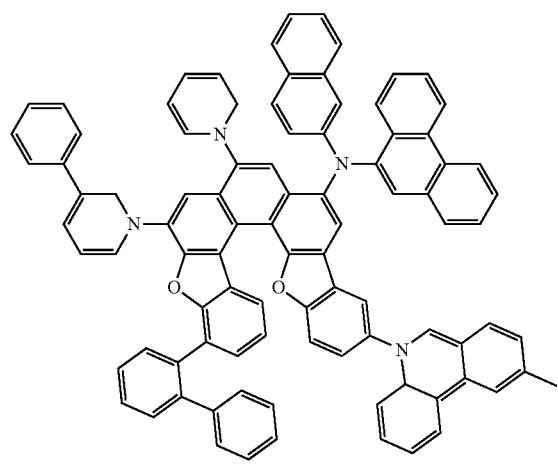    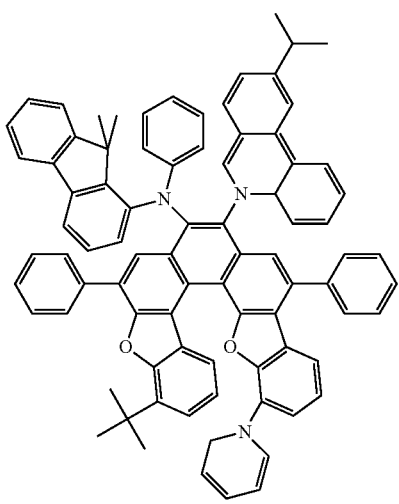

116
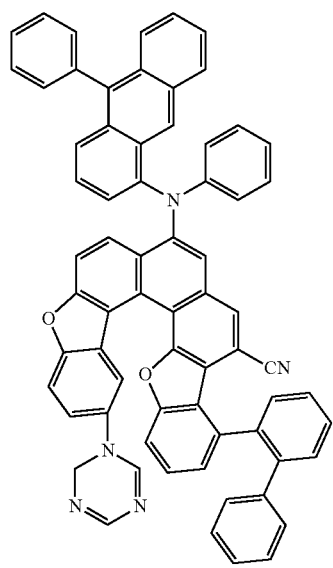
117
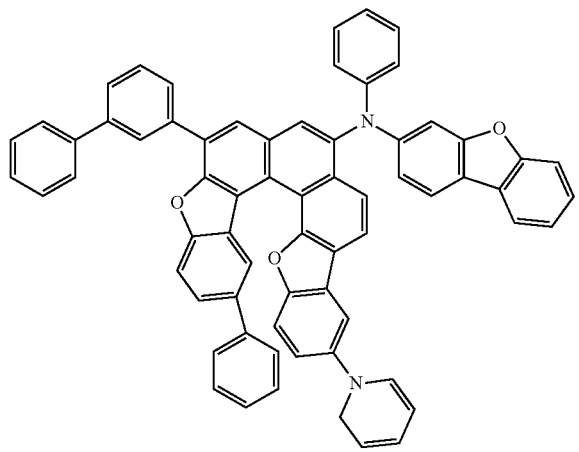
118
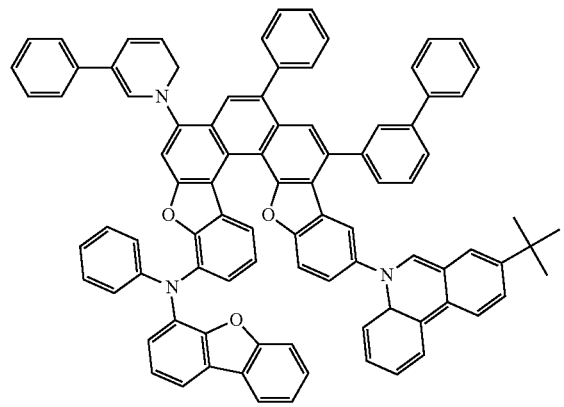
119
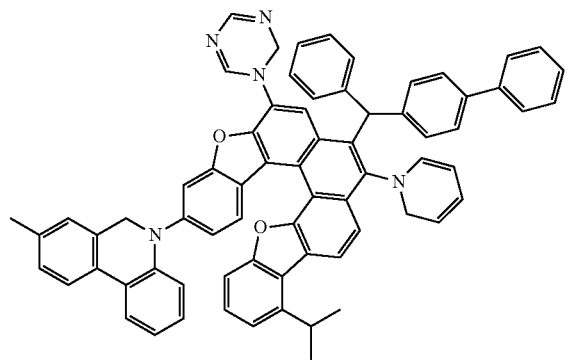
120
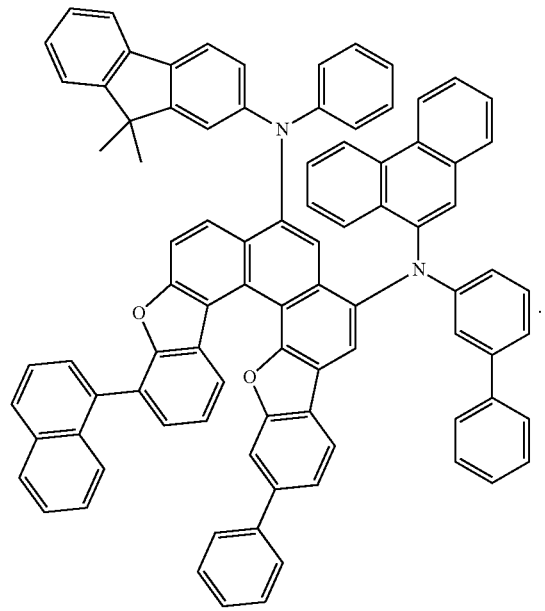

8. An organic electroluminescent device including an organic electroluminescent compound of the following structural formula:

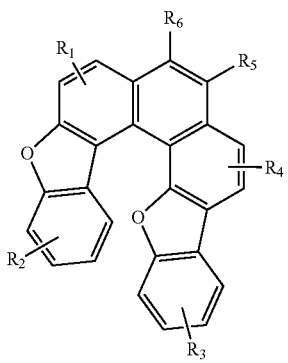

wherein $R_1$ is selected from hydrogen, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_2$ is selected from hydrogen, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_3$ is selected from hydrogen, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_4$ is selected from a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group;

$R_5$ and $R_6$ are, each dependently, selected from, a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group or a triazinyl group.

9. The blue fluorescence dopant according to claim 1, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group or a triazinyl group among $R_1$, at least one hydrogen atom thereof is substituted with a C1-C20 linear or branched alkyl group, a C3-C24 cyclic alkyl group, a C1-C20 alkoxyl group, a halogen atom, CN, $CF_3$, a $Si(CH_3)_3$ group, or a C6-C50 aryl group.

10. The organic electroluminescent device according to claim 8, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group among $R_2$, at least one hydrogen atom is substituted with a C1-C20 linear or branched alkyl group, a C3-C24 cyclic alkyl group, a C1-C20 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

11. The organic electroluminescent device according to claim 8, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group among $R_3$, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, or a C6-C60 aryl group.

12. The organic electroluminescent device according to claim 8, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, the pyrimidinyl group, the quinolyl group and the triazinyl group among $R_4$, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

13. The organic electroluminescent device according to claim 8, wherein for the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group among $R_5$ and $R_6$, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-40.
14. The organic electroluminescent device according to claim 8, wherein the organic electroluminescent compound is any one of the following compounds:
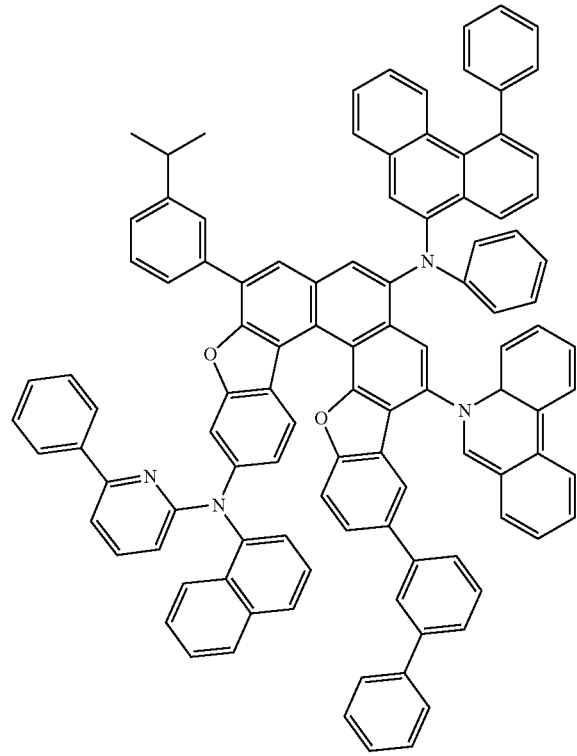
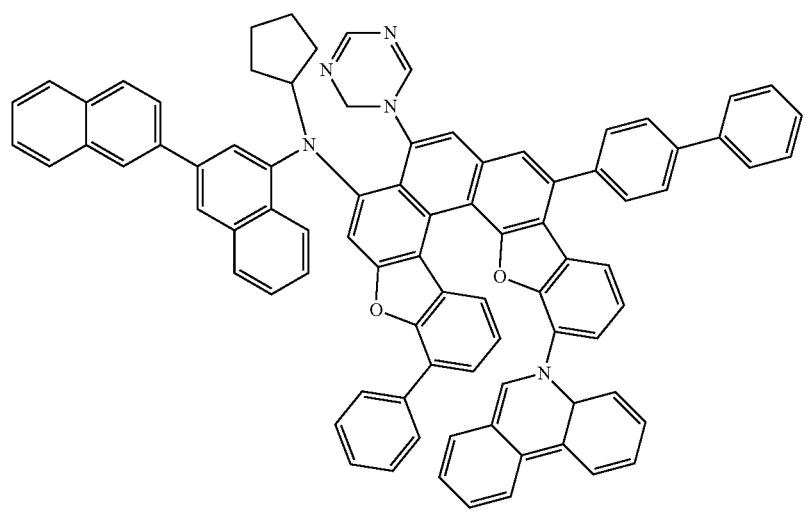

-continued
3
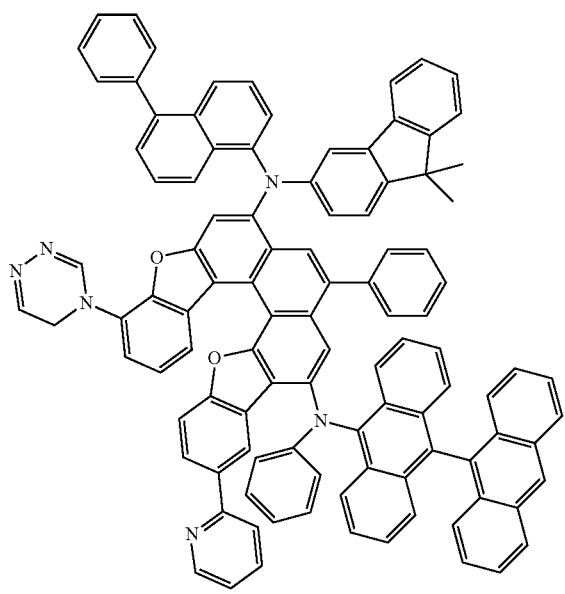
4
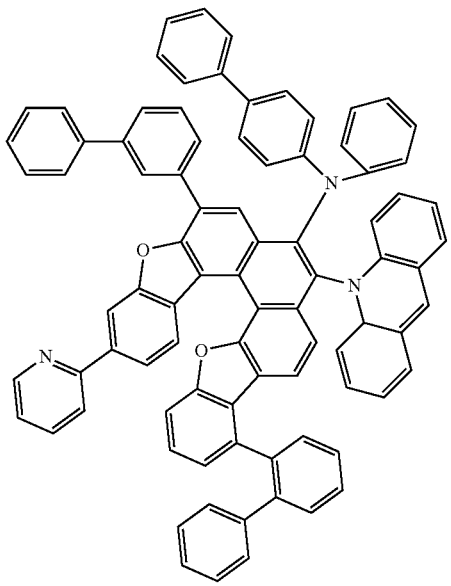
5
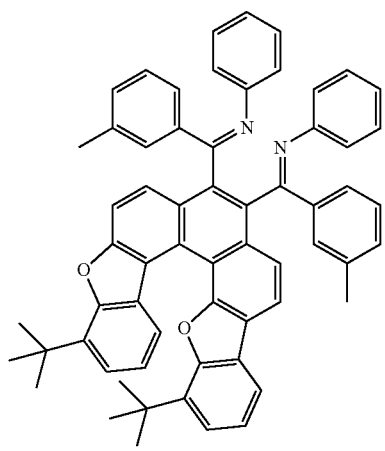
6
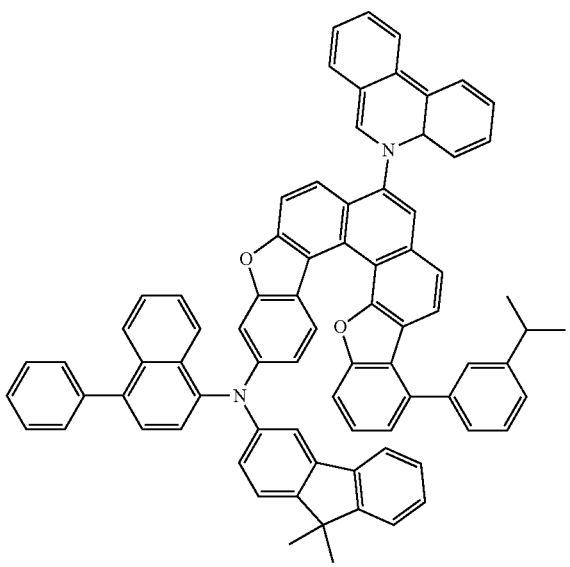

-continued
7
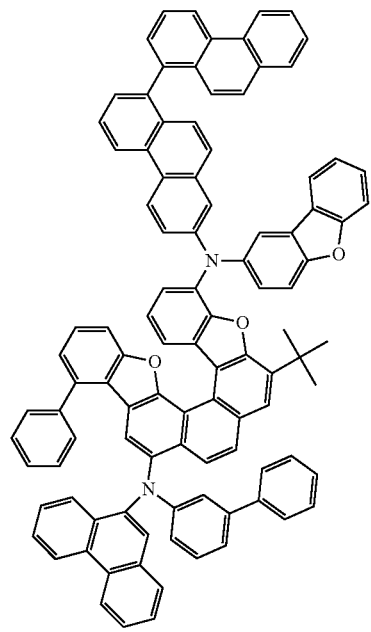
8
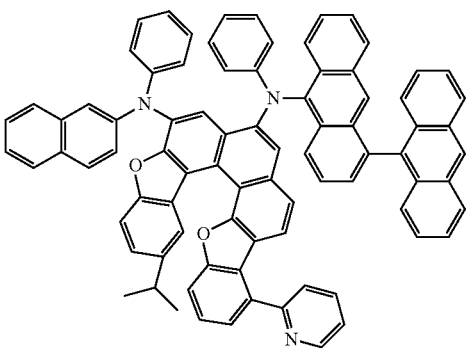
9
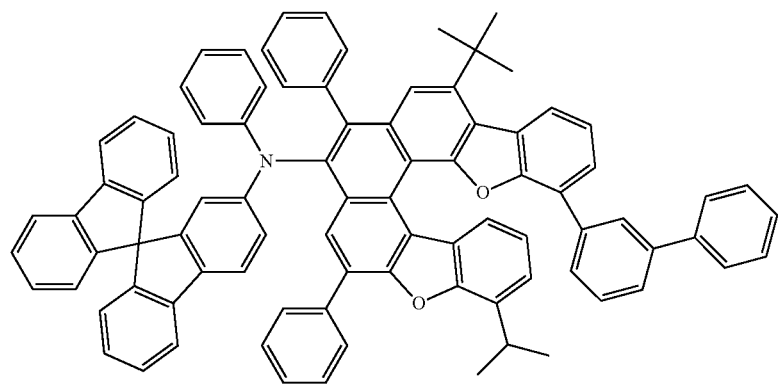
10
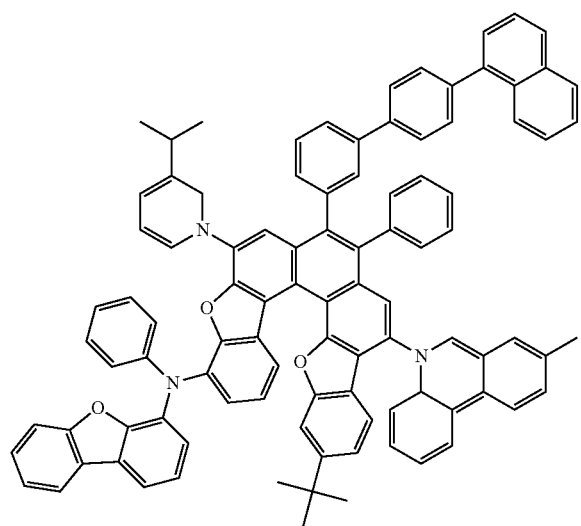
11
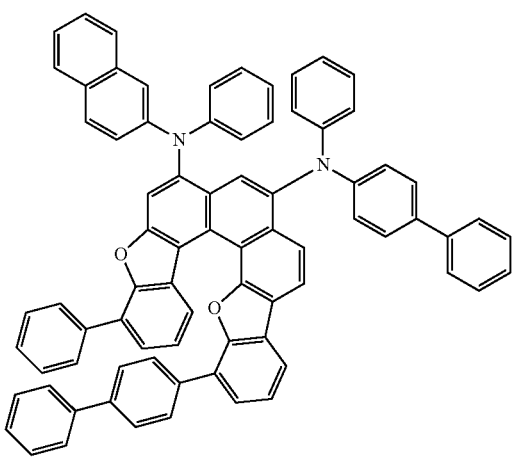

-continued
12
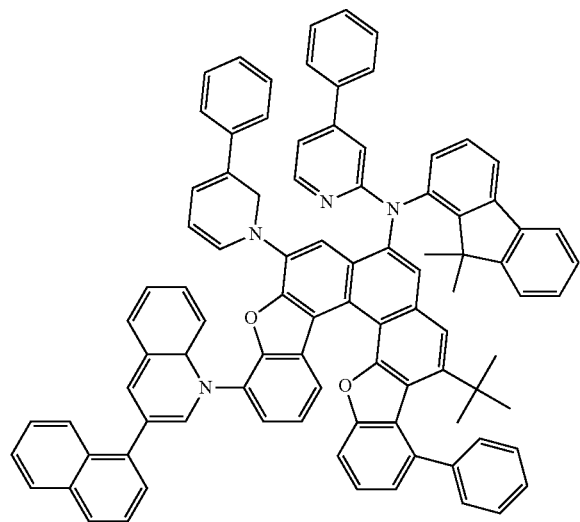
13
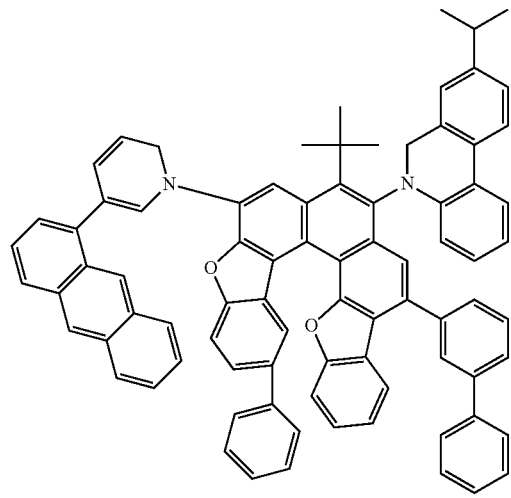
14
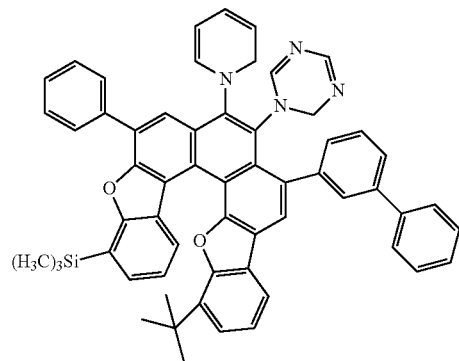
15
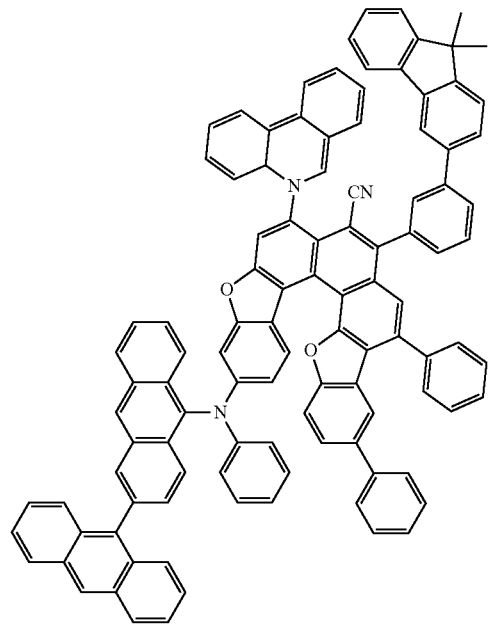

-continued
16
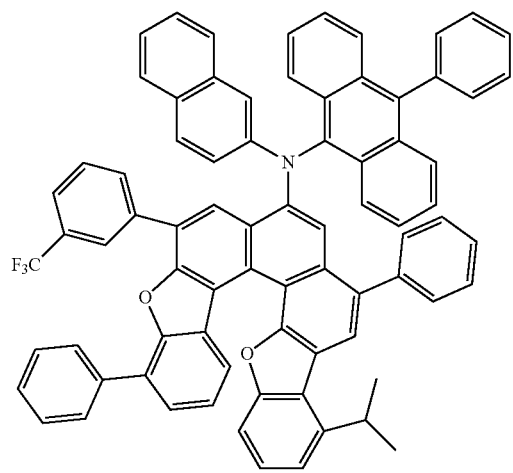
17
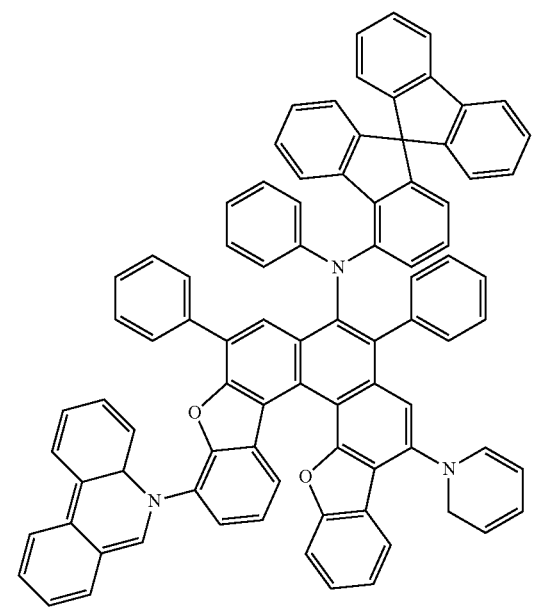
18
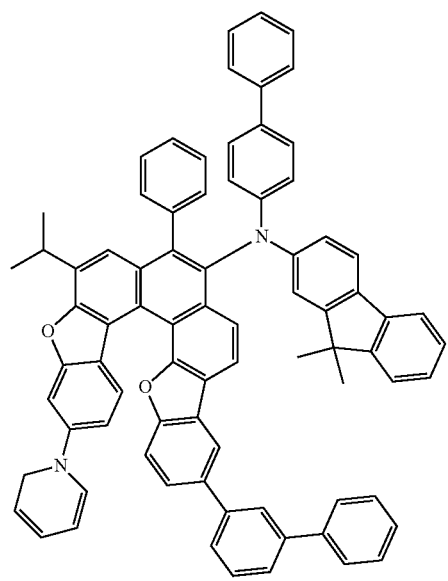
19
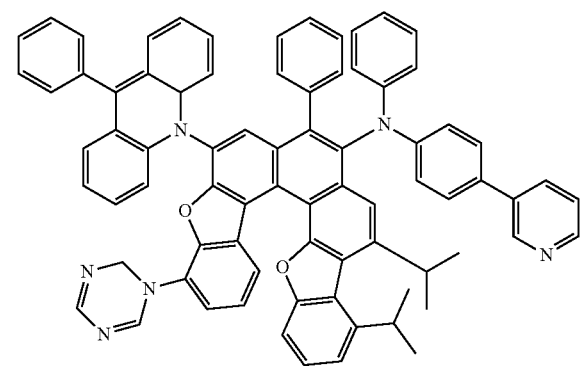

-continued
20
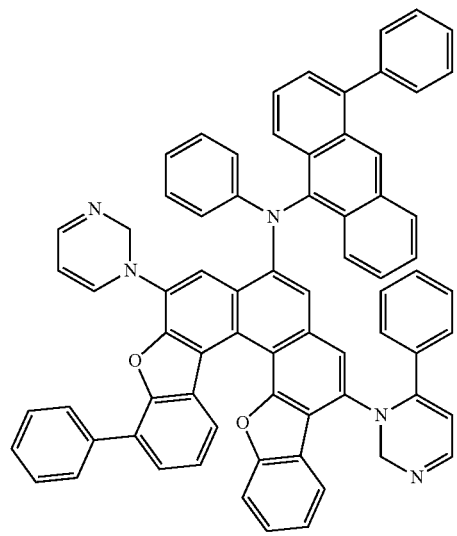
21
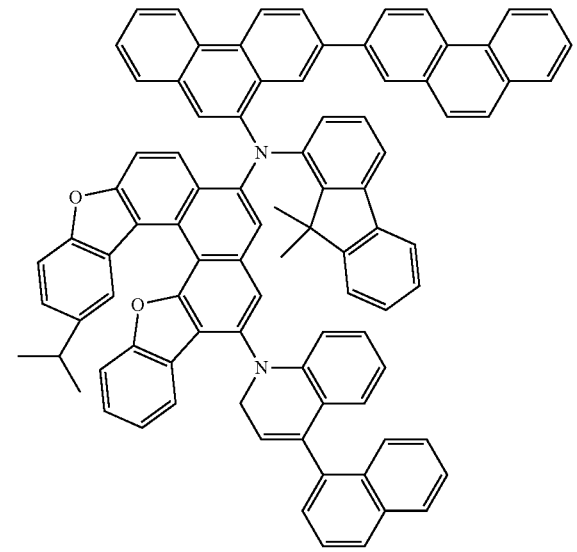
22
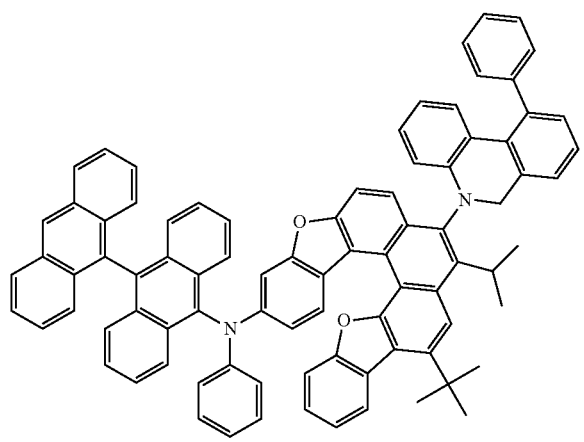
23
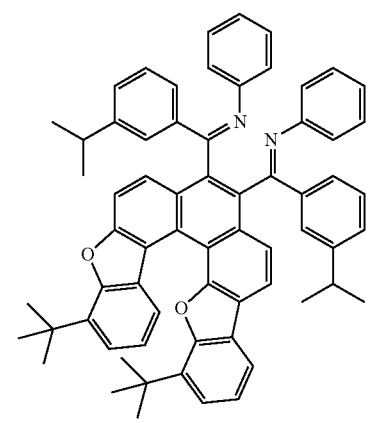
24
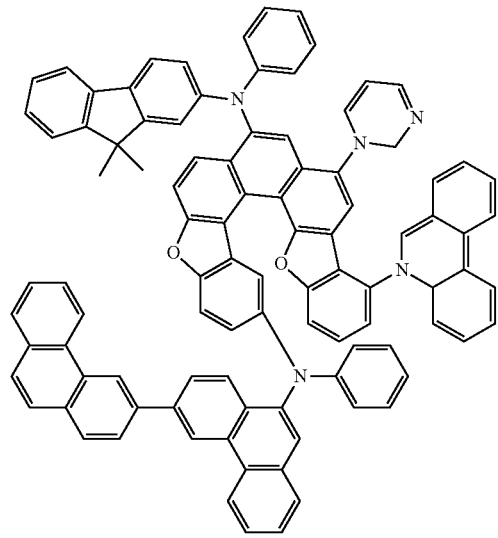
25
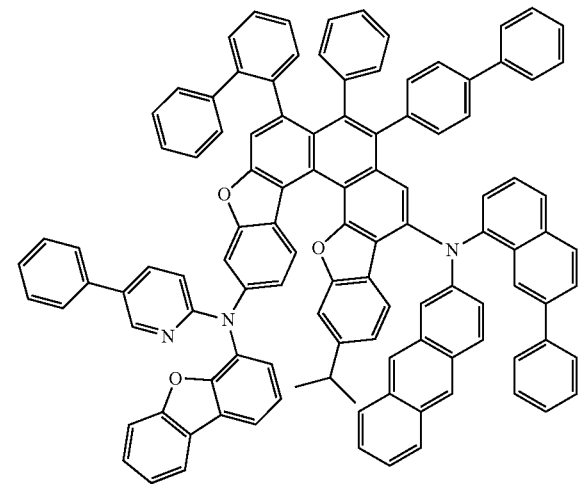

-continued
26
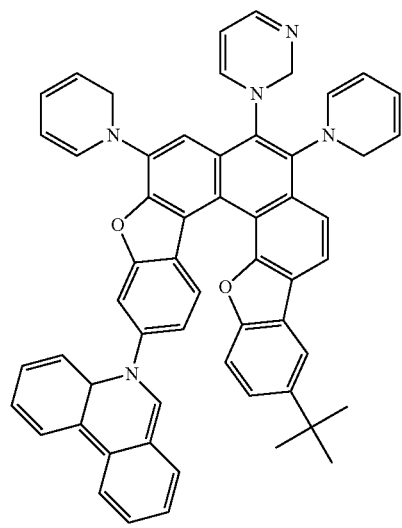
27
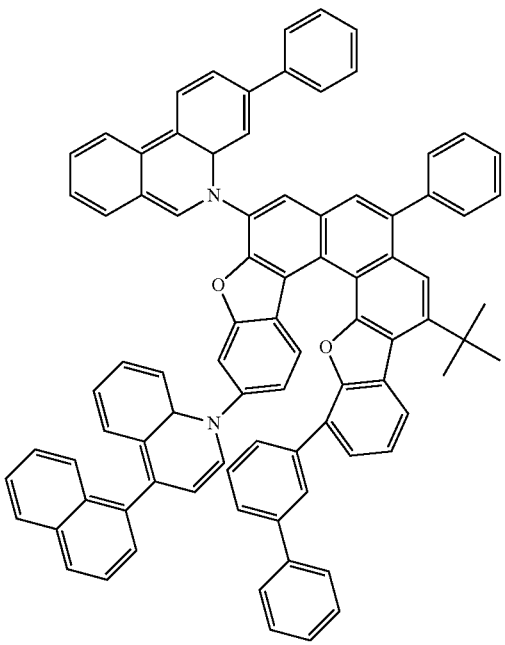
28
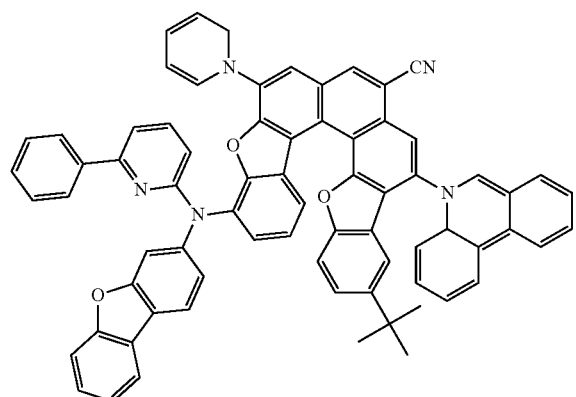
29
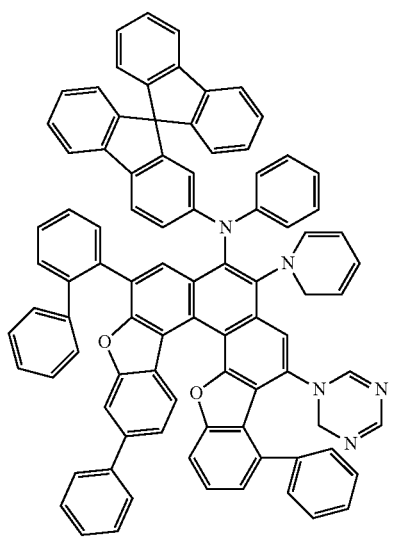

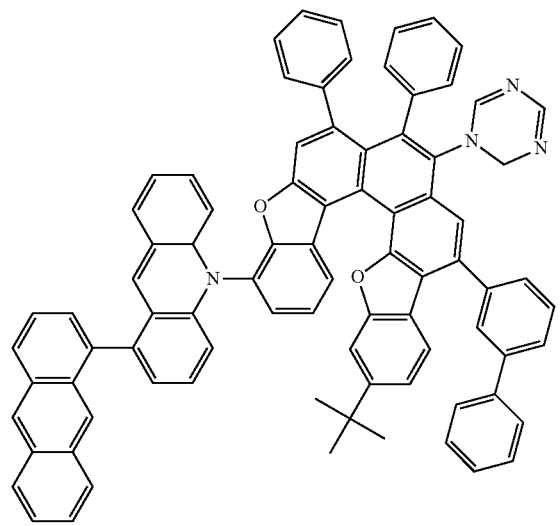
30
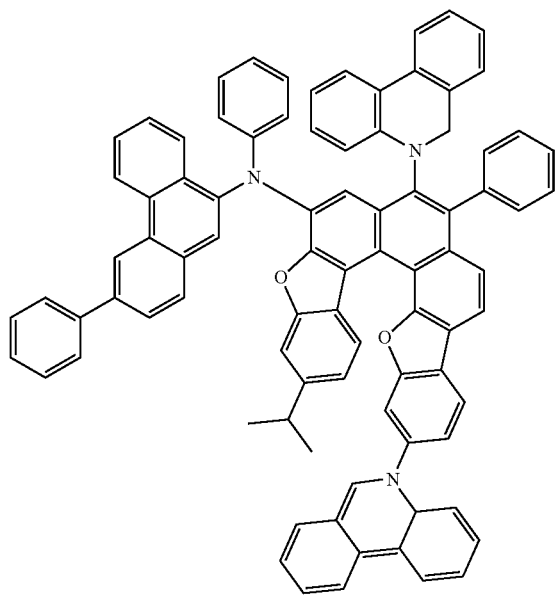
31
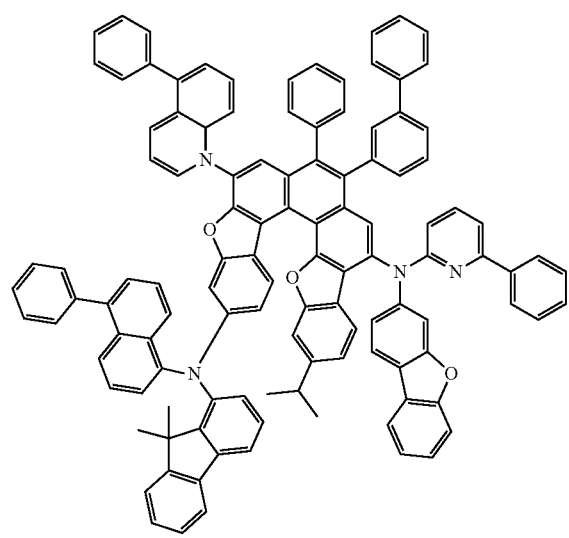
32
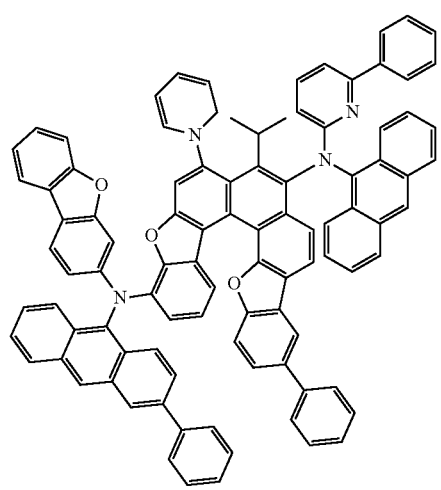
33

-continued
34
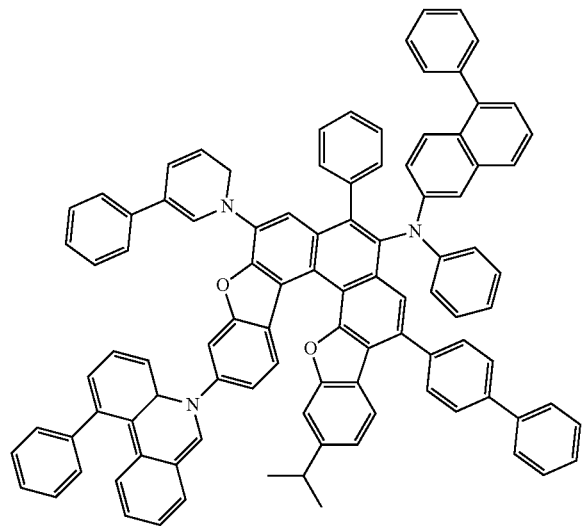
35
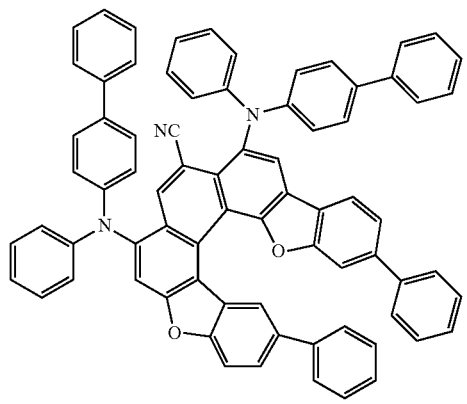
36
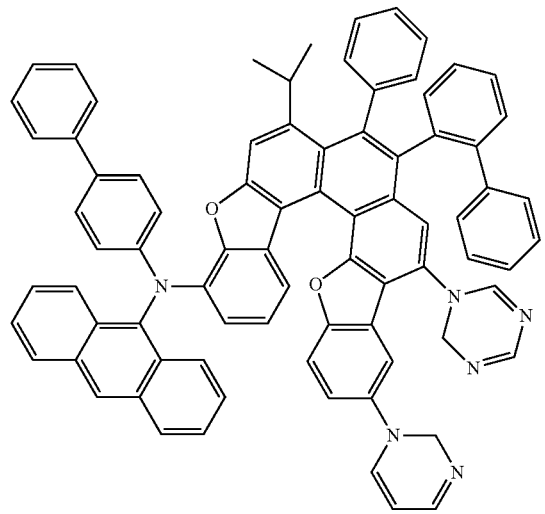
37
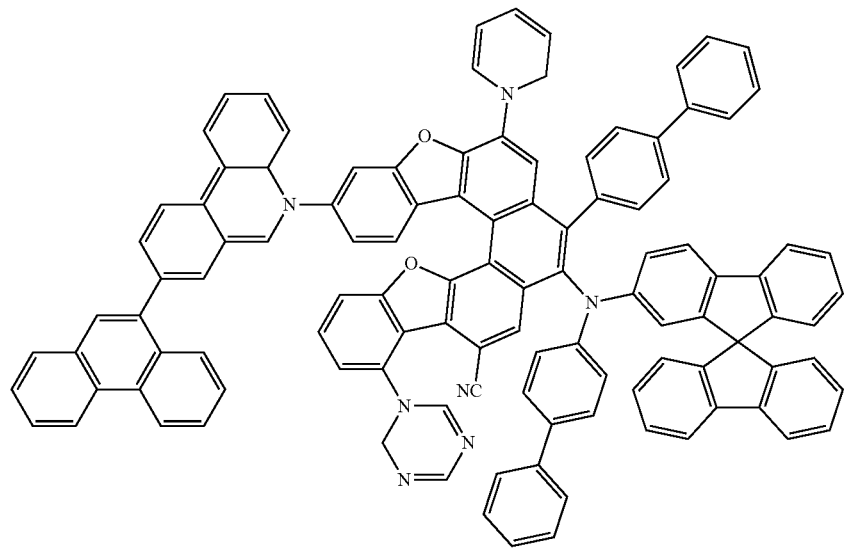

-continued
38
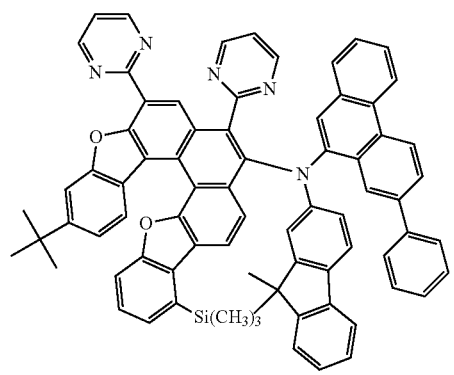
39
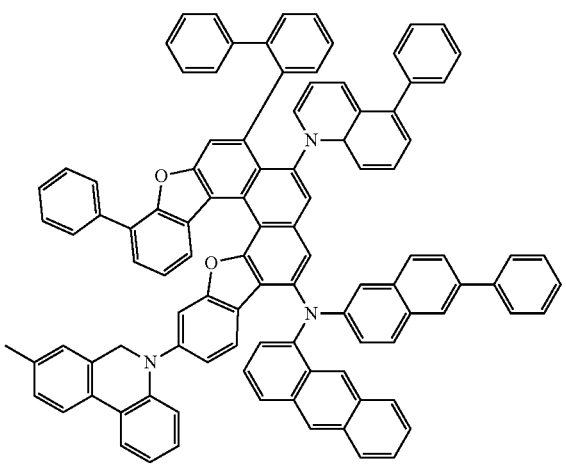
40
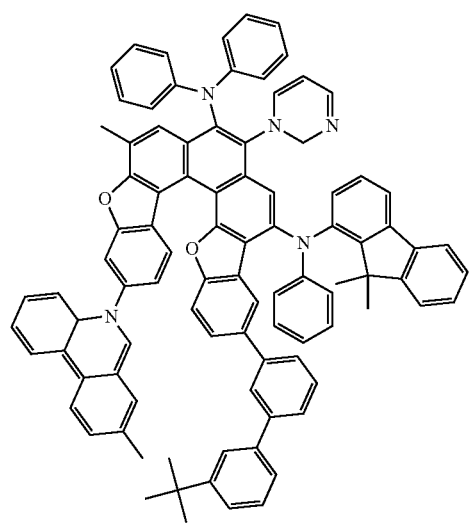
41
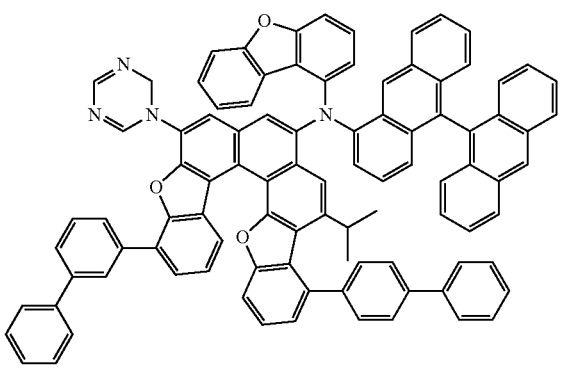
42
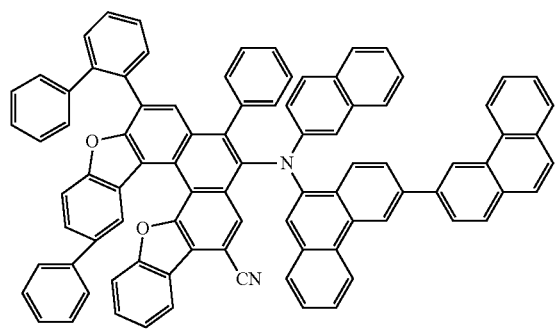
43
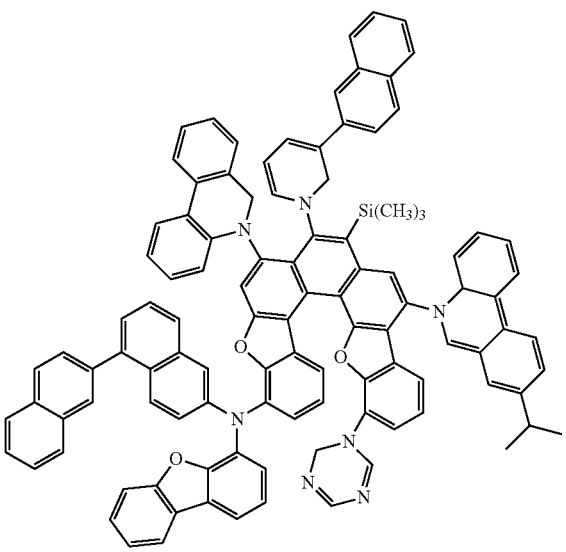

44
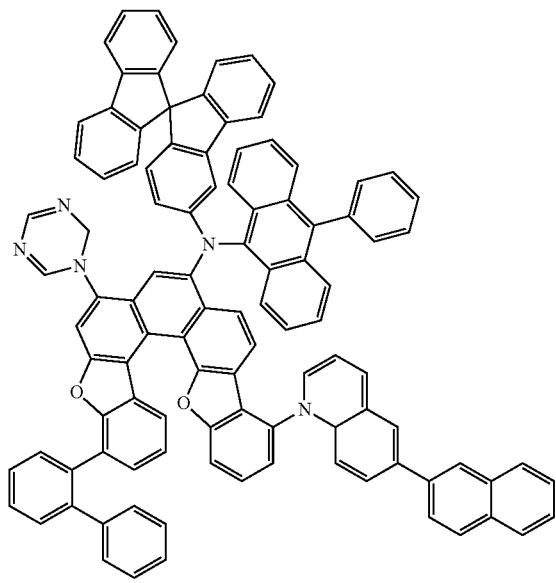
45
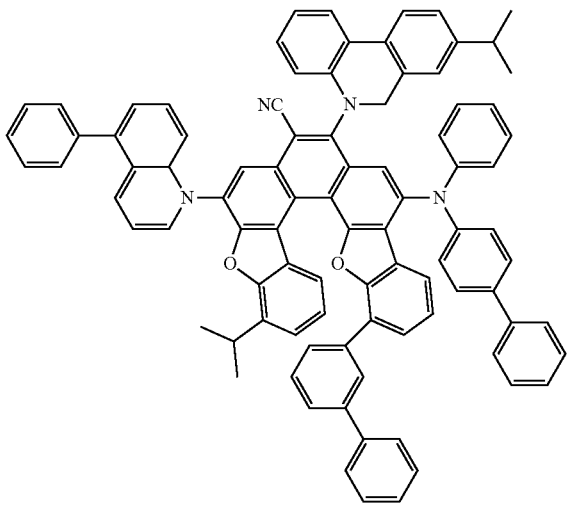
46
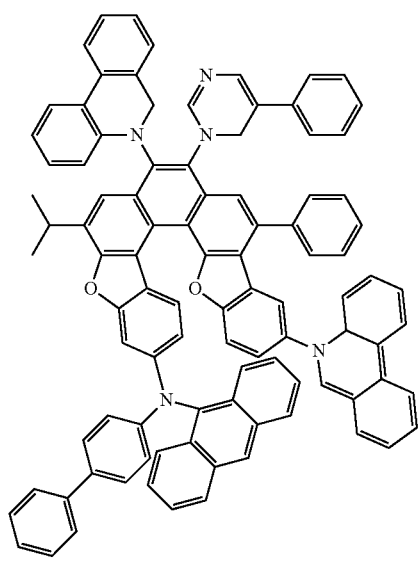
47
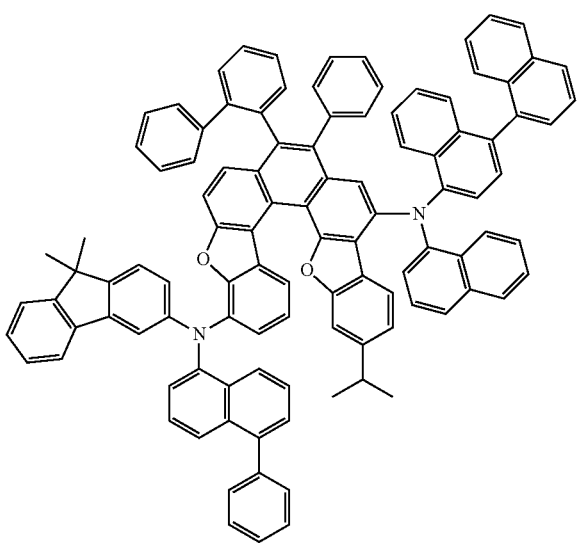

239 240
-continued
48 49
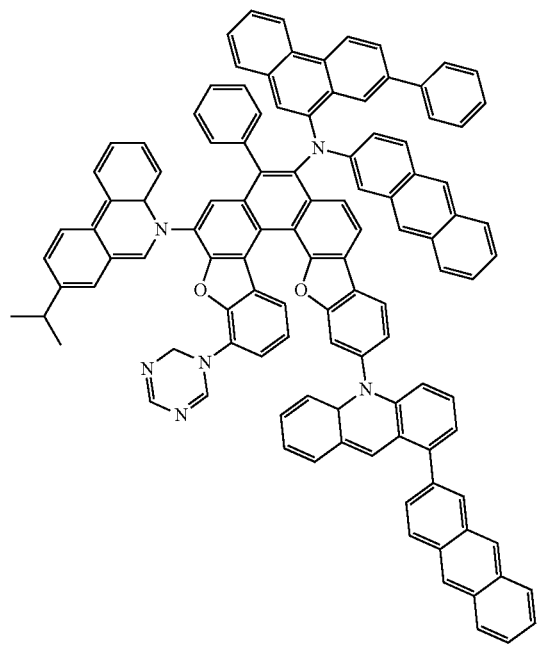 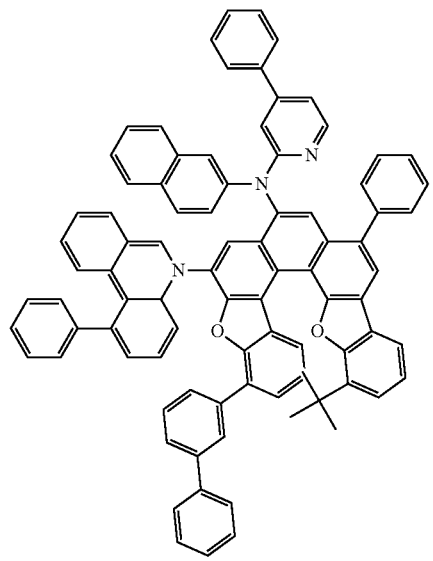
50 51
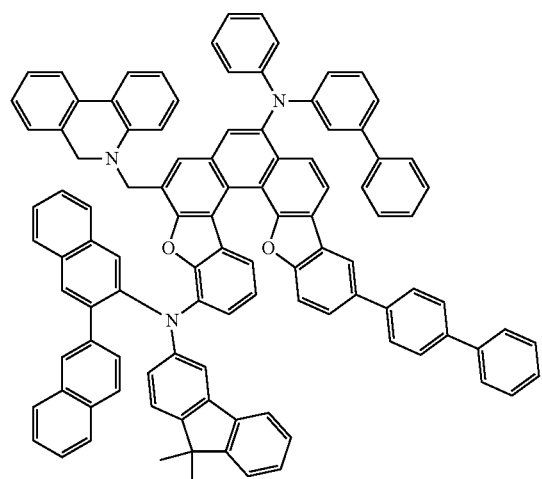 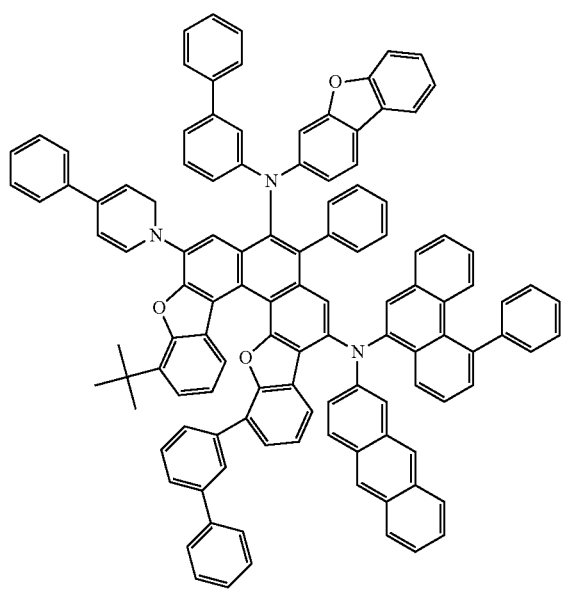

-continued
52
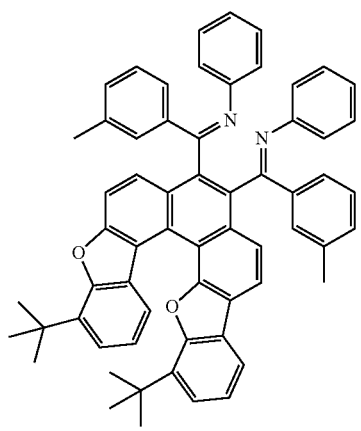
53
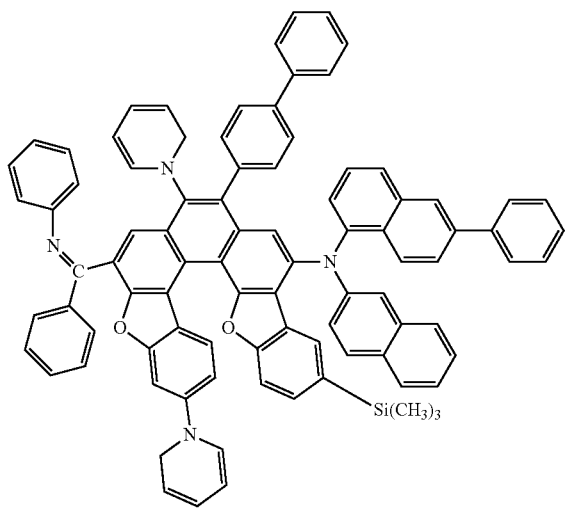
54
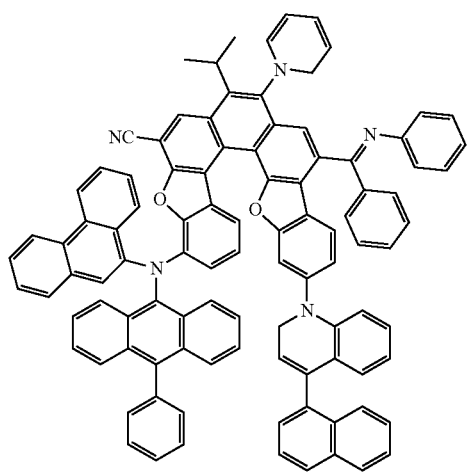
55
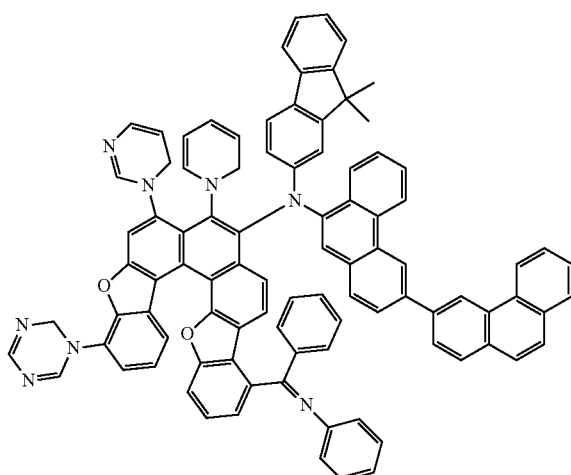
56
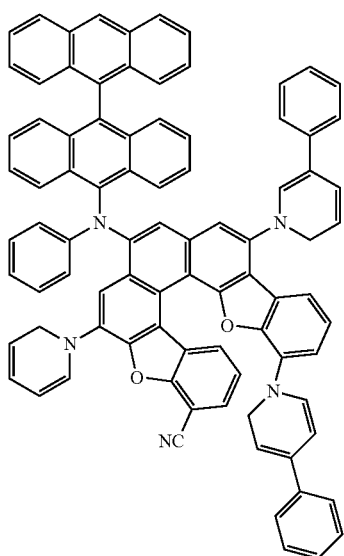
57
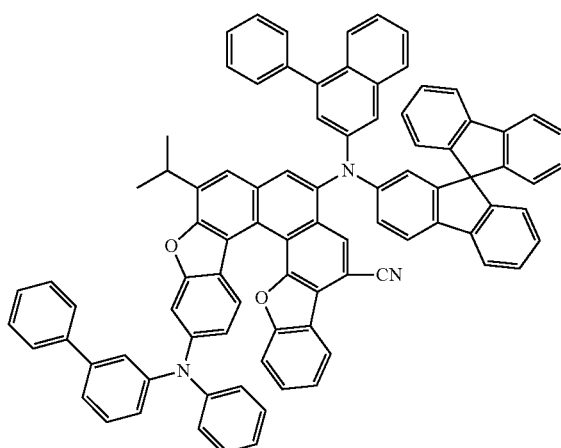

-continued
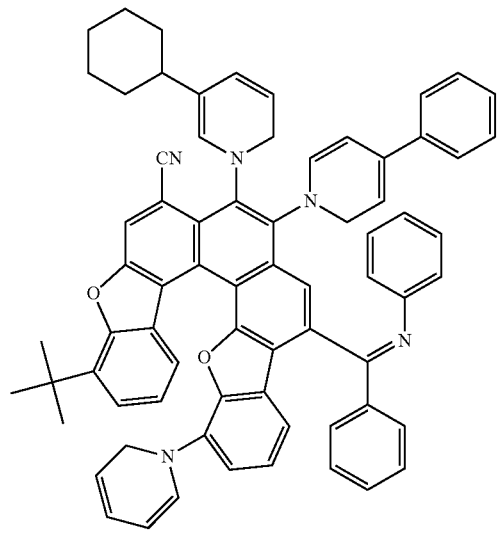
58
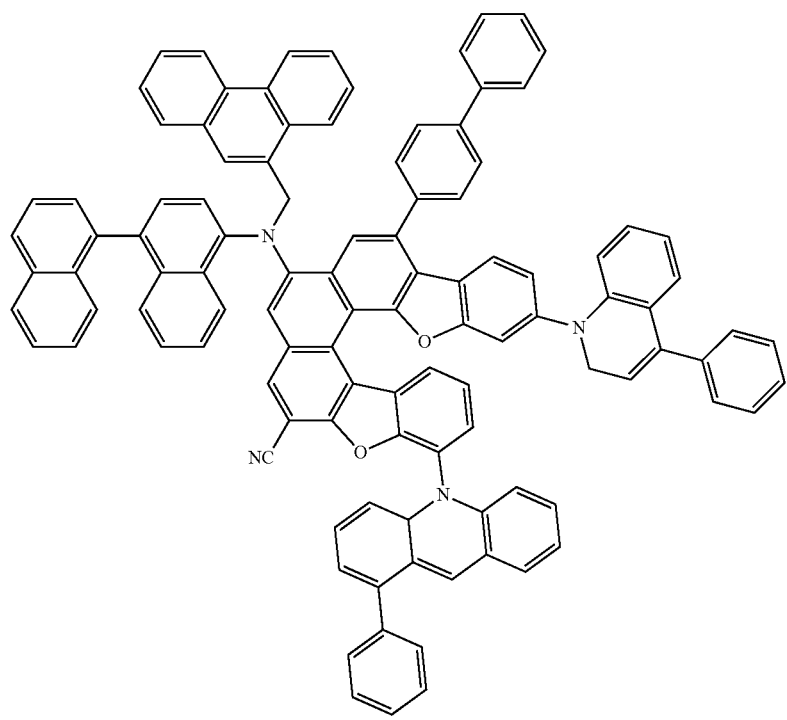
59

-continued
60
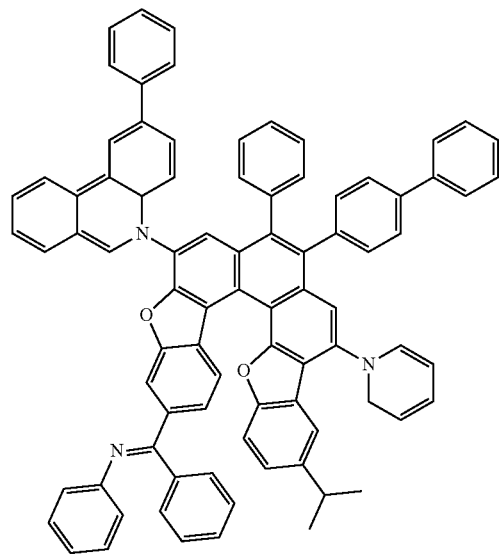
61
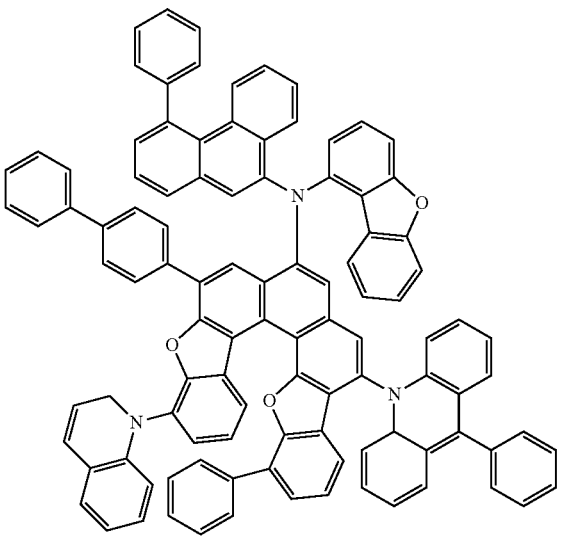
62
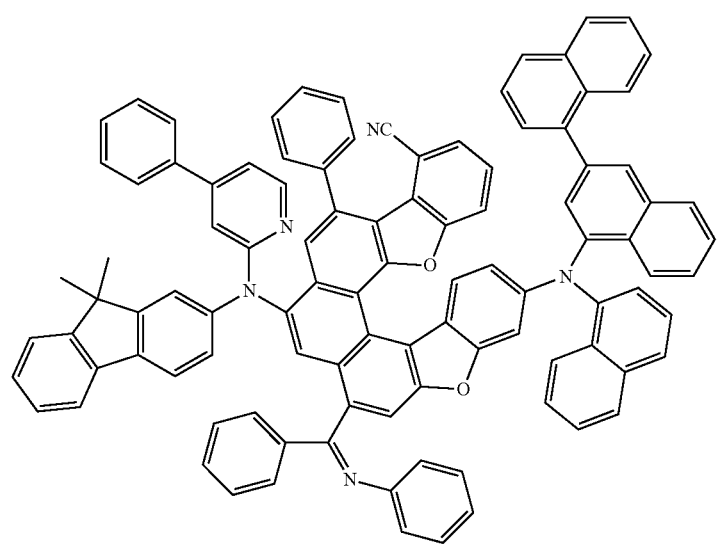
63
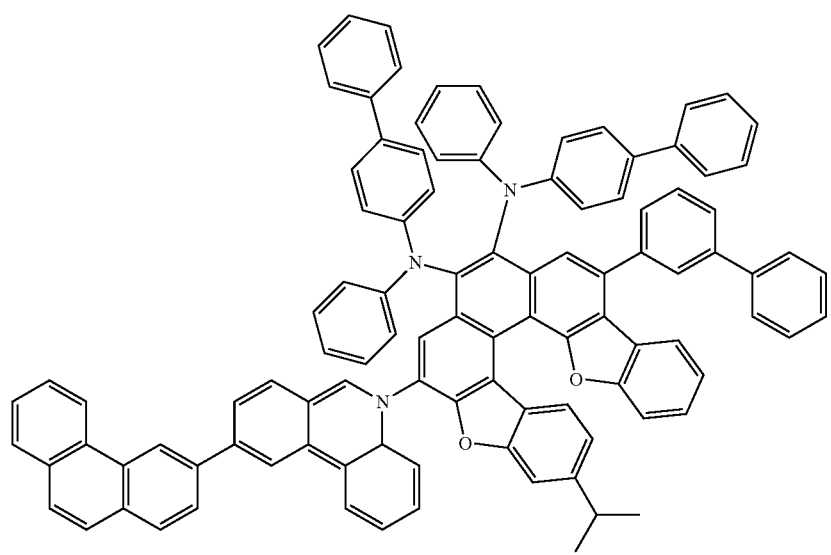

-continued
64
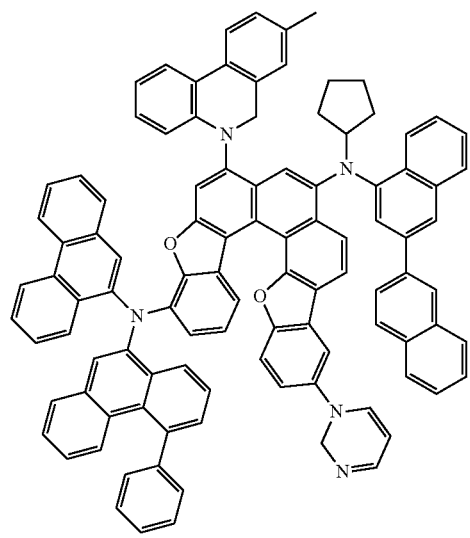
65
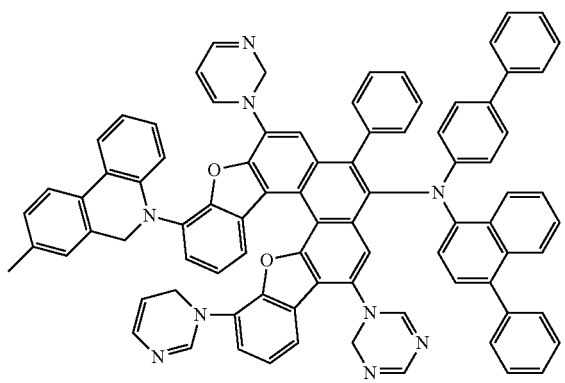
66
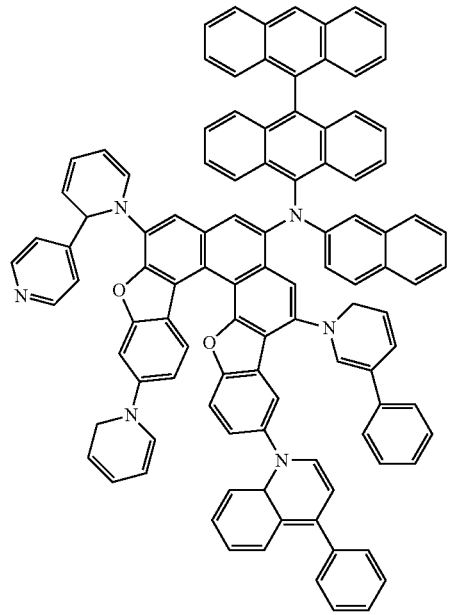
67
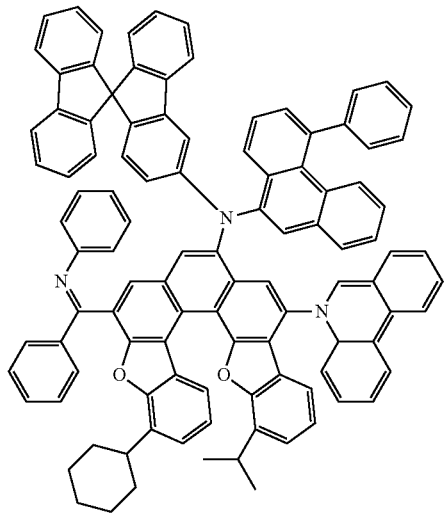

-continued
68
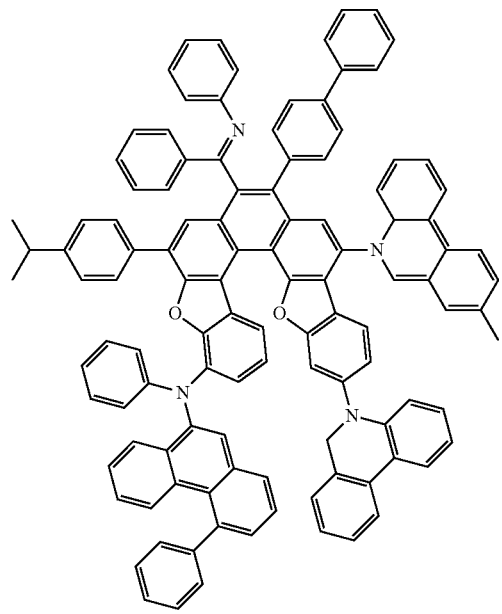
69
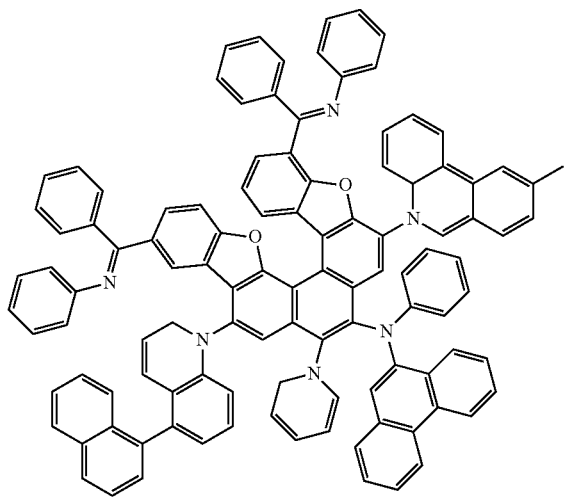
70
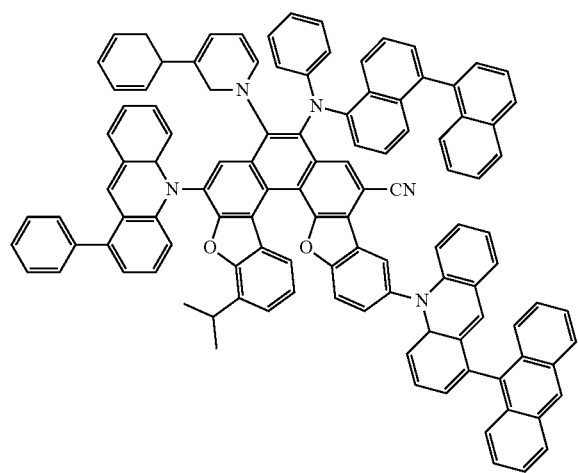
71
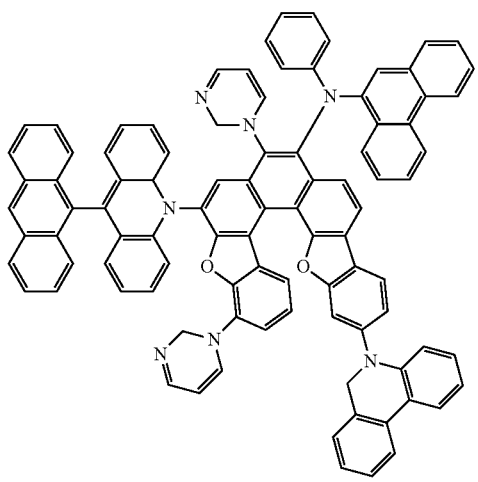

72
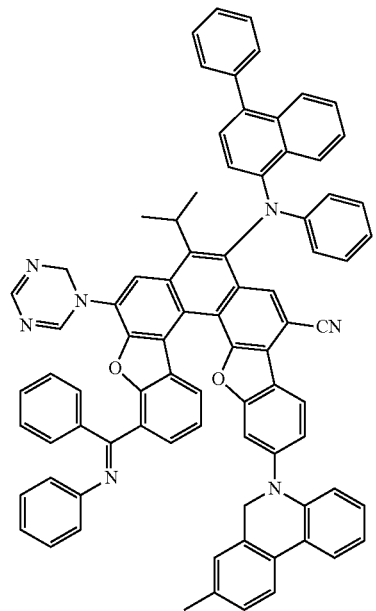
73
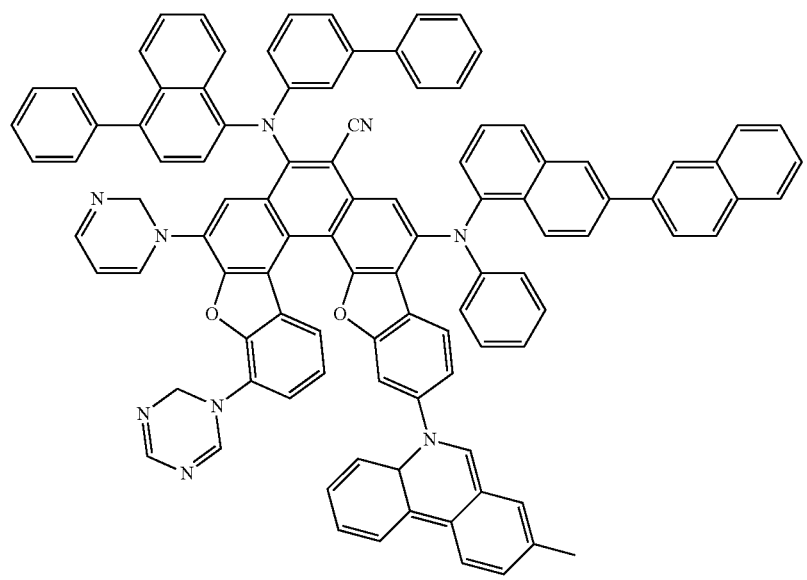

-continued
74
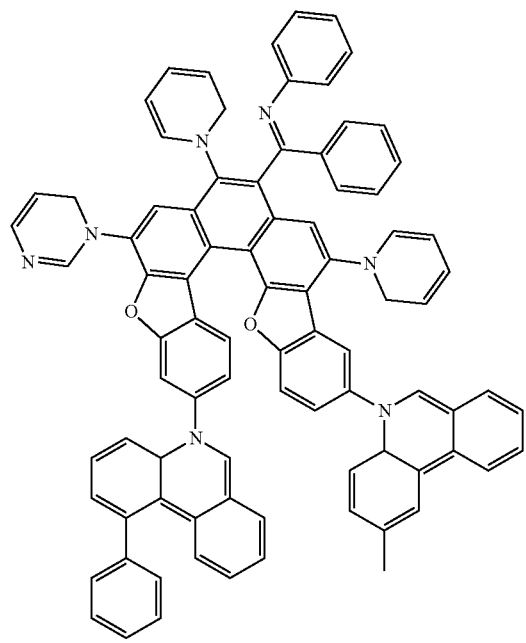
75
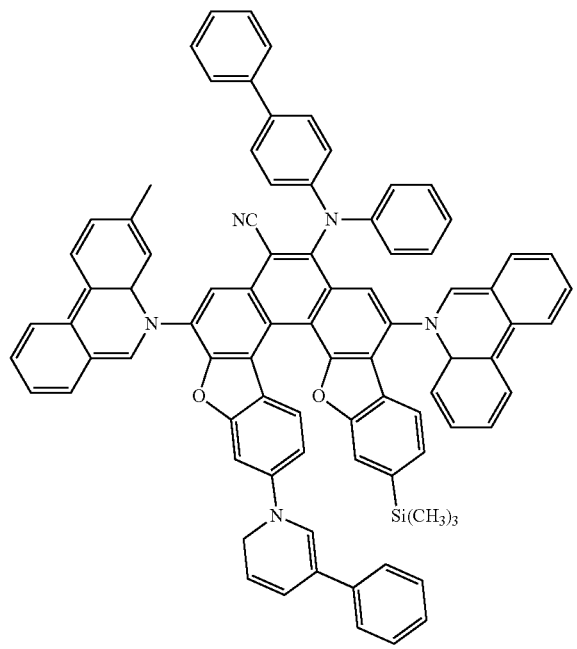
76
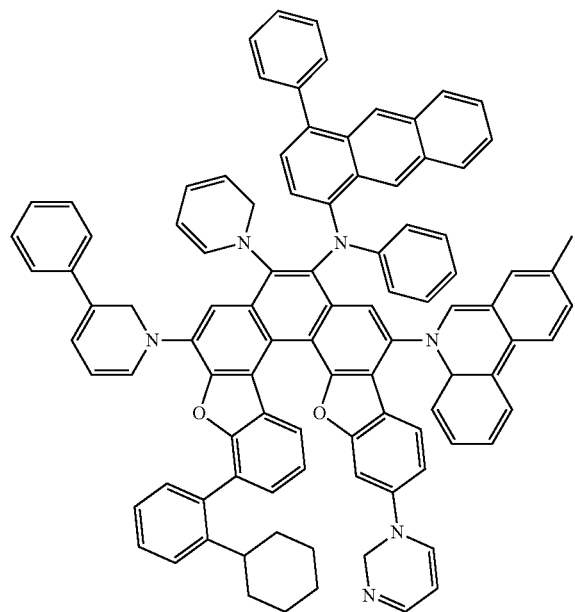
77
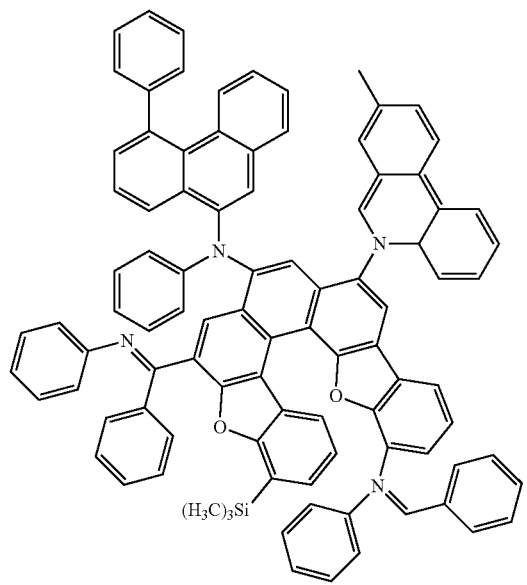

78
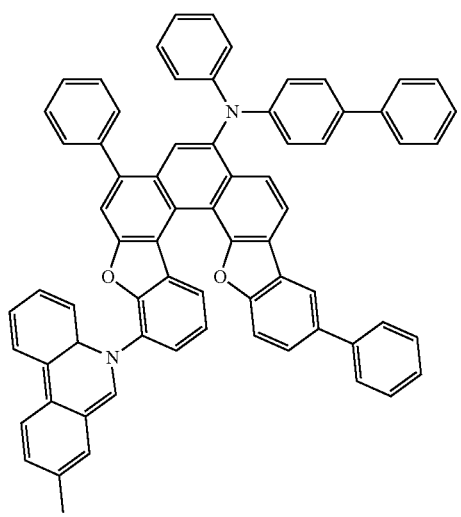
79
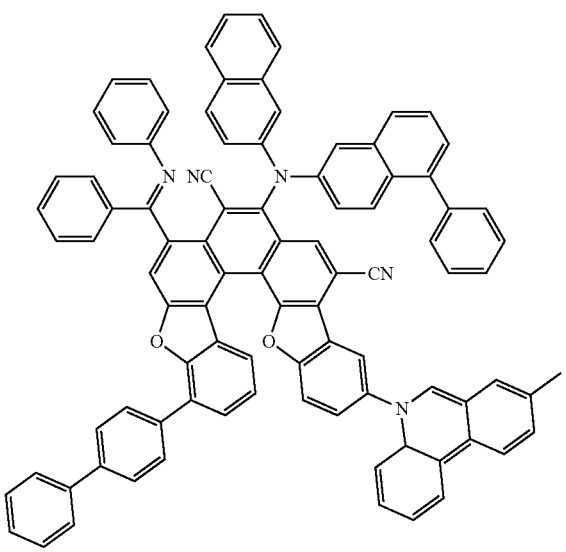
80
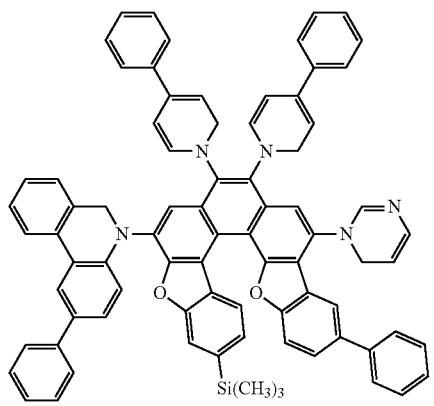
81
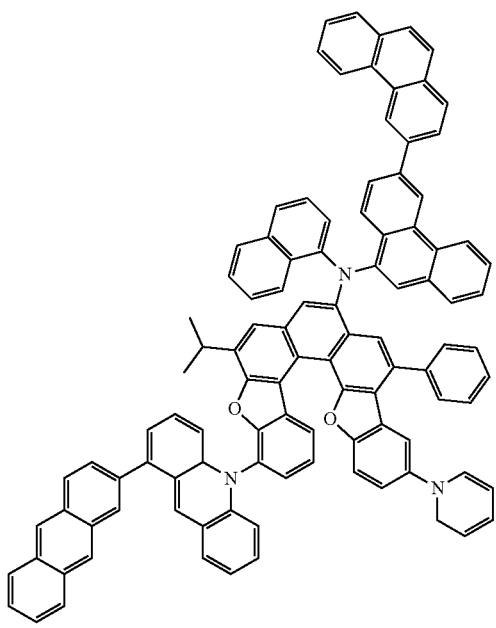

-continued
82
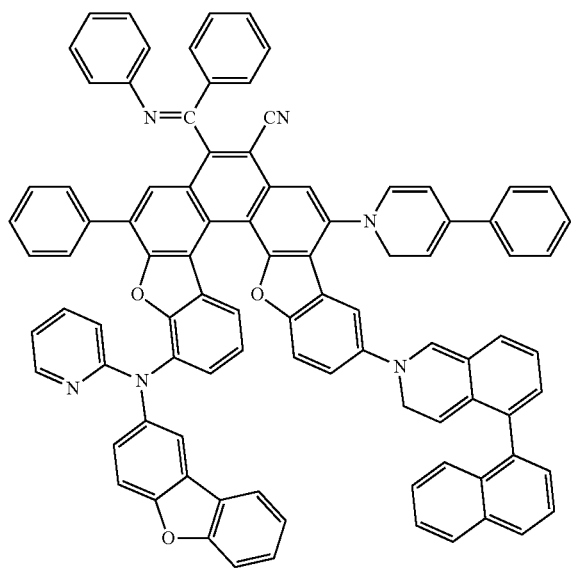
83
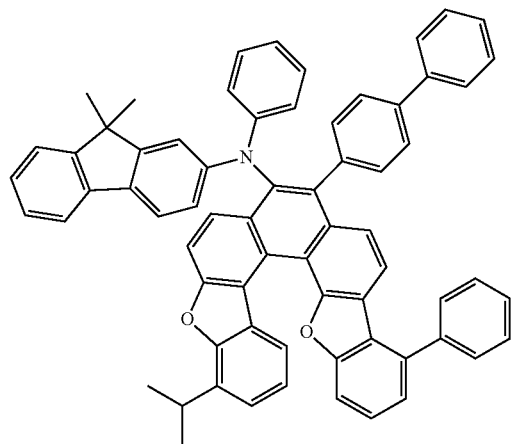
84
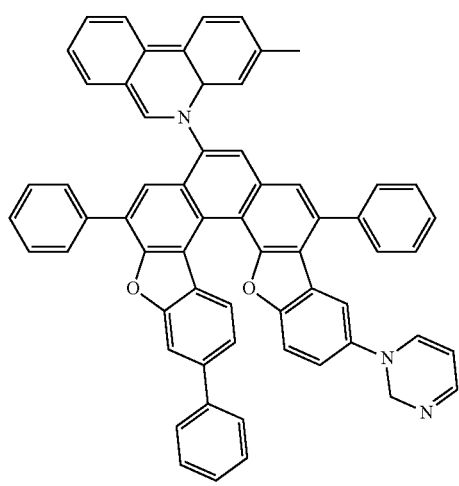
85
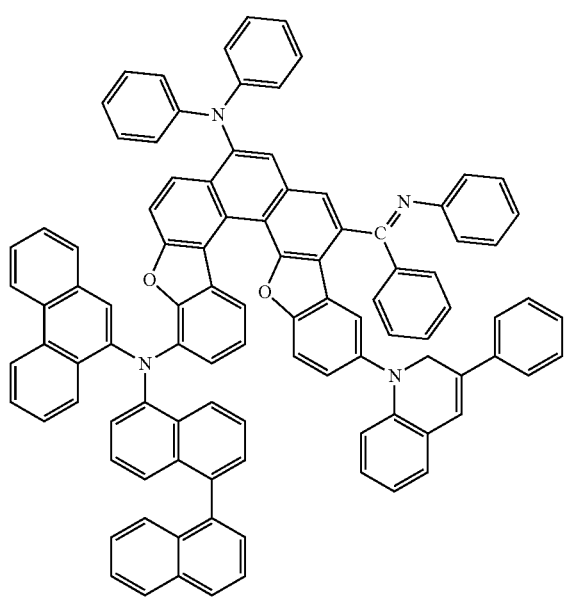

-continued
86
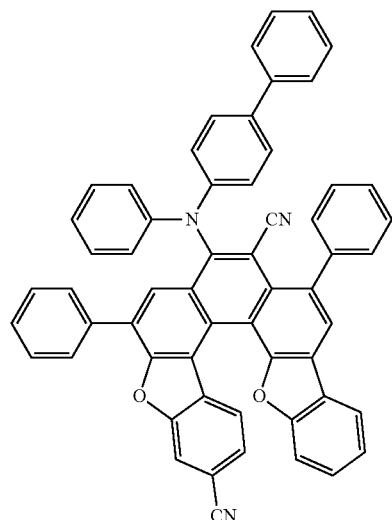
87
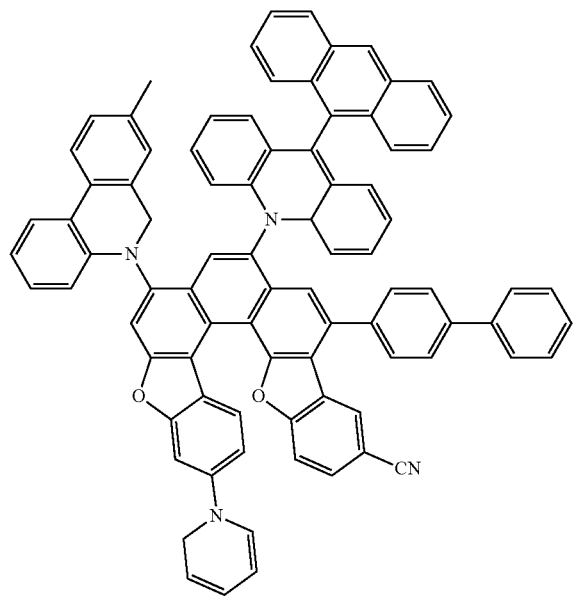
88
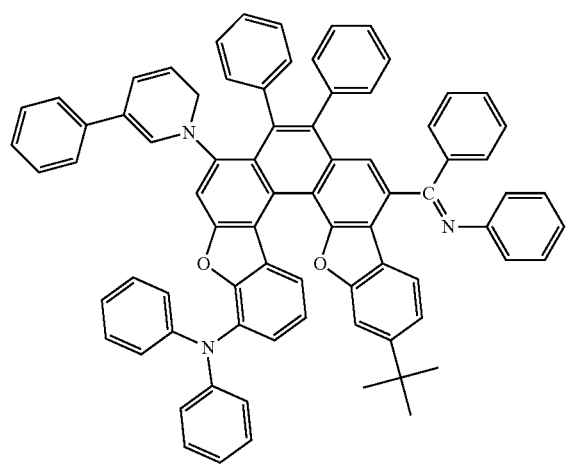
89
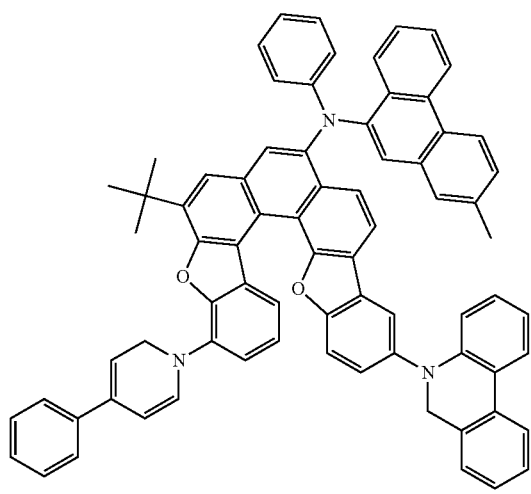

90
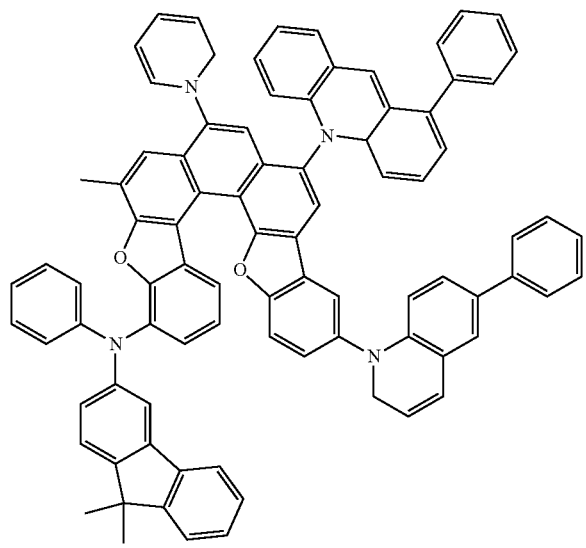
91
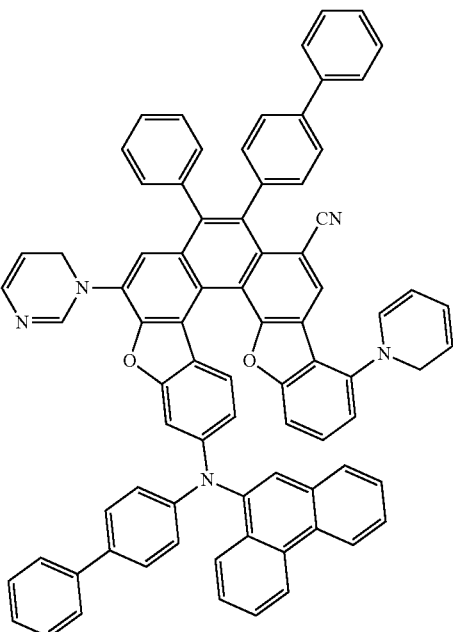
92
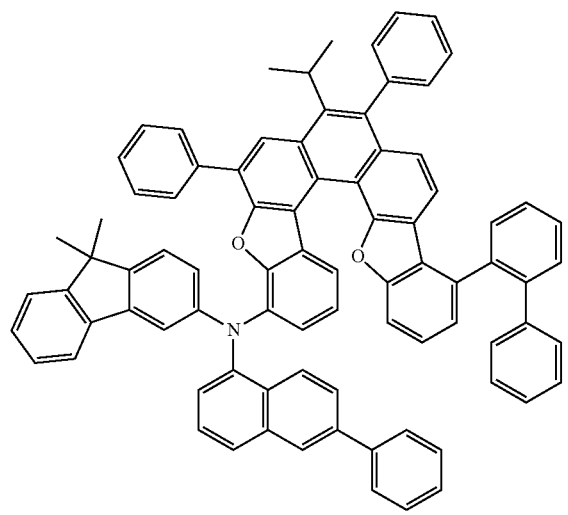
93
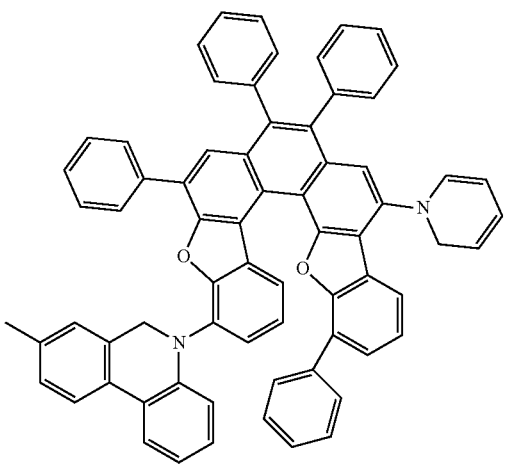

94
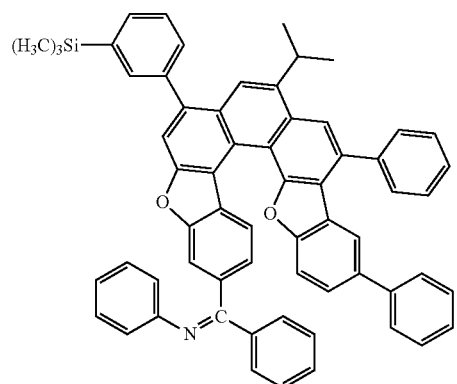
95
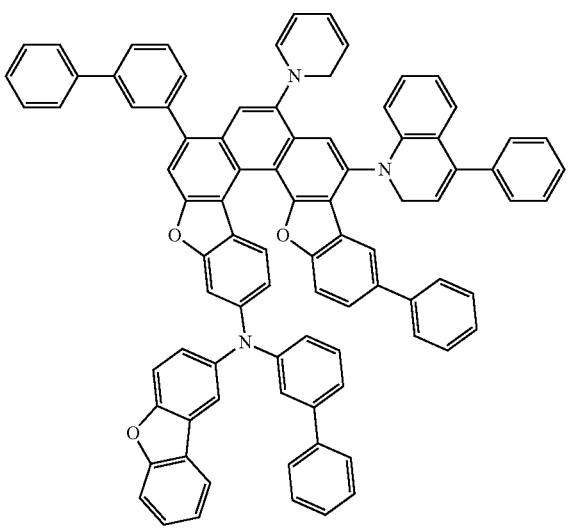
96
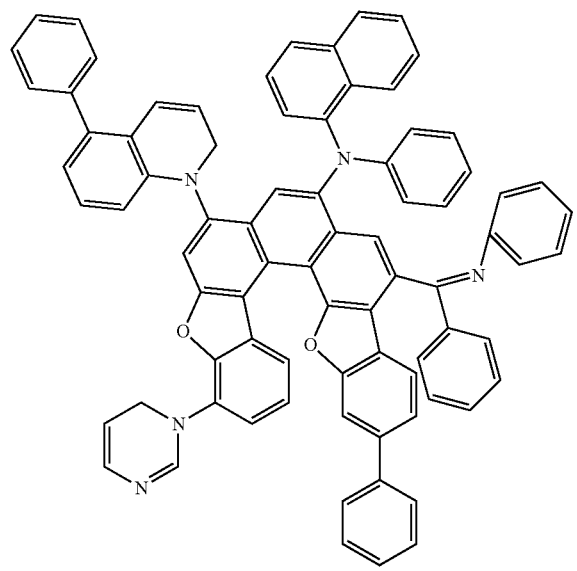
97
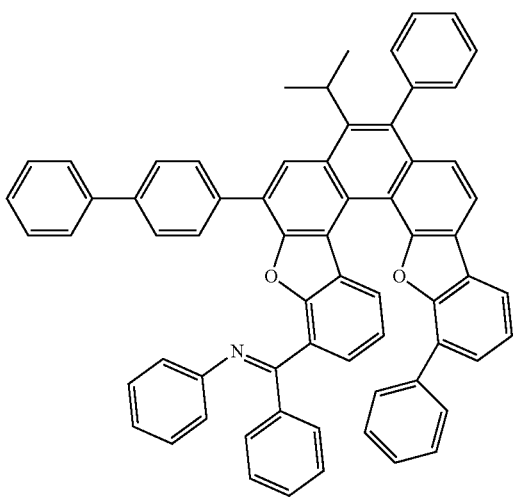

-continued
98
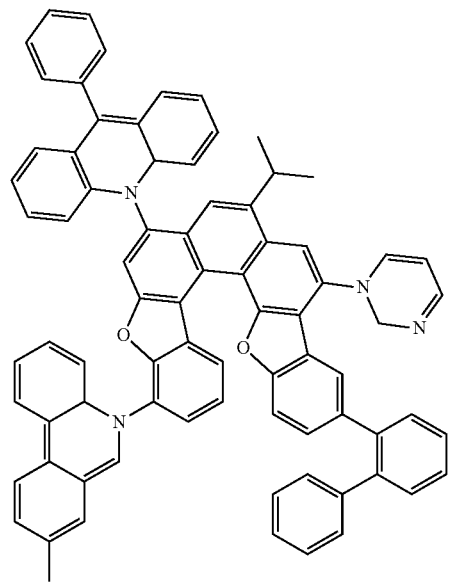
99
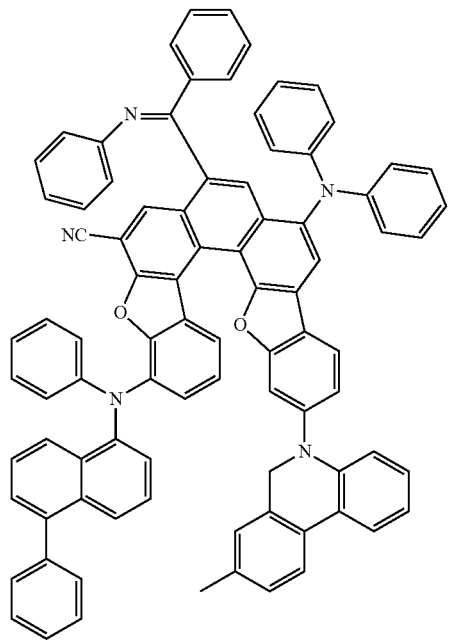
100
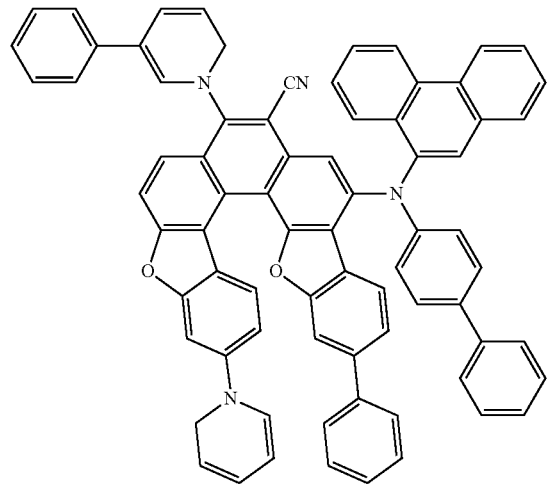
101
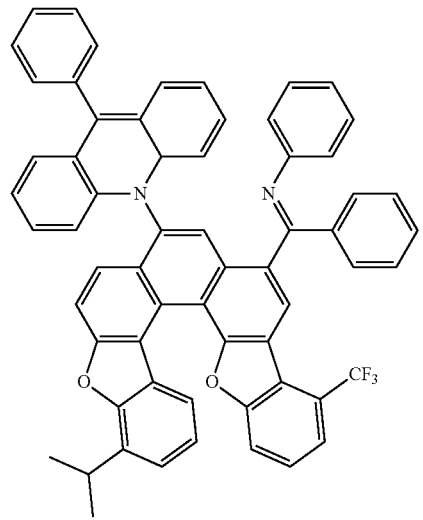

-continued
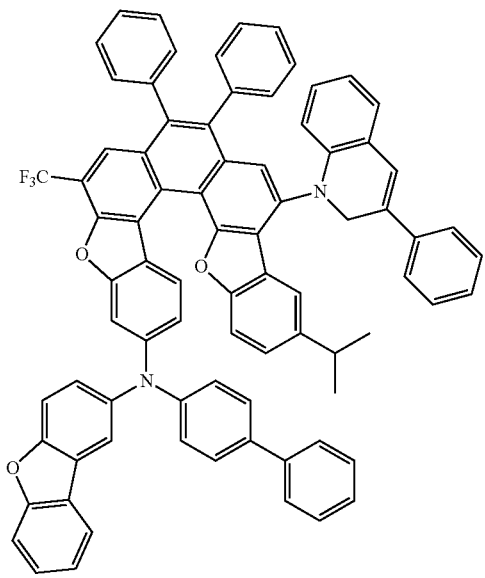
102
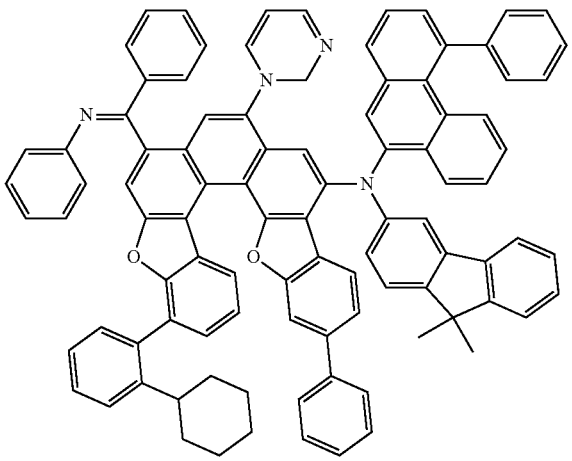
103
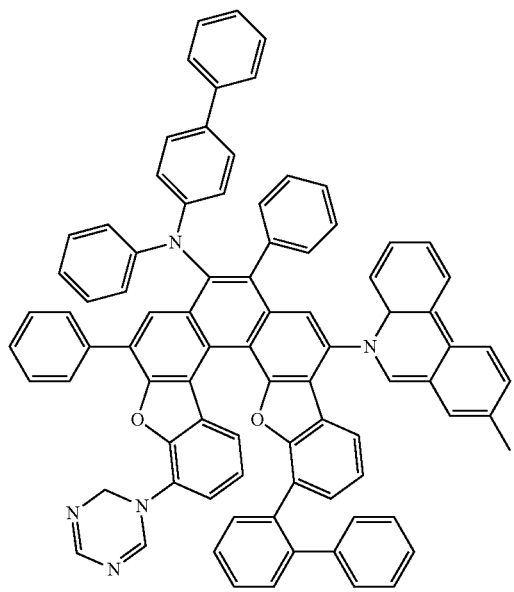
104
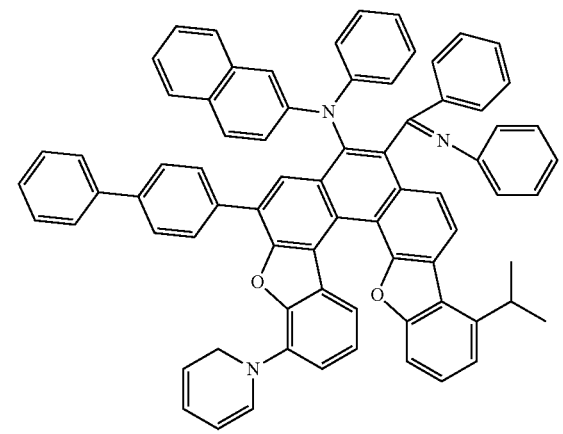
105
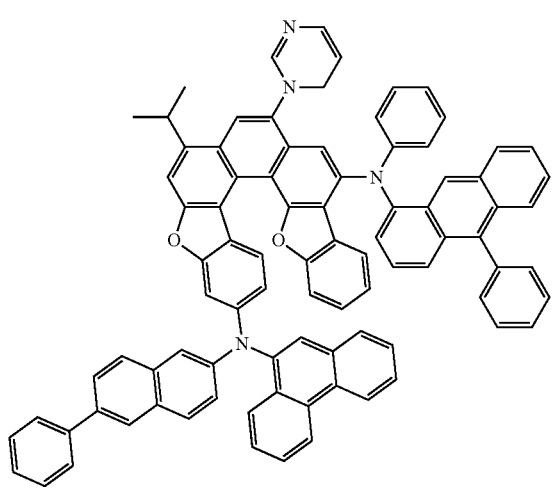
106
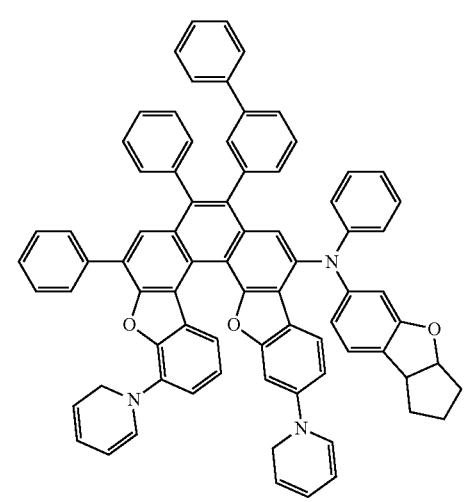
107

-continued
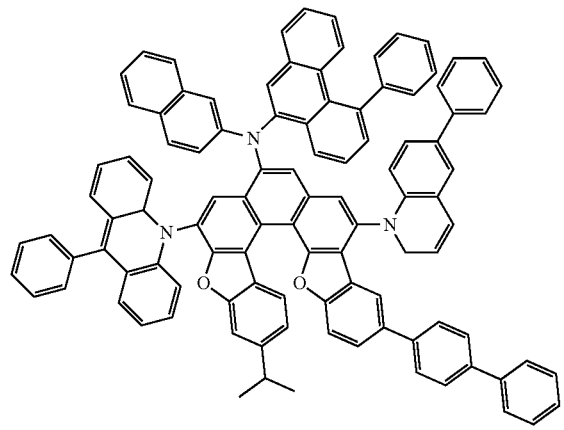
108
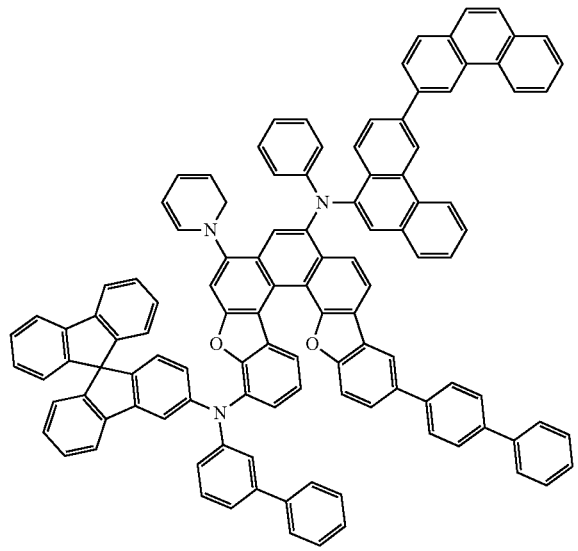
109
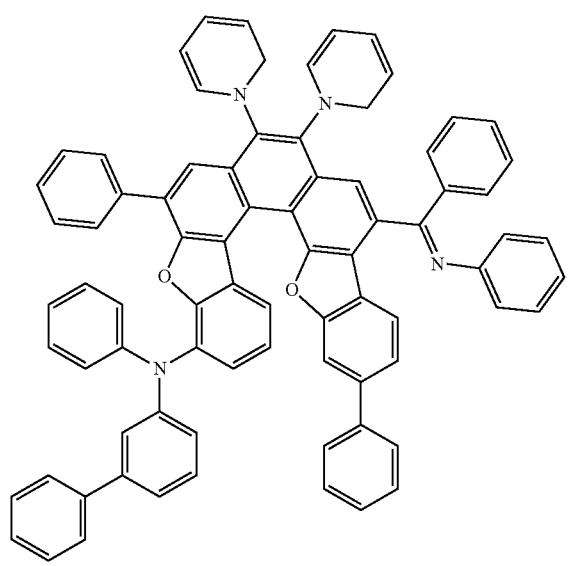
110
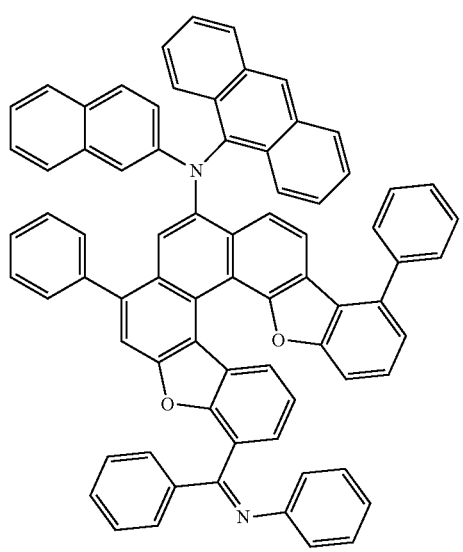
111

-continued
112
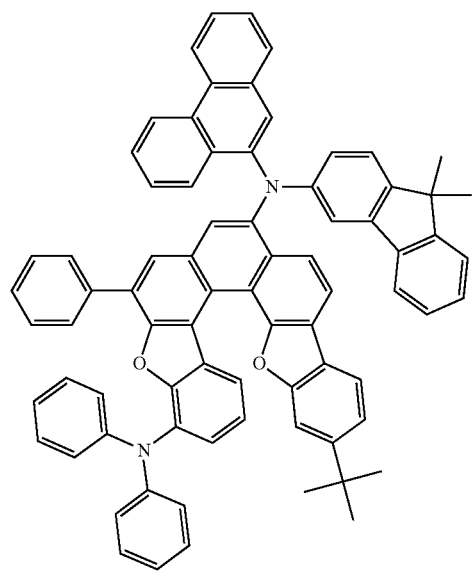
113
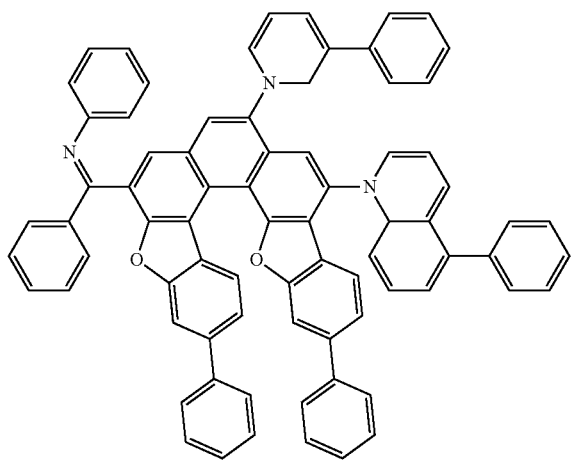
114
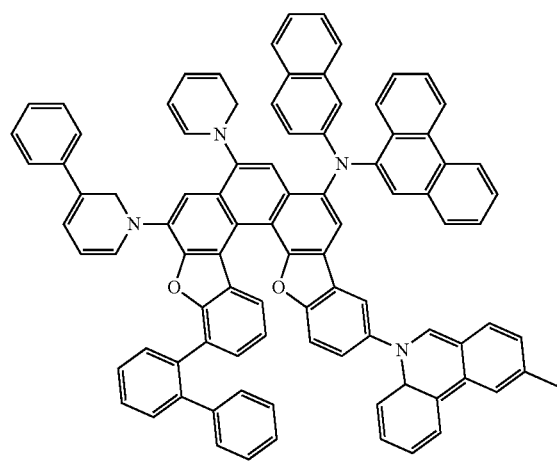
115
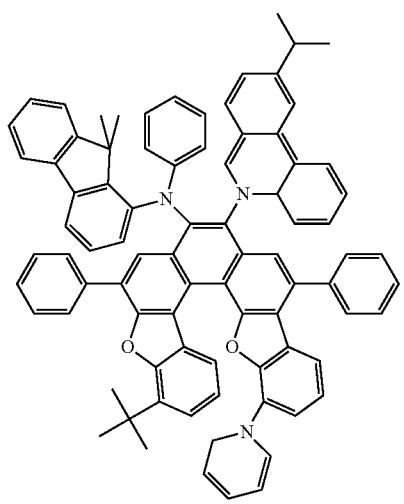

-continued
116
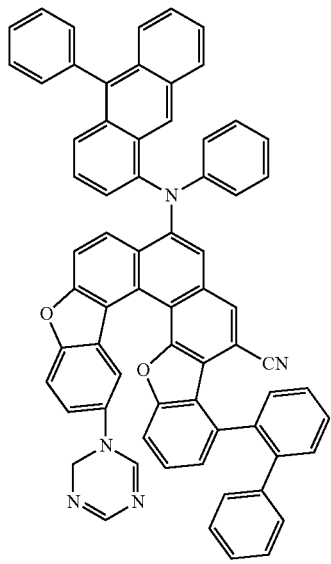
117
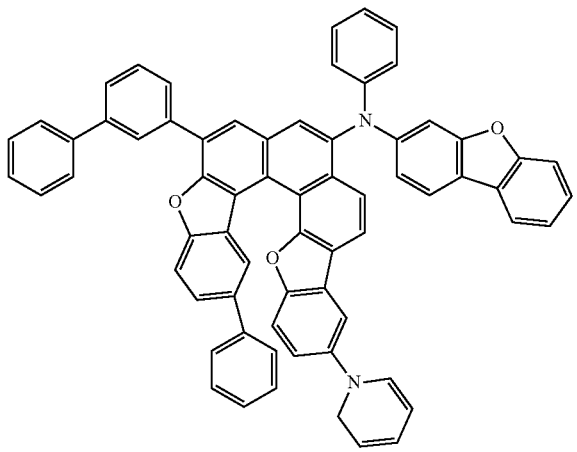
118
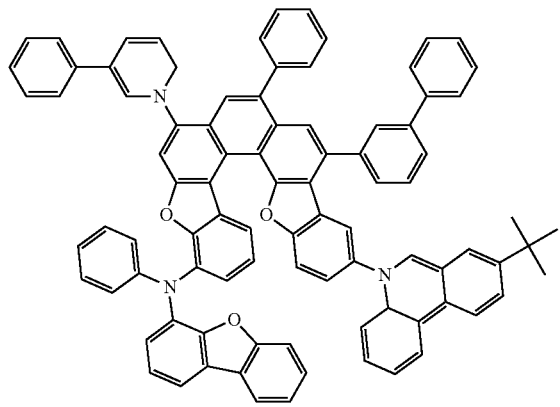
119
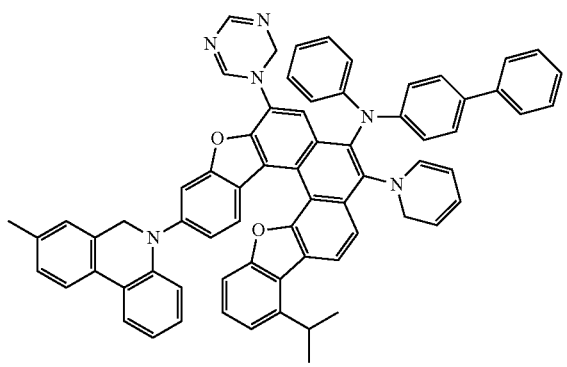
120
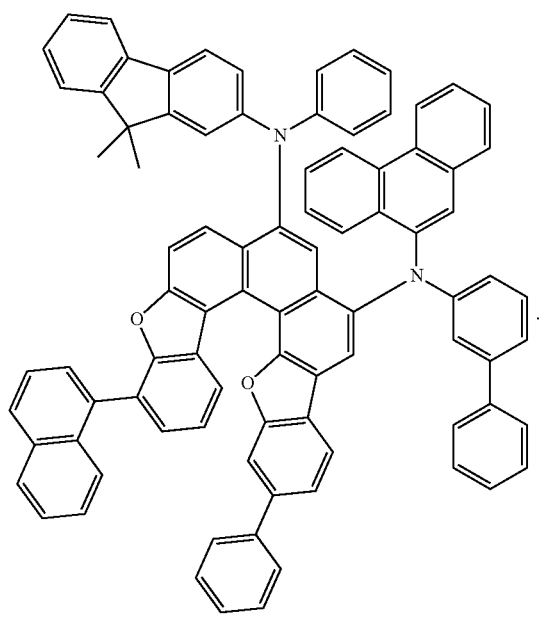
* * * * *

UNITED STATES PATENT AND TRADEMARK OFFICE
CERTIFICATE OF CORRECTION

PATENT NO. : 9,938,287 B1  
APPLICATION NO. : 15/828293  
DATED : April 10, 2018  
INVENTOR(S) : Jin Woo Kim, Chao Qian and Xiaowei Wang Page 1 of 1

It is certified that error appears in the above-identified patent and that said Letters Patent is hereby corrected as shown below:

On the Title Page

Insert Item --(30): Foreign Application Priority Data    Sep. 30, 2016 (CN) .........2016 1 0881333--

Signed and Sealed this  
Seventeenth Day of December, 2019

Andrei Iancu  
*Director of the United States Patent and Trademark Office*